US012492408B2

(12) United States Patent
Cannon et al.

(10) Patent No.: US 12,492,408 B2
(45) Date of Patent: Dec. 9, 2025

(54) METHODS FOR HYBRID CORN SEED PRODUCTION

(71) Applicant: Monsanto Technology LLC, St. Louis, MO (US)

(72) Inventors: Paul Cannon, Chesterfield, MO (US); Edward J. Cargill, Chesterfield, MO (US); Charles T. Foresman, St. Louis, MO (US); Michael A. Hall, Wildwood, MO (US); Scott C. Johnson, Wildwood, MO (US); John A. Miklos, Des Peres, MO (US)

(73) Assignee: Monsanto Tehnology LLC, St. Louis, MO (US)

( * ) Notice: Subject to any disclaimer, the term of this patent is extended or adjusted under 35 U.S.C. 154(b) by 0 days.

(21) Appl. No.: 18/182,207

(22) Filed: Mar. 10, 2023

(65) Prior Publication Data

US 2023/0323381 A1 Oct. 12, 2023

Related U.S. Application Data

(63) Continuation of application No. 17/101,202, filed on Nov. 23, 2020, now Pat. No. 11,632,921, which is a continuation of application No. 16/276,615, filed on Feb. 15, 2019, now Pat. No. 10,881,057.

(60) Provisional application No. 62/775,343, filed on Dec. 4, 2018, provisional application No. 62/631,199, filed on Feb. 15, 2018.

(51) Int. Cl.
*C12N 15/82* (2006.01)

(52) U.S. Cl.
CPC ..... *C12N 15/8262* (2013.01); *C12N 15/8218* (2013.01); *C12N 15/8297* (2013.01)

(58) Field of Classification Search
None
See application file for complete search history.

(56) References Cited

U.S. PATENT DOCUMENTS

| | | | |
|---|---|---|---|
| 4,368,592 A | 1/1983 | Welch | |
| 5,159,135 A | 10/1992 | Umbeck | |
| 5,188,958 A | 2/1993 | Moloney et al. | |
| 5,322,938 A | 6/1994 | McPherson et al. | |
| 5,352,605 A | 10/1994 | Fraley et al. | |
| 5,463,174 A | 10/1995 | Moloney et al. | |
| 5,510,474 A | 4/1996 | Quail et al. | |
| 5,538,880 A | 7/1996 | Lundquist et al. | |
| 5,550,318 A | 8/1996 | Adams et al. | |
| 5,591,616 A | 1/1997 | Hiei et al. | |
| 5,641,876 A | 6/1997 | McElroy et al. | |
| 5,750,871 A | 5/1998 | Moloney et al. | |
| 5,824,877 A | 10/1998 | Hinchee et al. | |
| 5,850,019 A | 12/1998 | Maiti et al. | |
| 5,939,539 A | 8/1999 | Lange et al. | |
| 6,153,812 A | 11/2000 | Fry et al. | |
| 6,160,208 A | 12/2000 | Lundquist et al. | |
| 6,198,021 B1 | 3/2001 | Lange et al. | |
| 6,372,211 B1 | 4/2002 | Isaac et al. | |
| 6,380,467 B1 | 4/2002 | Duclos | |
| 6,384,301 B1 | 5/2002 | Martinell et al. | |
| 6,399,861 B1 | 6/2002 | Anderson et al. | |
| 6,420,547 B1 | 7/2002 | Maiti et al. | |
| 6,429,357 B1 | 8/2002 | McElroy et al. | |
| 6,723,897 B2 | 4/2004 | Brown et al. | |
| 6,765,133 B2 | 7/2004 | Koehring | |
| 7,041,874 B2 | 5/2006 | Johal et al. | |
| 7,049,490 B2 | 5/2006 | Tanaka et al. | |
| 7,057,088 B2 | 6/2006 | Tanaka et al. | |
| 7,138,567 B2 | 11/2006 | Okawa et al. | |
| 7,154,028 B2 | 12/2006 | Tanaka et al. | |
| 7,597,055 B2 | 10/2009 | Choulet | |
| 8,835,353 B2 | 9/2014 | Fugiel et al. | |
| 9,012,722 B2 | 4/2015 | Narva et al. | |
| 9,040,774 B2 | 5/2015 | Ivashuta et al. | |
| 9,303,919 B2 | 4/2016 | Hultgren et al. | |
| 9,309,512 B2 | 4/2016 | Allen et al. | |
| 9,845,479 B2 | 12/2017 | Beghyn et al. | |
| 10,123,473 B2 | 11/2018 | Cavender-Bares et al. | |
| 10,472,684 B2 | 11/2019 | Barten et al. | |
| 10,724,047 B2 | 7/2020 | Allen et al. | |
| 10,881,057 B2 * | 1/2021 | Cannon | C12N 15/8262 |
| 11,627,736 B2 | 4/2023 | Barten et al. | |
| 11,632,921 B2 * | 4/2023 | Cannon | C12N 15/8262 800/290 |

(Continued)

FOREIGN PATENT DOCUMENTS

| | | |
|---|---|---|
| AU | 2016203359 B2 | 3/2018 |
| CN | 101440374 A | 5/2009 |

(Continued)

OTHER PUBLICATIONS

Pendleron et al. Crop Science 1961, vol. 1, No. 6; pp. 433-435.*
Begna et al .J. Agronomy & Crop Science (1997), 179:9-17.*
Cox et al . J. Prod. Agric. (1998) 11(1):128-134.*
Cox et al. J. Prod. Agric. (1997) 10(3):405-410.*
Da silva et al. Maringa (2014), vol. 36(2):175-181.*
Altschul, "Basic local alignment search tool." Journal of Molecular Biology, 15:403-410 (1990).
Chenna, et al., "Multiple sequence alignment with the Clustal series of programs," Nucleic Acids Research, 31(13): 3497-3500 (2003).
De Pater, et al., "The promoter of the rice gene GOS2 is active in various different monocot tissues and binds rice nuclear factor ASF-1," The Plant Journal, 2(6): 837-844 (1992).

(Continued)

*Primary Examiner* — Medina A Ibrahim
(74) *Attorney, Agent, or Firm* — Dentons US LLP; David Lanzotti

(57) ABSTRACT

Methods for improving the efficiency and productivity of hybrid corn seed production are provided herein. Various methods to improve the transfer of pollen from male corn plants to female corn plants, and thus increase yield, are provided herein. Without being limiting, these methods include varying the height of male and female corn plants in a field, as well as varying the number, arrangement, and ratio of male-to-female rows in a field.

41 Claims, 12 Drawing Sheets

Specification includes a Sequence Listing.

(56) References Cited

U.S. PATENT DOCUMENTS

| | | | |
|---|---|---|---|
| 12,274,205 | B2 | 4/2025 | Barten et al. |
| 2002/0053095 | A1 | 5/2002 | Brown et al. |
| 2002/0162142 | A1 | 10/2002 | Johal et al. |
| 2003/0172409 | A1 | 9/2003 | Horn |
| 2003/0233679 | A1 | 12/2003 | Brown et al. |
| 2004/0053411 | A1 | 3/2004 | Cullen et al. |
| 2004/0121321 | A1 | 6/2004 | Brown et al. |
| 2004/0268441 | A1 | 12/2004 | Vance et al. |
| 2005/0037988 | A1 | 2/2005 | Zamore et al. |
| 2005/0064474 | A1 | 3/2005 | Umov et al. |
| 2005/0144669 | A1 | 6/2005 | Reinhart et al. |
| 2005/0197253 | A1 | 9/2005 | Stoller et al. |
| 2005/0251883 | A1 | 11/2005 | Amasino et al. |
| 2006/0200878 | A1 | 9/2006 | Lutfiyya et al. |
| 2006/0253933 | A1 | 11/2006 | Brown et al. |
| 2007/0174931 | A1 | 7/2007 | Brown et al. |
| 2007/0294789 | A1 | 12/2007 | Ghiglione et al. |
| 2008/0034453 | A1 | 2/2008 | Cheikh et al. |
| 2009/0031441 | A1 | 1/2009 | Matsuoka et al. |
| 2009/0070898 | A1 | 3/2009 | Allen et al. |
| 2009/0117617 | A1 | 5/2009 | Holmes et al. |
| 2009/0313725 | A1 | 12/2009 | Yu et al. |
| 2010/0095406 | A1 | 4/2010 | Yu et al. |
| 2010/0107283 | A1 | 4/2010 | Dasgupta et al. |
| 2011/0004958 | A1 | 1/2011 | Aloni et al. |
| 2011/0035839 | A1 | 2/2011 | Lutfiyya et al. |
| 2011/0126310 | A1 | 5/2011 | Feng et al. |
| 2011/0145940 | A1 | 6/2011 | Voytas et al. |
| 2011/0167517 | A1 | 7/2011 | Danilevskaya et al. |
| 2011/0185456 | A1 | 7/2011 | Cheikh et al. |
| 2011/0296555 | A1 | 12/2011 | Ivashuta et al. |
| 2011/0301073 | A1 | 12/2011 | Gregory et al. |
| 2012/0142062 | A1 | 6/2012 | Doyon et al. |
| 2012/0174260 | A1 | 7/2012 | Narva et al. |
| 2012/0216318 | A1 | 8/2012 | La Rosa et al. |
| 2012/0297501 | A1 | 11/2012 | Beghyn et al. |
| 2013/0117869 | A1 | 5/2013 | Duchateau et al. |
| 2013/0121101 | A1 | 5/2013 | Ochampaugh et al. |
| 2013/0260012 | A1 | 10/2013 | Rommens et al. |
| 2013/0283461 | A1 | 10/2013 | Abad et al. |
| 2013/0345937 | A1 | 12/2013 | Strelioff et al. |
| 2014/0013464 | A1 | 1/2014 | Davie |
| 2014/0074360 | A1 | 3/2014 | Rosa et al. |
| 2014/0165228 | A1 | 6/2014 | Danilevskaya et al. |
| 2014/0344996 | A1 | 11/2014 | Inze et al. |
| 2015/0052634 | A1 | 2/2015 | Park et al. |
| 2015/0201619 | A1 | 7/2015 | Annigeri et al. |
| 2015/0247154 | A1 | 9/2015 | Ivashuta et al. |
| 2015/0307889 | A1 | 10/2015 | Petolino et al. |
| 2015/0376641 | A1 | 12/2015 | Etzioni et al. |
| 2016/0010109 | A1 | 1/2016 | Albertsen et al. |
| 2016/0017349 | A1 | 1/2016 | Ayele et al. |
| 2016/0046956 | A1 | 2/2016 | Yu et al. |
| 2016/0050865 | A1 | 2/2016 | Morse et al. |
| 2016/0050920 | A1 | 2/2016 | Ott et al. |
| 2016/0076046 | A1 | 3/2016 | Alexandrov et al. |
| 2016/0319375 | A1 | 11/2016 | Barten et al. |
| 2017/0079224 | A1 | 3/2017 | Jolliffe et al. |
| 2018/0051295 | A1 | 2/2018 | Allen et al. |
| 2019/0014730 | A1 | 1/2019 | Dong et al. |
| 2019/0014731 | A1 | 1/2019 | Ovadya et al. |
| 2019/0241903 | A1 | 8/2019 | Ellis et al. |
| 2019/0246586 | A1 | 8/2019 | Cannon et al. |
| 2019/0246619 | A1 | 8/2019 | Barten et al. |
| 2020/0140874 | A1 | 5/2020 | Barten et al. |
| 2021/0032649 | A1 | 2/2021 | Manjunath et al. |
| 2022/0039320 | A1 | 2/2022 | Barten et al. |
| 2022/0159905 | A1 | 5/2022 | Barten et al. |
| 2022/0159919 | A1 | 5/2022 | Cannon et al. |
| 2022/0162632 | A1 | 5/2022 | Barten et al. |
| 2022/0364108 | A1 | 11/2022 | Allen et al. |
| 2023/0110884 | A1 | 4/2023 | Allen et al. |
| 2023/0292733 | A1 | 9/2023 | Barten et al. |
| 2025/0221340 | A1 | 7/2025 | Barten et al. |

FOREIGN PATENT DOCUMENTS

| | | | |
|---|---|---|---|
| CN | 102149821 | A | 8/2011 |
| CN | 102174519 | A | 9/2011 |
| CN | 111778265 | | 10/2020 |
| EP | 1398382 | B1 | 11/2005 |
| JP | 3829157 | B2 | 10/2006 |
| KR | 20150045611 | A | 4/2015 |
| RU | 2013135491 | A | 2/2015 |
| RU | 2013151447 | A | 5/2015 |
| WO | WO 94/28141 | A1 | 12/1994 |
| WO | WO 99/09174 | A1 | 2/1999 |
| WO | WO 99/66029 | A2 | 12/1999 |
| WO | WO 00/009722 | A2 | 2/2000 |
| WO | WO 02/055725 | A2 | 7/2002 |
| WO | WO 03/008540 | A2 | 1/2003 |
| WO | 2004/092390 | | 10/2004 |
| WO | WO 2006/032916 | A2 | 3/2006 |
| WO | 2007/134234 | | 11/2007 |
| WO | WO 2008/034648 | A1 | 3/2008 |
| WO | WO 2010/002984 | A1 | 1/2010 |
| WO | WO 2011/023537 | A1 | 3/2011 |
| WO | WO 2013/037959 | A1 | 3/2013 |
| WO | WO 2013/086499 | A2 | 6/2013 |
| WO | WO 2014/055477 | A2 | 4/2014 |
| WO | WO 2014/151749 | A1 | 9/2014 |
| WO | WO 2015/168124 | A1 | 11/2015 |
| WO | 2016176286 | | 11/2016 |
| WO | 2017011791 | | 1/2017 |
| WO | 2018035354 | | 2/2018 |
| WO | 2018119225 | | 6/2018 |
| WO | 2018129302 | | 7/2018 |
| WO | 2019161143 | | 8/2019 |
| WO | 2019161145 | | 8/2019 |
| WO | 2019161149 | | 8/2019 |

OTHER PUBLICATIONS

Guo, et al., "RNA Silencing in Plants: Mechanism, Technologies and Applications in Horticulture Crops," Current Genomics, 17(6):476-489 (2016).

Hanway, "How a corn plant develops," Special Report No. 48, Iowa State University, CES, Ames, IA, (1966).

Inada, "Quality controls induced by aberrant translation," Nucleic Acids Research, 48(3): 1084-1096 (2020).

Israelsen, "Harvesting Corn Silage by Plant Moisture" article adapted from Crop and Soils Magazine, Utah State University Agricultural Extension Agents, (2009). Retrieved from <https://digitalcommons.usu.edu/cgi/viewcontent.cgi?article=1145&context=extension_curall>.

Karamyshev, et al., "Lost in Translation: Ribosome- Associated mRNA and Protein Quality Controls," Frontiers in Genetics, 9:431 (2018).

Larkin, et al., "Clustal W and Clustal X version 2.0," Bioinformatics, 23(21): 2947-48 (2007).

Last, et al., "pEmu: an improved promoter for gene expression in cereal cells," Theoretical and Applied Genetics, 81: 581-588 (1991).

Mcelroy, et al., "Construction of expression vectors based on the rice actin 1 (Actl) 5' region for use in monocot transformation," Molecular and General Genetics MGG, 231: 150-160 (1991).

Nickless, et al., "Control of gene expression through the nonsense-mediated RNA decay pathway," Cell & Bioscience, 7:26 (2017).

Ritchie, S.W. et al., "How corn plants develops," Special Report No. 48, Iowa State University, CES, Ames, IA, Reprinted 1996.

Szadeczky-Kardoss, et al., "The nonstop decay and the RNA silencing systems operate cooperatively in plants," Nucleic Acids Research, 46(9): 4632-4648 (2018).

Thompson, et al., "Clustal W: Improving the sensitivity of progressive multiple sequence alignment through sequence weighting, position-specific gap penalties and weight matrix choice," Nucleic Acids Research, 22: 4673-4680 (1994).

Wilson, et al., "Molecular Mechanisms of RNA Interference," Annual Review of Biophysics, 42: 217-39 (2013).

Goodman, Why do farmers leave dying corn in fields? Ask a farmer, Beef Runner, 2014.

(56) References Cited

OTHER PUBLICATIONS

Li et al., Difference in corn kernel moisture content between pre- and post-harvest, Journal of Integrative Agriculture 20 (7): 1775-1782, 2021.
Israelsen et al., Harvesting Corn Silage by Plant Moisture article adapted from Crop and Soils Magazine, Utah State University Agricultural Extension Agents, 2009.
U.S. Appl. No. 18/176,206, filed Feb. 28, 2023, Barten et al.
Crommelinck et al., "Simulating an Autonomously Operating Low-Cost Static Terrestrial LiDAR for Multitemporal Maize Crop Height Measurements," Remote Sensing, 8(3):205, pp. 1-17 (2016).
D'Andrea et al., "Genotypic Variability in Morphological and Physicological Traits among Maize Inbred Lines-Nitrogen Responses," Crop Sci., 46:1266-1276 (2006).
GenBank Accession No. AY366085, "Zea mays cultivar B73 PGP1 (pgpl) gene, complete cds" (2003).
International Search Report and Written Opinion mailed Aug. 8, 2019, in International Application No. PCT/US2019/018129.
International Search Report and Written Opinion mailed May 10, 2019, in International Application No. PCT/US2019/018127.
Kempton, "Heritable Characters of Maize, III. Brachytic Culms," Jour. Hexed., 11(1):111-115 (1920).
Mourtzinis et al., "Corn Grain and Stover Yield Prediction at RI Growth Stage," Agronomy Journal, 105(4):1045-1050 (2013).
Multani et al., "Loss of an MDR Transporter in Compact Stalks of Maize br2 and Sorghum dw3 Mutants," Science, 302:81-84 (2003).
Pilu et al., "Isolation and characterization of a new mutant allele of brachytic 2 maize gene," Molecular Breeding, 20:83-91 (2007).
Weng et al., "Genome-Wide Association Study Identifies Candidate Genes That Affect Plant Height in Chinese Elite Maize (*Zea mays* L.) Inbred Lines," PloS ONE, vol. 6, pp. 1-8 (2011).
Zaidi et al., "Phenotyping for Abiotic Stress Tolerance in Maize Heat Stress," CIMMYT, pp. 1-40 (2016).
"4 Series Sprayers," Published in May 2016, obtained from https://www.deere.com/en_CAF/docs/product/equipment/4_Series_Spr ayers.pdf (2016).
Amanullah et al., "Phenology, Growth, and Grain Yield of Maize as Influenced by Foliar Applied Urea at Different Growth Stages," Journal of Plant Nutrition 33:71-79 (2010).
"Corn Herbicide Application Timings," published online by PennState Extension; obtained from https://extension.psu.edu/corn-herbicide-application-timings (2015).
International Search Report and Written Opinion mailed Apr. 22, 2020, in International Application No. PCT/US2019/064270, pp. 1-14.
Lu, "Chapter 3 Research on Production Increase Technology in Late Harvesting of Maize in Optimum Period," Theory and Technology of Maize High Yield (2015).
Qiao et al., "The influence of RNAi targeting of OsGA20ox2 gene on plant height in rice," Plant Molecular Biology Reporting 29.4:952-960 (2011).
Wang et al., "Analysis of hormone sensitivity of a dwarf mutant of maize," Journal of Northwest A&F University (Nat. Sci. Ed.) 45(8) (2017).
Butzen, "Timing Corn Harvest," Crop Insights, (Sep. 2018).
Chen et al., "Identification and genetic mapping for rht-DM, a dominant dwarfing gene in mutant semi-dwarf maize using QTL-seq approach," Genes & Genomics 40, pp. 1091-1099 (Jun. 2018) (electronic publication).
Elmore et al., "In-Field Drydown Rates and Harvest," Iowa State University Extension and Outreach, https://crops.extension.iastate.edu/cropnews/2010/09/field-drydown-rates-and-harvest (Sep. 28, 2010).
Spelhaug, "Predicting Your Corn Harvest Date," Peterson Farms Seed (2013).
Supplementary European Search Report dated Oct. 11, 2022 in EP 19 89 2688.
Thomison et al., "Corn Response to Harvest Date a Affected by Plant Population and Hybrid," Agron J. 103, pp. 1765-1772 (Sep. 2011) (electronic publication).
Search Report dated Jul. 21, 2022, in Chinese Application 2017800639820 including English translation of related Office Action.
Allen, et al., "Evolution of microRNA genes by inverted duplication of target gene sequences in *Arabidopsis thaliana*," Nature Genetics, 36:1282-1290 (2004).
Allen, et al., "microRNA-directed phasing during Trans-acting siRNA Biogenesis in plants," Cell, 121(2):207-221 (2005).
Altschul, et al., "Basic Local Alignment Search Tool," Journal of Molecular Biology, 215(3):403-410 (1990).
Altschul, et al., "Gapped BLAST and PSI-BLAST: a new generation of protein database search programs," Nucleic Acids Research, 25 (17) : 3389-3402 (1997).
Ashikari, et al., "Loss-of-function of a Rice Gibberellin Biosynthetic Gene, GA20 oxidase (GA20ox-2), Led to the Rice 'Green Revolution'," Breeding Science, 52:143-150 (2002).
Axtell, et al., "A Two-Hit Trigger for siRNA Biogenesis in Plants," Cell, 127:565- 577 (2006).
Beurdeley, et al., "Compact designer TALENs for efficient genome engineering", Nature Communications, 4: 1762 (2013).
Cai, et al., "Molecular Cloning, Characterization, and Expression Analysis of Genes Encoding Gibberellin 20-Oxidase in *Dasypyrum villosum* Dwarf Mutant," Plant Molecular Biology Reporter, 30:1110-1116 (2012).
Carrera, et al.,"Changes in GA 20-oxidase gene expression strongly affect stem length, tuber induction and tuber yield of potato plants," The Plant Journal, 22(3):247-256 (2000).
Cermak, et al., "Efficient design and assembly of custom TALEN and other TAL effector-based constructs for DNA targeting," Nucleic Acids Research, 39(12):e82 (2011).
Chen, et al., "Identification and Functional Analysis of Flowering Related microRNAs in Common Wild Rice (*Oryza rufipogon* Griff.)," PLoS One, 8:e82844 (2013).
Chen, et al., "New insight in the Gibberellin biosynthesis and signal transduction," Plant Signaling & Behavior, 10(5):e1000140-1-e1000140-3:(2015).
Chen, et al., "The Maize DWARF1 Encodes a Gibberellin 3-Oxidase and Is Dual Localized to the Nucleus and Cytosol," Plant Physiology, 166:2028-2039 (2014).
Ciampitti, et al., "A comprehensive study of plant density consequences on nitrogen uptake dynamics of maize plants from vegetative to reproductive stages," Field Crops Research, 121(1):2-18 (2011).
Coles, et al., "Modification of gibberellin production and plant development in *Arabidopsis* by sense and antisense expression of gibberellin 20-oxidase genes," The Plant Journal, 17(5):547-556 (1999).
Davis, et al., "Gibberellin Biosynthesis in Maize. Metabolic Studies with $GA_{15}$, $GA_{24}$, $GA_{25}$, $GA_7$, and 2,3-Dehydro-$GA_9$[1]," Plant Physiology, 121(3):1037-1045 (1999).
Doyle, et al., "TAL Effector-Nucleotide Targeter (TALE-NT) 2.0: tools for TAL effector design and target prediction," Nucleic Acids Research, 40:W117-122 (2012).
Du, et al., "Cloning and characterization of an up-regulated GA 20-oxidase gene in hybrid maize," Natural Science, 19(2):161-166 (2009).
Eriksson, et al., "$GA_4$ Is the Active Gibberellin in the Regulation of LEAFY Transcription and *Arabidopsis* Floral Initiation," The Plant Cell, 18(9):2172-2181 (2006).
Extended European Search Report dated Mar. 9, 2020, in European Patent Application No. 17842139.2.
Fagoaga, et al., "Engineering of gibberellin levels in citrus by sense and antisense overexpression of a GA 20-oxidase gene modifies plant architecture," Journal of Experimental Botany, 58(6):1407-1420 (2007).
Fambrini, et al., "The extreme dwarf phenotype of the GA-sensitive mutant of sunflower, dwarf2, is generated by a deletion in the ent-kaurenoic acid oxidase1 (HaKAO1) gene sequence," Plant Molecular Biology, 75:431-450 (2011).
Franco-Zorrilla, et al., "Target mimicry provides a new mechanism for regulation of microRNA activity," Nature Genetics, 39: 1033-1037 (2007).

(56) References Cited

OTHER PUBLICATIONS

Gabsalilow, et al., "Site- and strand-specific nicking of DNA by fusion proteins derived from MutH and I-Scel or TALE repeats," Nucleic Acids Research, 41(7):e83 (2013).
Gaj, et al.. "ZFN, TALEN, and CRISPR/Cas-based methods for genome engineering," Trends Biotechnology, 31(7):397-405 (2013).
GenBank Accession No. AY105651.1, "*Zea mays* PC0130567 mRNA sequence," pp. 1-2, dated May 28, 2008.
GenBank Accession No. BT068785.2, "*Zea mays* full-length cDNA clone ZM_BFb0382B03 mRNA, complete cds," pp. 1-2, dated Jun. 15, 2012.
GenBank Accession No. EU963664.1, "*Zea mays* clone 265382 gibberellin 20 oxidase 2 mRNA, complete cds," pp. 1, dated Dec. 10, 2008.
Griffiths-Jones, et al., "Rfam: an RNA family database," Nucleic Acids Research, 31(1):439-441 (2003).
Gupta, et al., "Gibberellic acid in plant Still a mystery unresolved," Plant Signaling & Behavior, 8(9):e25504 (2013).
Han, et al., "Gibberellin-associated cisgenes modify growth, stature and wood properties in *Populus*," Plant Biotechnology Journal, 9(2):162-178 (2011).
Hedden, "Gibberellin Biosynthesis: Enzymes, Genes and Their Regulation," Annu. Rev. Plant Physiol. Plant Mol. Biol., 48:431-60 (1997).
Hedden, "The genes of the Green Revolution," TRENDS in Genetics, 19(1):5-9 (2003).
Helliwell, et al."Constructs and Methods for Hairpin RNA-Mediated Gene Silencing in Plants," Methods in Enzymology, 392:24-35 (2003).
Huang, et al., "A Gibberellin-Mediated DELLA-NAC Signaling Cascade Regulates Cellulose Synthesis in Rice," The Plant Cell, 27(6):1681-1696 (2015).
Copenheaver. International Search Report and Written Opinion mailed Dec. 28, 2017, in International Application No. PCT/US2017/047405.
Jia, et al., "GA-20 oxidase as a candidate for the semidwarf gene sdw1/denso in barley," Functional & Integrative Genomics, 9:255-262 (2009).
Jia, et al., "Molecular characterization and functional analysis of barley semi-dwarf mutant Riso No. 9265," BMC Genomics, 16(927):1-11 (2015).
Jones-Rhoades, et al., "Computational Identification of Plant MicroRNAs and Their Targets, Including a Stress-Induced miRNA," Molecular Cell, 14(6):787-799 (2004).
Kamthan, et al., "Small RNAs in plants: recent development and application for crop improvement" Frontiers in Plant Science, 6:1-17 (2015).
Katoh, et al., "Specific residues at every third position of siRNA shape its efficient RNAi activity," Nucleic Acids Research, 35(4):e27 (2007).
Khvorova, et al., "Functional siRNAs and miRNAs Exhibit Strand Bias," Cell, 115(2):209-216 (2003).
Kim, "MicroRNA Biogenesis: Coordinated Cropping and Dicing," Nature Reviews Molecular Cell Biology, 6:376-385 (2005).
King, et al., "Selective Deactivation of Gibberellins below the Shoot Apex is Critical to Flowering but Not to Stem Elongation of *Lolium*," Molecular Plant, 1(2):295-307 (2008).
Kobayashi, et al., "Gibberellin Metabolism in Maize," Plant Physiology, 110(2):413-418 (1996).
Kusaba, et al., "Isolation and expression analysis of gibberellin 20-oxidase homologous gene in apple," Journal of Experimental Botany, 52(335):375-376 (2001).
Lange, et al., "Gibberellin Biosynthesis and the Regulation of Plant Development," Plant Biology, 8(3):281-290 (2006).
Liu, et al., "Analysis of Complementarity Requirements for Plant MicroRNA Targeting Using a *Nicotiana benthamiana* Quantitative Transient Assay," The Plant Cell, 26(2):741-753 (2014).
McElroy, et al., "Construction of expression vectors based on the rice actin 1 (Act1) 5' region for use in monocot transformation," Molecular and General Genetics MGG, 231:150-160 (1991).
Mitchum, et al., "Distinct and overlapping roles of two gibberellin 3-oxidases in *Arabidopsis* development," The Plant Journal, 45(5):804-818 (2006).
Molina, et al., "Transformation of a Dwarf *Arabidopsis* Mutant Illustrates Gibberellin Hormone Physiology and the Function of a Green Revolution Gene," Biochemistry and Molecular Biology Education, 37(3): 170-177 (2009).
Mutasa-Gottgens, et al., "Gibberellin as a factor in floral regulatory networks," Journal of Experimental Botany, 60(7):1979-1989 (2009).
Offtype—Definition of Offtype by Merriam-Webster, pp. 1, retrieved Sep. 18, 2023 <https://www.merriam-webster.com/dictionary/offtype>.
Oikawa, et al., "A role of OsGA20ox1, encoding an isoform of gibberellin 20-oxidase, for regulation of plant stature in rice," Plant Molecular Biology, 55:687-700 (2004).
Ookawa, et al., "Precise estimation of genomic regions controlling lodging resistance using a set of reciprocal chromosome segment substitution lines in rice," Scientific Reports, 6(30572) pp. 1-12 (2016).
Parizotto, et al., "In vivo investigation of the transcription, processing, endonucleolytic activity, and functional relevance of the spatial distribution of a plant miRNA," Genes & Development, 18:2237-2242 (2004).
Pater, et al., "The promoter of the rice gene GOS2 is active in various different monocot tissues and binds rice nuclear factor ASF-1," The Plant Journal, 2(6):837-844 (1992).
Peiffer, et al., "The Genetic Architecture Of Maize Height," Genetics, 196(4):1337-1356 (2014).
Peng, et al., "'Green revolution' genes encode mutant gibberellin response modulators," Nature, 400:256-261 (1999).
Petti, et al., "Mapping of a Cellulose-Deficient Mutant Named dwarf1-1 in *Sorghum bicolor* to the Green Revolution Gene gibberellin20-oxidase Reveals a Positive Regulatory Association between Gibberellin and Cellulose Biosynthesis," Plant Physiology, 169(1):705-716 (2015).
Plackett, et al., "Analysis of the Developmental Roles of the Arabidopsis Gibberellin 20-Oxidases Demonstrates That GA200x1, -2, and -3 Are the Dominant Paralogs, " The Plant Cell, 24(3):941-960 (2012).
Qiao, et al., "Alteration of rice growth and development via antisense expression of OsGA20ox2 gene," African Journal of Biotechnology, 12(5):3898-3904 (2013).
Qiao, et al., "Modification of plant height via RNAi suppression of OsGA20ox2 gene in rice," Euphytica, 158-35-45 (2007).
Qiao, et al., "The Influence of RNAi Targeting of OsGA20ox2 Gene on Plant Height in Rice," Plant Molecular Biology Reporter, 29:952-960 (2011).
Reynolds, et al., "Rational siRNA design for RNA interference," Nature Biotechnology, 22(3):326-330 (2004).
Rhoades, et al., "Prediction of Plant MicroRNA Targets," Cell, 110(4):513-520 (2002).
Rieu, et al., "The gibberellin biosynthetic genes AtGA20ox1 and AtGA20ox2 act, partially redundantly, to promote growth and development throughout the *Arabidopsis* life cycle," The Plant Journal, 53 :488-504 (2008).
Ross, et al., "Gibberellin mutants," Physiologia Plantarum, 100(3):550-560 (1997).
Sarkar, et al., "Relationship between gibberellins, height, and stress tolerance in barley (*Hordeum vulgare* L.) seedlings," Plant Growth Regulation, 42:125-135 (2004).
Sasaki, et al., "A mutant gibberellin-synthesis gene in rice," Nature, 416:701-702 (2002).
Search Report dated Jun. 24, 2021, in Russian Patent Application 2019105536, and English translation of the same (pp. 1-4).
Singh, "The green revolution and the evolution of agricultural education and research in India," Genome, 42(4):557-561 (1999).
Song, et al., "Association of the molecular regulation of ear leaf senescence/stress response and photosynthesis/metabolism with heterosis at the reproductive stage in maize," Scientific Reports, 6: 29843 (2016).
Song, et al., "Flowering time regulation: photoperiod- and temperature-sensing in leaves," Trends in Plant Science, 18(10):575-583 (2013).

(56) References Cited

OTHER PUBLICATIONS

Song, et al., "Genome-wide identification of gibberellins metabolic enzyme genes and expression profiling analysis during seed germination in maize," Gene, 482(1-2):34-42 (2011).
Spielmeyer, et al., "Semidwarf (sd-1), "green revolution" rice, contains a defective gibberellin 20-oxidase gene," PNAS, 99(13):9043-9048 (2002).
Sun, "Gibberellin Metabolism, Perception and Signaling Pathways in *Arabidopsis*," The *Arabidopsis* Book, 2008(6): pp. 1-28 (2008).
Sunkar, et al., "Novel and Stress-Regulated MicroRNAs and Other Small RNAs from Arabidopsis," Plant Cell, 16(8):2001-2019 (2004).
Supplementary Partial European Search Report dated Jan. 14, 2020, in European Patent Application No. 17842139.2.
Svitashev, et al., "Targeted Mutagenesis, Precise Gene Editing, and Site-Specific Gene Insertion in Maize Using Cas9 and Guide RNA," Plant Physiology, 169(2):931-945 (2015).
Teng, et al., "ZmGA3ox2, a candidate gene for a major QTL, qPH3.1, for plant height in maize," The Plant Journal, 73(3):405-416 (2013).
Thompson, et al., "CLUSTAL W: improving the sensitivity of progressive multiple sequence alignment through sequence weighting, position-specific gap penalties and weight matrix choice," Nucleic Acids Research, 22(22):4673-4680 (1994).
Tollenaar, et al., "Effect of Defoliation on Kernel Development in Maize," Canadian Journal of Plant Science, 58(1):207-212 (1978).
Tong, et al., "Reply: Brassinosteroid Regulates Gibberellin Synthesis to Promote Cell Elongation in Rice: Critical Comments on Ross and Quittenden's Letter," The Plant Cell, vol. 28, pp. 833-835, (2016).
Traore, et al., "Bt and Non-Bt Maize Growth and Development as Affected by Temperature and Drought Stress," Agronomy Journal, 92(5): 1027-1035 (2000).
Unterholzner, et al., "Reply: Interaction Between Brassinosteroids and Gibberellins: Synthesis or Signaling? In *Arabidopsis* Both!," The Plant Cell, vol. 28, pp. 836-839, (2016).
Urakami, et al., "Immunomodulation of gibberellin biosynthesis using an anti-precursor gibberellin antibody confers gibberellin-deficient phenotypes," Planta, 228:863-873 (2008).
Voytas, "Plant Genome Engineering with Sequence-Specific Nucleases," Annual Review of Plant Biology, 64:327-50 (2013).
Wang, et al., "Gibberellin Biosynthetic Deficiency Is Responsible for Maize Dominant Dwarf11 (D11) Mutant Phenotype: Physiological and Transcriptomic Evidence," PLoS One, 8(6):e66466:1-8 (2013).
Wang, et al., "More than meets the eye? Factors that affect target selection by plant miRNAs and heterochromatic siRNAs," Current Opinion Plant Biology, 27:118-124 (2015).
Weng, et al.," Genome-Wide Association Study Identifies Candidate Genes That Affect Plant Height in Chinese Elite Maize (*Zea mays* L.) Inbred Lines," PLoS One, 6(12):e29229 pp. 1-8 (2011).
Wu, et al., "Target specificity of the CRISPR-Cas9 system," Quantitative Biology, 2(2):59-70 (2014).
Xiao, et al., "Dissection of GA 20-oxidase members affecting tomato morphology by RNAi-mediated silencing," Plant Growth Regulation, 50:179-189 (2006).
Yamaguchi, et al., "Gibberellin Acts Positively Then Negatively to Control Onset of Flower Formation in *Arabidopsis*," Science, 344(6184):638-641 (2014).
Yamaguchi, "Gibberellin Metabolism and its Regulation," Annual Review of Plant Biology, 59:225-251 (2008).
Yanik, et al., "TALE-Pvull Fusion Proteins—Novel Tools for Gene Targeting," PLoS One, 8(12):e82539 pp. 1-13 (2013).
Yin, et al., "In-Season Prediction of Corn Yield Using Plant Height under Major Production Systems," Agronomy Journal, 103(3):923-929 (2011).
Yoshikawa, et al., "A pathway for the biogenesis of trans-acting siRNAs in *Arabidopsis*," Genes & Development, 19:2164-2175 (2005).
Zeng, et al., "Both Natural and Designed Micro RNAs Can Inhibit the Expression of Cognate mRNAs When Expressed in Human Cells," Molecular Cell, 9(6): 1327-1333 (2002).
Rodriquez. Invitation to Pay Additional Fees for Application No. PCT/US23/62985 mailed May 23, 2023.
Rodriquez. International Search Report and Written Opinion for Application No. PCT/US23/62985 mailed Jul. 27, 2023.
Xia et al., "A book to understand high corn yield and disaster prevention and reduction technology", China Farmers Press, May 2016, p. 135.
Chinese Office Action regarding Chinese Patent Application No. 201980025083.0, dated Dec. 1, 2023, 19 pages.
Hill and Furrow, "Pinch or Push Your Corn: Scouting for Lodging Potential", University of Illinois Urbana-Champaign, Illinois Extension, Sep. 12, 2016, 2 pages.
Bage et al., Genetic characterization of novel and CRISPR-Cas9 gene edited maize brachytic 2 alleles, Plant Gene 21:100198, 2020.
Bolduc and Hake, The maize transcription factor KNOTTED1 directly regulates the gibberellin catabolismgene ga2ox1, Plant Cell 21:1647-1658, 2009.
R4038-sprayer by John Deere, available at https://kibbleeq.com/farmers/sprayers-&-applicators/self-propelled-sprayers/john-deere-sprayers/r4038-sprayer, accessed Apr. 29, 2024.
Sun et al., Identification and characterization of EI (Elongated Internode) gene in tomato (*Solanum lycopersicum*), Int. J. Mol. Sci. 20(2204):1-18, 2019.
Anonymous, Proceedings of the Caribbean Food Crops Society Fourth Annual Meeting, 1996.
Chen, et al. "Development of dwarfish and yield-effective GM maize through passivation of bioactive gibberellin." Transgenic Res, 28:589-599, (2019).
Kollner, et al. "Herbivore-Induced SABATH Methyltransferases of Maize that Methylate Anthranilic Acid Using S-Adenosyl-L-Methionine." Plant Physiology, vol. 153, pp. 1795-1807, (2010).
Zhang, et al. "Maize brachtic2 (br2) suppresses the elongation of lower internodes for excessive auxin accumulation in the intercalary meristem region." BMC Plant Biology, 19:589, (2019).
U.S. Appl. No. 18/866,453, filed Nov. 15, 2024, Cargill, et al.
GenBank AJ132435.1. "*Arabidopsis thaliana* mRNA for GA 2-oxidase, gene ga2ox1" Dated 1999. Retrieved from: <https://www.ncbi.nlm.nih.gov/nuccore/AJ132435>.
International Search Report and Written Opinion for International Application No. PCT/US2023/66999 mailed Nov. 2, 2023.
Dhaliwal, et al., "Comparative analysis of ABCB1 reveals novel structural and functional conservation between monocots and dicots." Frontiers in Plant Science, 2014, vol. 5, Article 657.
Knoller, et al., "Brachytic2/ZmABCB1 functions in IAA export from intercalary meristems." J. Exp. Botany, 61:3689-3696 (2010).
Uniprot A0A2P1BTK0_MAIZE. Brachytic 2. Accessed on Dec. 27, 2024. Accessed from <https://www.uniprot.org/uniprotkb/A0A2P1BTK0/entry>.
Abendroth & Elmore, presentation titled "Corn Growth and Development" available at https://www.ipm.iastate.edu/files/curriculum/03%20Corn%20Growth%20and%20Development_0.pdf, accessed Feb. 12, 2025.
Jayasundara et al., Energy and Greenhouse Gas Intensity of Corn (*Zea mays* L.) Production in Ontario: a Regional Assessment, Can J. Soil Sci. 94:77-95, 2014.
Lindsey & Zoller, Useful Tables: Adjustments and Conversions on Corn and Soybean Parameters, article on the Ohio State University Extension website https://ohioline.osu.edu/factsheet/agf-502, 2018.
Nielsen, Short Corn at Tasseling, article for Purdue Agronomy available at https://www.agry.purdue.edu/ext/corn/news/articles.01/short_corn-0712.html, 2001.
Xing, et al. "A rare SNP mutation in Brachytic2 moderately reduces plant height and increases yield potential in maize." Journal of Experimental Botany, vol. 66, Issue 13, pp. 3791-3802, (2015).
Thomas, et al. "Size constraints for targeting post-transcriptional gene silencing and for RNA-directed methylation in Nicotiana benthamiana using a potato virus X vector." The Plant Journal, vol. 25(4), pp. 417-425, (2001).
Macrobert, et al. "Maize Hybrid Seed Production Manual." International Maize and Wheat Improvement Center. (2014).

(56) References Cited

OTHER PUBLICATIONS

Haegele, et al. "Row Arrangement, Phosphorus Fertility, and Hybrid Contributions to Managing Increased Plant Density of Maize." Agronomy, vol. 106(5), pp. 1838-1846, (2014).
Guo, et al. "Protein tolerance to random amino acid change." Proc. Natl. Acad. Sci. U.S.A., vol. 101 (25), pp. 9205-9210, (2004).
Klahre, et al. "High molecular weight RNAs and small interfering RNAs induce systemic posttranscriptional gene silencing in plants." Proc. Natl. Acad. Sci. U.S.A., 99 (18) 11981-11986, (2002).
Elmore and Abendroth, How Fast Can Corn Dry Down? Iowa State University Extension and Outreach, available at https://crops.extension.iastate.edu/encyclopedia/how-fast-can-corn-dry-down, 2007.
Lo, et al. "Ectopic expression of specific GA2 oxidase mutants promotes yield and stress tolerance in rice." Plant. Biotech. J. 15:850-864, (2017).
Trellis. "When Should I Stop Irrigating?" (2018). Accessed from https://www.mytrellis.com/blog/when-should-I-stop-irrigating.
USPTO: Final Office Action regarding U.S. Appl. No. 17/530,873, mailed Jul. 31, 2025.

* cited by examiner

SEQUENCE LISTING

```
Sequence total quantity: 131
SEQ ID NO: 1           moltype = DNA  length = 1741
FEATURE                Location/Qualifiers
source                 1..1741
                       mol_type = other DNA
                       organism = Zea mays
SEQUENCE: 1
gacggtagtt ttcatctaaa gtttattctt cgtcacatgg gatggccgtt tgcttgtttg  60
ttgcttccgg gaggcggtgg tgaattgaag cagatcgaca agcatggctg cccactggtc  120
tcgatcgatc ggcctgccat gccatgccat gccactagag tccgtcctga ctggccgccc  180
gttcccccgt ataaaaaggc aggcaggcag gcagagcggg gacgagcaag caagcagttg  240
cagttgcagc ggcctcctcc tctgcttcct ccctcctcct cctcaccatg gtgctggctg  300
cgcacgatcc ccctcccctt gtgttcgacg ctgcccgcct gagcggcctc tccgacatcc  360
cgcagcagtt catctggccg gcggacgaga gcccccaccc ggactccgcc gaggagctgg  420
ccgtgccgct catcgacctc tccggggacg ccgccgaggt ggtccggcag gtccggcgcg  480
cctgcgacct gcacggcttc ttccaggtgg tggggcacgg catcgacgcg gcgctgacgg  540
cggaggccca ccgctgcatg gacgccttct tcacgctgcc gctcccggac aagcagcgcg  600
cgcagcgccg ccagggggac agctgcggct acgccagcag cttcacgggc cggttcgcgt  660
ccaagctgcc ctggaaggag acgctgtcgt tccgctacac cgacgacgac gacggcgaca  720
agtccaagga cgtcgtggcg tcctacttcg tggacaagct gggcgagggg taccggcacc  780
acggggaggt gtacgggcgc tactgctctg agatgagccg tctgtcgctg gagctcatgg  840
aggtgctagg cgagagcctg ggcgtgggcc ggcgccactt ccggcgcttc ttccagggga  900
acgactccat catgcgcctc aactactacc cgccgtgcca gcggccctac gacacgctgg  960
gcacggggcc gcattgcgac cccacgtcgc tcaccatcct gcaccaggac gacgtgggcg  1020
gactccaggt gttcgacgcc gccacgctcg cgtggcgctc catcaggccc cgcccgggcg  1080
ccttcgtcgt caacatcggc gacaccttca tggcgctctc caacgggcgc tacaggagct  1140
gcctccaccg cgccgtcgtc aacagccggg tggcacgccg ctcgctcgcc ttcttcctgt  1200
gcccggagat ggacaaggtg gtcaggccgc ccaaggagct ggtggacgac gccaacccga  1260
gggcgtaccc ggacttcacg tggaggacgc tgctggactt caccatgagg cactacaggt  1320
cggacatgag gacgctcgag gccttctcca actggctcag caccagtagc aatggcggac  1380
agcacctgct ggagaagaag taggcatgct atttgggtat ggaagatggt ggatgtaagc  1440
aaacaaagcc aaattaagca gagtaggtta attaaggttg gctgatgatc catttaggga  1500
aggagctgat ctccctgact ccctcctcca attttctcaa ccaaatttat atagtataat  1560
aataataata aaatagcaag taatagttgt atcgtattat tattaattaa tttattagct  1620
ggtaggcaag tagtattaaa taccatttgt agtacgatgg gcgtatttct attttggcgt  1680
tttgctctgt gttttttgac gtttcctttg gatttggggg gacctcagat cagctcggcc  1740
t                                                                  1741

SEQ ID NO: 2           moltype = DNA  length = 1116
FEATURE                Location/Qualifiers
source                 1..1116
                       mol_type = other DNA
                       organism = Zea mays
SEQUENCE: 2
atggtgctgg ctgcgcacga tccccctccc cttgtgttcg acgctgcccg cctgagcggc  60
ctctccgaca tcccgcagca gttcatctgg ccggcggacg agagccccac ccggactcc  120
gccgaggagc tggccgtgcc gctcatcgac ctctccgggg acgccgccga ggtggtccgg  180
caggtccggc gcgcctgcga cctgcacggc ttcttccagg tggtggggca cggcatcgac  240
gcggcgctga cggcggaggc ccaccgctgc atggacgcct tcttcacgct gccgctcccg  300
gacaagcagc gcgcgcagcg ccgccagggg gacagctgcg gctacgccag cagcttcacg  360
ggccggttcg cgtccaagct gccctggaag gagacgctgt cgttccgcta caccgacgac  420
gacgacggcg acaagtccaa ggacgtcgtg gcgtcctact tcgtggacaa gctgggcgag  480
gggtaccggc accacgggga ggtgtacggg cgctactgct ctgagatgag ccgtctgtcg  540
ctggagctca tggaggtgct aggcgagagc ctgggcgtgg gccggcgcca cttccggcgc  600
ttcttccagg ggaacgactc catcatgcgc ctcaactact acccgccgtg ccagcggccc  660
```

```
tacgacacgc tgggcacggg gccgcattgc gaccccacgt cgctcaccat cctgcaccag  720
gacgacgtgg gcggactcca ggtgttcgac gccgccacgc tcgcgtggcg ctccatcagg  780
ccccgcccgg gcgccttcgt cgtcaacatc ggcgacacct tcatggcgct ctccaacggg  840
cgctacagga gctgcctcca ccgcgccgtc gtcaacagcc gggtggcacg ccgctcgctc  900
gccttcttcc tgtgcccgga gatggacaag gtggtcaggc cgcccaagga gctggtggac  960
gacgccaacc cgagggcgta cccggacttc acgtggagga cgctgctgga cttcaccatg  1020
aggcactaca ggtcggacat gaggacgctc gaggccttct ccaactggct cagcaccagt  1080
agcaatggcg gacagcacct gctggagaag aagtag                            1116
```

```
SEQ ID NO: 3           moltype = AA  length = 371
FEATURE                Location/Qualifiers
source                 1..371
                       mol_type = protein
                       organism = Zea mays
SEQUENCE: 3
MVLAAHDPPP LVFDAARLSG LSDIPQQFIW PADESPTPDS AEELAVPLID LSGDAAEVVR  60
QVRRACDLHG FFQVVGHGID AALTAEAHRC MDAFFTLPLP DKQRAQRRQG DSCGYASSFT  120
GRFASKLPWK ETLSFRYTDD DDGDKSKDVV ASYFVDKLGE GYRHHGEVYG RYCSEMSRLS  180
LELMEVLGES LGVGRRHFRR FFQGNDSIMR LNYYPPCQRP YDTLGTGPHC DPTSLTILHQ  240
DDVGGLQVFD AATLAWRSIR PRPGAFVVNI GDTFMALSNG RYRSCLHRAV VNSRVARRSL  300
AFFLCPEMDK VVRPPKELVD DANPRAYPDF TWRTLLDFTM RHYRSDMRTL EAFSNWLSTS  360
SNGGQHLLEK K                                                     371
```

```
SEQ ID NO: 4           moltype = DNA  length = 1517
FEATURE                Location/Qualifiers
source                 1..1517
                       mol_type = other DNA
                       organism = Zea mays
SEQUENCE: 4
caggaataaa ataagcctcc gcccggcttc gttgcatcca cgcacgcagc aagcgatcgg  60
atttcgccag catggcggcg gcggccgtgg tgttcgacgc cgaggcgctg agccgggagg  120
agcacatccc ggcgcagttc gtgtggccca ccgaggagcg ggcgccggcg ggcggcgtgg  180
aggaggtcgc catccccgtg gtcgacctcg gcgagttcct ccgccgcggg gtgctcccgc  240
gcggcgtggc ggaggcgtgc gagcgccacg gcgtcttcca ggtggtgaac cacggcgtgg  300
gcgccgcgct gctcgccgag gcctaccgct gttgcgacgc cttttacgcg ctcccgctcg  360
cggacaagca gcgcgcgcag cgccggcacg gggagaacca cggctacgcc agcagcttca  420
cgggccgctt ccactgctgc ctgccgtgga aggagacgct gtccttcaac tgccccgccg  480
gtgccgggac tgcgcgcgcc gtcgtcggct acttcgtcga cgtcctcggc gaggactacc  540
gccacatggg ggaggtgtac caggagtact gcgacgcgat gacgcgtctg gcgctggacg  600
tgacggaggt gctggcggca gcgctggggc tggaccgcgg cgcactgcgc ggcttcttcg  660
agggcggcga ctccgtcatg cggctgaacc actacccggc gtgccggcag ccgcacctga  720
cgctggggac gggcccgcac cgggacccga cgtcgctgac gctgctgcac caggacgacg  780
tgggcgggct gcaggtgcgc gccggcggcg ggccgtggcg cgcggtgcgg ccccgcgcgg  840
acgcgttcgt ggtcaacatt ggcgacacct tcgccgcgct caccgacggg cgtcacacca  900
gctgcctgca ccgcgccgtg gtgaccggcg gcggctcccg ccggtcgctc gccttcttcc  960
tcaacccgcc gctggaccgc gtcgtccgcc cgccgggcgc gctcctccag gagaacaagc  1020
aggcgggccg cccgcgcgcg ttcccggact tcacgtggcg cgagttcctc gagttcacgc  1080
agaagcacta ccggtcggac gcgggcacca tggacgcctt cgtgtcgtgg atcgcgggag  1140
gccgccgcca ccatggcgga caggaggagg gcaactgaga tcgatgcatc tctagctgta  1200
ggcagcagcg cagcagctac caagaataat ggccggcgac ggagatgcag ctacgacgca  1260
caaataaatt gagtgtttgt ggtacaataa ggacgaggac gatcaatggc gacctgtaac  1320
cggtgcagtt ttagttaatc tttcatggcg atatggcatt aaccaatcgt tggtgtaaaa  1380
tgcgtgcatg ctttgcatgc caatgttggc catgtgatgg cacagcgtga gtgtagctca  1440
cccaccgtga caacgtgcta atttcgtgtg gtcctagata ccaaggtcgt ctaatgaact  1500
tgatggattg atgattt                                                 1517
```

```
SEQ ID NO: 5           moltype = DNA  length = 1107
FEATURE                Location/Qualifiers
source                 1..1107
                       mol_type = other DNA
                       organism = Zea mays
SEQUENCE: 5
atggcggcgg cggccgtggt gttcgacgcc gaggcgctga gccgggagga gcacatcccg  60
gcgcagttcg tgtggcccac cgaggagcgg gcgccggcgg gcggcgtgga ggaggtcgcc  120
atccccgtgg tcgacctcgg cgagttcctc cgccgcgggg tgctcccgcg cggcgtggcg  180
gaggcgtgcg agcgccacgg cgtcttccag gtggtgaacc acggcgtggg cgccgcgctg  240
ctcgccgagg cctaccgctg ttgcgacgcc ttttacgcgc tcccgctcgc ggacaagcag  300
cgcgcgcagc gccggcacgg ggagaaccac ggctacgcca gcagcttcac gggccgcttc  360
cactgctgcc tgccgtggaa ggagacgctg tccttcaact gccccgccgg tgccgggact  420
gcgcgcgccg tcgtcggcta cttcgtcgac gtcctcggcg aggactaccg ccacatgggg  480
gaggtgtacc aggagtactg cgacgcgatg acgcgtctgg cgctggacgt gacggaggtg  540
ctggcggcag cgctggggct ggaccgcggc gcactgcgcg gcttcttcga gggcggcgac  600
tccgtcatgc ggctgaacca ctacccggcg tgccggcagc cgcacctgac gctggggacg  660
ggcccgcacc gggacccgac gtcgctgacg ctgctgcacc aggacgacgt gggcgggctg  720
caggtgcgcg ccggcggcgg gccgtggcgc gcggtgcggc cccgcgcgga cgcgttcgtg  780
gtcaacattg gcgacacctt cgccgcgctc accgacgggc gtcacaccag ctgcctgcac  840
cgcgccgtgg tgaccggcgg cggctcccgc cggtcgctcg ccttcttcct caacccgccg  900
ctggaccgcg tcgtccgccc gccgggcgcg ctcctccagg agaacaagca ggcgggccgc  960
ccgcgcgcgt tcccggactt cacgtggcgc gagttcctcg agttcacgca gaagcactac  1020
```

```
cggtcggacg cgggcaccat ggacgccttc gtgtcgtgga tcgcgggagg ccgccgccac  1080
catggcggac aggaggaggg caactga                                      1107

SEQ ID NO: 6           moltype = AA  length = 368
FEATURE                Location/Qualifiers
source                 1..368
                       mol_type = protein
                       organism = Zea mays
SEQUENCE: 6
MAAAAVVFDA EALSREEHIP AQFVWPTEER APAGGVEEVA IPVVDLGEFL RRGVLPRGVA  60
EACERHGVFQ VVNHGVGAAL LAEAYRCCDA FYALPLADKQ RAQRRHGENH GYASSFTGRF  120
HCCLPWKETL SFNCPAGAGT ARAVVGYFVD VLGEDYRHMG EVYQEYCDAM TRLALDVTEV  180
LAAALGLDRG ALRGFFEGGD SVMRLNHYPA CRQPHLTLGT GPHRDPTSLT LLHQDDVGGL  240
QVRAGGGPWR AVRPRADAFV VNIGDTFAAL TDGRHTSCLH RAVVTGGGSR RSLAFFLNPP  300
LDRVVRPPGA LLQENKQAGR PRAFPDFTWR EFLEFTQKHY RSDAGTMDAF VSWIAGGRRH  360
HGGQEEGN                                                           368

SEQ ID NO: 7           moltype = DNA  length = 1522
FEATURE                Location/Qualifiers
source                 1..1522
                       mol_type = other DNA
                       organism = Zea mays
SEQUENCE: 7
gcacactcgc agctcgcaca tctcatggtg tcctaagaac ggcaagagcc agctctgcct  60
agcagcagcg cacagccaca tccatggacg ccagcccgac ccccaccgctc cccctccgcg 120
ccccaactcc cagcattgac ctccccgctg gcaaggacag ggccgacgcg gcggctaaca  180
aggccgcggc tgtgttcgac ctgcgccggg agcccaagat cccggagcca ttcctgtggc  240
cgcacgaaga ggcgcggccg acctcggccg cggagctgga ggtgccggtg gtggacgtgg  300
gcgtgctgcg caatggcgac ggcgcggggc tccgccgcgc cgcggcgcaa gtggcggcgg  360
cgtgcgcgac gcacgggttc ttccaggtgt gcgggcacgg cgtggacgcg gcgctggggc  420
gcgccgcgct ggacggcgcc agcgacttct tccggctgcc gctggctgag aagcagcggg  480
cccggcgcgt ccccggcacc gtgtccgggt acacgagcgc gcacgccgac cggttcgcgt  540
ccaagctccc ctggaaggag accctgtcct tcggcttcca cgacggcgcc gcggcgcccg  600
tcgtcgtgga ctacttcacc ggcaccctcg gccaagattt cgagccagtg ggcgggtgt   660
accagaggta ctgcgaggag atgaaggagc tgtcgctgac gatcatggag ctgctggagc  720
tgagcctggg cgtggagcgc ggctactacc gggagttctt cgaggacagc cgctccatca  780
tgcggtgcaa ctactacccg ccgtgcccgg tgccggagcg cacgctgggc acgggcccgc  840
actgcgaccc cacggcgctg accatcctcc tgcaggacga cgtcggcggg ctggaggtcc  900
tggtggacgg cgagtggcgc cccgtccggc ccgtcccagg cgccatggtc atcaacatcg  960
gcgacacctt catggcgctg tccaacgggc ggtacaagag ctgcctgcac cgcgcggtgg  1020
tgaaccggcg gcaggagcgg caatcgctgg ccttcttcct gtgcccgcgc gaggaccggg  1080
tggtgcgccc gccggccagc gccgcgccgc ggcagtaccc ggacttcacc tgggccgacc  1140
tcatgcgctt cacgcagcgc cactaccgcg ccgacacccg cacgctggac gccttcaccc  1200
gctggctctc ccacggcccg gcggcggcgg ctccctgcac ctaacgagcc ggccgtctct  1260
ttcgccgggg cccgcgcggg gttcgcccac gtggtgatca ggtggcagac atgtggccca  1320
cgggccccgc gccgccttcc ccatttttgg acgaccctac tgctactact actagtgtac  1380
atatgcaaaa aaatacatat atatataggt actttctcta atatttttat atataagcaa  1440
ggcggcctgg tgttcttttc tttgttttgt cgacaactgt ttgatcccat cctatggacg  1500
atggatagtt caatgtttgt ac                                           1522

SEQ ID NO: 8           moltype = DNA  length = 1161
FEATURE                Location/Qualifiers
source                 1..1161
                       mol_type = other DNA
                       organism = Zea mays
SEQUENCE: 8
atggacgcca gcccgacccc accgctcccc ctccgcgccc caactcccag cattgacctc  60
cccgctggca aggacagggc cgacgcggcg gctaacaagg ccgcggctgt gttcgacctg  120
cgccgggagc ccaagatccc ggagccattc ctgtggccgc acgaagaggc gcggccgacc  180
tcggccgcgg agctggaggt gccggtggtg gacgtgggcg tgctgcgcaa tggcgacggc  240
gcggggctcc gccgcgccgc ggcgcaagtg gcggcggcgt gcgcgacgca cgggttcttc  300
caggtgtgcg ggcacggcgt ggacgcggcg ctggggcgcg ccgcgctgga cggcgccagc  360
gacttcttcc ggctgccgct ggctgagaag cagcgggccc ggcgcgtccc cggcaccgtg  420
tccgggtaca cgagcgcgca cgccgaccgg ttcgcgtcca agctcccctg gaaggagacc  480
ctgtccttcg gcttccacga cggcgccgcg gcgcccgtcg tcgtggacta cttcaccggc  540
accctcggcc aagatttcga gccagtgggg cgggtgtacc agaggtactg cgaggagatg  600
aaggagctgt cgctgacgat catggagctg ctggagctga gcctgggcgt ggagcgcggc  660
tactaccggg agttcttcga ggacagccgc tccatcatgc ggtgcaacta ctacccgccg  720
tgcccggtgc cggagcgcac gctgggcacg ggcccgcact gcgaccccac ggcgctgacc  780
atcctcctgc aggacgacgt cggcgggctg gaggtcctgg tggacggcga gtggcgcccc  840
gtccggcccg tcccaggcgc catggtcatc aacatcggcg acaccttcat ggcgctgtcc  900
aacgggcggt acaagagctg cctgcaccgc gcggtggtga accggcggca ggagcggcaa  960
tcgctggcct tcttcctgtg cccgcgcgag gaccgggtgg tgcgcccgcc ggccagcgcc  1020
gcgccgcggc agtacccgga cttcacctgg gccgacctca tgcgcttcac gcagcgccac  1080
taccgcgccg acacccgcac gctggacgcc ttcacccgct ggctctccca cggcccggcg  1140
gcggcggctc cctgcaccta a                                            1161

SEQ ID NO: 9           moltype = AA  length = 386
FEATURE                Location/Qualifiers
```

```
source                  1..386
                        mol_type = protein
                        organism = Zea mays
SEQUENCE: 9
MDASPTPPLP LRAPTPSIDL PAGKDRADAA ANKAAAVFDL RREPKIPEPF LWPHEEARPT  60
SAAELEVPVV DVGVLRNGDG AGLRRAAAQV AAACATHGFF QVCGHGVDAA LGRAALDGAS  120
DFFRLPLAEK QRARRVPGTV SGYTSAHADR FASKLPWKET LSFGFHDGAA APVVVDYFTG  180
TLGQDFEPVG RVYQRYCEEM KELSLTIMEL LELSLGVERG YYREFFEDSR SIMRCNYYPP  240
CPVPERTLGT GPHCDPTALT ILLQDDVGGL EVLVDGEWRP VRPVPGAMVI NIGDTFMALS  300
NGRYKSCLHR AVVNRRQERQ SLAFFLCPRE DRVVRPPASA APRQYPDFTW ADLMRFTQRH  360
YRADTRTLDA FTRWLSHGPA AAAPCT                                       386

SEQ ID NO: 10           moltype = DNA  length = 1457
FEATURE                 Location/Qualifiers
source                  1..1457
                        mol_type = other DNA
                        organism = Zea mays
SEQUENCE: 10
taatcacctc atcacaggtc cccccagcct cactctcgcg ccggctcaag gtacattgcg  60
tgtcctagcc aagacacgca gctcatctca gcctcacacg cacagcaaga gcgaggcgtg  120
attcgccatg ggcggcctca ctatggacca ggccttcgtg caggcccccg agcaccgccc  180
caagcccatc gtcaccgagg ccaccggcat ccctctcatc gacctctcgc ctctggccgc  240
cagcggcggc gccgtggacg cgctggccgc cgaggtgggc gcggcgagcc gggactgggg  300
cttcttcgtg gtcgtgggcc acggcgtgcc cgcagagacc gtggcgcgcg cgacggaggc  360
gcagcgagcg ttcttcgcgc tgccggcaga gcggaaggcc gccgtgcgga ggaacgaggc  420
ggagccgctc gggtactacg agtcggagca caccaagaac gtgagggact ggaaggaggt  480
gtacgacctc gtgccgcgcg agccgccgcc gccggcagcc gtggccgacg gcgagcttgt  540
gttcgataac aagtggcccc aggatctacc gggcttcaga gaggcgctgg aggagtacgc  600
gaaagcgatg gaagagctgg cgttcaagct gctggagctg atcgcccgga gcctgaagct  660
gaggcccgac cggctgcacg gcttcttcaa ggaccagacg accttcatcc ggctgaacca  720
ctaccctcct tgcccgagcc ccgacctggc cctcggcgtg gggcggcaca aggacgccgg  780
cgccctgacc atcctgtacc aggacgacgt cggggggctc gacgtccggc ggcgctccga  840
cggcgagtgg gtccgcgtca ggcccgtgcc cgactcgttc atcatcaacg tcggcgacct  900
catccaggta cgagagcgcg gagcaccggg tgtcggtgaa ctcggcgagg gagaggttct  960
ccatgcccta cttcttcaac ccggcgacct acaccatggt ggagccggtg gaggagctgg  1020
tgagcaagga cgatccgccc aggtacgacg cctacaactg gggcgacttc ttcagcacca  1080
ggaagaacag caacttcaag aagctcaacg tggagaacat tcagatcgcg catttcaaga  1140
agagcctcgt cctcgcctaa ctactgctac tgctaggatc catgccattg ccatgtcgtc  1200
ttcagattca gagcacgcca tgtcgtcgct agcttcgtgg tagaacaaat aatgatgtgc  1260
gtgctgtgtg taagcatgga tatggatgtg aatatgtaat atgatgagca ctcctacttt  1320
ggtatgtttg ggaataacag acttgtgttg gtctggttca ttatttgtaa gaaaatcaaa  1380
aagagttagt agggcaggag gctaaccaca gtcatgctgc accacatccc tggtggaaag  1440
ctggccgggt tacgcta                                                 1457

SEQ ID NO: 11           moltype = DNA  length = 1116
FEATURE                 Location/Qualifiers
source                  1..1116
                        mol_type = other DNA
                        organism = Zea mays
SEQUENCE: 11
atgggcggcc tcactatgga ccaggccttc gtgcaggccc ccgagcaccg ccccaagccc  60
atcgtcaccg aggccaccgg catccctctc atcgacctct cgcctctggc cgccagcggc  120
ggcgccgtgg acgcgctggc cgccgaggtg ggcgcggcga gccgggactg gggcttcttc  180
gtggtcgtgg gccacggcgt gcccgcagag accgtggcgc gcgcgacgga ggcgcagcga  240
gcgttcttcg cgctgccggc agagcggaag gccgccgtgc ggaggaacga ggcggagccg  300
ctcgggtact acgagtcgga gcacaccaag aacgtgaggg actggaagga ggtgtacgac  360
ctcgtgccgc gcgagccgcc gccgccggca gccgtggccg acggcgagct tgtgttcgat  420
aacaagtggc cccaggatct accgggcttc agagaggcgc tggaggagta cgcgaaagcg  480
atggaagagc tggcgttcaa gctgctggag ctgatcgccc ggagcctgaa gctgaggccc  540
gaccggctgc acggcttctt caaggaccag acgaccttca tccggctgaa ccactaccct  600
ccttgcccga gccccgacct ggccctcggc gtggggcggc acaaggacgc cggcgccctg  660
accatcctgt accaggacga cgtcgggggg ctcgacgtcc ggcggcgctc cgacggcgag  720
tgggtccgcg tcaggcccgt gcccgactcg ttcatcatca acgtcggcga cctcatccag  780
gtacgagagc gcggagcacc gggtgtcggt gaactcggcg agggagaggt tctccatgcc  840
ctacttcttc aacccggcga cctacaccat ggtggagccg gtggaggagc tggtgagcaa  900
ggacgatccg cccaggtacg acgcctacaa ctggggcgac ttcttcagca ccaggaagaa  960
cagcaacttc aagaagctca acgtggagaa cattcagatc gcgcatttca agaagagcct  1020
cgtcctcgcc taactactgc tactgctagg atccatgcca ttgccatgtc gtcttcagat  1080
tcagagcacg ccatgtcgtc gctagcttcg tggtag                            1116

SEQ ID NO: 12           moltype = AA  length = 371
FEATURE                 Location/Qualifiers
source                  1..371
                        mol_type = protein
                        organism = Zea mays
SEQUENCE: 12
MGGLTMDQAF VQAPEHRPKP IVTEATGIPL IDLSPLAASG GAVDALAAEV GAASRDWGFF  60
VVVGHGVPAE TVARATEAQR AFFALPAERK AAVRRNEAEP LGYYESEHTK NVRDWKEVYD  120
LVPREPPPPA AVADGELVFD NKWPQDLPGF REALEEYAKA MEELAFKLLE LIARSLKLRP  180
```

```
DRLHGFFKDQ TTFIRLNHYP PCPSPDLALG VGRHKDAGAL TILYQDDVGG LDVRRRSDGE  240
WVRVRPVPDS FIINVGDLIQ VRERGAPGVG ELGEGEVLHA LLLQPGDLHH GGAGGGAGEQ  300
GRSAQVRRLQ LGRLLQHQEE QQLQEAQRGE HSDRAFQEEP RPRLTTATAR IHAIAMSSSD  360
SEHAMSSLAS W                                                       371

SEQ ID NO: 13          moltype = DNA  length = 1733
FEATURE                Location/Qualifiers
source                 1..1733
                       mol_type = other DNA
                       organism = Zea mays
SEQUENCE: 13
atgaggccgc gcctccctcc aaatgttccc tccctgcctt cgtctttgtc gttgctcgca  60
aactccctgt cctcccctgt tacaaatacc cccacccgcc cggacagctt ccctgcatac  120
ttgcagctcg cacatctcat ggtgtcgcag gaacgacaag agccagctgt gcctagcagc  180
agcagcagca gcgccaagcg cgcagccacg tccatggacg ccagcccggc cccgccgctc  240
ctcctccgcg cccccactcc cagccccagc attgacctcc ccgctggcaa ggacaaggcc  300
gacgcggcgg ccagcaaggc cggcgcggcc gtgttcgacc tgcgccggga gcccaagatc  360
cccgcgccat tcctgtggcc gcaggaagag gcgcggccgt cctcggccgc ggagctggag  420
gtgccgatgg tggacgtggg cgtgctgcgc aatggcgacc gcgcggggct gcggcgcgcc  480
gcggcgcagg tggccgcggc gtgcgcgacg cacgggttct tccaggtgtg cgggcacggc  540
gtggacgcgg cgctggggcg cgccgcgctg gacggcgcca gcgacttctt ccggctgccg  600
ctcgccgaga agcagcgcgc ccggcgcgtc cccggcaccg tgtccgggta cacgagcgcg  660
cacgccgacc ggttcgcggc caagctcccc tggaaggaga ccctgtcgtt cggctaccac  720
gacggcgccg cgtcgcctgt cgtcgtggac tacttcgtcg gcaccctcgg ccaggatttc  780
gagccaatgg ggtgggtgta ccagaggtac tgcgaggaga tgaaggagct gtcgctgacg  840
atcatggagc tgctggagct gagcctgggc gtggagctgc gcggctacta ccgggagttc  900
ttcgaggaca gccggtccat catgcggtgc aactactacc cgccgtgccc ggagccggag  960
cgcacgctgg gcacgggccc gcactgcgac ccccacggcgc tcaccatcct cctgcaggac  1020
gacgtgggcg ggctggaggt gctggtggac ggtgagtggc gccccgtccg gcccgtcccg  1080
ggcgccatgg tcatcaacat cggcgacacc ttcatggcgc tgtcgaacgg gaggtacaag  1140
agctgcctgc accgcgcggt ggtgaaccag cggcgggcgc ggcggtcgct ggccttcttc  1200
ctgtgcccgc gcgaggaccg ggtggtgcgc ccgccggcca gtgctgcgcc gcggcgctac  1260
ccggacttca cctgggccga cctcatgcgc ttcacgcagc gccactaccg cgccgacacc  1320
cgcacgctgg acgccttcac ccgctggctc tcccacggcc cggcccaggc ggcggcgcct  1380
ccctgcacct agcgagccgg gccaaggccg tctctttcgc cccacgtgcg cgcccagctg  1440
ggcaggtggc cagacacgcg gcccgcgggc cccgcgccgc cttgccattt tttgacgctg  1500
gccctactgc tgtgctacta gtgtacatat gcaagagtac atatatatat atatatatac  1560
gtattttcta tatattatat ataaaagcaa ggcggcccgg tgcccttctc ttgttttgtc  1620
cacaactgtt tgatcccatt attctatgga ccatggatac ttcaatgttt gtactaagac  1680
cgtgaacgtg ggattctttt ccttcctctg tgttttttct gagaaaaatt aaa         1733

SEQ ID NO: 14          moltype = DNA  length = 1392
FEATURE                Location/Qualifiers
source                 1..1392
                       mol_type = other DNA
                       organism = Zea mays
SEQUENCE: 14
atgaggccgc gcctccctcc aaatgttccc tccctgcctt cgtctttgtc gttgctcgca  60
aactccctgt cctcccctgt tacaaatacc cccacccgcc cggacagctt ccctgcatac  120
ttgcagctcg cacatctcat ggtgtcgcag gaacgacaag agccagctgt gcctagcagc  180
agcagcagca gcgccaagcg cgcagccacg tccatggacg ccagcccggc cccgccgctc  240
ctcctccgcg cccccactcc cagccccagc attgacctcc ccgctggcaa ggacaaggcc  300
gacgcggcgg ccagcaaggc cggcgcggcc gtgttcgacc tgcgccggga gcccaagatc  360
cccgcgccat tcctgtggcc gcaggaagag gcgcggccgt cctcggccgc ggagctggag  420
gtgccgatgg tggacgtggg cgtgctgcgc aatggcgacc gcgcggggct gcggcgcgcc  480
gcggcgcagg tggccgcggc gtgcgcgacg cacgggttct tccaggtgtg cgggcacggc  540
gtggacgcgg cgctggggcg cgccgcgctg gacggcgcca gcgacttctt ccggctgccg  600
ctcgccgaga agcagcgcgc ccggcgcgtc cccggcaccg tgtccgggta cacgagcgcg  660
cacgccgacc ggttcgcggc caagctcccc tggaaggaga ccctgtcgtt cggctaccac  720
gacggcgccg cgtcgcctgt cgtcgtggac tacttcgtcg gcaccctcgg ccaggatttc  780
gagccaatgg ggtgggtgta ccagaggtac tgcgaggaga tgaaggagct gtcgctgacg  840
atcatggagc tgctggagct gagcctgggc gtggagctgc gcggctacta ccgggagttc  900
ttcgaggaca gccggtccat catgcggtgc aactactacc cgccgtgccc ggagccggag  960
cgcacgctgg gcacgggccc gcactgcgac ccccacggcgc tcaccatcct cctgcaggac  1020
gacgtgggcg ggctggaggt gctggtggac ggtgagtggc gccccgtccg gcccgtcccg  1080
ggcgccatgg tcatcaacat cggcgacacc ttcatggcgc tgtcgaacgg gaggtacaag  1140
agctgcctgc accgcgcggt ggtgaaccag cggcgggcgc ggcggtcgct ggccttcttc  1200
ctgtgcccgc gcgaggaccg ggtggtgcgc ccgccggcca gtgctgcgcc gcggcgctac  1260
ccggacttca cctgggccga cctcatgcgc ttcacgcagc gccactaccg cgccgacacc  1320
cgcacgctgg acgccttcac ccgctggctc tcccacggcc cggcccaggc ggcggcgcct  1380
ccctgcacct ag                                                     1392

SEQ ID NO: 15          moltype = AA  length = 463
FEATURE                Location/Qualifiers
source                 1..463
                       mol_type = protein
                       organism = Zea mays
SEQUENCE: 15
MRPRLPPNVP SLPSSLSLLA NSLSSPVTNT PTRPDSFPAY LQLAHLMVSQ ERQEPAVPSS  60
```

```
SSSSAKRAAT SMDASPAPPL LLRAPTPSPS IDLPAGKDKA DAAASKAGAA VFDLRREPKI  120
PAPFLWPQEE ARPSSAAELE VPMVDVGVLR NGDRAGLRRA AAQVAAACAT HGFFQVCGHG  180
VDAALGRAAL DGASDFFRLP LAEKQRARRV PGTVSGYTSA HADRFAAKLP WKETLSFGYH  240
DGAASPVVVD YFVGTLGQDF EPMGWVYQRY CEEMKELSLT IMELLELSLG VELRGYYREF  300
FEDSRSIMRC NYYPPCPEPE RTLGTGPHCD PTALTILLQD DVGGLEVLVD GEWRPVRPVP  360
GAMVINIGDT FMALSNGRYK SCLHRAVVNQ RRARRSLAFF LCPREDRVVR PPASAAPRRY  420
PDFTWADLMR FTQRHYRADT RTLDAFTRWL SHGPAQAAAP PCT                    463

SEQ ID NO: 16          moltype = DNA  length = 1510
FEATURE                Location/Qualifiers
source                 1..1510
                       mol_type = other DNA
                       organism = Zea mays
SEQUENCE: 16
aaagagcgcg cgacggcggc ccctgggaga gccatgcgag actggaggcg gaaccgcgca  60
cgacaccaag ctgccgcgcc ggactgctgc acgcaagcgc agcgcaggac cgaccgacct  120
ccgtaggcac gcacggcgcc ggcggcatgg cggagcacct cctgtcgacg gccgtgcacg  180
acacgctgcc ggggagctac gtgcggccgg agccggagcg cccgcgcctc gcggaggtcg  240
tgaccggcgc gcgcatcccc gtcgtggacc tgggcagccc cgaccgcggc gcggtcgtgg  300
ccgccgtcgg cgacgcctgc cgctcgcacg gcttcttcca ggtcgtcaac cacgggatac  360
acgccgccct ggtcgcggcg gtgatggccg cggggcgcgg cttcttccgg ctgccccccg  420
aggagaaggc caagctctac tccgacgacc ccgccaggaa gatccggctg tccaccagct  480
tcaacgtgcg caaggagacg gtgcacaact ggcgcgacta cctccgcctg cactgccatc  540
ccctcgacga gttcctgccc gattggccgt ccaacccgcc cgatttcaag gagaccatgg  600
gcacctactg caaggaggtc cgggagctcg ggttcaggct gtacgccgcg atctcggaga  660
gcctgggcct agaggcgagc tacatgaagg aagcgctggg ggagcaggag cagcacatgg  720
cggtcaactt ctacccgccg tgcccggagc cggagctcac ctacggcctc ccggcgcaca  780
ccgaccccaa cgcgctcacc atcctgctca tggacccgga cgtcgccggc ctgcaggtgc  840
tccacgccgg ccagtgggtc gccgtcaacc cgcagcccgg cgcgctcatc atcaacatcg  900
gcgaccagct gcaggcgctg agcaacgggc agtaccggag cgtgtggcac cgcgcggtgg  960
tgaactcgga ccgggagcgc atgtccgtgg cgtcgttcct gtgcccgtgc aaccacgtcg  1020
tgctcggccc cgcgcggaag ctcgtcaccg aggacacccc ggccgtgtac aggaactaca  1080
cgtacgacaa gtactacgcc aagttctgga gcaggaacct ggaccaggag cactgcctcg  1140
agctcttcag aacctagcga atcggatacg gatggatgga tacattacat acgcgccctc  1200
tgtttttctc catgacgtta gaagaacacg ttctgcaatg tttgtccatt caaggtggta  1260
tcaatcaagg ctgtggtcgt tgcaattctt ccgctccata tacatgatta aatgctttga  1320
aagaaaaaga aaaaaaagaa acacaagtat tatggcacta ctagtgtttt taggaacaag  1380
gaaagagggg ttgcccctgc tggctatata tattaaatat aaataaaggt aaggctgtag  1440
acattggtga ataagagaaa gtatttgagt ttctctattg tcactccaga acagactcct  1500
ttgcctcgat                                                         1510

SEQ ID NO: 17          moltype = DNA  length = 1011
FEATURE                Location/Qualifiers
source                 1..1011
                       mol_type = other DNA
                       organism = Zea mays
SEQUENCE: 17
atggcggagc acctcctgtc gacggccgtg cacgacacgc tgccggggag ctacgtgcgg  60
ccggagccgg agcgcccgcg cctcgcggag gtcgtgaccg gcgcgcgcat ccccgtcgtg  120
gacctgggca gccccgaccg cggcgcggtc gtggccgccg tcggcgacgc ctgccgctcg  180
cacggcttct tccaggtcgt caaccacggg atacacgccg ccctggtcgc ggcggtgatg  240
gccgcggggc gcggcttctt ccggctgccc cccgaggaga aggccaagct ctactccgac  300
gaccccgcca ggaagatccg gctgtccacc agcttcaacg tgcgcaagga gacggtgcac  360
aactggcgcg actacctccg cctgcactgc catcccctcg acgagttcct gcccgattgg  420
ccgtccaacc cgcccgattt caaggagacc atgggcacct actgcaagga ggtccgggag  480
ctcgggttca ggctgtacgc cgcgatctcg gagagcctgg gcctagaggc gagctacatg  540
aaggaagcgc tgggggagca ggagcagcac atggcggtca acttctaccc gccgtgcccg  600
gagccggagc tcacctacgg cctcccggcg cacaccgacc ccaacgcgct caccatcctg  660
ctcatggacc cggacgtcgc cggcctgcag gtgctccacg ccggccagtg ggtcgccgtc  720
aacccgcagc ccggcgcgct catcatcaac atcggcgacc agctgcaggc gctgagcaac  780
gggcagtacc ggagcgtgtg gcaccgcgcg gtggtgaact cggaccggga gcgcatgtcc  840
gtggcgtcgt tcctgtgccc gtgcaaccac gtcgtgctcg gccccgcgcg gaagctcgtc  900
accgaggaca ccccggccgt gtacaggaac tacacgtacg acaagtacta cgccaagttc  960
tggagcagga acctggacca ggagcactgc ctcgagctct tcagaaccta g           1011

SEQ ID NO: 18          moltype = AA  length = 336
FEATURE                Location/Qualifiers
source                 1..336
                       mol_type = protein
                       organism = Zea mays
SEQUENCE: 18
MAEHLLSTAV HDTLPGSYVR PEPERPRLAE VVTGARIPVV DLGSPDRGAV VAAVGDACRS  60
HGFFQVVNHG IHAALVAAVM AAGRGFFRLP PEEKAKLYSD DPARKIRLST SFNVRKETVH  120
NWRDYLRLHC HPLDEFLPDW PSNPPDFKET MGTYCKEVRE LGFRLYAAIS ESLGLEASYM  180
KEALGEQEQH MAVNFYPPCP EPELTYGLPA HTDPNALTIL LMDPDVAGLQ VLHAGQWVAV  240
NPQPGALIIN IGDQLQALSN GQYRSVWHRA VVNSDRERMS VASFLCPCNH VVLGPARKLV  300
TEDTPAVYRN YTYDKYYAKF WSRNLDQEHC LELFRT                            336

SEQ ID NO: 19          moltype = DNA  length = 1387
```

```
FEATURE                Location/Qualifiers
source                 1..1387
                       mol_type = other DNA
                       organism = Zea mays
SEQUENCE: 19
gttttctttt tgaacgtaac tgacagaagc tatctgccta gctacggcgt gtcggttgct  60
tgtctcacca aagcagcgac atggaagcct gacagctcgt cgcgtcgcgc catttccacc  120
caacaaagcg gcggcgccag cacgcactgc ttctgcttgt gcgtgctcct ccgttccggg  180
cacgcctcta aagtctatac agcctcgaat ccatcccggc cgccgctcct gggggatact  240
acagcgagcc gaagcgggga tggcggagat ccctgtgatc gacctgcgcg tcgccggctc  300
ggcggccgag gagtccgcgc ggctgcgggc cgcgtgcgag cgcctgggct gcttccgggt  360
gaccggccac ggcgtgccct cggtgctcct ggcagagatg aaggccgccg tgcgcgcgct  420
cttcgacctc cccgacgacg ccaagcgccg caacgccgac gtcatcaccg gcagcggcta  480
cgtcgccccc agcccgacca acccgctcta cgaggccttc gggctcctcg acgccgccgt  540
gcccaccgac gtcgacgcct ttgcgcgct cctcgacgcg ccgcccaaca tcagggagac  600
cgtcaaggcc tacgcggaga agatgcacga tgtgatcgtt ggcgtcgccc gcgagctggc  660
gtctagcctg gggctagtcg aggagcactc gttccaggac tggccgtgcc agttccgcat  720
caacaggtac aactacacgc gggagacggt gggctcctcc ggcgtgcaga cccacacgga  780
ctcgggcttc ctcaccgtgc tccatgagga cgagtgtgtc ggcggcctcg aggtcctgga  840
cccgggcacc ggcgagttcg tgcccgtgga ccccgtcgcg ggctcctttc tcgtaaacat  900
cggcgacgtc ggcacggcgt ggagcaacgg gaggctgcac aacgtgaagc accgggtgcg  960
gtgcgtcgca cccgtgccgc gcatctccat cgccatgttc ctgctcgcac ccaaggacga  1020
cagcgtgagc gcaccggcgg cgttcgtgga cgcggaccac ccgcgcaggt acaaggtgtt  1080
caactacaac gactatcgga ggctcagact gtccaccggc gagcacgcag gcgaggcgct  1140
cgcacggatg gcggcgtgac gtggctggag ctgcaaattg gattggaagc cgagacaagc  1200
cgttagttat ttaccatgcc cgtgcgttca ccgcacacaa tcatattcaa aagccataaa  1260
ataaaaaata attttaatat cagtcaacat atggtttaaa tatcatatgg agtacaatat  1320
tccgaatttt tttttgtaat ttagtctgtc ttttgaaaaa aatgcacatc tagacctccg  1380
gatgact                                                            1387

SEQ ID NO: 20          moltype = DNA  length = 900
FEATURE                Location/Qualifiers
source                 1..900
                       mol_type = other DNA
                       organism = Zea mays
SEQUENCE: 20
atggcggaga tccctgtgat cgacctgcgc gtcgccggct cggcggccga ggagtccgcg  60
cggctgcggg ccgcgtgcga gcgcctgggc tgcttccggg tgaccggcca cggcgtgccc  120
tcggtgctcc tggcagagat gaaggccgcc gtgcgcgcgc tcttcgacct ccccgacgac  180
gccaagcgcc gcaacgccga cgtcatcacc ggcagcggct acgtcgcccc cagcccgacc  240
aacccgctct acgaggcctt cgggctcctc gacgccgccg tgcccaccga cgtcgacgcc  300
ttttgcgcgc tcctcgacgc gccgcccaac atcagggaga ccgtcaaggc ctacgcggag  360
aagatgcacg atgtgatcgt tggcgtcgcc cgcgagctgg cgtctagcct ggggctagtc  420
gaggagcact cgttccagga ctggccgtgc cagttccgca tcaacaggta caactacacg  480
cgggagacgg tgggctcctc cggcgtgcag acccacacgg actcgggctt cctcaccgtg  540
ctccatgagg acgagtgtgt cggcggcctc gaggtcctgg acccgggcac cggcgagttc  600
gtgcccgtgg accccgtcgc gggctccttt ctcgtaaaca tcggcgacgt cggcacggcg  660
tggagcaacg ggaggctgca caacgtgaag caccgggtgc ggtgcgtcgc acccgtgccg  720
cgcatctcca tcgccatgtt cctgctcgca cccaaggacg acagcgtgag cgcaccggcg  780
gcgttcgtgg acgcggacca cccgcgcagg tacaaggtgt tcaactacaa cgactatcgg  840
aggctcagac tgtccaccgg cgagcacgca ggcgaggcgc tcgcacggat ggcggcgtga  900

SEQ ID NO: 21          moltype = AA  length = 299
FEATURE                Location/Qualifiers
source                 1..299
                       mol_type = protein
                       organism = Zea mays
SEQUENCE: 21
MAEIPVIDLR VAGSAAEESA RLRAACERLG CFRVTGHGVP SVLLAEMKAA VRALFDLPDD  60
AKRRNADVIT GSGYVAPSPT NPLYEAFGLL DAAVPTDVDA FCALLDAPPN IRETVKAYAE  120
KMHDVIVGVA RELASSLGLV EEHSFQDWPC QFRINRYNYT RETVGSSGVQ THTDSGFLTV  180
LHEDECVGGL EVLDPGTGEF VPVDPVAGSF LVNIGDVGTA WSNGRLHNVK HRVRCVAPVP  240
RISIAMFLLA PKDDSVSAPA AFVDADHPRR YKVFNYNDYR RLRLSTGEHA GEALARMAA   299

SEQ ID NO: 22          moltype = DNA  length = 1496
FEATURE                Location/Qualifiers
source                 1..1496
                       mol_type = other DNA
                       organism = Zea mays
SEQUENCE: 22
gtcggtctct tgtctcacca aaccggcgac atggtacatg gaggccagcc cgtcgcttgg  60
cgcccacaagt ctcggtgccg tccgtccgac aagcggcgcc agcgcacgct ggctgctcgt  120
gcacgcctct aaatacggcc ccggacccgc caccaagcga aggccaatcc cgtccgccgc  180
cccccaccaa ccacgaacca cgcaagcgaa cccggccggc gcggggcagc ggcgatggcg  240
gagatcccgg tgatcgacct gcgcctcgcc ggctcgtcgc ccgacgagtc ggcgcggctg  300
cgcgacgcgt gcgagcgcct gggctgcttt cgggtgaccg gccacggcgc gcccgcgggg  360
ctcctggccg acatgaaggc cgccgtgcgc gcgctcttcg acctccccga cgacgccaag  420
cgccgcaacg ccgacgtcat ccccggcagc ggctacgtcg cgccctgccc cgccaacccg  480
ctctacgagg ccttcgggct cctcgacgcc gccgcgcccg ccgacgtcga cgccttctgc  540
```

```
gcgcgcctcg acgcgccgcc caaagtcagg gagaccgtca agacctacgc ggagaagatg  600
cacgacgtga tcgtcggcgt cgccggcgag ctggccacca gcctggggct gggcctggag  660
gagcactcgt tccaggactg gccgtgccag ttccgcatca acaggtacaa ctacacgcag  720
gagacggtgg gctcctccgg cgtgcagacc cacacggact cgggcttcct caccgtgctc  780
caggaggacg agtgcgtcgg cggcctcgag gtgctggacc ccgccgccgg tgagttcgtg  840
cccgtggacc ccgtcgccgg ctccttcctc gtcaacatcg gcgacgtcgg cacggcgtgg  900
agcaacggga ggctccacaa cgtgaagcac cgggtgcggt gcgtcgcgcc cgtgccgcgc  960
atctccatcg ccatgttcct gctggcgccc aaggacgacc gcgtgagcgc cccggaggcg  1020
ttggtcgacg cgggccaccc gcgtcggtac aagccgttca actacgacga ctaccggagg  1080
ctccggctgt ccaccggcga gcgcgcaggc gaggcgctcg cgcggatggc ggcgtgatgt  1140
cgtcacgcac gtgcaagccg ttaattatag gctcgcgcat gcatacgcct acacgagagg  1200
ttgtctcgtt aagccgttct attaaaatgt gtgggggaga aagatgacta ccgtggtgcc  1260
atgtggattg ctatcgggtc tgatcaataa aatcttgcaa cacttgcacg tgcgattcca  1320
tatcctagca cgggtgggcg ccacgctagt aggtagagac cggagcggcc aaaaaatggc  1380
tacagcacca gtaggtgaac tctcaagcaa cactggctat cccacttctg acgttgtctc  1440
tctcatcact atgtatgacc agcgaatgaa gtgtttaaaa atctgacgcc gtgaaa      1496

SEQ ID NO: 23           moltype = DNA  length = 903
FEATURE                 Location/Qualifiers
source                  1..903
                        mol_type = other DNA
                        organism = Zea mays
SEQUENCE: 23
atggcggaga tcccggtgat cgacctgcgc ctcgccggct cgtcgcccga cgagtcggcg  60
cggctgcgcg acgcgtgcga gcgcctgggc tgctttcggg tgaccggcca cggcgcgccc  120
gcggggctcc tggccgacat gaaggcgcgc gtgcgcgcgc tcttcgacct ccccgacgac  180
gccaagcgcc gcaacgccga cgtcatcccc ggcagcggct acgtcgcgcc ctgccccgcc  240
aacccgctct acgaggcctt cggctcctcc gacgccgccg cgcccgccga cgtcgacgcc  300
ttctgcgcgc gcctcgacgc gccgcccaaa gtcagggaga ccgtcaagac ctacgcggag  360
aagatgcacg acgtgatcgt cggcgtcgcc ggcgagctgg ccaccagcct ggggctgggc  420
ctggaggagc actcgttcca ggactggccg tgccagttcc gcatcaacag gtacaactac  480
acgcaggaga cggtgggctc ctccggcgtg cagacccaca cggactcggg cttcctcacc  540
gtgctccagg aggacgagtg cgtcggcggc ctcgaggtgc tggaccccgc cgccggtgag  600
ttcgtgcccg tggaccccgt cgccggctcc ttcctcgtca acatcggcga cgtcggcacg  660
gcgtggagca acgggaggct ccacaacgtg aagcaccggg tgcggtgcgt cgcgcccgtg  720
ccgcgcatct ccatcgccat gttcctgctg gcgcccaagg acgaccgcgt gagcgccccg  780
gaggcgttgg tcgacgcggg ccacccgcgt cggtacaagc cgttcaacta cgacgactac  840
cggaggctcc ggctgtccac cggcgagcgc gcaggcgagg cgctcgcgcg gatggcggcg  900
tga                                                                903

SEQ ID NO: 24           moltype = AA  length = 300
FEATURE                 Location/Qualifiers
source                  1..300
                        mol_type = protein
                        organism = Zea mays
SEQUENCE: 24
MAEIPVIDLR LAGSSPDESA RLRDACERLG CFRVTGHGAP AGLLADMKAA VRALFDLPDD  60
AKRRNADVIP GSGYVAPCPA NPLYEAFGLL DAAAPADVDA FCARLDAPPK VRETVKTYAE  120
KMHDVIVGVA GELATSLGLG LEEHSFQDWP CQFRINRYNY TQETVGSSGV QTHTDSGFLT  180
VLQEDECVGG LEVLDPAAGE FVPVDPVAGS FLVNIGDVGT AWSNGRLHNV KHRVRCVAPV  240
PRISIAMFLL APKDDRVSAP EALVDAGHPR RYKPFNYDDY RRLRLSTGER AGEALARMAA  300

SEQ ID NO: 25           moltype = DNA  length = 1614
FEATURE                 Location/Qualifiers
source                  1..1614
                        mol_type = other DNA
                        organism = Zea mays
SEQUENCE: 25
accacacgaa ttgcacatct ccacagctca cgattccaac actagctaca tatatatgta  60
gctttctagg ctactatata cactcaccac caagtgtgaa gtgtgtatat atagtgacag  120
ctactgcaat atatacatac gcgtcaccta tatattagcc aagctagcta tatgagcttg  180
gttgcggcgc caatggcgat cgtcgacgtg gccaacgccc agctgcagca agcagcagca  240
gcagctgcca agaaagacga ggacggccat gagcagcagg agtcgtccta cgactacggc  300
gcgctgatga aggcgtgag gcacctgtcg gacagcggca ttaccaggct gcccgacagg  360
tacgtcctgc ccgcgtccga ccgcccccggc gtccttgccg tctcgtcgtc cgtggcgggc  420
agcggcaggg tcaagctccc tgtcgtcaac ctcgccggcc tccgcgaccc ctgccagcgc  480
gccgccgtgc tggccacgct cgacgccgcg tgccgggagt acggcttctt tcaggtggta  540
aaccacgggt tcgggagcga cgtgagcggc gggatgctgg acgtggcgca gcgcttcttc  600
gagctgccgc tggccgagcg agcgcggcac atgtcggcgg acgtgcgggc gccggtgcgc  660
tacggcacca gcttcaacca ggccaaggac gacgtgctct gctggcgcga cttcctcaag  720
ctcgtctgcc agccgctgca ggcggtgctc ccgtactggc cccagcagcc ggcggacctc  780
agggacgtgg ccaccaggta cgccacggcg agccaccggc tgttcatgga ggtcatggag  840
gcggcgctgg aggccctggg catcccccacg gccggcggcg tgctcgggga gctggcagcg  900
tcgtcgtcgc acatgatgac ggtgaactgc tacccggcgt gcccgcagcc tgagctcacg  960
ctggggatgc cctcgcactc ggactacggc ctcttcacgt tcgtcctgca ggaccacgtc  1020
gagggcctcc aggtcatgca cgacggccgc tggctcacca tcgaccccat cccgggatcg  1080
ttcgtcgtca acgtcggcga ccacctagag atctacagca acgggcggta caagagcgcg  1140
ctgcaccggg tgcacgtgaa ctccacgcgg ccgcgcatct cggtggcgtc gttccacagc  1200
ctgccggcgg agcgagtgat cgggccggcg ccggagctgg tggacgacga ggccggcaac  1260
```

```
ccgcggcggt acatggacac cgacttcgct accttcctcg cctacctcgc atccgcggac  1320
ggcaagaaca agaccttcct ccagtcaagg aagctgcctg ctgctgctcc tccatgcctc  1380
tagctaacta gatagctgct tattaatctg acagaataaa attaatcagt tcagcgcaca  1440
attccacaag cgaaaacaaa cctggatttg ttttaattag ctctgccctt cattattaca  1500
ttcaagctag ctcttggtca acgcatgcac acaagcttga gcattgactg gtcccttttc  1560
aatcggttgc attgtactcc ctccgtacca aaattggttg tcgctatagt attt        1614

SEQ ID NO: 26          moltype = DNA  length = 1212
FEATURE                Location/Qualifiers
source                 1..1212
                       mol_type = other DNA
                       organism = Zea mays
SEQUENCE: 26
atgagcttgg ttgcggcgcc aatggcgatc gtcgacgtgg ccaacgccca gctgcagcaa  60
gcagcagcag cagctgccaa gaaagacgag gacggccatg agcagcagga gtcgtcctac  120
gactacggcg cgctgatgaa aggcgtgagg cacctgtcgg acagcggcat taccaggctg  180
cccgacaggt acgtcctgcc cgcgtccgac cgccccggcg tccttgccgt ctcgtcgtcc  240
gtggcgggca gcggcagggt caagctccct gtcgtcaacc tcgccggcct ccgcgacccc  300
tgccagcgcg ccgccgtgct ggccacgctc gacgccgcgt gccgggagta cggcttcttt  360
caggtggtaa accacgggtt cgggagcgac gtgagcggcg ggatgctgga cgtggcgcag  420
cgcttcttcg agctgccgct ggccgagcga gcgcggcaca tgtcggcgga cgtgcgggcg  480
ccggtgcgct acggcaccag cttcaaccag gccaaggacg acgtgctctg ctggcgcgac  540
ttcctcaagc tcgtctgcca gccgctgcag gcggtgctcc cgtactggcc ccagcagccg  600
gcggacctca gggacgtggc caccaggtac gccacggcga gccaccggct gttcatggag  660
gtcatggagg cggcgctgga ggccctgggc atccccacgg ccggcggcgt gctcggggag  720
ctggcagcgt cgtcgtcgca catgatgacg gtgaactgct acccggcgtg cccgcagcct  780
gagctcacgc tggggatgcc ctcgcactcg gactacggcc tcttcacgtt cgtcctgcag  840
gaccacgtcg agggcctcca ggtcatgcac gacggccgct ggctcaccat cgaccccatc  900
ccgggatcgt tcgtcgtcaa cgtcggcgac cacctagaga tctacagcaa cgggcggtac  960
aagagcgcgc tgcaccgggt gcacgtgaac tccacgcggc cgcgcatctc ggtggcgtcg  1020
ttccacagcc tgccggcgga gcgagtgatc gggccggcgc cggagctggt ggacgacgag  1080
gccggcaacc cgcggcggta catggacacc gacttcgcta ccttcctcgc ctacctcgca  1140
tccgcggacg gcaagaacaa gaccttcctc cagtcaagga agctgcctgc tgctgctcct  1200
ccatgcctct ag                                                     1212

SEQ ID NO: 27          moltype = AA  length = 403
FEATURE                Location/Qualifiers
source                 1..403
                       mol_type = protein
                       organism = Zea mays
SEQUENCE: 27
MSLVAAPMAI VDVANAQLQQ AAAAAAKKDE DGHEQQESSY DYGALMKGVR HLSDSGITRL  60
PDRYVLPASD RPGVLAVSSS VAGSGRVKLP VVNLAGLRDP CQRAAVLATL DAACREYGFF  120
QVVNHGFGSD VSGGMLDVAQ RFFELPLAER ARHMSADVRA PVRYGTSFNQ AKDDVLCWRD  180
FLKLVCQPLQ AVLPYWPQQP ADLRDVATRY ATASHRLFME VMEAALEALG IPTAGGVLGE  240
LAASSSHMMT VNCYPACPQP ELTLGMPSHS DYGLFTFVLQ DHVEGLQVMH DGRWLTIDPI  300
PGSFVVNVGD HLEIYSNGRY KSALHRVHVN STRPRISVAS FHSLPAERVI GPAPELVDDE  360
AGNPRRYMDT DFATFLAYLA SADGKNKTFL QSRKLPAAAP PCL                   403

SEQ ID NO: 28          moltype = DNA  length = 1863
FEATURE                Location/Qualifiers
source                 1..1863
                       mol_type = other DNA
                       organism = Zea mays
SEQUENCE: 28
tgccaccata ccactagtgc aaggtcctag atttacactt ggtgctacac cttgcttcgc  60
ccccttcctt ccttccttcc ttccttccct ccttccttgg tctctaggca gctagcagtg  120
tggtgctgct gccggccgcc tattggccgc ctgggactgg gatccattaa ttactgcgcg  180
cgcgcggcta accaaccaat cccagcgtgc gtaatctatt gcccacatgc cgacgccgtc  240
gcacctcaac aagaacccgc gctacctgga cttccgggcg gcgcggcggg tgccggagtc  300
gcacgcctgg ccgggcctgc acgaccaccc cgtcgtggac ggcggcgcgc cgggccccga  360
cgccgtgccg gtggtggacc tgggcgccgc ggacccggcg ccggcgccgg cggcggcggt  420
ggcccgcgcc gccgagcaat ggggcgcgtt cctgctcacg ggccacggcg tccccgcgga  480
cctgctggcg ccgtggagg accggatcgc caccatgttc gcgctgccgg ccgacgacaa  540
gatgcgcgcc gtgcgcgggc ccggcgacgc ctgcggctac ggctccccgc ccatctcctc  600
cttcttctcc aagtgcatgt ggtccgaggg ctacaccttc tcgccggcct ccctccgcgc  660
cgacctccgc aagctctggc ccaaggccgg cgacgactac accagcttct gtgatgtgat  720
ggaggagttc cacaagcaca tgcgcgccct cgcggacaag ctgctggagc tgttcctcat  780
ggcgctgggg ctcaccgacg agcaggccag cgccgtcgag gccgagcgga ggatcgccga  840
gacgatgacc gccaccatgc atctcaactg gtacccgagg tgcccggacc cgcggcgcgc  900
gctggggctg atcgcgcaca ccgactcggg cttcttcacc ttcgtgatgc agagcctcgt  960
gcccgggctg cagctcttcc gccacgcccc ggaccggtgg gtggcggtgc cggccgtgcc  1020
gggcgccttc gtcgtcaacg tgggcgacct cttccacatc ctcaccaacg gccggttcca  1080
cagcgtgtac caccgcgccg tcgtgaaccg ggacctcgac aggatctcgc tcggctactt  1140
cctcggcccg ccgccgcacg ccaaggtggc gccgctgcgc gaggccgtgc cgcccggccg  1200
ggcccccgcg taccgcgccg tcacgtggcc cgagtacatg ggcgtccgca agaaggcctt  1260
caccaccggc gcctccgcgc tcaagatggt cgccctcgcc gccgccgccg acctcgacga  1320
cgacggcgac gccgccgtcg tccatcagca gcagcagcta gtcgtctcgt cgtagccgag  1380
accgatcgcc ggagactgat gctgatgatg atgcatatat acatgagaga aatcgtcgag  1440
```

```
tagactagcc gattgcaaaa gcaaccccag ctgccgaaac ctggcatatc gatcccattc  1500
tctgctgcgc acatgtatgc atgcatgcgc ttcgtccgtt cgactcgtgt gtgcttgctt  1560
gcttgcgcgt gcagcagaac taattccgtt ccgcagctag ctgctctgct ctgctctgct  1620
ggaatgtaat taagtagtag tatatggtag tagagaaaag attagctagg cgatcgatat  1680
agatgacggg ccggggaaga agacgaatta attaagatcg atcgacgacg acgagctgtg  1740
cgtggctggc tgtgttcttc tctagcctag ttacagaggc cggctgctgc tgcttccaat  1800
cgggctgctt gtcgctactg acgatcgtta gtggatccat taactaatct ggaattctgg  1860
att                                                                1863

SEQ ID NO: 29          moltype = DNA  length = 1149
FEATURE                Location/Qualifiers
source                 1..1149
                       mol_type = other DNA
                       organism = Zea mays
SEQUENCE: 29
atgccgacgc cgtcgcacct caacaagaac ccgcgctacc tggacttccg ggcggcgcgg  60
cgggtgccgg agtcgcacgc ctggccgggc ctgcacgacc accccgtcgt ggacggcggc  120
gcgccgggcc ccgacgccgt gccggtggtg gacctgggcg ccgcggaccc ggcgccggcg  180
ccggcggcgg cggtggcccg cgccgccgag caatggggcg cgttcctgct cacgggccac  240
ggcgtccccg cggacctgct ggcgcgcgtg gaggaccgga tcgccaccat gttcgcgctg  300
ccggccgacg acaagatgcg cgccgtgcgc gggcccggcg acgcctgcgg ctacggctcc  360
ccgcccatct cctccttctt ctccaagtgc atgtggtccg agggctacac cttctcgccg  420
gcctccctcc gcgccgacct ccgcaagctc tggcccaagg ccggcgacga ctacaccagc  480
ttctgtgatg tgatggagga gttccacaag cacatgcgcg ccctcgcgga caagctgctg  540
gagctgttcc tcatggcgct ggggctcacc gacgagcagg ccagcgccgt cgaggccgag  600
cggaggatcg ccgagacgat gaccgccacc atgcatctca actggtaccc gaggtgcccg  660
gacccgcggc gcgcgctggg gctgatcgcg cacaccgact cgggcttctt caccttcgtg  720
atgcagagcc tcgtgcccgg gctgcagctc ttccgccacg ccccggaccg gtgggtggcg  780
gtgccggccg tgccgggcgc cttcgtcgtc aacgtgggcg acctcttcca catcctcacc  840
aacggccggt tccacagcgt gtaccaccgc gccgtcgtga accgggacct cgacaggatc  900
tcgctcggct acttcctcgg cccgccgccg cacgccaagg tggcgccgct gcgcgaggcc  960
gtgccgcccg gccgggcccc cgcgtaccgc gccgtcacgt ggcccgagta catgggcgtc  1020
cgcaagaagg ccttcaccac cggcgcctcc gcgctcaaga tggtcgccct cgccgccgcc  1080
gccgacctcg acgacgacgg cgacgccgcc gtcgtccatc agcagcagca gctagtcgtc  1140
tcgtcgtag                                                          1149

SEQ ID NO: 30          moltype = AA  length = 382
FEATURE                Location/Qualifiers
source                 1..382
                       mol_type = protein
                       organism = Zea mays
SEQUENCE: 30
MPTPSHLNKN PRYLDFRAAR RVPESHAWPG LHDHPVVDGG APGPDAVPVV DLGAADPAPA  60
PAAAVARAAE QWGAFLLTGH GVPADLLARV EDRIATMFAL PADDKMRAVR GPGDACGYGS  120
PPISSFFSKC MWSEGYTFSP ASLRADLRKL WPKAGDDYTS FCDVMEEFHK HMRALADKLL  180
ELFLMALGLT DEQASAVEAE RRIAETMTAT MHLNWYPRCP DPRRALGLIA HTDSGFFTFV  240
MQSLVPGLQL FRHAPDRWVA VPAVPGAFVV NVGDLFHILT NGRFHSVYHR AVVNRDLDRI  300
SLGYFLGPPP HAKVAPLREA VPPGRAPAYR AVTWPEYMGV RKKAFTTGAS ALKMVALAAA  360
ADLDDDGDAA VVHQQQQLVV SS                                           382

SEQ ID NO: 31          moltype = DNA  length = 1439
FEATURE                Location/Qualifiers
source                 1..1439
                       mol_type = other DNA
                       organism = Zea mays
SEQUENCE: 31
gacctccatt ttgattatct ctatcctgta cgtgccgaga gtccttcaaa gccgacgacg  60
agacgacgat gcagtcgtcg tcgtcatcag cctcgacgcc ggctgccgct tccggcctcg  120
tcttcgatct cgggtctgcg gcgggcgtgc cggagacaca cgcgtggccg ggggtgaacg  180
agtacccgtc ggtggagtcc gctggccgcg acgtggtccc ggtggtggac atgggggtgg  240
cctgcccgga cgcgacgcgg gcgttggcgc gcgccgcaga cgagtggggc gtgtttctgc  300
tcgtcggcca cggcgtgccc cgggaagtgg cggcgcgtgc cgaggagcag gtcgcgcgcc  360
tgttcgtgct cccggctcct gacaaggccc gcgcggggcg ccgcccggg gagcccacgg  420
ccaccggcta cggcaggccg cccctggcac tccgcttctc caagctcatg tggtccgagg  480
ggtacacgtt ccgcgccgcc accgtccgcg aagagttccg ccgcgtctgg cccgacggcg  540
gcgacgacta cctccgcttc tgcgacgtga tggaggagta cgacagagag atgagggctc  600
tcggtggcag gctgctcgac ctcttcttca tggcgctcgg cctcaccgac gtccagttcg  660
ccaccggcga gacggagcgg aggatccgcg agacctggac ggcgacgatg cacccaatcc  720
tgtgtccgga accggagcgc gccatcggcc tgacggcgca cacggactcg ggcttcatca  780
cgctcatcat gcagagcccc gtgcccgggc tgcagctgct ccgccgcggg ccggaccggt  840
gggtgacggt gccggcgccg ccgggcgcgc tcatcgtcat gctcggcgac ctgttccagg  900
tgctcacgaa cggccgcttc cggagcccta tccaccgcgc cgtcgtaagc cgagagcgcg  960
agcggatctc cgtgccctac ttcctctgcc cgccggagga catgacggtg gcgccgctcg  1020
cgtccgctct gctgccgggg aggaaggccg tgttccgggc cgtgacgtgg ccagagtaca  1080
tggaggtcaa gcacaaggtg ttcggcacgg atgcgccggc cctggagatg ctgcagctgc  1140
aggtggatga ggaagaacaa ggtgaaaggg ccgccaccac ctaagcccta aggaactact  1200
agctgaatcc ataaactaat aaagaattcg tgaataaggg cgttggaaga ctggacacaa  1260
cacaagagag ttgctatata tcgtatttct gaaatttaag gcaaatatct tagttaaaaa  1320
actggtatat ttaaatagac aatatatatc taaaataaag atagttcacc atttttacgg  1380
```

```
tcgaacaatg ataaagttat atattgtctg aatagtaaca aattaaagat ttccaggag   1439

SEQ ID NO: 32          moltype = DNA  length = 1116
FEATURE                Location/Qualifiers
source                 1..1116
                       mol_type = other DNA
                       organism = Zea mays
SEQUENCE: 32
atgcagtcgt cgtcgtcatc agcctcgacg ccggctgccg cttccggcct cgtcttcgat  60
ctcgggtctg cggcgggcgt gccggagaca cacgcgtggc cgggggtgaa cgagtacccg  120
tcggtggagt ccgctggccg cgacgtggtc ccggtggtgg acatgggggt ggcctgcccg  180
gacgcgacgc gggcgttggc gcgcgccgca gacgagtggg gcgtgtttct gctcgtcggc  240
cacggcgtgc cccgggaagt ggcggcgcgt gccgaggagc aggtcgcgcg cctgttcgtg  300
ctcccggctc ctgacaaggc ccgcgcgggg cgccgccccg gggagcccac ggccaccggc  360
tacggcaggc cgcccctggc actccgcttc tccaagctca tgtggtccga ggggtacacg  420
ttccgcgccg ccaccgtccg cgaagagttc cgccgcgtct ggcccgacgg cggcgacgac  480
tacctccgct tctgcgacgt gatggaggag tacgacagag agatgagggc tctcggtggc  540
aggctgctcg acctcttctt catggcgctc ggcctcaccg acgtccagtt cgccaccggc  600
gagacggagc ggaggatccg cgagacctgg acggcgacga tgcacccaat cctgtgtccg  660
gaaccggagc gcgccatcgg gctgacggcg cacacggact cgggcttcat cacgctcatc  720
atgcagagcc ccgtgcccgg gctgcagctg ctccgccgcg ggccggaccg gtgggtgacg  780
gtgccggcgc cgccgggcgc gctcatcgtc atgctcggcg acctgttcca ggtgctcacg  840
aacggccgct tccggagccc tatccaccgc gccgtcgtaa gccgagagcg cgagcggatc  900
tccgtgccct acttcctctg cccgccggag gacatgacgg tggcgccgct cgcgtccgct  960
ctgctgccgg ggaggaaggc cgtgttccgg gccgtgacgt ggccagagta catggaggtc  1020
aagcacaagg tgttcggcac ggatgcgccg gccctggaga tgctgcagct gcaggtggat  1080
gaggaagaac aaggtgaaag ggccgccacc acctaa                            1116

SEQ ID NO: 33          moltype = AA  length = 371
FEATURE                Location/Qualifiers
source                 1..371
                       mol_type = protein
                       organism = Zea mays
SEQUENCE: 33
MQSSSSSAST PAAASGLVFD LGSAAGVPET HAWPGVNEYP SVESAGRDVV PVVDMGVACP  60
DATRALARAA DEWGVFLLVG HGVPREVAAR AEEQVARLFV LPAPDKARAG RRPGEPTATG  120
YGRPPLALRF SKLMWSEGYT FRAATVREEF RRVWPDGGDD YLRFCDVMEE YDREMRALGG  180
RLLDLFFMAL GLTDVQFATG ETERRIRETW TATMHPILCP EPERAIGLTA HTDSGFITLI  240
MQSPVPGLQL LRRGPDRWVT VPAPPGALIV MLGDLFQVLT NGRFRSPIHR AVVSRERERI  300
SVPYFLCPPE DMTVAPLASA LLPGRKAVFR AVTWPEYMEV KHKVFGTDAP ALEMLQLQVD  360
EEEQGERAAT T                                                       371

SEQ ID NO: 34          moltype = DNA  length = 4095
FEATURE                Location/Qualifiers
source                 1..4095
                       mol_type = genomic DNA
                       organism = Zea mays
SEQUENCE: 34
taaatttgtg atccttgtga agttgttata tcatgaattg tgaacttgtt gcatttgtga  60
tcttttgtca actttgttgt attgtgaagt ttgatatgtt taccgatcgt attttagatt  120
tcgatcgtta ccggtgtatt ttccgcacca aacttttgtt tccgatgttt tcgaaatacc  180
gatatcgttt ccgtttctat agttaccctt ttcaatttta tttccgatta aaaatatgaa  240
aacggtaatg gttttagtgt ttatcgaccg ttttcatctc taatcatccc tgccggtgaa  300
gtttaatttt tcccttggct aaagagatgc aagctgctgt aaaatacgtt aaaacaggca  360
aggcagcccc agcagccagc atcgcgtgcc cgtctatgta catcagtgga tacgtagcat  420
ctctagtgag taatataacg attgcatttg gctggaggac gtatgttata taagtatgtc  480
atttaccagt tgcattagta tcttccctaa ctcctataat aactctcttc gtggaatgga  540
cgtagacgta tgctatataa gtattaaaaa atagtttttt aagctggtgt cctcaatttt  600
gctattgttc tcgtttttat ctttagttgt gtcacaaatt taatccgtac aacaaatcaa  660
aaataccata cccttcttat attaattttc taacataaca tttgtttaga tattttcagt  720
cgtgaaaata caattctaat tctaacgtcg tagtatcaaa tcaaaccatc cagaatttga  780
ccaagcttaa ttataaaaaa tataaaattt atgatactga atagatagca ttagatttgt  840
tatataatat atttttataa aataccattt ttatggtata aatattggta ctcctttact  900
ttaaactata gatagttttg actaaggatg caactagaat tgcatcctct tttcactgca  960
ccttcattag ttttaatatt tatttagatg ggcccttgca aactgtagat atcatctctt  1020
gcaacattct ttctatagca ccacgaaaat gtattgcggc tttgaaatta taattgaatt  1080
agttgtatca tttctttcac cgatgcgtta aattcaaaat taagtgttat atttcttcat  1140
aatttgttaa atatatagac cctataatcc accattattt actataatag catacattaa  1200
cattggtttt agcctacact acgacactcg aggcattgaa ttttcctcta tcaaagaatt  1260
atatgtgtag tagtattgtt cttgacaaaa agggggatta aaattaaact accaatattg  1320
atacttatct tatcacatcc atgaatacaa tcaacactct tacaaaagat aagatacaag  1380
attaaaaagt accatgataa tacattaaga ttattagcaa tgcattaaat taaataaatg  1440
tgcaagtgaa tcatgatttt agttttatct attttacttt taaaatatga tattctctga  1500
ctacttctaa gcataaatgt gattctaagt catgaccgat cgtgcttatt cagaaaaatg  1560
aaggagacac agatttctat aaaaaaaggt tgtcatggga ctattgggtc aaccatctta  1620
ttcatttggg aaaataagtt tagaacacat caacccattt tagatgttga gtttggccct  1680
aatggtccat tgaccttact tttgtgggtt gacatagacc atctatccca agttattgtt  1740
gtgtcacatt ccctgatatc atgaatctat attttagctt tccgttttca tatttttagt  1800
cgttacatat tttttatccg cgtactagat taaaactcta gttgttgcaa tacattttgt  1860
```

```
tcattttttt ctatttcttc tttactaaca acatattcta gttcctagct acattcttaa  1920
gtaccatagt gctataaaca ttttttatcc tacattattc cacttaagaa attgaatttt  1980
ctgcataaaa aaattatatg tccagtagtg ttgtcttata aaagcataaa gtgattaaaa  2040
ttaaaaccat tattgatatc ttatttttca aaaaaaaata taagcttata gaaagtgaat  2100
taatttcatg gtaaattaat atagtttaaa ttgaattatt agtgttatta ctatgtttat  2160
tatcaatgaa acatttttca tggttgatat aacttagtgt tacttatttt agtatttttt  2220
atataattct agttaacttt tagtttttga tttaaaaaaa cgagaattgt gtccttttgt  2280
ggagtgagta taaagaaagt aatatctgtt catcataatt tggtttttta aggtacgtga  2340
aacttgcttt atatttggac tcaagctatg tctaaataca tagtaaaaaa gcaatatttc  2400
tagaaaagac aaaacatctt ataatttaga atcaaggaaa tatatagatt ttatgtgcag  2460
tgagaagcca tttacaatgg aacgttcaac gttgggccaa tagatatttt gcgatatgat  2520
gatgggcata tttttgcatg gttgtccctc cactagctat agtttgatga tacgatacgc  2580
tgcacacacc attgggttgt accatgttag tgtagcaaca gtagaaaccc aattgtggcc  2640
gtgaaccatg ataatactag gtagagtgct agctagaggt ttcaggctat tgatgcgtga  2700
attaaacttt ctgttgtgtt gcgaggaaac gagtattgtg aaatatttga aacggttttt  2760
tttgtgaaag atttgaaacg gtatttttgt tgtgaaataa agatcaaggc taaataaatt  2820
caaactaata aaacatatta attgacggcc tgaagccccc gcccccatgg ccccatgcca  2880
tagcatcagg tcccacatga catgaggccg cgcctccctc tatgttggct ccctgccttc  2940
gccgttgtcg tcgctcccga actccctctc ctcccctgtt acaaataccc ccacccgccc  3000
ggacagcttc cctgcacact cgcagctcgc acatctcatg gtgtcctaag aacggcaaga  3060
gccagctctg cctagcagca gcgcacagcc acatccatgg acgccagccc gaccccaccg  3120
ctccccctcc gcgccccaac tcccagcatt gacctccccg ctggcaagga cagggccgac  3180
gcggcggcta acaaggccgc ggctgtgttc gacctgcgcc gggagcccaa gatcccggag  3240
ccattcctgt ggccgcacga agaggcgcgg ccgacctcgg ccgcggagct ggaggtgccg  3300
gtggtggacg tgggcgtgct gcgcaatggc gacggcgcgg ggctccgccg cgccgcggcg  3360
caagtggcgg cggcgtgcgc gacgcacggg ttcttccagg tgtgcgggca cggcgtggac  3420
gcggcgctgg ggcgcgccgc gctggacggc gccagcgact tcttccggct gccgctggct  3480
gagaagcagc gggcccggcg cgtccccggc accgtgtccg ggtacacgag cgcgcacgcc  3540
gaccggttcg cgtccaagct cccctggaag gagaccctgt ccttcggctt ccacgacggc  3600
gccgcggcgc ccgtcgtcgt ggactacttc accggcaccc tcggccaaga tttcgagcca  3660
gtggggtgag taaagaagaa gatggcgccg aatttacatt tataagtagg accagcagaa  3720
gcccctgccc ctgggggcct tagcattgca ttcgactgat gaatacgcat ggcaggcggg  3780
tgtaccagag gtactgcgag gagatgaagg agctgtcgct gacgatcatg gagctgctgg  3840
agctgagcct gggcgtggag cgcggctact accgggagtt cttcgaggac agccgctcca  3900
tcatgcggtg caactactac ccgccgtgcc cggtgccgga gcgcacgctg ggcacgggcc  3960
cgcactgcga ccccacggcg ctgaccatcc tcctgcagga cgacgtcggc gggctggagg  4020
tcctggtgga cggcgagtgg cgccccgtcc ggcccgtccc aggcgccatg gtcatcaaca  4080
tcggcgacac cttca                                                   4095
```

```
SEQ ID NO: 35           moltype = DNA  length = 7404
FEATURE                 Location/Qualifiers
source                  1..7404
                        mol_type = genomic DNA
                        organism = Zea mays
```

```
SEQUENCE: 35
cctattttgt gtctaatact cttcttatat taattgtttg gtcaaacttt agataaattt  60
gactaatgat gcaattaaaa ctgcatcacc tttactaagg tactgcttta tatgtttcga  120
caaaatttc aattattctc tatgtgtttt aatctttgcg ctacacctcc attgatttaa  180
atactcattt attttaaacc ataacttaaa ttatatcgga tctttgcatc ctttctatgg  240
caccatacat gaatcgatat tttggctgca aatttttaat catgttagtt ttagcatttt  300
ttcatatcca tgtgttaagt ttgaatcatg tgttgttttt atataattta ttgaaaatat  360
agatcctaaa cttcactaat acttacaaca atagcatcat catgtgtttt aatccacgcc  420
acaacactca aggcattgaa ttttcttcta ccaaagagtt gtatgtgtgt attgttcttt  480
aaaaaataga gtgattataa ttaaactacc agtattcata tgtaaaatgt atagacatct  540
aaaataaaat ttgcaaaaaa cattgttgca gactttcaat ataattaaga atgggtttta  600
gggtcatgat atatggtttg ttaaagaaac ttgttttttt ttgcaattga taaactataa  660
aatacatttt cactattgtg tgcatatgta cttggtatac atagtggcat atatcatttt  720
tgtttacttt gaggtttgaa ttatctatgt taaaattgga taacatagat acattggtgt  780
gcgtcctttg gcccatttac ttgactgagg agcaatacta taaagtaaaa catatttgga  840
tattttatct taaactccta gcataatatt gatttaatta tgaacaaata tatgtttagg  900
tgatagtttc atgggtggta aactatataa gaaggcttac catgatcttt gcaaactcta  960
ggctatgaaa gagttccatg atttgtctta gaagcataga caaaacagtg ataatgatct  1020
aaatcacact tatggcactg atgaccatat atgcaaagct aaatgcatgt taagttgtat  1080
tatatcatat gtttacaatg actatcgcat ataacgagga atacattgtc tatatagata  1140
gctattactg tagtagtgcc aaatgttgga caacatgaat cataatcttc aaacctagag  1200
aaattgtagt cagtcgtaca catatcgtct agtaagttgt ctatactttt tatttattgt  1260
atcaaatttt attgttatct tgcttgcttg tttgtttgta ccatagacac aatatggtca  1320
aaaagtggtc aatcgattcg aagaagattg caattgacga gtgctaacag ttgatccttt  1380
tgttgtgcac gctagcggag tagcatgaaa agagtaaaat atgaaattag cgttctaaac  1440
tgtttgtgct ataggtactt cgtatttaat ggagtgacta actataggaa ggtgagagct  1500
cagaagtcag caccctcaca cagagttcta gagttagtgg tcatcgaacc acgacaaact  1560
acatgatgag cagaagaggc aacatcaaga ctatgatcaa tagtttcggg tcaatgaatg  1620
acatcgtgat gagtatttat ctaactatat agaacaacaa cacatgatgt tttaagtaag  1680
ttcaactgat cttctattgc tatctttaag tatttaacgt agcgaataat gttttatcta  1740
tttcattcat aaataatgtt gtgacaaaag gggataacca tcacttttac catgttctag  1800
ataccacaac catctccacc atcataatgg gttcttcatt ggtgcttgga cctcaaataa  1860
tcatatctat agccaactta gctcaattct aataaaatta ggcaacttgg cttcattgta  1920
gcaaaaatag ccaacttagc tcaattttat ctaaacttag ctaatctagc acaacttaga  1980
tcaatattag gaaaaactaa tcaatctaat ctagctcaac tatagcgaaa gatagatatt  2040
```

```
gtagcataac ttagtagatc tatctcaaat tttagcaaaa actaatcaat ttagataaac  2100
tctataaaat tttaatcatt atgacttatt tccaactaat tgtaacttgc atgattttta  2160
tgttccttct ttataattag caacacctaa agacacgaat gatgaggggt ctaacgcatt  2220
cattaaccag ttgttaaata atactctagg tagatgataa gaactctaat tattctatga  2280
atctaagcta aaagatgttt aatatttaag tattggtgtt tattatgtta tttagaacga  2340
ttcatgttac ttaaagattt gttatgattt ttaaatatga ttatgataat ttatgtggtg  2400
tggattaact tgtgaacata tgtgatgtag atgaatatgt atgttgtgga tggaaccata  2460
tgaatatata tacacactca tatactattc gttggtgtag gtaaagcttc atccatcggt  2520
aattactaaa tggtcttcag tcattaccac taggtgaagc ttcacacgac cgataattat  2580
tgaagaacgc tcattaattt ccggtaatgg cttattggcc ttcactagtc ggtgaaaatt  2640
agctattttt ataccaataa aaattagcta atatatgtaa accaggtcta atttttatgg  2700
gcctcttacc gaccaaaatt gattagatta ttgttacaat agttttagtc aaaagctagc  2760
tatgctataa aaattttgaa ttaaagtgag tttcgtaata aaaattgcat acttttaaaa  2820
taaaataatt aaaaaacagt ttttagaaat acaatcaaac accttatgct ataaaaaaat  2880
tgtaatgtac ctacaaatat ataatacttt actttaaaat aggcctgtgc cttctcggct  2940
ctatatgggc tgcctccaac gaagcgccat ggccatgggc tccactgtgt cgggtcccac  3000
atgaggccgc gcctccctcc aaatgttccc tccctgcctt cgtctttgtc gttgctcgca  3060
aactccctgt cctcccctgt tacaaatacc cccacccgcc cggacagctt ccctgcatac  3120
ttgcagctcg cacatctcat ggtgtcgcag gaacgacaag agccagctgt gcctagcagc  3180
agcagcagca gcgccaagcg cgcagccacg tccatggacg ccagcccggc cccgccgctc  3240
ctcctccgcg cccccactcc cagccccagc attgacctcc ccgctggcaa ggacaaggcc  3300
gacgcggcgg ccagcaaggc cggcgcggcc gtgttcgacc tgcgccggga gcccaagatc  3360
cccgcgccat tcctgtggcc gcaggaagag gcgcggccgt cctcggccgc ggagctggag  3420
gtgccgatgg tggacgtggg cgtgctgcgc aatggcgacc gcgcggggct gcggcgcgcc  3480
gcggcgcagg tggccgcggc gtgcgcgacg cacgggttct tccaggtgtg cgggcacggc  3540
gtggacgcgg cgctggggcg cgccgcgctg gacggcgcca gcgacttctt ccggctgccg  3600
ctcgccgaga agcagcgcgc ccggcgcgtc cccggcaccg tgtccgggta cacgagcgcg  3660
cacgccgacc ggttcgcggc caagctcccc tggaaggaga ccctgtcgtt cggctaccac  3720
gacggcgccg cgtcgcctgt cgtcgtggac tacttcgtcg gcaccctcgg ccaggatttc  3780
gagccaatgg ggtaagtaag gtagtaagaa ggagcgccgg tttacattta ccgcacgtcg  3840
gcgtgcggtc gagtcgggac tcgggagacg tatgaacccc cgtcccgtcc catgcatgtg  3900
tggcaggtgg gtgtaccaga ggtactgcga ggagatgaag gagctgtcgc tgacgatcat  3960
ggagctgctg gagctgagcc tgggcgtgga gctgcgcggc tactaccggg agttcttcga  4020
ggacagccgg tccatcatgc ggtgcaacta ctacccgccg tgcccggagc cggagcgcac  4080
gctgggcacg ggcccgcact gcgaccccac ggcgctcacc atcctcctgc aggacgacgt  4140
gggcgggctg gaggtgctgg tggacggtga gtggcgcccc gtccggcccg tcccgggcgc  4200
catggtcatc aacatcggcg acaccttcat ggtaacgaaa cgaaagcgct cgctcctctg  4260
ttttccttgg ccgctcttgt cctgtgtgta tattcagttg agctctctct gtgctgttat  4320
ttcccgaatc ctagtggacc taaacgggca ggttattaca gcacgcacac gtaggcatgt  4380
catgtagcta gtacatacat agcgatgccg atgcaaatgc aatagagaca tgcgttcgag  4440
ttggttccta tctcggcggg ctacggcagg tacacgcggc cgcggcgcgc tctctctagt  4500
ctatccgcgg ccgcgcccag gccgatcgag gcttccgggg gagagttgcg acaagagaac  4560
ggaccgaggg ggtcggctag cggtagcaag ttccctgttg gtttgtggcg ttggagcgtt  4620
gcggagaggc ttgcgcggcg gcggggacgt cgacggggac gtggcgggga gacgatacga  4680
tgggtgccgg gcaggtttcc gaattccaaa cgtttttgtg gcgtgcgtcc atggggcgcc  4740
cccaaacttc ggacgtttcc ggcgctccaa caaatcttct cgcttcacac gtcaccgtcg  4800
tcccggattc atttgcctcg tcgctccacc attcgctgct ctcctctcca cgtactctta  4860
ccctgacctt tgggaaagaa ctgaacattc gagatgcaca acagttcaaa tataacatat  4920
gcagcacaag atcgttcgac tgctatccga caagccaaca acgtgcccag tagaactgaa  4980
tgtacctgtg atttccagca ctaacttaca gcaacgttgt gaaaaaacaa aaacgaaaac  5040
aaacggcaga aaaaacagat gtattgttct acagttacac caaatatttt ctggtccttt  5100
cagcaccaac aagagccata cgcatatcta gaagacaaaa ttcctctaat ttcaccccta  5160
cgtggtagca gttcctcctc aacacagttc acgtgctagc gtcgagttct ttgggccgcc  5220
acatcgactt ctcgacgcag agcaggccct cgctgccctt ggtgtaggtc atccgcacct  5280
cccactgcac ggacttggcc atgctctcca gctcatttat cgtgtccgcg gtgtccctca  5340
cgatcagctt gccctgtggc ctcagtacac ggtcgacctc ggcgaaaact gcagccagtt  5400
tgcatctgta aacaggcaac acagattttt agtatctaaa acactgcagg caaacgccac  5460
aggttttagt cgcaagaagc aataaaagca tgcaaacaat gctacgtgta cgtatcaaag  5520
gaacatgtca aaactcgttg catgaacgat cattgatgtt tccttgctga actagtcaca  5580
tcagtctgct tcaacttctg ggtttcacta gtagatatac cagaagggta gaataatgtg  5640
aagagcaaga aatacagacc tctttctgag ctttgagaac agatggtccg cgtgcagaag  5700
gtcatacgtt cttgggtaag tgctgaaaga ctcgcaccag tcatggtaca tgccaaacaa  5760
accgcgctcg tagatgatgg gcagcgtgtc tggtgaatcg atcggcacga tattcatgac  5820
ccagaccttt tggtccctca gagctgcagc aaaactgcca tgcaacaatg taaagcatta  5880
gtcaagaaga aggtgtacag tgcatttctc cttgtcaaca gtcttcagta acaaaaaaaa  5940
agtgttatgc ttgactgaat ctttcaaaga aatatgcttg atgacttatg gtggacaagt  6000
tgcctgttat agtgttatgt tttaattaac tatgtgccag cttgggtaac tagtagttat  6060
gtagtgtgat ctgaattacc aaaatataaa taaataaata aacatgccca agaaactacg  6120
aaaaccattt acttaccctc catagacagc tctcatgtcc atgacatttc tcactttgga  6180
ccagtcaatt cccatgccat tcacatacga tttacttaca acccgtttcc agtgggcatt  6240
atctgcctca aaatcttcat ttgcaggctt tccatagaca ccaaccttgg aaccatcaat  6300
ccagaaaggg gtcttctcaa gcctttgcgg ccataactct ggccattttg atcctcggac  6360
ttttgagcca ccaggcagtt tgtgcatgca tgcttccaac ggtacattcc tgcaaatcaa  6420
aaggctgtgt aagcaaagca gagaagcact tttctccatt gaaaatatac tcttctcaaa  6480
gaaccgaaac cataccaagc agcatctgca tcatcagatt ccttgcacaa tggcgggctg  6540
ttttcagatc ttttctcata gcaaatattg tccattggtt tctgatatat gaccatacca  6600
acttggttta acttatcctt agtcttgttg accatcttcc agcacatgga ctttgtcaaa  6660
gtagacatgg ctgaaaaggg tatgtggcca catgttatgt tagaaataaa attcaatttt  6720
gaacagttgg tccatagcat gtattttgaa caaatgcaat ccttctccat ccatgaaaga  6780
```

```
agttgaccct tcatacttag gattattcag tactttcact catgtctgct gaatttgttc  6840
tcttggtagt tgctatacaa gaaaggggga agtacagagt agctaaactt atacaagcta  6900
tagtctgata tttgtatgaa acataaattt tggtatggat gtcttattaa aatgggaggt  6960
tgtataatat ttttctagcc tacctcaact tgcttgagac taaaaggctt tgttgttgtt  7020
gttgaggctg tatggtgctt tgactttaca aatcaagtta tcagctaccc tacttatgga  7080
tatacacctc tcataaaatg atggtaagaa gtttcgatat gtcacattaa cataagaact  7140
tcattcagtt agggtacaac gaagttaagt agttacggaa ataccattcc aaatctcaac  7200
atcctctggg agcttttggt aaacaggagt ggcagaccag acaaagtaac caccagggcg  7260
taacaagcgg ttcaattcca gcaaaagcat gccacctaaa agtagcgagc cagcaataag  7320
attcagttct atagcaaatc aataaatgaa aggaggacat gtcaatatgt aaccagcagg  7380
acaaaccttc gatgtgccaa ggga                                         7404

SEQ ID NO: 36          moltype = DNA  length = 1788
FEATURE                Location/Qualifiers
source                 1..1788
                       mol_type = genomic DNA
                       organism = Zea mays
SEQUENCE: 36
aatcccagcg tgcgtaatct attgcccaca tgccgacgcc gtcgcacctc aacaagaacc  60
cgcgctacct ggacttccgg gcggcgcggc gggtgccgga gtcgcacgcc tggccgggcc  120
tgcacgacca ccccgtcgtg gacggcggcg cgccgggccc cgacgccgtg ccggtggtgg  180
acctgggcgc cgcggacccg gcgccggcgc cggcggcggc ggtggcccgc gccgccgagc  240
aatggggcgc gttcctgctc acgggccacg gcgtccccgc ggacctgctg gcgcgcgtgg  300
aggaccggat cgccaccatg ttcgcgctgc cggccgacga caagatgcgc gccgtgcgcg  360
ggcccggcga cgcctgcggc tacggctccc cgcccatctc ctccttcttc tccaagtgca  420
tgtggtccga gggctacacc ttctcgccgg cctccctccg cgccgacctc cgcaagctct  480
ggcccaaggc cggcgacgac tacaccagct tctggtacgt tgcgttgcgt gcttgtgtgc  540
gcgcacacct gccgaccgcg gccacaccgt acgcaaccca cgcgtacgta cgtgcgctag  600
ctacctgctt cgctcgcttc gctcctctcg cctcgccatg catatgcacg tacggccgta  660
caggtacagc agcaggtcac acgcacgaac gcacgcacgc accagcaccg atatgataca  720
tcatcgacgt gtcgtccccc cgtctaaggc catgcatgca tgcaagcacg cctagctagc  780
ccttttggct tgctagctga cgaggggagc taggacgagc atacttactg tgcgcgtcat  840
gctcaattgc tcacactata ctactacttg ttactacagt gatgtgatgg aggagttcca  900
caagcacatg cgcgccctcg cggacaagct gctggagctg ttcctcatgg cgctggggct  960
caccgacgag caggccagcg ccgtcgaggc cgagcggagg atcgccgaga cgatgaccgc  1020
caccatgcat ctcaactggt gggtatatat tattgtctgt catgttgtcg tcgtcgtacg  1080
cgttgcggtt gggtgtacat gtatataaca caaacaacaa aaaactaacg ccgtgccgac  1140
gacgacgacg atcatcaggt acccgaggtg cccggacccg cggcgcgcgc tggggctgat  1200
cgcgcacacc gactcgggct tcttcacctt cgtgatgcag agcctcgtgc ccgggctgca  1260
gctcttccgc cacgccccgg accggtgggt ggcggtgccg gccgtgccgg gcgccttcgt  1320
cgtcaacgtg ggcgacctct tccacatcct caccaacggc cggttccaca gcgtgtacca  1380
ccgcgccgtc gtgaaccggg acctcgacag gatctcgctc ggctacttcc tcggcccgcc  1440
gccgcacgcc aaggtggcgc cgctgcgcga ggccgtgccg cccggccggg cccccgcgta  1500
ccgcgccgtc acgtggcccg agtacatggg cgtccgcaag aaggccttca ccaccggcgc  1560
ctccgcgctc aagatggtcg ccctcgccgc cgccgccgac ctcgacgacg acggcgacgc  1620
cgccgtcgtc catcagcagc agcagctagt cgtctcgtcg tagccgagac cgatcgccgg  1680
agactgatgc tgatgatgat gcatatatac atgagagaaa tcgtcgagta gactagccga  1740
ttgcaaaagc aaccccagct gccgaaacct ggcatatcga tcccattc               1788

SEQ ID NO: 37          moltype = DNA  length = 1698
FEATURE                Location/Qualifiers
source                 1..1698
                       mol_type = genomic DNA
                       organism = Zea mays
SEQUENCE: 37
cgtgccgaga gtccttcaaa gccgacgacg agacgacgat gcagtcgtcg tcgtcatcag  60
cctcgacgcc ggctgccgct tccggcctcg tcttcgatct cgggtctgcg gcgggcgtgc  120
cggagacaca cgcgtggccg ggggtgaacg agtacccgtc ggtggagtcc gctggccgcg  180
acgtggtccc ggtggtggac atggggtgg cctgcccgga cgcgacgcgg gcgttggcgc  240
gcgccgcaga cgagtggggc gtgtttctgc tcgtcggcca cggcgtgccc cgggaagtgg  300
cggcgcgtgc cgaggagcag gtcgcgcgcc tgttcgtgct cccggctcct gacaaggccc  360
gcgcggggcg ccgccccggg gagcccacgg ccaccggcta cggcaggccg cccctggcac  420
tccgcttctc caagctcatg tggtccgagg ggtacacgtt ccgcgccgcc accgtccgcg  480
aagagttccg ccgcgtctgg cccgacggcg gcgacgacta cctccgcttc tggtacgtac  540
gagcgccatg tcacgtgctt gtgctttcat gcctcgtacc gtcgtcgtgc tgtacgtgtt  600
atgtttatcg gccggtacgt cacgcgtgct acactggtta acgacgtgag cgtgcccacg  660
ttgactgcat gcatgtgcat gcgcgcgccc agcgacgtga tggaggagta cgacagagag  720
atgagggctc tcggtggcag gctgctcgac ctcttcttca tggcgctcgg cctcaccgac  780
gtccagttcg ccaccggcga gacggagcgg aggatccgcg agacctggac ggcgacgatg  840
cacccaatcc tgtacgtacg tcaaaaacga atatctgacc aatgcaaacg tttttctgca  900
atgccagtca tccactcatc ctgtacgtac ctctggactc tgcttgtcca tctactgatg  960
acacgtatgg taggtacccc aggtgtccgg aaccggagcg cgccatcggg ctgacggcgc  1020
acacggactc gggcttcatc acgctcatca tgcagagccc cgtgcccggg ctgcagctgc  1080
tccgccgcgg gccggaccgg tgggtgacgg tgccggcgcc gccgggcgcg ctcatcgtca  1140
tgctcggcga cctgttccag gtgctcacga acggccgctt ccggagccct atccaccgcg  1200
ccgtcgtaag ccgagagcgc gagcggatct ccgtgcccta cttcctctgc ccgccggagg  1260
acatgacggt ggcgccgctc gcgtccgctc tgctgccggg gaggaaggcc gtgttccggg  1320
ccgtgacgtg gccagagtac atggaggtca agcacaaggt gttcggcacg gatgcgccgg  1380
ccctggagat gctgcagctg caggtggatg aggaagaaca aggtgaaagg gccgccacca  1440
```

```
cctaagccct aaggaactac tagctgaatc cataaactaa taaagaattc gtgaataagg  1500
gcgttggaag actggacaca acacaagaga gttgctatat atcgtatttc tgaaatttaa  1560
ggcaaatatc ttagttaaaa aactggtata tttaaataga caatatatat ctaaaataaa  1620
gatagttcac catttttacg gtcgaacaat gataaagtta tatattgtct gaatagtaac  1680
aaattaaaga tttccagg                                                1698

SEQ ID NO: 38          moltype = DNA  length = 4095
FEATURE                Location/Qualifiers
source                 1..4095
                       mol_type = genomic DNA
                       organism = Zea mays
SEQUENCE: 38
cggtctaagt gaccgtttga gagaggaaaa gggttgaaag agacccggtc tttgtgacca  60
cctcaacggg gagtaggttt ataagaaccg aacctcggta aaacgaatca ccgtgtcatc  120
cgccttattt gcttgtgatt tgttttcgcc ctctctttcg gactcgttta tatttctaac  180
gctaaccccg acttgtagtt gtgcttaaag tttgtaaatt tcagattcgc cctattcacc  240
ccctctaggc gactttcata taaatattgg gagaaatatg aaaaacaaat gaaggtcgaa  300
cgagtcagag acaccataaa aaagaggtcg tcttaactag ggtgctaaac ctcaacattg  360
tagtagatct tagtactgag tttgacatct ttgacaccaa caagatggtg atacgttact  420
ttctacgtta acttgggtag gtatatcgac tatagtggcc tataacacta ggctatgtaa  480
tatgatattg tgttgagtct ttataaacat gatttttttt aaaaaaaaga gctaaaataa  540
aaaatagaaa tcgacggtac gatgcaagtt cttctcaaga caaccaaacg cacccttgcc  600
cctttattga aattgaagta tgtgctttat caaatgttta aatactaatt ataagtatta  660
aatataattt aattataata ctaattatat agataaagac taaataacaa gacaaattta  720
ttaaatataa ttaattcatt attaacaaat acttaatgta gcacgatcga atcatggact  780
aattagtctt gatagactcg tcttaccatt taatcataat tagttttgta tactgtttat  840
aatatttcta actagctagt attaaacttt tgatgtaacc taactaaagt ttagtcacgc  900
caatacataa ggactcggat cgttcgatca cccatgacat cacgtatact aagagcatct  960
ccaaaagctc tccagaagtc tcccctaaat ctattttttt gggaaaaaca caaaaacatg  1020
tctccaacag ttcccttaaa gcgcccccaa ctttttcata gcccttaaaa ctccctcatt  1080
tgtagctaca aatgaggggt tttttgggct ccccagaaac aaactgttga tttaagggat  1140
ctgttggaga aaggattaaa atttaccctc acttattatt tagatgtccc ttaaaactga  1200
ttttgaggag tcgttttatg tagagctctt ggagatgctc taacacaccg agcacaaccg  1260
catcatcaat caaaacaacc caaagtttgt tcggtacaag tcatcagcct gtgtacacac  1320
atcagcctcg gccccgggag aagcgctagc aaacaaggtt cacctaaaaa tccatccaga  1380
ttcattgaat ccaaccagca caaacgtccc atttattaat cacctcatca caggtccccc  1440
cagcctcact ctcgcgccgg ctcaaggtac attgcgtgtc ctagccaaga cacgcagctc  1500
atctcagcct cacacgcaca gcaagagcga ggcgtgattc gccatgggcg gcctcactat  1560
ggaccaggcc ttcgtgcagg cccccgagca ccgccccaag cccatcgtca ccgaggccac  1620
cggcatccct ctcatcgacc tctcgcctct ggccgccagc ggcggcgccg tggacgcgct  1680
ggccgccgag gtgggcgcgg cgagccggga ctggggcttc ttcgtggtcg tgggccacgg  1740
cgtgcccgca gagaccgtgg cgcgcgcgac ggaggcgcag cgagcgttct tcgcgctgcc  1800
ggcagagcgg aaggccgccg tgcggaggaa cgaggcggag ccgctcgggt actacgagtc  1860
ggagcacacc aagaacgtga gggactggaa ggaggtgtac gacctcgtgc cgcgcgagcc  1920
gccgccgccg gcagccgtgg ccgacggcga gcttgtgttc gataacaagt ggccccagga  1980
tctaccgggc ttcaggtgac gaaattaact atatatccct ttcgatcata gttgcgttaa  2040
taaattaagg gaatcgtgag cgtacgtacg taagtttccg cagagaggcg ctggaggagt  2100
acgcgaaagc gatggaagag ctggcgttca agctgctgga gctgatcgcc cggagcctga  2160
agctgaggcc cgaccggctg cacggcttct tcaaggacca gacgaccttc atccggctga  2220
accactaccc tccttgcccg agccccgacc tggccctcgg cgtggggcgg cacaaggacg  2280
ccggcgccct gaccatcctg taccaggacg acgtcggggg gctcgacgtc cggcggcgct  2340
ccgacggcga gtgggtccgc gtcaggcccg tgcccgactc gttcatcatc aacgtcggcg  2400
acctcatcca ggtacgtgcc cacctgatga actgagctga acgtaggttg catgcactgc  2460
atgtgtatag gcttctcaga tcgcttcgtg tggcgtaagg tgtggagcaa cgacaggtac  2520
gagagcgcgg agcaccgggt gtcggtgaac tcggcgaggg agaggttctc catgccctac  2580
ttcttcaacc cggcgaccta caccatggtg gagccggtgg aggagctggt gagcaaggac  2640
gatccgccca ggtacgacgc ctacaactgg ggcgacttct tcagcaccag gaagaacagc  2700
aacttcaaga agctcaacgt ggagaacatt cagatcgcgc atttcaagaa gagcctcgtc  2760
ctcgcctaac tactgctact gctaggatcc atgccattgc catgtcgtct tcagattcag  2820
agcacgccat gtcgtcgcta gcttcgtggt agaacaaata atgatgtgcg tgctgtgtgt  2880
aagcatggat atggatgtga atatgtaata tgatgagcac tcctactttg gtatgtttgg  2940
gaataacaga cttgtgttgg tctggttcat tatttgtaag aaaatcaaaa agagttagta  3000
gggcaggagg ctaaccacag tcatgctgca ccacatccct ggtggaaagc tggccgggtt  3060
acgctacgct cgtgcagcca gattactgca gggccgggat atgcttccgg tggaaggaag  3120
gggacggtgg ctgaggacca tggggctgga gcctgggaga gaggtcgagc tagaagaaag  3180
ggggagagag aagacgcaca acgaagatgg gtcagccagg gatttcgacc caagggggag  3240
ctagtggatt ttgggagaaa acagaaaaga gaaaagagaa aagaagaaaa atttgttggt  3300
gtgaacacaa ggttgatttg tcttttctta tttggattga tgatgagtcg tggactaacc  3360
gacccgtgag ctattgtgtc gtataatcat gtctctcggt ttctggtgtg caggtttgaa  3420
gcacagagac ggtggtcgac gcaaaggtga acgtcatgca ggttcgtgcc gatggaccgg  3480
gagcagtgaa agacgagcgt tgggacttga acaagggacc agagtcgccg gatgactagc  3540
cgcagtggct gacgcctgga acacgcatag acgtgaggac gtggtagagc aggtgaaaat  3600
cgcctagagg gggggggggt gaatagacaa aacctaaaaa ttataaactt tgaacacaaa  3660
ctttacctga ggttaccgtt agaacgagta ttaatgaaat cggagtgcgg aaggcaagtt  3720
cttcttgcta cgagttgctt aatcaatatt gataactttg ggagtcaact caaaatgatc  3780
acaagcaaaa gaactagaga gagaggagag gaagaatcaa ctcgcaaagt aatgatcaac  3840
acaaatgaac acaatgattt atttctcgag gtttggttcc gaagaaccta ctccccgttc  3900
aggagtccac ataggacatg tctctttcaa ccctttctct ctctcaaatg gtcacataga  3960
ctggttcagt tgagagcacc tagagggggg tgaataggtg atcttgtaaa atcaaacact  4020
```

```
aatagccaca aaacttagtt taaagtgtta gtacggctaa gtagctttga agcgagttat  4080
tgtgaacaca acaat                                                   4095

SEQ ID NO: 39          moltype = DNA  length = 726
FEATURE                Location/Qualifiers
source                 1..726
                       mol_type = genomic DNA
                       organism = Rice tungro bacilliform virus
SEQUENCE: 39
tcctacaaaa gggagtagta atatttaatg agcttgaagg aggatatcaa ctctctccaa  60
ggtttattgg agacctttat gctcatggtt ttattaaaca aataaacttc acaaccaagg  120
ttcctgaagg gctaccgcca atcatagcgg aaaaacttca agactataag ttccctggat  180
caaataccgt cttaatagaa cgagagattc ctcgctggaa cttcaatgaa atgaaaaagag  240
aaacacagat gaggaccaac ttatatatct tcaagaatta tcgctgtttc tatggctatt  300
caccattaag gccatacgaa cctataactc ctgaagaatt tgggtttgat tactacagtt  360
gggaaaatat ggttgatgaa gacgaaggag aagttgtata catctccaag tatactaaga  420
ttatcaaagt cactaaagag catgcatggg cttggccaga acatgatgga gacacaatgt  480
cctgcaccac atcaatagaa gatgaatgga tccatcgtat ggacaatgct taaagaagct  540
ttatcaaaag caactttaag tacgaatcaa taaagaagga ccagaagata taaagcggga  600
acatcttcac atgctaccac atggctagca tctttacttt agcatctcta ttattgtaag  660
agtgtataat gaccagtgtg cccctggact ccagtatata aggagcacca gagtagtgta  720
atagat                                                             726

SEQ ID NO: 40          moltype = DNA  length = 165
FEATURE                Location/Qualifiers
source                 1..165
                       mol_type = genomic DNA
                       organism = Rice tungro bacilliform virus
SEQUENCE: 40
acgaatcaat aaagaaggac cagaagatat aaagctggaa catcttcaca tgctaccaca  60
tggctagcat ctttacttta gcatctctat tattgtaaga gtgtataatg accagtgtgc  120
ccctggactc cagtatataa ggagcaccag agtagtgtaa tagat                 165

SEQ ID NO: 41          moltype = DNA  length = 2000
FEATURE                Location/Qualifiers
source                 1..2000
                       mol_type = genomic DNA
                       organism = Zea mays
SEQUENCE: 41
ctgcaatata tacaccaaaa gtattataaa ctgtcatata tatgaccaaa accttttttat  60
tttagaaaag tatattaatc atggtatatt aatcaaagtt gttgttgggg ctgcaaaaat  120
catacccttc ttccacaagc tgttccttga actgcaggta ctcaggaact ctcagctcct  180
caacagcgag ctcactgacg ttgaccctca catactccca gacaccaggc ctagggcgga  240
tggcaagtgc aacccatggg gggatgacaa tcgcctcctg taagataata gagctagaat  300
gattaaagaa ggtgcacact acaaaaggaa cagtgctgtc cagcgagatc tgaatctgat  360
gcaaacctga gctgccctca ggacatcctc aaaagcacca tccttgagct tctcgcgctc  420
agcctcaggg atcgcattgt tgtactcggc aatgatctgg tggggctgca gcatacccttt  480
tccaaggttt ttcagcctgc gcaaaacgat gtgccaaata acatcagact atgccagatc  540
tataaactca tcaaacatat acaatttcaa gaaatagttt agacgtatga tcagcagtca  600
gtagcgtggg aacatatgca acatagcgaa gaggcacaac agcaaattca ttcgaaaaaa  660
tgaaaacaaa gattcctctc ttttaactga acttctcgaa accccttttca tgcctacaca  720
tccgatctag tcagatgcct atgcgttcat gctgaacaga acgtgtcaga actaagcata  780
aactggttag caagcattat cgtattcgat agacccttta gtaacaagct atacattggg  840
taagttcaga ctccaatcat tctgttcaga aacatcgtat tgaatataaa actaaagaac  900
acacatgcag gtgcagccag atctaacagc agtttacagt cggtactaaa aaaagcatgg  960
tgtatgtatg tatcatcagt atccagtact aggtttcgac aaaatcctgg atgctaatta  1020
aatactcatc ttattaggga acacaggaac attatgtcta cagcattgaa tgatggccac  1080
atcatgctag atctaacaat acataatatg atggaactgg tcttaaaaag tcgcattcgc  1140
tcaaataata cccgtagcaa aataaatgta aacttgcaga cgaagcgggg gaaatgaggg  1200
cagacctggt gaagacggcg acaagctcat tggggtgggc agagagtgag tcgccaatgc  1260
gctccctgac gctgtggagg cggctcagga cacggtcacc tgcaccttcc cccattgctg  1320
tcctcttcct ggatcctcag gcctgcacag cgaaaccgaa acggaagcgg aagcttcagt  1380
cagcagagaa aactgaaacc gaaaaacggt tcagatccgt tgacataaaa gctgcgatga  1440
catcctaaaa ctaaaacccc tccagcaaga cataaaccca actgccaaca accagtcttt  1500
taagtctcga cacaccccttg acgctgcgcc acgaaactat attgcaggca agaaaccaac  1560
agaacctaac tctggaaggg gggaaagaaa cggcagacag gagcaagacc caaaaaaaaa  1620
cgactcagat cctggtacta tagtcctagt acctagacca gaaagaagaa acaaccaata  1680
caacaagagg catacaagaa ctgaatcgat gaactgaaac gcttcagagg accgaggaat  1740
ggcggagaag ggaggcgcct atttatacag atctgacgag agaaccgaac aaaaacacat  1800
cgatgggaac catggagaag aaaagggctg gccgcatggc accaatggcc tcggcctcca  1860
aaaagccgtt gaatccaaag caggcgagga cgaagcgtga cgcggcaggg tacttctcta  1920
gaaaagcacg gcatcagcaa ggtggggggg ctggggttcc ttattgcagg caatcacgag  1980
gtgattagca caaacggaag                                             2000

SEQ ID NO: 42          moltype = DNA  length = 2000
FEATURE                Location/Qualifiers
source                 1..2000
                       mol_type = genomic DNA
                       organism = Oryza sativa
```

```
SEQUENCE: 42
ctgaaatata catcagagat attacaatga catatatatc gataaaagaa aaataataaa  60
attaagtttt aaattttaag aatatatgtt tttagtatcc caattatgca gatttcatac  120
ccttcttcca caagctgttc cttgaactgc aagtactcgg ggactgtcag caactcaaca  180
gcgagctcgc tcacattgac cctcacatac tcccagacac cgggcctcgg gcggatggca  240
agggcaaccc atggggagat aacaatcccc tcctgcatga taaaaaaacaa ttacaagtta  300
agttagagca agcggtagag taaagatgga tctctgtgat gcaatgaaat ctgaatctga  360
ttcaaacctg tgcactcctc aggacatcct caaaagcacc gtccttcagc ttctcacgat  420
cagcctcaga gattgcgttg ttgtactcag caatgatctg gtgggcctga agcattccct  480
ttccgaggtt aaccagcctg cgcaaataac agtgtcaaca aaaatatcag gccagatcta  540
tcaactcagc ctataaatat ctcaataaga taattttagc acttgagcat ttgcgcataa  600
taagaaaatt tgctattagc cacttaaaaa gaccatatat gatctgtttg cattgagatg  660
aattaaaaat ttcattgtag atatgaaatg attagttttg accatttaat tggacttaat  720
gaaatatgcg cgataatcag atctacgcgc tcgcgccaat agatctagta agatgtaggt  780
tttttatttt ttttgtgaaa ctttgctacc acaacaagca tctgtaccag tgcagaattc  840
attacttgta ttcagtttgt aaaccgtata tataatataa ataacatgca catgcagtca  900
gatctagcac taccagtcca cagtaatcca aaactacatt tgtatatttc atcattattc  960
agtagtacta ggtttgtaca aaatcttggc tgcagaaggc cgcacttaaa tattcattct  1020
aatcagaaac ttaaaaaaaa agtgactaca aaatgattgc atccaattca gtaaatatga  1080
gccattcctg gccagatcta acaatctcaa caacaaagat cctatatgaa catctccttc  1140
taaaagaaaa tacagtaaca tctgaaggca gtagactaga aaccaacaaa atctaatgct  1200
gggaaatcac taaatcagca cgaacctggt gaagacggcg acgagctcat tggggtgggc  1260
ggagagggag tcgccgatgc gctccctgac gctgtggagg cggctcagga cgcggtcgcc  1320
ggcagcttcc cccattgctc tcctcttcct cttggctcct caagcctgcg tgcacaacca  1380
accaccatca tcagatacat ccagacccag tcaacacaat cactccagga aaaaaaaaag  1440
tcaagccata aaccccaacc aaaaaccacg cctttgacaa acactggaag aaaaagaaaa  1500
tcgcagcttt ttcacaagca atctagaaga aaagaaaaag aaaagactac atagcagcta  1560
taattgactg agaagcatac aggaatcaaa caatggagaa ggggagggag gaagaacaat  1620
gatgctccag gctgaggacc gaggaactgg gtgaagcggg gtaggcgcgt atttatgcag  1680
atctgaggag agaaaccacc aaaacaatcc gatggtttca acgaaaaaga tcgtcgcttc  1740
ttgctgcacc agctcaccca tagccgttga gatcgaagct aagctagcag cagcaaagct  1800
ggaacgaaga gtgacgcatt caagctcctc tcctctcctc tcctctcctc cggagcacga  1860
ggccagcatg ggatggattg gggtttcttg ttggccatgg caaaggagga ggtcattaac  1920
gttgacacgg cgtaatttaa ttaaatctta tcttaaaata tgatttaagt ggtagtaaca  1980
aggaagatta atactatgaa                                            2000

SEQ ID NO: 43          moltype = DNA  length = 2000
FEATURE                Location/Qualifiers
source                 1..2000
                       mol_type = genomic DNA
                       organism = Oryza sativa
SEQUENCE: 43
gctgtttaag aaaaacagaa gtaaaattca gtcactgtta ttttgcttca gttataatct  60
gcaaatcgtc gttctggtac ttactgtcca tcaacaagct gttccttgaa tgccaagtac  120
tcagaaacac tcagctcttc cactgccaac tcacttacat tcacccgaat gtagtcccag  180
acaccaggcc ttggcctgat ggccagtgca acccagggcg gcagcacaat ggcttcctac  240
atacagtcaa ggaagtaagt tagaaagact ggtatttgac tttgagttga ctatcataac  300
catcctggct cattgccaaa tttacctgag cagcccggag aatgtcttca aagggagcat  360
atttctcttt gtcagcttcg atcaaggcat cgaactccgc aagcagctgg tgacgctgga  420
gcattcccct tccctggtta acatacctgc atagagtgat atttaagaaa tagaaccaat  480
gcttagatct cacatccttt ctgcggctga actatgttaa tggcactacc acataaacct  540
gatttttact tcttattttt aagaccacat gatctgtact taatctagct atgaacaaac  600
aatatttcaa catcatctaa gattcatgac tcaagacaaa aatgttagag ctcatcacag  660
attattatag ataccatcat taaaactaaa gagatgcata accttgtcag ctaagaattt  720
gtaacatact aacatgttat cgtttcacat ctgggttgac taagaactaa ccaactgtat  780
ggataaaatc attgaaaact caaaacaatt agtagcaggt tccaagaaga cacaagatat  840
tatattgaga tcttcaccta gagaagagtg caatcaactc attgggatga gacgagaagg  900
tggcaccgag gcgttcgcgg agactgtgga ggcgagctag cttggcagcc atgactcaat  960
ttcaggaact gcaaagaaag gttacactta gcaacacgta ccaaaaccac tcacttgcac  1020
aagaataatt agtcaacagc catcactaag cattgcaaga ctatctctga acaggaaagc  1080
catgctaaat caacactaat aacatcacac aaaagcattg gaagatcaaa acataactaa  1140
aaacagctgt ttcatctaca caactgaaag catctatggt ttacgaagca gagtgcgagt  1200
actgattcaa aataaatcaa cctgaaccaa tatactctga caatgttttc aaagggataa  1260
aagaaccagc tttatcaaat ggatttgttg ggttttagta agtatcattg agataccgat  1320
ggcatatctc aaactttgca aaattataat ggcatggttc caaattaccc tttagtatta  1380
gcaccagtta gatcctaatt cctaaatccg ataggacaga gcgaaagatc cctggagata  1440
tgaagatttg gctacagatt aagcagagcc aacatgaagt tccgaatatt atgaatccgc  1500
aagcggggag atcaaagaga agaatacgga aggtcgcgac tccatgaaag aatccaacca  1560
aaaacccaaa gatttttctc agttcaaaaa aaaaaaaccc ttcatttttg gttcgccatc  1620
caccgacagg caccaagaca ttcctcagga agcaaaaaag attaagcaga acaagtgata  1680
agcaagacac agtatcaacg gactacgagt cgagaaaatc actgaggcgc gattcttact  1740
gcaccaagta aaaaaaaatt tgggggcaaa aagaactctg caatggggcg gagcaacgtg  1800
gcagcaaaac taaaggtcga ggatttgagg ttttttgccg gtttcctcg aaaccccgaa  1860
tccgctcata gtaaacccac taaactgcag cagaaacccc cctcttggtt cagatttacc  1920
gaaagcagta aacccaagaa catgtcagca aaaactcctg caagattcag ctgacgaccc  1980
accaaagaat cgcaagaaat                                            2000

SEQ ID NO: 44          moltype = DNA  length = 2000
FEATURE                Location/Qualifiers
```

```
source                  1..2000
                        mol_type = genomic DNA
                        organism = Oryza sativa
SEQUENCE: 44
tggcggacgc gccacgcaca aacacaaacc tgcacacccc tgtgtcagag gaggagaggc  60
caagaaagga aatcgagtgg aggaagtgag gagcggcgga gacgtaggag gaggaggggg  120
agatggaaat ggaaagccgc gcgagagagg aggcgcgtgc tggatgggag gaggaggagg  180
aggtggtggg tttgtgtttg gagagacgag cgagagaggc gaagcattta aagggaggaa  240
gagggggaga gagagagaga gagagagaga gagagagaga gagagagaaa ggaggaatat  300
aataaagggt ggtgcacctg ccaactgcta tgctcaccaa cactttgtac acacccagtt  360
acacccccct gcctttatta tttccagtgc agtaataact tcaacaatta ttgaaatgaa  420
aatggaatta atggagttag tatcggatta gcgacacgct tgccgagctt ctagacggtg  480
cgattatttc agcgggaacg actttctgta ggtgaattta atagaggagt gttttaaatc  540
cactcgacgt tgtaatagct ggtttaattc gtttgtactg tcgagtagtt atccaaaatc  600
aattttggat atttaaaaga aaaaaaaaca gatccgaagt attggaccta ctggcaaata  660
ggaattttgc tatatatagg tgtgcgttca tttataatgg agtagcatgg agttttatta  720
atccagtaaa tgttttcatt gatttaatta atataacgaa tttcgcttga ggccatattt  780
gttaaacgct tttatctcta tcatcattca tcctaccagt aaagagcacc ggagatcgca  840
cttcatttaa atatatgtcc atgttggata aaccatagtt tattatagtg ttcttttata  900
tgttttgtgg ggaatttaga ttgtttaata tggcatacat atccatccat cattattata  960
ttctaacaca actggataag tgttctaaac tattgtagaa taactttgta gtatgatcga  1020
tcttgtggaa taaaaaaagt ctgacaataa cctttcataa aggaatatga atacccgtaa  1080
tcaacgcatc aaatcattca cggtgtacgc ctagcgaatt cgttggcgag tgctcgtgcg  1140
gccgtgggct cgctgtgatg catgcatggc tctctggcta cgtcgagata gcgattagta  1200
gcaaaattaa gcaagccact tattaattaa tctttggaga tatcatatga ttaaggcatt  1260
aattcgtacg tactcgtcgt cagcgtttc tgcaaagtcc actacagttt tttctttctt  1320
tgctgaaaat gctgatgtgt tggagatgga gtgacgtgca caacctgccg ccacgtggat  1380
ggttgctgga gcctacgtgt catcttaatt tgaacaaaaa aaaaagagga ataatacatc  1440
aatacatttt cgaatttcag ttctgccatt gaccagtaat acacatgtcg gcctcacatt  1500
ttaccctgat cttagtaacg ggtggtcgcc tggtcggtca ctgaaaaaag ttcaggaaat  1560
tatagtcaaa ctgaaacgaa catattcact ccttaaaaaa actaaatctt tttatatatt  1620
tgtgatattg taaaatagct acgggataat gatatagata tatatagtga taagggatag  1680
atggatcgag atatggagtt gtgctttctt taatttccac tacttgggct accatattat  1740
ggtagttggt atgaaaagat acacagcagt atagtgatgt gatcaatgac atgtatatct  1800
cacatgctcc catgttggag tcaaattttg ctagactaaa atccaattcc aagcagtccc  1860
tagccaagaa caaacaaaat tcagtgaggt cactgctgca ccaaggactg catgcatgca  1920
ggagaagggc attttctctt ttttcttttg gagactcgat tcaattcggt cggtcggtcg  1980
caatggtcag cttaattaaa                                              2000

SEQ ID NO: 45           moltype = DNA  length = 2000
FEATURE                 Location/Qualifiers
source                  1..2000
                        mol_type = genomic DNA
                        organism = Oryza sativa
SEQUENCE: 45
tgtgaaaggt ggcggcacca gcttagccgc agcttctctc gtcgtctccc tgaaacgaga  60
gggaggaagt tggtagcgtg atatatttag gcatgtcatc tcttgtataa gaagtcttat  120
ctgtgctaat tcacacggtt ctctaatctc tctccattct gtttttgtaa attggttcag  180
tagatagcgt agggttatgc ttatatatac tccgtgaagt atatatttaa aaattagtca  240
cacgtaaagt actatacatg ttttatcgtc taataacaat aaaaacacta atcataaaat  300
ttttttaaat aatacgaatg gttaaacgtt gaatatgaac cgtgcaaaac tatatttatt  360
ttgtaacaga gaaaatattt cacattaatt agattgttgt tttatggaag gttggagagc  420
tgcgccgccg ttgcgcagac ctaggaggct gcttataagt tataatcaat caattcacgg  480
atgccggctg ggacgcggcc catcgtccgg gaagacgaca actcaacgca aaaagccgat  540
atgcctccaa attgccattg ccacctctac ggctgtttat actgctccaa atcaaaagcg  600
tccatggaag aatctagtat ttcccgcaaa gacgatgatg atatgcagga ttggatatat  660
agggggttgt tgcatgattg ctagaactcc cgtttccgaa gttgttcgtc catttttaaa  720
gctgccaaat aggaatttat tttgttttca agtgtaatag agttctgtcc agatgagtga  780
attataattt ggttcacatt ttatttgcta agtttcagtt tgaacattct caaataactt  840
ttttcttcac tttttaaccg agtaacttag ttattttttc cgtttggacc acccaacaat  900
ttgttgctaa gtgcatctca cccgtcaaat aattcctttg aatccaaatt caattatatc  960
ccaaaaataa aaaacttctg aattccacat caattcaaac cccaaccatt ttaatttctc  1020
tccatatttt ccatttctct atttttacct ttctcttttt tccatctatt tattttttc  1080
cttttctatt tctttctttc tccttccttt ctctgtttcc ttcttcttct cctcggctag  1140
gcccgagcca gcccgtgccg cctcgcgcca accctgtgcc gccttacgcc gcgcttgcgt  1200
gcgctcgcgc ccacctcgtg cccaacccgc gcacgccaca cgcacacacg aggacgatcg  1260
acggacgaat gcaatcatat ccccttcctt actcagctag aaggctcaag aaccgcaact  1320
ttgatctctt ccaccctctc aaatccgccc caacccctgc tgactcaatc gccattaccg  1380
gaggaaaaat ccccgaaacc ctattaccgg cgccactaac agagctccaa aattcgtcgc  1440
ataattcgaa aatattctga aattgaaggt aaaaatggaa tctacatgcg aagtactccc  1500
tttcccctcc aatccgtcac tggaacgccg ccggcgccgc ctcccgctgc cactgccctg  1560
tttggccgcc gacagccgca cggcgcgccg ctgctccagg ccgccctagc ttcaaccacc  1620
gccacctttg gctccgcctc cctcctctta tgctcaccaa gcccgcctcc ctcgccggag  1680
atcgccggaa ccaccgccgc catggccgcc accgcctcct gcttctggcc gccgccgcca  1740
gcctcgccac cggcgcctat gccaccgccg accacggaaa cggagtccct acaccttggg  1800
gaccacaaaa ccggcggcat ccctcccaaa accggcctcc tccaccgccg gcgttcgtgg  1860
gattccggcc agttctgtgc agagcgagag aagaagagga aaaatagatt ttcctattga  1920
aagataaatc agaaaattcc tttttctttt cctatcaagt tgaccatccg tttgacctca  1980
aaatcaaaat ctgagaccta                                              2000
```

```
SEQ ID NO: 46          moltype = DNA  length = 786
FEATURE                Location/Qualifiers
source                 1..786
                       mol_type = genomic DNA
                       organism = Zea mays
SEQUENCE: 46
gacatggagg tggaaggcct gacgtagata gagaagatgc tcttagcttt cattgtcttt  60
cttttgtagt catctgattt acctctctcg tttatacaac tggtttttta aacactcctt  120
aacttttcaa attgtctctt tctttaccct agactagata attttaatgg tgattttgct  180
aatgtggcgc catgttagat agaggtaaaa tgaactagtt aaaagctcag agtgataaat  240
caggctctca aaaattcata aactgttttt taaatatcca aatattttta catggaaaat  300
aataaaattt agtttagtat taaaaaattc agttgaatat agttttgtct tcaaaaatta  360
tgaaactgat cttaattatt tttccttaaa accgtgctct atctttgatg tctagtttga  420
gacgattata taattttttt tgtgcttaac tacgacgagc tgaagtacgt agaaatacta  480
gtggagtcgt gccgcgtgtg cctgtagcca ctcgtacgct acagcccaag cgctagagcc  540
caagaggccg gaggtggaag gcgtcgcggc actatagcca ctcgccgcaa gagcccaaga  600
gaccggagct ggaaggatga gggtctgggt gttcacgaat tgcctggagg caggaggctc  660
gtcgtccgga gccacaggcg tggagacgtc cgggataagg tgagcagccg ctgcgatagg  720
ggcgcgtgtg aaccccgtcg cgccccacgg atggtataag aataaaggca ttccgcgtgc  780
aggatt                                                             786

SEQ ID NO: 47          moltype = DNA  length = 1160
FEATURE                Location/Qualifiers
source                 1..1160
                       mol_type = genomic DNA
                       organism = Zea mays
SEQUENCE: 47
atgtgctggt gccccataag gtaggcacct aggtctgtgt ttgaagcatc gacagatttg  60
taaacatgtt cctatgaacc tatttctgat tgataatttg tcaaaactca tcatttgtct  120
tcatccttgc ctgcttgcgt tcacgtgaca aagtacgtgt atgtcttcgg cctttgctgt  180
gtatgtttcg cattgcttag atgtggtgaa agaacatcag aagatgcatt gatggcgtgc  240
ttaaaccagt gatgtgctcc aggtgttcct gcagtctgca gagatattta ctcttgtagt  300
cttgttgaca gcacagttgt atgtgatttc ttggatgtaa tgtaaaccaa atgaaagata  360
ggaacagttc gtcctcttcc gtatacgaag gtcactgtat catttgtcgt ggcacaagat  420
gatctgcagg caggactgca acatggtttc ttggactgtc ctgaatgccc gttcttgttc  480
tttagttgag ccagagcagc agcctggtgt cggtgcctga gacctgacga agcacacggc  540
aaacaaacaa gtcgcagcag ctagcagggg cgttgccatc gccacaagcc cccaagagac  600
ccgccgagga aaagaaaaaa aaactacggc cgccgttgcc aagccgagcg tgcgaaccga  660
tccacggatg ggagatcaga gatcacccac cgcaggcggg cggcagtggc tggcgaggtg  720
cgtccacaga acctgctgca ggtccctgtc cgtcccggcg accccttttc taggcgagca  780
actccccatg gcagagctgc acgcagcagg gcccgtcgtt ggttgcagct ttaacccttt  840
ttgttttaac catacaatgc agagtcgcag aggtgaaaca ggacggaaat tacagaaaag  900
atggtggtgt gccagcagcc ccagcatgaa gaagatcagg acaaaagaaa agcttgtgat  960
tggtgacagc aacaggattg gattggagcc aagctaggca gtgagaggca ggcagcaaga  1020
cgcgtcagcc actgaaatcc agagggcaac ctcggcctca caactcatat ccccttgtgc  1080
tgttgcgcgc cgtggttagc caggtgtgct gcaggcctcc tccttgttta tatatgggag  1140
atgctctcac cctctaaggt                                              1160

SEQ ID NO: 48          moltype = DNA  length = 1532
FEATURE                Location/Qualifiers
source                 1..1532
                       mol_type = genomic DNA
                       organism = Oryza sativa
SEQUENCE: 48
tagtcctcta atatatgaaa ttttgatata ggtaaagaag ggtattgcaa ggataagaat  60
gtaaaaagaa ataagagtaa tccttaccga taatagtatt ccttctctac cgttaaaagt  120
taaacctgtg cgtgtagcat tttaatccag gatctatcga atccgtccct cgttggcgtg  180
ggcgacgaac acgtgcagaa gaagctttcc ccagaaagca cctcaccgcc tcgccgtctg  240
gcagactggc acgcggggcc ctaccctcgc tgcgcctggg cccgtccgcc ttctgcacac  300
tgtcacgccc ccacccgctc gccgcctcgc gcctctctct ccgcctccgc cgcggccgcc  360
cgacgtgata gcgacacgta ggactcgcca aacacaaaaa atccatcgcg atttttggaa  420
ttttgttaca aaccaaatcc cgcattagag atttaatttg atttaattta attacgtagg  480
agtaccagat aaggagatcg agttaaaaaa gctaacggcg cggcgtggtt atctccgaat  540
cggctgtggc tccccgcgtc ggcgtcggcg cggcggcggc gcgccggccg aaccctggcc  600
gtcggatcgg gcgtcgtcct gggccccacg cgccacgggc ggctgtcgtt tgctcctcgg  660
agcggggtgg gcccaccatg gccaccacca caggtcgcgg tcgcggctga cctggcggtg  720
gtcccgtgct cgcggtgttt tttttttttc actctctttc tctcggtgga cagtagcggg  780
ggccgcggcc cgcgggggca gagattgcaa aaacagcgga aacggaagat tgcaaaattg  840
caactgcttt cctgttttta attcgggatc aaaaagattc tttcgtcggg gtccccgtgc  900
cattgttgta ttgcgcgtag gtccttgctt gtaaaagata atctccttaa tttttttcttt  960
gtactactag tgtatatgca gtaagaatat accatgagta aaatgaacca caaaactaat  1020
tacgatatac cattctcatg tagacgttct cttttctttt gctagtcata cgtgcatata  1080
taaccaaaca aaaaaatgtt tgaagtactc ctatccaatt tattactcca gtagacaaca  1140
aaagaaaatg tttgaagtaa taactgatcc atggtacagt agggttgtcg tcaatcttgt  1200
gtttctttca ttccattgta cttacaatcg tactccagct agcacagcac aatgggctta  1260
agctttggac cccaaattct gatcttgtcg gggacccgta cgaaaatact cccgtagaga  1320
tgcagatacc gtcacaacct acaaccaacg aatgttaaga aaacaaaggg aaaaaaaaag  1380
aggcgaattc ggaggagaaa aaacggtggc taaaatatag tgcgggtgtg gggacgcgac  1440
```

```
gcgagcgacg aaagaggaga gaggatgggt tggcctgccc ccccctcccc tgtctataaa  1500
tgcagaggcg ccgagtgccc tagtcgccgc tc                                1532

SEQ ID NO: 49          moltype = DNA  length = 841
FEATURE                Location/Qualifiers
source                 1..841
                       mol_type = genomic DNA
                       organism = Oryza sativa
SEQUENCE: 49
tcgaggtcat tcatatgctt gagaagagag tcgggatagt ccaaaataaa acaaaggtaa  60
gattacctgg tcaaaagtga aaacatcagt taaaaggtgg tataaagtaa aatatcggta  120
ataaaaggtg gcccaaagtg aaatttactc ttttctacta ttataaaaat tgaggatgtt  180
tttgtcggta ctttgatacg tcatttttgt atgaattggt ttttaagttt attcgctttt  240
ggaaatgcat atctgtattt gagtcgggtt ttaagttcgt ttgcttttgt aaatacagag  300
ggatttgtat aagaaatatc tttagaaaaa cccatatgct aatttgacat aatttttgag  360
aaaaatatat attcaggcga attctcacaa tgaacaataa taagattaaa atagctttcc  420
cccgttgcag cgcatgggta ttttttctag taaaaataaa agataaactt agactcaaaa  480
catttacaaa aacaacccct aaagttccta aagcccaaag tgctatccac gatccatagc  540
aagcccagcc caacccaacc caacccaacc caccccagtc cagccaactg gacaatagtc  600
tccacacccc cccactatca ccgtgagttg tccgcacgca ccgcacgtct cgcagccaaa  660
aaaaaaaaga aagaaaaaaa agaaaaagaa aaaacagcag gtgggtccgg gtcgtggggg  720
ccggaaacgc gaggaggatc gcgagccagc gacgaggccg gccctccctc cgcttccaaa  780
gaaacgcccc ccatcgccac tatatacata cccccccctc tcctcccatc cccccaaccc  840
t                                                                  841

SEQ ID NO: 50          moltype = DNA  length = 1392
FEATURE                Location/Qualifiers
source                 1..1392
                       mol_type = genomic DNA
                       organism = Oryza sativa
SEQUENCE: 50
ctcgaggtca ttcatatgct tgagaagaga gtcgggatag tccaaaataa aacaaaggta  60
agattacctg gtcaaaagtg aaaacatcag ttaaaaggtg gtataagtaa aatatcggta  120
ataaaaggtg gcccaaagtg aaatttactc ttttctacta ttataaaaat tgaggatgtt  180
ttgtcggtac tttgatacgt catttttgta tgaattggtt tttaagttta ttcgcgattt  240
tggaaatgca tatctgtatt tgagtcgggt tttaagttcg tttgcttttg taaatacaga  300
gggatttgta taagaaatat ctttaaaaaa acccatatgc taatttgaca taatttttga  360
gaaaaatata tattcaggcg aattctcaca atgaacaata ataagattaa aatagcttgc  420
ccccgttgca gcgatgggta ttttttctag taaaataaaa gataaactta gactcaaaac  480
atttacaaaa acaaccccta aagtcctaaa gcccaaagtg ctatgcacga tccatagcaa  540
gcccagccca acccaaccca acccaaccca ccccagtgca gccaactggc aaatagtctc  600
cacaccccgg cactatcacc gtgagttgtc cgcaccaccg cacgtctcgc agccaaaaaa  660
aaaaaaagaa agaaaaaaaa gaaaaagaaa aaacagcagg tgggtccggg tcgtgggggc  720
cggaaaagcg aggaggatcg cgagcagcga cgaggccggc cctccctccg cttccaaaga  780
aacgcccccc atcgccacta tatacatacc ccccctctc ctcccatccc cccaacccta  840
ccaccaccac caccaccacc tcctcccccc tcgctgccgg acgacgagct cctcccccct  900
ccccctccgc cgccgccggt aaccaccccg cgtccctctc ctctttcttt ctccgttttt  960
tttttccgtc tcgtctcgat ctttggcctt ggtagtttgg gggcgagagg cggcttcgtc  1020
gcccagatcg gtgcgcggga ggggcgggat ctcgcggctg ggtctcggcg tgcggccgga  1080
tcctcgcggg gaatggggct ctcggatgta gatctgatcc gccgttgttg ggggagatga  1140
tggggcgttt aaaatttcgc catgctaaac aagatcagga agaggggaaa agggcactat  1200
ggtttatatt tttatatatt tctgctgctg ctcgtcaggc ttagatgtgc tagatctttc  1260
tttcttcttt ttgtgggtag aatttgaatc cctcagcatt gttcatcggt agtttttctt  1320
ttcatgattt gtgacaaatg cagcctcgtg cggagctttt ttgtaggtag aagatggctg  1380
acgccgagga ta                                                      1392

SEQ ID NO: 51          moltype = DNA  length = 743
FEATURE                Location/Qualifiers
source                 1..743
                       mol_type = genomic DNA
                       organism = Oryza sativa
SEQUENCE: 51
gaattcccgg acctccatgc ctacatcaac taatttgatt ccttgagttt acgtttagtg  60
atatgtctat ttttagagct tgttggggct tcggcctcag ctctagccag ccaaacatgt  120
tctaccaagt accctatgtt ggcatgatat agtgatgcat tataacaata aatgagcgag  180
ggattgctgg ctgaaaaagc tatactagct gcatttggtt atagttaacc gaactattaa  240
ttgcgtgtac aacaaaataa aaaaaatgca tgttgcacat tctttcatta acattatgtt  300
ttggtagtgt gaattagaaa tttgattgac agtagatcga caaacatagt ttcaatatgc  360
ttaagttagt tatgacttta acatatcagt ctccttgata ttttcgtttt agattcgtct  420
ctctactagt gtgtatgtcc accttccata gcagtgaagg gttccattcc atccctggta  480
aaaaaaaatc aaccactact atttatttcc taaaaagcaa aatgataaaa tatcattttt  540
ttaataaaaa taaaaaaatt ttggggtaca taattgatgt tgccccttgg gattaacctt  600
aaaaaagggc gaattttcta gggtttggcc aagttttgca atgcaccaaa ttattcccct  660
tgggccggcc gccaccccaa aaaaaacccc aacccccaac tttccattga aggccgggcc  720
cccttaaatc ctcatccccc caa                                          743

SEQ ID NO: 52          moltype = DNA  length = 144
FEATURE                Location/Qualifiers
source                 1..144
```

```
                        mol_type = genomic DNA
                        organism = Oryza sativa
SEQUENCE: 52
taaaaaaggg cgaattttct agggtttggc caagttttgc aatgcaccaa attattcccc  60
ttgggccggc cgccacccca aaaaaaaccc caaccccaa ctttccattg aaggccgggc  120
cccctaaat cctcatcccc ccaa                                         144

SEQ ID NO: 53           moltype = DNA  length = 612
FEATURE                 Location/Qualifiers
source                  1..612
                        mol_type = genomic DNA
                        organism = Cauliflower mosaic virus
SEQUENCE: 53
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga gg                                                     612

SEQ ID NO: 54           moltype = DNA  length = 837
FEATURE                 Location/Qualifiers
source                  1..837
                        mol_type = genomic DNA
                        organism = Coix lacryma-jobi
SEQUENCE: 54
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacat     837

SEQ ID NO: 55           moltype = DNA  length = 947
FEATURE                 Location/Qualifiers
source                  1..947
                        mol_type = genomic DNA
                        organism = Oryza sativa
SEQUENCE: 55
aatccgaaaa gtttctgcac cgttttcacg tcctaactaa caatataggg aacgtgtgct  60
aaatataaaa tgagacctta tatatgtagc gctgataact agaactatgt aagaaaaact  120
catccaccta ctttagtggc aatcgggcta aataaaaaag agtcgctaca ctagtttcgt  180
tttccttagt aattaagtgg gaaaatgaaa tcattattgc ttagaatata cgttcacatc  240
tctgtcatga agttaaatta ttcgaggtag ccataattgt catcaaactc ttcttgaata  300
aaaaaatctt tctagctgaa ctcaatgggt aaagagagat attttttttt aaaaaaaaat  360
agaatgaaga tattctgaac gtatcggcaa agatttaaac atataattat ataattttat  420
agtttgtgca ttcgttatat cgcacgtcat taaggacatg tcttactcca tctcaatttt  480
tatttagtaa ttaaagacaa ttgacttatt tttattattt atctttttc gattagatgc  540
aaggtactta cgcacacact ttgtgctcat gtgcatgtgt gagtgcacct cctcaataca  600
cgttcaacta gcgacacatc tccaatatca ctcgcctatt taatacattt aggtagcaat  660
atctgaattc aagcactcca ccatcaccag accactttta ataatatcta aaatacaaaa  720
aataatttta cagaatagca tgaaaagtat gaaacgaact atttaggttt ttcacataca  780
aaaaaaaaaa gaattttgct cgtgcgcgag cgccaatctc ccatattggg cacacaggca  840
acaacagagt ggctgcccac agaacaaccc acaaaaaacg atgatctaac ggaggacagc  900
aagtccgcaa caacctttta acagcaggct ttgcggccag gagagag                947

SEQ ID NO: 56           moltype = DNA  length = 721
FEATURE                 Location/Qualifiers
source                  1..721
                        mol_type = genomic DNA
                        organism = Mirabilis mosaic virus
SEQUENCE: 56
tggagattca gaaaaatctc catcaacaaa taatccaagt aaggattaat ggattgatca  60
acatccttac cgctatgggt aagattgatg aaaagtcaaa aacaaaaatc aattatgcac  120
accagcatgt gttgatcacc agctattgtg ggacaccaat ttcgtccaca gacatcaaca  180
tcttatcgtc ctttgaagat aagataataa tgttgaagat aagagtggga gccaccacta  240
```

```
aaacattgct ttgtcaaaag ctaaaaaaga tgatgcccga cagccacttg tgtgaagcat  300
gtgaagccgg tccctccact aagaaaatta gtgaagcatc ttccagtggt ccctccactc  360
acagctcaat cagtgagcaa caggacgaag gaaatgacgt aagccatgac gtctaatccc  420
acaagaattt ccttatataa ggaacacaaa tcagaaggaa gagatcaatc gaaatcaaaa  480
tcggaatcga aatcaaaatc ggaatcgaaa tctctcatct ctctctacct tctctctaaa  540
aaacacttag atgtgtgagt aatcacccac ttggggttgt aatatgtagt agtaaataag  600
ggaaccttag ggtataccat tgttgtaata ttattttcag tatcaataaa ataatctttc  660
agtttatctt atattcattt gtgtgacacc gtattcccat aaaaccgatc ctaatctctc  720
c                                                                    721

SEQ ID NO: 57          moltype = DNA  length = 352
FEATURE                Location/Qualifiers
source                 1..352
                       mol_type = genomic DNA
                       organism = Peanut chlorotic streak virus
SEQUENCE: 57
acagagggat ttctctgaag atcatgtttg ccagctatgc gaacaatcat cgggagatct  60
tgagccaatc aaagaggagt gatgtagacc taaagcaata atggagccat gacgtaaggg  120
cttacgccat tacgaaataa ttaaaggctg atgtgacctg tcggtctctc agaaccttta  180
ctttttatat ttggcgtgta tttttaaatt tccacggcaa tgacgatgtg acctgtgcat  240
ccgctttgcc tataaataag ttttagtttg tattgatcga cacgatcgag aagacacggc  300
catttggacg atcatttgag agtctaaaag aacgagtctt gtaatatgtt tt          352

SEQ ID NO: 58          moltype = DNA  length = 7139
FEATURE                Location/Qualifiers
source                 1..7139
                       mol_type = genomic DNA
                       organism = Zea mays
SEQUENCE: 58
gctctgccac tctgctgagg tgggggggaga ggagctcccc ctccctcctc tcccctcctc  60
gccatgtcta gcagcgaccc ggaggagatc agggcgcgcg tcgtcgttct cggttcgccc  120
catgccgacg gcggcgacga gtgggcccgg cccgagctcg aggccttcca tctgccgtct  180
cccgcccacc agcctcctgg cttcctagcc gggcaaccgg aagcagcaga gcaacccacg  240
ctccctgctc ctgctggccg cagcagcagc agcagcaaca cgcctactac atctgccggt  300
ggcggcgctg ctcctcctcc tccttcttcg cctccccctc cgccggcttc tctggagacc  360
gagcagccgc ccaatgccag gccagcctcc gccggcgcca atgacagcaa gaagcccacc  420
ccgcccgccg ccctgcgcga cctcttccgc ttcgccgacg gcctcgactg cgcgctcatg  480
ctcatcggca ccctcggcgc gctcgtccac gggtgctcgc tccccgtctt cctccgcttc  540
ttcgccgacc tcgtcgactc cttcggctcc cacgccgacg acccggacac catggtccgc  600
ctcgtcgtca agtacgcctt ctacttcctc gtcgtcggag cggcaatctg ggcatcctcg  660
tgggcaggta cgctatccct cctcctcctg ccgccccagc ttgtgtgcgt cgcgaattgg  720
cggtcaattt ggattggatg acaaatcacg tcggtcagcc aatcgccgtg gctacaaacg  780
agatgttcaa atcgttcgcc ccgctcgcaa gagatctctt gctggatgtg gaccggcgag  840
cggcagtcga cgcggatgcg gattcggtac ctggacgcgg cgctgcggca ggacgtgtcc  900
ttcttcgaca ccgacgtgcg ggcctcggac gtgatctacg ccatcaacgc ggacgccgtg  960
gtggtgcagg acgccatcag ccagaaactg ggcaacctca tccactacat ggccaccttc  1020
gtggccggct tcgtcgtggg gttcacggcc gcgtggcagc tggcgctggt cacgctggcc  1080
gtggtgccgc tcatcgccgt catcggcggg ctgagcgccg ccgcgctcgc caagctctcg  1140
tcccgcagcc aggacgcgct ctcgggcgcc agcggcatcg cggagcaggc gctcgcgcag  1200
atacggatcg tgcaggcgtt cgttggcgag gagcgcgaga tgcgggccta ctcggcggcg  1260
ctggccgtgg cgcagaggat cggctaccgc agcggcttcg ccaaggggct cggcctcggc  1320
ggcacctact tcaccgtctt ctgctgctac gggctcctgc tctggtacgg cggccacctc  1380
gtgcgcgccc agcacaccaa cggcgggctc gccatcgcca ccatgttctc cgtcatgatc  1440
ggcggactgt aaggcccacc acaccacgca ctctctcctt ctgctgtcct cggccgcccc  1500
cgtcgtcatt gctgctgacg gtatctgtgg atcgcgtgca ggcctcggca gtcggcgccg  1560
agcatggccg cgttcgccaa ggcgcgtgtg gcggctgcca agatcttccg catcatcgac  1620
cacaggccgg gcatctcctc gcgcgacggc gcggagccag agtcggtgac ggggcgggtg  1680
gagatgcggg gcgtggactt cgcgtacccg tcgcggccgg acgtccccat cctgcgcggc  1740
ttctcgctga gcgtgcccgc cgggaagacc atcgcgctgg tgggcagctc cggctccggg  1800
aagagcacgg tggtgtcgct catcgagaga ttctacgacc ccagcgcagg tatacctagt  1860
actgttacta cttttagcgc attaatctga ggatgtccag ttcgcttgct tgccaatcgc  1920
cattgccatc gcaacaacaa tacttcgcca actgccattg ctgggtagat tagtacagta  1980
gcagttagaa gaagcctcca ctgtacattg cattgccaaa caaaagtgaa ttgtgcagta  2040
actctgtacc accacattga catggaaatg aagtgaatgc ttggagcatg cagagctggc  2100
cggcctcatg ggctgctgct acctgctagc tagccaacca gaaccagcca tcctctttct  2160
tgcttttctt tttactttct ttggtcgtgg ctgtttgtgg tcatacatac attcacgcag  2220
agcagaagag ctagctaagc taggtgggtg tgcctgcaac gcgggacaaa gaaaactatt  2280
tgttgcctgg caagatgcta ctgttgccta gcacatgcct gccattgacc gactgctcag  2340
tgagaagtgg ttcagttgtg ctgttgacag tatagataga tatatatagt agccctgtag  2400
attttttttt cagacaaaaa aagaagaaga acgagatgaa gtctgcaatt cggttttggc  2460
agggcaaatc ctgctggacg ggcacgacct caggtcgctg gagctgcggt ggctgcggcg  2520
gcagatcggg ctggtgagcc aggagccggc gctgttcgcg acgagcatca gggagaacct  2580
gctgctgggg cgggacagcc agagcgcgac gctggcggag atggaggagg cggccagggt  2640
ggccaacgcc cactccttca tcatcaaact ccccgacggc tacgacacgc aggtccgtcc  2700
cgtatagcta gctcactagc tgcactgcca cttctctcgc ttgctccccc accgttgctg  2760
cctgttgctc tccaatccac ttgtcggtgt ctggaccaca cgtgctgctt gcctagctgc  2820
tccacatctg ctttccctgt ccaaccttat gcaactcact ctaatactat atcaaataca  2880
tttctagagt ttaaagctta tcttagaata aatgcatctt tagctacgag acaacctaac  2940
ttcagttgtt gttgttgttt tttttacttt ctctcttctc acaaatacta tgattacgtc  3000
```

```
tttacagcga tctttttttat tccaaaccta aaaatgcatg cactcactct aaaagcgcaa  3060
agggagcatc tttttttccc ccatcatctg cacgcagcct tttcttttcc tcatgtcacg  3120
aagggactga aggtgtgtat gcagcgtcaa gtcatccatc cgttccactc cactcactca  3180
tgcgtcgcgc actctgcgct cgtgcctgcc cggggctaaa gctttagtag ctagcctcag  3240
atcagatact gttcgtgttt gttaggccgc ggcagctgca catgagctca tgacagccgg  3300
cagcaccacc accaacgcca tggaagaggg gtcggggtcc atcacataga cataatgcct  3360
gttgtagact aggacgggag ggcaattgtt aggcgcctgt tgccatcgca tttgctgctg  3420
tgggttgcca acaagtaaca tgccaggatg ctttgctatc acgcacagga caggagaggt  3480
cctttttctc gacacaagct ctacagcctc tactaaacta gcacttgctg atgagtgcag  3540
aggatgaatg gacgatgaac atctagagtg agagagaaaa aaatgttaat aataataaaa  3600
agtagtagca ggattaagaa tcaacctggg gtacgtagga agaggtacaa tccctaggaa  3660
tctagagtat gagaagtatg ggaggagttg ggggagtgaa acggaacaaa ttccgagttg  3720
gtattttgtc gggaatgtca agttgatttt tgatcctagt gcaagcaaga attatcaatc  3780
actcagactc agcctgtctg tgtctgtcca ccccagctct tgctactcta cttactactg  3840
tgctactagt gggtagggta ggtatcttac ataaactgtt attataaact gtcatctgag  3900
aaagagagcc agtcaaaccc atgctgctgc ttattttaat cactgtcaaa tggcaggcag  3960
gcaggcagtc tggttagtta ataacatctg ggaagggttt aatcaaacca aatcaaatca  4020
gacgaaatct agaggccaca tgggatgggg ccatatgtac tgtactagca taactagcgg  4080
ctagatttta ttagaacacg gactcacact cccataacta taactgactt gatcatgatt  4140
ccttgccaag caatgctcgc atgcccatgc atgcatcatc cctggtcaaa ctcaaacact  4200
ctccaccgtc agggaataag acttattatt ttattaacaa ttcaattttt atttattaat  4260
tacgtctgga cgaggagtac tggtttattt gatgagagac atggcagtcc aagtcaaact  4320
cgtttgtctg accatggcgg tgatggccgg tgcaggttgg ggagcgcggc ctgcagctct  4380
ccggtgggca gaagcagcgc atcgccatcg cccgcgccat gctcaagaac cccgccatcc  4440
tgctgctgga cgaggccacc agcgcgctgg actccgagtc tgagaagctc gtgcaggagg  4500
cgctggaccg cttcatgatg gggcgcacca cccttggtga tcgcgcaaca ggctgtccac  4560
catccgcaaa ggccgacgtg gtggccgtgc tgcagggcgg cgccgtctcc gagatgagcg  4620
cgcacgacga gctgatggcc aagggcgaga acggcaccta cgccaagctc atccgcatgc  4680
aggagcaggc gcacgaggcg gcgctcgtca acgcccgccg cagcagcgcc aggccctcca  4740
gcgcccgcaa ctccgtcagc tcgcccatca tgacgcgcaa ctcctcctac ggccgctccc  4800
cctactcccg ccgcctctcc gacttctcca cctccgactt caccctctcc atccacgacc  4860
cgcaccacca ccaccggacc atggcggaca agcagctggc gttccgcgcc ggcgccagct  4920
ccttcctgcg cctcgccagg atgaactcgc ccgagtgggc ctacgcgctc gccggctcca  4980
tcggctccat ggtctgcggc tccttcagcg ccatcttcgc ctacatcctc agcgccgtgc  5040
tcagcgtcta ctacgcgccg gacccgcggt acatgaagcg cgagatcgca aaatactgtt  5100
acctgctcat cggcatgtcc tccgcggcgc tgctgttcaa cacggtgcag cacgtgttct  5160
gggacacggt gggcgagaac ttgaccaagc gggtgcgcga gaagatgttc gccgccgtgt  5220
tccgcaacga gatcgcctgg ttcgacgcgg acgagaacgc cagcgcgcgc gtgaccgcca  5280
ggctagcgct ggacgcccag aacgtgcgct ccgccatcgg ggaccgcatc tccgtcatcg  5340
tccagaactc ggcgctgatg ctggtggcct gcaccgcggg gttcgtcctc cagtggcgcc  5400
tcgcgctcgt gctcctcgcc gtgttcccgc tcgtcgtggg cgccaccgtg ctgcagaaga  5460
tgttcatgaa gggcttctcg ggggacctgg aggccgcgca cgccagggcc acgcagatcg  5520
cgggcgaggc cgtggccaac ctgcgcaccg tggccgcgtt caacgcggag cgcaagatca  5580
cggggctgtt cgaggccaac ctgcgcggcc cgctccggcg ctgcttctgg aaggggcaga  5640
tcgccggcag cggctacggc gtggcgcagt tcctgctgta cgcgtcctac gcgctggggc  5700
tgtggtacgc ggcgtggctg gtgaagcacg gcgtgtccga cttctcgcgc accatccgcg  5760
tgttcatggt gctgatggtg tccgcgaacg gcgccgccga gacgctgacg ctggcgccgg  5820
acttcatcaa aggcgggcgc gcgatgcggt cggtgttcga gacaatcgac cgcaagacgg  5880
aggtggagcc ccacgacgtg gacgcggcgc cggtgccgga cggcccaggg gcgaaggtgg  5940
aacttaagca cgtggacttt ttgtacccgt cgcggccgga catccaagtg ttccgcgacc  6000
tgagcctccg tgcgcgcgcc ggaaaaacgt tggcgctggt ggggccgagc gggtccggca  6060
agagctcggt cctggctctg gtgcagcggt tctacaagcc cacgtccggg cgcgtgctct  6120
tggacggcaa ggacgtgcgc aagtacaacc tgcgggcgct gcggcgcgtg gtggcggtgg  6180
taccgcagga gccgttcctg ttcgcggcga gcatccacga gaacatcgcg tacgggcgcg  6240
agggcgcgac ggaggcggag gtggtggagg cggcggcgca ggcgaacgcg caccggttca  6300
tcgcggcgct gccggagggg taccggacgc aggtgggcga gcgcggggtg cagctgtcgg  6360
gggggcagcg gcagcggatc gcgatcgcgc gcgcgctggt gaagcaggcg gccatcgtgc  6420
tgctggacga ggcgaccagc gcgctggacg ccgagtcgga gcggtgcgtg caggaggcgc  6480
tggagcgcgc ggggtccggg cgcaccacca tcgtggtggc gcaccggctg gccacggtgc  6540
gcggcgcgca caccatcgcg gtcatcgacg acggcaaggt ggcggagcag gggtcgcact  6600
cgcacctgct caagcaccat cccgacgggt gctacgcgcg gatgctgcag cttgcagcgg  6660
ctgacgggcg cggcggccgg gcccgggccg tcgtcctcgt gcaacggggc cgcgtaggac  6720
ggaatggatg gatggatggg tttggttcct cgagagattg atgggtgagg aagctgaagc  6780
tccggatcaa atggtggtac tccatgatcg caacaatgag gggaaaaaag gaaaggagaa  6840
aatacggtgg ttcatatgat tgtacaattt gacgatctgt ttgagtcggg gttttaggat  6900
gatgtaaacc ttcactcgcc ttttttttac tcttgtttct catccgcatc agtatcatct  6960
atctacatac agtgtcagag atgggaactg atcccgcatc atcatctacc tcccaaggca  7020
ccccagattg tattaatgta cttagttagc ctgttttata tatacttata agtaccaaat  7080
agcagaattt tactccttat ctgcagtagc acgaaagaaa aaaaaaaaaa gctaaacct   7139
```

```
SEQ ID NO: 59          moltype = DNA  length = 143
FEATURE                Location/Qualifiers
source                 1..143
                       mol_type = genomic DNA
                       organism = Zea mays
SEQUENCE: 59
ttgcctagca catgcctgcc attgaccgac tgctcagtga gaagtggttc agttgtgctg  60
ttgacagtat atatagatat atatagtagc cctgtagatt ttttttcag acaaaaaaag  120
aagaagaacg agatgaagtc tgc                                         143
```

```
SEQ ID NO: 60          moltype = DNA  length = 143
FEATURE                Location/Qualifiers
source                 1..143
                       mol_type = genomic DNA
                       organism = Zea mays
SEQUENCE: 60
ctagcacatg cctgccattg accgactgct cagtgagaag tggttcagtt gtgctgttga  60
cagtatagat atatatatat agtagccctg tagatttttt tttcagacaa aaaaagaaga  120
agaacgagat gaagtctgca att                                          143

SEQ ID NO: 61          moltype = DNA  length = 143
FEATURE                Location/Qualifiers
source                 1..143
                       mol_type = genomic DNA
                       organism = Zea mays
SEQUENCE: 61
acatgcctgc cattgaccga ctgctcagtg agaagtggtt cagttgtgct gttgacagta  60
tagatagata tgtatagtag ccctgtagat tttttttca gacaaaaaaa gaagaagaac  120
gagatgaagt ctgcaattcg gtt                                          143

SEQ ID NO: 62          moltype = DNA  length = 142
FEATURE                Location/Qualifiers
source                 1..142
                       mol_type = genomic DNA
                       organism = Zea mays
SEQUENCE: 62
catgcctgcc attgaccgac tgctcagtga gaagtggttc agttgtgctg ttgacagtat  60
agatagatat agtagccctg tagatttttt tttcagacaa aaaaagaaga agaacgagat  120
gaagtctgca attcggtttt gg                                           142

SEQ ID NO: 63          moltype = DNA  length = 140
FEATURE                Location/Qualifiers
source                 1..140
                       mol_type = genomic DNA
                       organism = Zea mays
SEQUENCE: 63
gctgttgaca gtatagatag atatatatag tagccctgta gatttttttt tcagacaaaa  60
aaagaagaac gagatgaagt ctgcaattcg gttttggcag ggcaaatcct gctggacggg  120
cacgacctca ggtcgctgga                                              140

SEQ ID NO: 64          moltype = DNA  length = 141
FEATURE                Location/Qualifiers
source                 1..141
                       mol_type = genomic DNA
                       organism = Zea mays
SEQUENCE: 64
tgacagtata gatagatata tatagtagcc ctgtagattt tttttcaga caaaaaaaga  60
agaagaacgg gatgaagtct gcaattcggt tttggcaggg caaatcctgc tggacgggca  120
cgacctcagg tcgctggagc t                                            141

SEQ ID NO: 65          moltype = DNA  length = 141
FEATURE                Location/Qualifiers
source                 1..141
                       mol_type = genomic DNA
                       organism = Zea mays
SEQUENCE: 65
tgacagtata gatagatata tatagtagcc ctgtagattt tttttcaga caaaaaaaga  60
agaagaacgg gatgaagtct gcaattcggt tttggcaggg caaatcctgc tggacgggca  120
cgacctcagg tcgctggagc t                                            141

SEQ ID NO: 66          moltype = DNA  length = 144
FEATURE                Location/Qualifiers
source                 1..144
                       mol_type = genomic DNA
                       organism = Zea mays
SEQUENCE: 66
aggcggccag ggtggccaac gcccactcct tcatcatcaa actccccgac ggctacgaca  60
cgcaggtccg tgtccgtccc gtatagctag ctcactagct gcactgccac ttctctcgct  120
tgctccccca ccgttgctgc ctgt                                         144

SEQ ID NO: 67          moltype = DNA  length = 136
FEATURE                Location/Qualifiers
source                 1..136
                       mol_type = genomic DNA
                       organism = Zea mays
SEQUENCE: 67
caacgcccac tccttcatca tcaaactccc cgacggctac gacacgcagg tccgtcccgt  60
atagcggtag ctcactagct gcactgccac ttctctcgct tgctccccca ccgttgctgc  120
```

```
ctgttgctct ccaatc                                                   136

SEQ ID NO: 68          moltype = DNA  length = 136
FEATURE                Location/Qualifiers
source                 1..136
                       mol_type = genomic DNA
                       organism = Zea mays
SEQUENCE: 68
gcccactcct tcatcatcaa actccccgac ggctacgaca cgcaggtccg tcccgtatag  60
ctatagctca ctagctgcac tgccacttct ctcgcttgct cccccaccgt tgctgcctgt  120
tgctctccaa tccact                                                   136

SEQ ID NO: 69          moltype = DNA  length = 133
FEATURE                Location/Qualifiers
source                 1..133
                       mol_type = genomic DNA
                       organism = Zea mays
SEQUENCE: 69
ctccttcatc atcaaactcc ccgacggcta cgacacgcag gtccgtcccg tatagctagc  60
taactagctg cactgccact tctctcgctt gctcccccac cgttgctgcc tgttgctctc  120
caatccactt gtc                                                      133

SEQ ID NO: 70          moltype = DNA  length = 141
FEATURE                Location/Qualifiers
source                 1..141
                       mol_type = genomic DNA
                       organism = Zea mays
SEQUENCE: 70
cacacgcaca cacacagatc gcctgacaag ccagccattg cttcagatca aagaaactgc  60
gtaataattt ctttctttct ttctttcttt ctttccagag cacaagggag gggggttata  120
atggctagta cctgactgac t                                             141

SEQ ID NO: 71          moltype = DNA  length = 143
FEATURE                Location/Qualifiers
source                 1..143
                       mol_type = genomic DNA
                       organism = Zea mays
SEQUENCE: 71
agccagccat tgcttcagat caaagaaact gcgtaataat tcctttcttt ctttctttct  60
ttctttccag atcacaaggg agggggggtta taatggctag tacctgactg actgtacgag  120
ccgagattaa cggcagtcac ctc                                           143

SEQ ID NO: 72          moltype = DNA  length = 143
FEATURE                Location/Qualifiers
source                 1..143
                       mol_type = genomic DNA
                       organism = Zea mays
SEQUENCE: 72
atcgccctgc tggccatttg gcaccaccta gtcgtacatg tgttcagtca tttccgtcca  60
ttactactac ggccgtgctc acccgtgccg acgcgccgtg catggtcccc gtcccggctg  120
gaacgcgtcc tcggaagaga gag                                           143

SEQ ID NO: 73          moltype = DNA  length = 143
FEATURE                Location/Qualifiers
source                 1..143
                       mol_type = genomic DNA
                       organism = Zea mays
SEQUENCE: 73
ccattactac tacgaccgtg ctcacccgtg ccgacgcgcc gtgcatggtc cccgtcccgg  60
ctggaacgcg tgctcggaag agagagatag agcacagcag acagggagac agggatggaa  120
ggatggcgtt cgcccggtac agg                                           143

SEQ ID NO: 74          moltype = DNA  length = 143
FEATURE                Location/Qualifiers
source                 1..143
                       mol_type = genomic DNA
                       organism = Zea mays
SEQUENCE: 74
cattactact acgaccgtgc tcacccgtgc cgacgcgccg tgcatggtcc ccgtcccggc  60
tggaacgcgt catcggaaga gagagataga gcacagcaga cagggagaca gggatggaag  120
gatggcgttc gcccggtaca ggt                                           143

SEQ ID NO: 75          moltype = DNA  length = 143
FEATURE                Location/Qualifiers
source                 1..143
                       mol_type = genomic DNA
                       organism = Zea mays
SEQUENCE: 75
attactacta cgaccgtgct cacccgtgcc gacgcgccgt gcatggtccc cgtcccggct  60
```

```
ggaacgcgtc cccggaagag agagatagag cacagcagac agggagacag ggatggaagg  120
atggcgttcg cccggtacag gtt                                          143

SEQ ID NO: 76          moltype = DNA  length = 143
FEATURE                Location/Qualifiers
source                 1..143
                       mol_type = genomic DNA
                       organism = Zea mays
SEQUENCE: 76
ttactactac gaccgtgctc acccgtgccg acgcgccgtg catggtcccc gtcccggctg  60
gaacgcgtcc tgggaagaga gagatagagc acagcagaca gggagacagg gatggaagga  120
tggcgttcgc ccggtacagg ttg                                          143

SEQ ID NO: 77          moltype = DNA  length = 143
FEATURE                Location/Qualifiers
source                 1..143
                       mol_type = genomic DNA
                       organism = Zea mays
SEQUENCE: 77
tactactacg accgtgctca cccgtgccga cgcgccgtgc atggtccccg tcccggctgg  60
aacgcgtcct ccgaagagag agatagagca cagcagacag ggagacaggg atggaaggat  120
ggcgttcgcc cggtacaggt tgc                                          143

SEQ ID NO: 78          moltype = DNA  length = 143
FEATURE                Location/Qualifiers
source                 1..143
                       mol_type = genomic DNA
                       organism = Zea mays
SEQUENCE: 78
ctactacgac cgtgctcacc cgtgccgacg cgccgtgcat ggtccccgtc ccggctggaa  60
cgcgtcctcg gtagagagag atagagcaca gcagacaggg agacagggat ggaaggatgg  120
cgttcgcccg gtacaggttg cta                                          143

SEQ ID NO: 79          moltype = DNA  length = 143
FEATURE                Location/Qualifiers
source                 1..143
                       mol_type = genomic DNA
                       organism = Zea mays
SEQUENCE: 79
tactacgacc gtgctcaccc gtgccgacgc gccgtgcatg gtccccgtcc cggctggaac  60
gcgtcctcgg acgagagaga tagagcacag cagacaggga gacagggatg gaaggatggc  120
gttcgcccgg tacaggttgc tag                                          143

SEQ ID NO: 80          moltype = DNA  length = 146
FEATURE                Location/Qualifiers
source                 1..146
                       mol_type = genomic DNA
                       organism = Zea mays
SEQUENCE: 80
actacgaccg tgctcacccg tgccgacgcg ccgtgcatgg tccccgtccc ggctggaacg  60
cgtcctcgga actcggagag agatagagca cagcagacag ggagacaggg atggaaggat  120
ggcgttcgcc cggtacaggt tgctag                                       146

SEQ ID NO: 81          moltype = DNA  length = 143
FEATURE                Location/Qualifiers
source                 1..143
                       mol_type = genomic DNA
                       organism = Zea mays
SEQUENCE: 81
caggaggcgc tggaccgctt catgatcggg cgcaccaccc tggtgatcgc gcacaggctg  60
tccaccatcc gcaaggccga cgtggtggcc gtgctgcagg gcggcgccgt ctccgagatg  120
ggcgcgcacg acgagctgat ggc                                          143

SEQ ID NO: 82          moltype = DNA  length = 143
FEATURE                Location/Qualifiers
source                 1..143
                       mol_type = genomic DNA
                       organism = Zea mays
SEQUENCE: 82
tccatcggct ccatggtctg cggctccttc agcgccatct tcgcctacat cctcagcgcc  60
gtgctcagcg tctactacgc gccggacccg cggtacatga agcgcgagat cgcaaaatac  120
tgctacctgc tcatcggcat gtc                                          143

SEQ ID NO: 83          moltype = DNA  length = 143
FEATURE                Location/Qualifiers
source                 1..143
                       mol_type = genomic DNA
                       organism = Zea mays
SEQUENCE: 83
```

```
gcctacatcc tcagcgccgt gctcagcgtc tactacgcgc cggacccgcg gtacatgaag  60
cgcgagatcg caaaatactg ctacctgctc atcggcatgt cctccgcggc gctgctgttc  120
aacacggtgc agcacgtgtt ctg                                          143

SEQ ID NO: 84          moltype = DNA  length = 143
FEATURE                Location/Qualifiers
source                 1..143
                       mol_type = genomic DNA
                       organism = Zea mays
SEQUENCE: 84
ctggttcgac gcggacgaga acgccagcgc gcgcgtggcc gccaggctag cgctggacgc  60
ccagaacgtg cgctccgcca tcggggaccg catctccgtc atcgtccaga actcggcgct  120
gatgctggtg gcctgcaccg cgg                                          143

SEQ ID NO: 85          moltype = DNA  length = 143
FEATURE                Location/Qualifiers
source                 1..143
                       mol_type = genomic DNA
                       organism = Zea mays
SEQUENCE: 85
cagaacgtgc gctccgccat cggggaccgc atctccgtca tcgtccagaa ctcggcgctg  60
atgctggtgg cctgcaccgc ggggttcgtc ctccagtggc gcctcgcgct cgtgctcctc  120
gccgtgttcc cgctcgtcgt ggg                                          143

SEQ ID NO: 86          moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 86
ttgcctagca catgcctgcc attgaccgac tgctcagtga gaagtggttc agttgtgctg  60
ttgacagtat anatagatat atatagtagc cctgtagatt ttttttcag acaaaaaaag  120
aagaagaacg agatgaagtc tgc                                          143

SEQ ID NO: 87          moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 87
ctagcacatg cctgccattg accgactgct cagtgagaag tggttcagtt gtgctgttga  60
cagtatagat anatatatat agtagccctg tagatttttt tttcagacaa aaaaagaaga  120
agaacgagat gaagtctgca att                                          143

SEQ ID NO: 88          moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 88
acatgcctgc cattgaccga ctgctcagtg agaagtggtt cagttgtgct gttgacagta  60
tagatagata tntatagtag ccctgtagat tttttttca gacaaaaaaa gaagaagaac  120
gagatgaagt ctgcaattcg gtt                                          143

SEQ ID NO: 89          moltype = DNA  length = 146
FEATURE                Location/Qualifiers
variation              72..75
                       note = a, c, t, g, or absent
source                 1..146
                       mol_type = genomic DNA
                       note = See specification as filed for detailed description
                        of, substitutions and preferred embodiments
                       organism = Zea mays
SEQUENCE: 89
catgcctgcc attgaccgac tgctcagtga gaagtggttc agttgtgctg ttgacagtat  60
agatagatat annnngtagc cctgtagatt ttttttcag acaaaaaaag aagaagaacg  120
agatgaagtc tgcaattcgg ttttgg                                       146
```

```
SEQ ID NO: 90          moltype = DNA  length = 143
FEATURE                Location/Qualifiers
variation              70..72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 90
gctgttgaca gtatagatag atatatatag tagccctgta gatttttttt tcagacaaaa  60
aaagaagaan nncgagatga agtctgcaat tcggttttgg cagggcaaat cctgctggac  120
gggcacgacc tcaggtcgct gga                                          143

SEQ ID NO: 91          moltype = DNA  length = 141
FEATURE                Location/Qualifiers
variation              70
                       note = a, c, t, g, or absent
source                 1..141
                       mol_type = genomic DNA
                       note = See specification as filed for detailed description
                        of, substitutions and preferred embodiments
                       organism = Zea mays
SEQUENCE: 91
tgacagtata gatagatata tatagtagcc ctgtagattt ttttttcaga caaaaaaaga  60
agaagaacgn gatgaagtct gcaattcggt tttggcaggg caaatcctgc tggacgggca  120
cgacctcagg tcgctggagc t                                            141

SEQ ID NO: 92          moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 92
ttttttttc agacaaaaaa agaagaagaa cgagatgaag tctgcaattc ggttttggca  60
gggcaaatcc tnctggacgg gcacgacctc aggtcgctgg agctgcggtg gctgcggcgg  120
cagatcgggc tggtgagcca gga                                          143

SEQ ID NO: 93          moltype = DNA  length = 144
FEATURE                Location/Qualifiers
variation              72..77
                       note = a, c, t, g, or absent
source                 1..144
                       mol_type = genomic DNA
                       note = See specification as filed for detailed description
                        of, substitutions and preferred embodiments
                       organism = Zea mays
SEQUENCE: 93
aggcggccag ggtggccaac gcccactcct tcatcatcaa actccccgac ggctacgaca  60
cgcaggtccg tnnnnnnccc gtatagctag ctcactagct gcactgccac ttctctcgct  120
tgctccccca ccgttgctgc ctgt                                         144

SEQ ID NO: 94          moltype = DNA  length = 136
FEATURE                Location/Qualifiers
variation              66..67
                       note = a, c, t, g, or absent
source                 1..136
                       mol_type = genomic DNA
                       note = See specification as filed for detailed description
                        of, substitutions and preferred embodiments
                       organism = Zea mays
SEQUENCE: 94
caacgcccac tccttcatca tcaaactccc cgacggctac gacacgcagg tccgtcccgt  60
atagcnntag ctcactagct gcactgccac ttctctcgct tgctccccca ccgttgctgc  120
ctgttgctct ccaatc                                                  136

SEQ ID NO: 95          moltype = DNA  length = 136
FEATURE                Location/Qualifiers
variation              64..65
                       note = a, c, t, g, or absent
source                 1..136
                       mol_type = genomic DNA
                       note = See specification as filed for detailed description
                        of, substitutions and preferred embodiments
```

```
                       organism = Zea mays
SEQUENCE: 95
gcccactcct tcatcatcaa actccccgac ggctacgaca cgcaggtccg tcccgtatag  60
ctanngctca ctagctgcac tgccacttct ctcgcttgct cccccaccgt tgctgcctgt  120
tgctctccaa tccact                                                  136

SEQ ID NO: 96          moltype = DNA  length = 133
FEATURE                Location/Qualifiers
variation              62
                       note = a, c, t, g, or absent
source                 1..133
                       mol_type = genomic DNA
                       note = See specification as filed for detailed description
                        of, substitutions and preferred embodiments
                       organism = Zea mays
SEQUENCE: 96
ctccttcatc atcaaactcc ccgacggcta cgacacgcag gtccgtcccg tatagctagc  60
tnactagctg cactgccact tctctcgctt gctcccccac cgttgctgcc tgttgctctc  120
caatccactt gtc                                                     133

SEQ ID NO: 97          moltype = DNA  length = 141
FEATURE                Location/Qualifiers
variation              70
                       note = a, c, t, g, or absent
source                 1..141
                       mol_type = genomic DNA
                       note = See specification as filed for detailed description
                        of, substitutions and preferred embodiments
                       organism = Zea mays
SEQUENCE: 97
cacacgcaca cacacagatc gcctgacaag ccagccattg cttcagatca aagaaactgc  60
gtaataattn ctttctttct ttctttcttt ctttccagag cacaagggag gggggttata  120
atggctagta cctgactgac t                                            141

SEQ ID NO: 98          moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 98
agccagccat tgcttcagat caaagaaact gcgtaataat tcctttcttt ctttctttct  60
ttctttccag ancacaaggg agggggggtta taatggctag tacctgactg actgtacgag  120
ccgagattaa cggcagtcac ctc                                          143

SEQ ID NO: 99          moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 99
atcgccctgc tggccatttg gcaccaccta gtcgtacatg tgttcagtca tttccgtcca  60
ttactactac gnccgtgctc acccgtgccg acgcgccgtg catggtcccc gtcccggctg  120
gaacgcgtcc tcggaagaga gag                                          143

SEQ ID NO: 100         moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 100
ccattactac tacgaccgtg ctcacccgtg ccgacgcgcc gtgcatggtc cccgtcccgg  60
ctggaacgcg tnctcggaag agagagatag agcacagcag acagggagac agggatggaa  120
ggatggcgtt cgcccggtac agg                                          143

SEQ ID NO: 101         moltype = DNA  length = 143
FEATURE                Location/Qualifiers
variation              72
```

```
                         note = a, c, t, g, or absent
source                   1..143
                         mol_type = genomic DNA
                         note = See specification as filed for detailed description
                          of, substitutions and preferred embodiments
                         organism = Zea mays
SEQUENCE: 101
cattactact acgaccgtgc tcacccgtgc cgacgcgccg tgcatggtcc ccgtcccggc  60
tggaacgcgt cntcggaaga gagagataga gcacagcaga cagggagaca gggatggaag  120
gatggcgttc gcccggtaca ggt                                          143

SEQ ID NO: 102           moltype = DNA  length = 143
FEATURE                  Location/Qualifiers
variation                72
                         note = a, c, t, g, or absent
source                   1..143
                         mol_type = genomic DNA
                         note = See specification as filed for detailed description
                          of, substitutions and preferred embodiments
                         organism = Zea mays
SEQUENCE: 102
attactacta cgaccgtgct cacccgtgcc gacgcgccgt gcatggtccc cgtcccggct  60
ggaacgcgtc cncggaagag agagatagag cacagcagac agggagacag ggatggaagg  120
atggcgttcg cccggtacag gtt                                          143

SEQ ID NO: 103           moltype = DNA  length = 143
FEATURE                  Location/Qualifiers
variation                72
                         note = a, c, t, g, or absent
source                   1..143
                         mol_type = genomic DNA
                         note = See specification as filed for detailed description
                          of, substitutions and preferred embodiments
                         organism = Zea mays
SEQUENCE: 103
ttactactac gaccgtgctc acccgtgccg acgcgccgtg catggtcccc gtcccggctg  60
gaacgcgtcc tnggaagaga gagatagagc acagcagaca gggagacagg gatggaagga  120
tggcgttcgc ccggtacagg ttg                                          143

SEQ ID NO: 104           moltype = DNA  length = 143
FEATURE                  Location/Qualifiers
variation                72
                         note = a, c, t, g, or absent
source                   1..143
                         mol_type = genomic DNA
                         note = See specification as filed for detailed description
                          of, substitutions and preferred embodiments
                         organism = Zea mays
SEQUENCE: 104
ttactactac gaccgtgctc acccgtgccg acgcgccgtg catggtcccc gtcccggctg  60
gaacgcgtcc tnggaagaga gagatagagc acagcagaca gggagacagg gatggaagga  120
tggcgttcgc ccggtacagg ttg                                          143

SEQ ID NO: 105           moltype = DNA  length = 143
FEATURE                  Location/Qualifiers
variation                72
                         note = a, c, t, g, or absent
source                   1..143
                         mol_type = genomic DNA
                         note = See specification as filed for detailed description
                          of, substitutions and preferred embodiments
                         organism = Zea mays
SEQUENCE: 105
ctactacgac cgtgctcacc cgtgccgacg cgccgtgcat ggtccccgtc ccggctggaa  60
cgcgtcctcg gnagagagag atagagcaca gcagacaggg agacagggat ggaaggatgg  120
cgttcgcccg gtacaggttg cta                                          143

SEQ ID NO: 106           moltype = DNA  length = 143
FEATURE                  Location/Qualifiers
variation                72
                         note = a, c, t, g, or absent
source                   1..143
                         mol_type = genomic DNA
                         note = See specification as filed for detailed description
                          of, substitutions and preferred embodiments
                         organism = Zea mays
SEQUENCE: 106
tactacgacc gtgctcaccc gtgccgacgc gccgtgcatg gtccccgtcc cggctggaac  60
gcgtcctcgg angagagaga tagagcacag cagacaggga gacagggatg gaaggatggc  120
```

```
gttcgcccgg tacaggttgc tag                                         143

SEQ ID NO: 107         moltype = DNA  length = 146
FEATURE                Location/Qualifiers
variation              72..75
                       note = a, c, t, g, or absent
source                 1..146
                       mol_type = genomic DNA
                       note = See specification as filed for detailed description
                        of, substitutions and preferred embodiments
                       organism = Zea mays
SEQUENCE: 107
actacgaccg tgctcacccg tgccgacgcg ccgtgcatgg tccccgtccc ggctggaacg  60
cgtcctcgga annnngagag agatagagca cagcagacag ggagacaggg atggaaggat  120
ggcgttcgcc cggtacaggt tgctag                                      146

SEQ ID NO: 108         moltype = DNA  length = 143
FEATURE                Location/Qualifiers
variation              72..77
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 108
ttgcctagca catgcctgcc attgaccgac tgctcagtga gaagtggttc agttgtgctg  60
ttgacagtat annnnnntat atatagtagc cctgtagatt tttttttcag acaaaaaaag  120
aagaagaacg agatgaagtc tgc                                         143

SEQ ID NO: 109         moltype = DNA  length = 148
FEATURE                Location/Qualifiers
variation              76..77
                       note = a, c, t, g, or absent
source                 1..148
                       mol_type = genomic DNA
                       note = See specification as filed for detailed description
                        of, substitutions and preferred embodiments
                       organism = Zea mays
SEQUENCE: 109
catgcctgcc attgaccgac tgctcagtga gaagtggttc agttgtgctg ttgacagtat  60
agatagatat atatanngta gccctgtaga tttttttttc agacaaaaaa agaagaagaa  120
cgagatgaag tctgcaattc ggttttgg                                    148

SEQ ID NO: 110         moltype = DNA  length = 142
FEATURE                Location/Qualifiers
variation              66..69
                       note = a, c, t, g, or absent
source                 1..142
                       mol_type = genomic DNA
                       note = See specification as filed for detailed description
                        of, substitutions and preferred embodiments
                       organism = Zea mays
SEQUENCE: 110
caacgcccac tccttcatca tcaaactccc cgacggctac gacacgcagg tccgtcccgt  60
atagcnnnnt agctcactag ctgcactgcc acttctctcg cttgctcccc caccgttgct  120
gcctgttgct ctccaatcca ct                                          142

SEQ ID NO: 111         moltype = DNA  length = 146
FEATURE                Location/Qualifiers
variation              71..76
                       note = a, c, t, g, or absent
source                 1..146
                       mol_type = genomic DNA
                       note = See specification as filed for detailed description
                        of, substitutions and preferred embodiments
                       organism = Zea mays
SEQUENCE: 111
tttctagagt ttaaagctta tcttagaata aatgcatctt tagctacgag acaacctaac  60
ttcagttgtt nnnnnngttt tttttacttt ctctcttctc acaaatacta tgattacgtc  120
tttacagcga tcttttttat tccaaa                                      146

SEQ ID NO: 112         moltype = DNA  length = 146
FEATURE                Location/Qualifiers
variation              77
                       note = a, c, t, g, or absent
source                 1..146
                       mol_type = genomic DNA
                       note = See specification as filed for detailed description
```

```
                         of, substitutions and preferred embodiments
                        organism = Zea mays
SEQUENCE: 112
tttctagagt ttaaagctta tcttagaata aatgcatctt tagctacgag acaacctaac  60
ttcagttgtt gttgttnttt tttttacttt ctctcttctc acaaatacta tgattacgtc  120
tttacagcga tcttttttat tccaaa                                      146

SEQ ID NO: 113          moltype = DNA  length = 105
FEATURE                 Location/Qualifiers
variation               60..61
                        note = a, c, t, g, or absent
source                  1..105
                        mol_type = genomic DNA
                        note = See specification as filed for detailed description
                         of, substitutions and preferred embodiments
                        organism = Zea mays
SEQUENCE: 113
attccaaacc taaaaatgca tgcactcact ctaaaagcgc aaagggagca tctttttttn  60
ncccccatca tctgcacgca gccttttctt ttcctcatgt cacga                 105

SEQ ID NO: 114          moltype = DNA  length = 181
FEATURE                 Location/Qualifiers
variation               63..111
                        note = a, c, t, g, or absent
source                  1..181
                        mol_type = genomic DNA
                        note = See specification as filed for detailed description
                         of, substitutions and preferred embodiments
                        organism = Zea mays
SEQUENCE: 114
tcggtgctgg ctctggtgca gcggttctac gagcccacgt ccgggcgcgt gctcctggac  60
ggnnnnnnnn nnnnnnnnnn nnnnnnnnnn nnnnnnnnnn nnnnnnnnnn ncaaggacgt  120
gcgcaagtac aacctgcggg cgctgcggcg cgtggtggcg gtggtaccgc aggagccgtt  180
c                                                                 181

SEQ ID NO: 115          moltype = DNA  length = 185
FEATURE                 Location/Qualifiers
variation               51..135
                        note = a, c, t, g, or absent
source                  1..185
                        mol_type = genomic DNA
                        note = See specification as filed for detailed description
                         of, substitutions and preferred embodiments
                        organism = Zea mays
SEQUENCE: 115
agaacacgga ctcacactcc cataactata actgacttga tcatgattcc nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnatttt attaacaatt caatttttat ttattaatta cgtctggacg  180
aggag                                                             185

SEQ ID NO: 116          moltype = DNA  length = 140
FEATURE                 Location/Qualifiers
variation               52..69
                        note = a, c, t, g, or absent
source                  1..140
                        mol_type = genomic DNA
                        note = See specification as filed for detailed description
                         of, substitutions and preferred embodiments
                        organism = Zea mays
SEQUENCE: 116
ccaccgtcag ggaataagac ttattatttt attaacaatt caatttttat tnnnnnnnnn  60
nnnnnnnnnt attaattacg tctggacgag gagtactggt ttatttgatg agagacatgg  120
cagtccaagt caaactcgtt                                             140

SEQ ID NO: 117          moltype = DNA  length = 711
FEATURE                 Location/Qualifiers
variation               66..644
                        note = a, c, t, g, or absent
source                  1..711
                        mol_type = genomic DNA
                        note = See specification as filed for detailed description
                         of, substitutions and preferred embodiments
                        organism = Zea mays
SEQUENCE: 117
actgaaggtg tgtatgcagc gtcaagtcat ccatccgttc cactccactc actcatgcgt  60
cgcgcnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnnnn nnnnnnnnnn  240
nnnnnnnnnn nnnnnnnnnn nnnnnnnnnn nnnnnnnnnn nnnnnnnnnn nnnnnnnnnn  300
```

```
nnnnnnnnnn nnnnnnnnnn nnnnnnnnnn nnnnnnnnnn nnnnnnnnnn nnnnnnnnnn  360
nnnnnnnnnn nnnnnnnnnn nnnnnnnnnn nnnnnnnnnn nnnnnnnnnn nnnnnnnnnn  420
nnnnnnnnnn nnnnnnnnnn nnnnnnnnnn nnnnnnnnnn nnnnnnnnnn nnnnnnnnnn  480
nnnnnnnnnn nnnnnnnnnn nnnnnnnnnn nnnnnnnnnn nnnnnnnnnn nnnnnnnnnn  540
nnnnnnnnnn nnnnnnnnnn nnnnnnnnnn nnnnnnnnnn nnnnnnnnnn nnnnnnnnnn  600
nnnnnnnnnn nnnnnnnnnn nnnnnnnnnn nnnnnnnnnn nnnnactctg cgctcgtgcc  660
tgcccggggc taaagcttta gtagctagcc tcagatcaga tactgttcgt g           711

SEQ ID NO: 118          moltype = DNA  length = 114
FEATURE                 Location/Qualifiers
variation               68..80
                        note = a, c, t, g, or absent
source                  1..114
                        mol_type = genomic DNA
                        note = See specification as filed for detailed description
                         of, substitutions and preferred embodiments
                        organism = Zea mays
SEQUENCE: 118
gcactcagga ctcgcagcga gagaattttt ttaatcaagc ctaaaattca ctttcggaca  60
aatcgaannn nnnnnnnnnn ctactcataa atattaacca tgagaccttt tcgc        114

SEQ ID NO: 119          moltype = DNA  length = 141
FEATURE                 Location/Qualifiers
variation               71
                        note = a, c, t, g, or absent
source                  1..141
                        mol_type = genomic DNA
                        note = See specification as filed for detailed description
                         of, substitutions and preferred embodiments
                        organism = Zea mays
SEQUENCE: 119
ttagcgcatt aatctgagga tgtccagttc gcttgcttgc caatcgccat tgccatcgca  60
acaacaatac ntcgccaact gccattgctg ggtagactag tacagtagca gttagaagaa  120
gcctccactg tacattgcat t                                            141

SEQ ID NO: 120          moltype = DNA  length = 141
FEATURE                 Location/Qualifiers
variation               73
                        note = a, c, t, g, or absent
source                  1..141
                        mol_type = genomic DNA
                        note = See specification as filed for detailed description
                         of, substitutions and preferred embodiments
                        organism = Zea mays
SEQUENCE: 120
ttagcgcatt aatctgagga tgtccagttc gcttgcttgc caatcgccat tgccatcgca  60
acaacaatac ttngccaact gccattgctg ggtagactag tacagtagca gttagaagaa  120
gcctccactg tacattgcat t                                            141

SEQ ID NO: 121          moltype = DNA  length = 144
FEATURE                 Location/Qualifiers
variation               72..73
                        note = a, c, t, g, or absent
source                  1..144
                        mol_type = genomic DNA
                        note = See specification as filed for detailed description
                         of, substitutions and preferred embodiments
                        organism = Zea mays
SEQUENCE: 121
ccatcctctt tcttgctttt ctttttactt tctttggtcg tggctgtttg tggtcataca  60
tacattcacg cnnagagcag aagagctagc taagctaggt gggtgtgcct gcaacgcggg  120
acaaagaaaa ctatttgttg cctg                                         144

SEQ ID NO: 122          moltype = DNA  length = 138
FEATURE                 Location/Qualifiers
variation               70
                        note = a, c, t, g, or absent
source                  1..138
                        mol_type = genomic DNA
                        note = See specification as filed for detailed description
                         of, substitutions and preferred embodiments
                        organism = Zea mays
SEQUENCE: 122
tgtgtctgtc caccccagct cttgctactc tacttactac tgtgctacta gtggtagggt  60
aggtatcttn cataaactgt tattataaac tgtcatctga gaaagagagc cagtcaaacc  120
catgctgctg cttatttt                                                138

SEQ ID NO: 123          moltype = DNA  length = 142
FEATURE                 Location/Qualifiers
```

```
variation              70
                       note = a, c, t, g, or absent
source                 1..142
                       mol_type = genomic DNA
                       note = See specification as filed for detailed description
                        of, substitutions and preferred embodiments
                       organism = Zea mays
SEQUENCE: 123
tcttacataa actgttatta taaactgtca tctgagaaag agagccagtc aaacccatgc  60
tgctgcttan ttttaatcac tgtcaaatgg caggcaggca ggcagtctgg ttagttaata  120
acatctggga agggtttaat ca                                           142

SEQ ID NO: 124         moltype = DNA  length = 141
FEATURE                Location/Qualifiers
variation              70
                       note = a, c, t, g, or absent
source                 1..141
                       mol_type = genomic DNA
                       note = See specification as filed for detailed description
                        of, substitutions and preferred embodiments
                       organism = Zea mays
SEQUENCE: 124
ggcaggcagg caggcagtct ggttagttaa taacatctgg gaagggttta atcaaaccaa  60
atcaaatcan acgaaatcta gaggccacat gggatggggc catatgtact gtactagcat  120
aactagcggc tagattttat t                                            141

SEQ ID NO: 125         moltype = DNA  length = 141
FEATURE                Location/Qualifiers
variation              71
                       note = a, c, t, g, or absent
source                 1..141
                       mol_type = genomic DNA
                       note = See specification as filed for detailed description
                        of, substitutions and preferred embodiments
                       organism = Zea mays
SEQUENCE: 125
caaaccaaat caaatcagac gaaatctaga ggccacatgg gatggggcca tatgtactgt  60
actagcataa ntagcggcta gattttatta gaacacggac tcacactccc ataactataa  120
ctgacttgat catgattcct t                                            141

SEQ ID NO: 126         moltype = DNA  length = 143
FEATURE                Location/Qualifiers
variation              72
                       note = a, c, t, g, or absent
source                 1..143
                       mol_type = genomic DNA
                       note = See specification as filed for detailed description
                        of, substitutions and preferred embodiments
                       organism = Zea mays
SEQUENCE: 126
tactgtacta gcataactag cggctagatt ttattagaac acggactcac actcccataa  60
ctataactga cnttgatcat gattccttgc caagcaatgc tcgcatgccc atgcatgcat  120
catccctggt caaactcaaa cac                                          143

SEQ ID NO: 127         moltype = DNA  length = 141
FEATURE                Location/Qualifiers
variation              71
                       note = a, c, t, g, or absent
source                 1..141
                       mol_type = genomic DNA
                       note = See specification as filed for detailed description
                        of, substitutions and preferred embodiments
                       organism = Zea mays
SEQUENCE: 127
catcatccct ggtcaaactc aaacactctc caccgtcagg gaataagact tattatttta  60
ttaacaattc nattttttatt tattaattac gtctggacga ggagtactgg tttatttgat  120
gagagacatg gcagtccaag t                                            141

SEQ ID NO: 128         moltype = DNA  length = 141
FEATURE                Location/Qualifiers
variation              71
                       note = a, c, t, g, or absent
source                 1..141
                       mol_type = genomic DNA
                       note = See specification as filed for detailed description
                        of, substitutions and preferred embodiments
                       organism = Zea mays
SEQUENCE: 128
aacactctcc accgtcaggg aataagactt attattttat taacaattca atttttattt  60
```

-continued

```
attaattacg nctggacgag gagtactggt ttatttgatg agagacatgg cagtccaagt  120
caaactcgtt tgtctgacca t                                            141

SEQ ID NO: 129          moltype = DNA  length = 139
FEATURE                 Location/Qualifiers
variation               71
                        note = a, c, t, g, or absent
source                  1..139
                        mol_type = genomic DNA
                        note = See specification as filed for detailed description
                         of, substitutions and preferred embodiments
                        organism = Zea mays
SEQUENCE: 129
gggaataaga cttattattt tattaacaat tcaattttta tttattaatt acgtctggac  60
gaggagtact ngtttatttg atgagagaca tggcagtcca agtcaaactc gtttgtctga  120
ccatggcggt gatggccgg                                               139

SEQ ID NO: 130          moltype = DNA  length = 134
FEATURE                 Location/Qualifiers
variation               68
                        note = a, c, t, g, or absent
source                  1..134
                        mol_type = genomic DNA
                        note = See specification as filed for detailed description
                         of, substitutions and preferred embodiments
                        organism = Zea mays
SEQUENCE: 130
tttatttgat gagagacatg gcagtccaag tcaaactcgt ttgtctgacc atggcggtga  60
tggccggntg caggttgggg agcgcggcct gcagctctcc ggtgggcaga agcagcgcat  120
cgccatcgcc cgcg                                                    134

SEQ ID NO: 131          moltype = DNA  length = 141
FEATURE                 Location/Qualifiers
variation               65..74
                        note = a, c, t, g, or absent
source                  1..141
                        mol_type = genomic DNA
                        note = See specification as filed for detailed description
                         of, substitutions and preferred embodiments
                        organism = Zea mays
SEQUENCE: 131
gtcgtacatg tgttcagtca tttccgtcca ttactactac gaccgtgctc acccgtgccg  60
acgcnnnnnn nnnngccgtg catggtcccc gtcccggctg gaacgcgtcc tcggaagaga  120
gagatagagc acagcagaca g                                            141
```

METHODS FOR HYBRID CORN SEED PRODUCTION

CROSS REFERENCE TO RELATED APPLICATIONS

This application is a continuation of U.S. patent application Ser. No. 17/101,202, filed Nov. 23, 2020, which is a continuation of U.S. patent application Ser. No. 16/276,615, filed Feb. 15, 2019, which claims the benefit of U.S. Provisional Patent Application No. 62/631,199, filed Feb. 15, 2018; and U.S. Provisional Patent Application No. 62/775,343, filed Dec. 4, 2018, both each of which are incorporated herein by reference in their entireties.

FIELD OF THE INVENTION

The present disclosure relates to methods of improving hybrid corn seed production.

INCORPORATION OF SEQUENCE LISTING

A sequence listing contained in the filed named MONS544USC2 ST26, which is 228 kilobytes (measured in MS-Windows®) and created on Mar. 10, 2023, comprises 131 sequences, and is filed electronically herewith and incorporated by reference in its entirety.

BACKGROUND

Hybrid corn seeds are produced by crossing two different parental inbred corn lines. Increasing the profitability of commercial corn seed production largely relies on the ability to improve female inbred plant yield. A need continues to exist in the art for further improvements in the efficiency and productivity of corn seed production, especially if agricultural demand and costs of production continue to rise.

SUMMARY

In an aspect, this disclosure provides a method comprising: (a) fertilizing a plurality of female inbred corn plants with pollen from at least one male inbred corn plant to produce hybrid corn seeds, where the female inbred corn plants have an average height that is at least 2.5% lower than the average height of the least one male inbred corn plant; and (b) harvesting the hybrid corn seeds from one or more of the female inbred corn plants.

In an aspect, this disclosure provides a method comprising: (a) crossing at least one male inbred corn plant with a plurality of female inbred corn plants to produce hybrid corn seeds, where the female inbred corn plants have an average height that is at least 2.5% lower than the height of the at least one male inbred corn plant; and (b) harvesting the hybrid corn seeds from one or more of the female inbred corn plants.

In an aspect, this disclosure provides a method comprising: (a) planting at least one male inbred corn plant in proximity to a plurality of female inbred corn plants to produce hybrid corn seeds, where the female inbred corn plants have an average height that is at least 2.5% lower than the height or average height of the at least one male inbred corn plant; and (b) harvesting said hybrid corn seeds from one or more of the female inbred corn plants.

DETAILED DESCRIPTION

Figure 1:
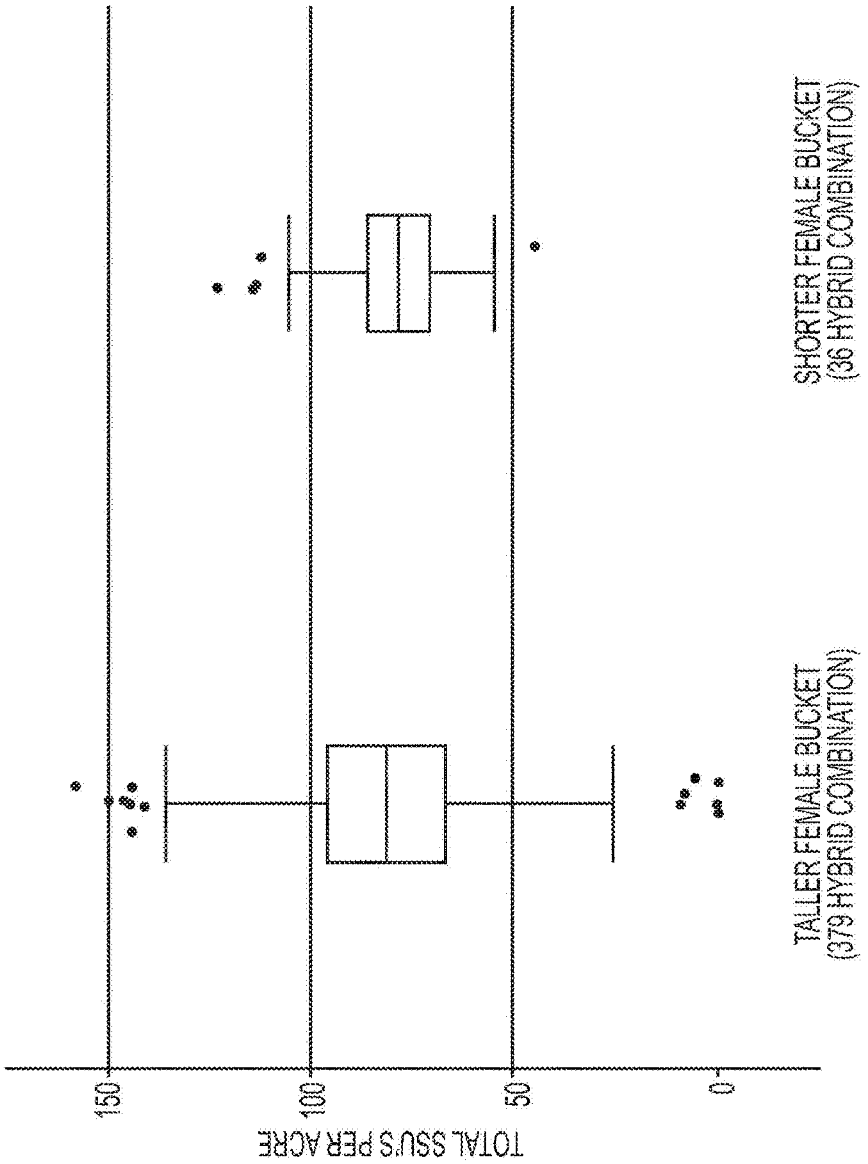
FIG. 1 is a chart illustrating the variability in hybrid corn seed yield produced for a set of 415 different hybrid corn combinations separated into two groupings based upon the average female to male parent plant height ratio for each combination.

Unless defined otherwise, all technical and scientific terms used have the same meaning as commonly understood by one of ordinary skill in the art to which this disclosure belongs. Where a term is provided in the singular, the inventors also contemplate aspects of the disclosure being described by the plural of that term. Where there are discrepancies in terms and definitions used in references that are incorporated by reference, the terms used in this application shall apply. Other technical terms that are used herein have their ordinary meaning in the art in which they are used, as can be exemplified or defined by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives are specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B— i.e., A alone, B alone, or A and B in combination. The expression "A, B and/or C" is intended to mean A alone, B alone, C alone, A and B in combination, A and C in combination, B and C in combination, or A, B, and C in combination.

As used herein, terms in the singular, and the singular forms "a," "an," and "the," for example, include plural referents unless the content clearly dictates otherwise.

As is well understood in the art, metric measurement values provided herein can be easily converted to standard (S.I.) units and vice versa.

As used herein, "plant" includes an explant, plant part, seedling, plantlet or whole plant at any stage of regeneration or development. As commonly understood, a "corn plant" or "maize plant" refers to any plant of species *Zea mays* and includes all plant varieties that can be bred with corn, including wild maize species. In an aspect, corn plants disclosed herein are selected from the subspecies *Zea mays* L. ssp. *mays*. In an additional aspect, corn plants disclosed herein are selected from the group *Zea mays* L. subsp. *mays* Indentata, otherwise known as dent corn. In another aspect, corn plants disclosed herein are selected from the group *Zea mays* L. subsp. *mays* Indurata, otherwise known as flint corn. In an aspect, corn plants disclosed herein are selected from the group *Zea mays* L. subsp. *mays Saccharata*, otherwise known as sweet corn. In another aspect, corn plants disclosed herein are selected from the group *Zea mays* L. subsp. *mays* Amylacea, otherwise known as flour corn. In a further aspect, corn plants disclosed herein are selected from the group *Zea mays* L. subsp. *mays* Everta, otherwise known as popcorn. Plants disclosed herein also include hybrids, inbreds, partial inbreds, or members of defined or undefined populations.

As used herein, the term "inbred" refers to a plant line that has been bred for genetic homogeneity. In an aspect, a corn plant provided herein can be an inbred corn plant.

As used herein, the term "parent" refers to a member of a parental line which, when crossed with another parent, produces seed that can be used to generate a set of offspring plants, which can be referred to as the first filial (F1) generation. A "parent" can be a male or female parent used to produce the seed or offspring.

As used herein, the term "hybrid" means a progeny of mating between at least two genetically dissimilar parents or inbreds. Without limitation, examples of mating schemes include single crosses (A×B), modified single cross ((A×A')×B), double modified single cross ((A×A')×(B×B')), three-way cross ((A×B)×C), modified three-way cross ((A×B)×(C×C')), and double cross ((A×B)×(C×D)) where at least one parent in a modified cross is the progeny of a cross between sister lines. In an aspect, a corn plant provided herein is a hybrid corn plant. In another aspect, a corn seed provided herein is a hybrid corn seed. In an aspect, a hybrid corn seed can be produced by crossing two different inbred corn plants or populations.

As used herein, a "female" corn plant refers to a corn plant that comprises one or more female reproductive structures that are capable of producing corn ear(s) and kernels (seed). In an aspect, a corn plant provided herein is a female corn plant. In an aspect, a female corn plant is male sterile. In another aspect, a female corn plant is detasseled. In an aspect, the male reproductive organs or flowers (e.g., tassels) of a female corn plant are chemically sterilized (e.g., by application of an herbicide to plants lacking tolerance to the herbicide in those male reproductive organs, flowers or tassels), such as with a Roundup® Hybridization System (RHS). In another aspect, the male reproductive organs or flowers (e.g., tassels) of a female corn plant are sterilized due to cytoplasmic male sterility (or CMS). It is appreciated in the art that a corn plant is monoecious and can be considered both a male corn plant and a female corn plant. In an aspect, a female corn plant is capable of producing pollen. For purposes of the present disclosure, a corn plant having one or more male reproductive organ or structure, such as tassels, and/or capable of producing pollen, is considered a "female" plant if used to generate a corn ear(s) and/or corn seed (i.e., kernels) for production and harvest. A corn plant lacking a male reproductive organ or structure, such as tassels, having a sterilized male reproductive organ or structure, and/or incapable of producing pollen, is also considered a "female" plant if used to generate a corn ear(s) and/or seed (i.e., kernels) for production and harvest. A "female" corn plant may include any pollen-receiving corn plant that produces an ear or female reproductive organ, which can receive pollen from a pollen-bearing corn plant.

As used herein, a "male" corn plant refers to a corn plant that is capable of producing pollen (e.g., form one or more tassels) and is used to pollinate and/or fertilize one or more female corn plant(s) for seed production and harvest, even if the male plant further has a female reproductive structure(s) that is/are capable of producing a corn ear and kernels (seed), which may or may not be harvested. A "male" corn plant may include any pollen-bearing (or pollen-producing) corn plant, which can provide its pollen to a pollen-receiving corn plant.

As used herein, the term "plurality" in reference to an item means two or more of such items. For example, a "plurality of plants" means two or more plants.

As used herein, the phrase "at least one" in reference to something (e.g., any object, method step, etc.) means one or more of that something. For example, "at least one plant" or "at least one plants" each means one or more plants. Accordingly, "at least one" can include one or a plurality. Thus, where the present disclosure provides "one or more" of something or "at least one" of something, then the description further supports a plurality of that something.

As used herein, a "control plant" refers to a wild-type plant that does not have or exhibit a trait or phenotype to be analyzed, such as reduced plant height or stature.

In an aspect, the corn plants provided herein are dwarf corn plants. In another aspect, the female inbred corn plants provided herein are dwarf inbred corn plants. As used herein, a "dwarf" plant refers to an atypically small plant. Generally, such a "dwarf plant" has a stature or height that is reduced relative to a control plant (e.g., a wild-type sibling plant comprising all other traits except the dwarf trait) by about 30%, 35%, 40%, 45%, 50%, 55%, 60% or greater. In an aspect, corn plants provided herein are semi-dwarf inbred corn plants.

In another aspect, the female inbred corn plants provided herein are semi-dwarf inbred corn plants. As used herein, a "semi-dwarf plant" refers to a plant having a stature or height that is reduced relative to a control plant (e.g., a wild-type sibling plant comprising all other traits except the semi-dwarf trait) by about 5%, 10%, 15%, 20%, 25%, 30%, 35%, 40%, 45% or less. Such a semi-dwarf plant can be characterized by a reduced stem, stalk, or trunk length when compared to a control wild-type plant under comparable growth conditions, which can result from fewer internodes or shorter average internode length.

As used herein, the term "polynucleotide" refers to a nucleic acid molecule containing multiple nucleotides and generally comprises at least 2, at least 5, at least 10, at least 20, at least 30, at least 40, at least 50, at least 100, at least 250, at least 500, at least 1,000, at least 1,500, at least 2,000, at least 2,500, at least 3,000, at least 5,000, or at least 10,000 nucleotide bases. As an example, a polynucleotide provided herein can be a plasmid. The use of the terms "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. In an aspect, a polynucleotide provided herein is single-stranded. In another aspect, a polynucleotide provided herein is double-stranded.

As used herein, a "gene" refers to a polynucleotide that can produce a functional unit (without being limiting, for example, a mRNA and/or protein or a non-coding RNA molecule). A polynucleotide sequence encoding a non-coding RNA molecule can also be described as a transcribable DNA sequence. A non-coding RNA molecule can act as a suppression element that targets one or more gene(s) in a plant cell, such as one or more endogenous GA20 or GA3 oxidase gene(s), or as a RNA molecule, such as a guide RNA, etc., that guides a sequence-specific nuclease to cut and trigger a genome editing event at a target site in the genome. Non-limiting examples of non-coding RNA molecules include a microRNA (miRNA), a miRNA precursor (pre-miRNA), a small interfering RNA (siRNA), a small RNA (18-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA). In an aspect, a non-coding RNA provided herein is selected from the group consisting of a microRNA, a small interfering RNA, a secondary small interfering RNA, a transfer RNA, a ribosomal RNA, a trans-acting small interfering RNA, a naturally occurring antisense small interfering RNA, a heterochromatic small interfering RNA, and precursors thereof. In another aspect, a non-coding RNA provided herein is selected from the group consisting of a miRNA, a pre-miRNA, a siRNA, a hc-siRNA, a piRNA, a hairpin dsRNA, a ta-siRNA, a nat-siRNA, a crRNA, a tracrRNA, a gRNA, and a sgRNA. In another aspect, a non-coding RNA provided herein is a miRNA. In another aspect, a non-coding RNA provided herein is a siRNA.

As used herein, the term "genome" refers to the genetic material of an organism, consisting of DNA. The genome includes both coding and noncoding regions of DNA molecules. A genome can be a nuclear genome, a plastid genome, or a mitochondrial genome.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, the term "transgene" refers to a recombinant DNA molecule, construct, or sequence comprising a gene and/or transcribable DNA sequence and integrated or inserted into a plant genome.

As used herein, a "transgenic plant" refers to a plant whose genome has been altered by the integration or insertion of a recombinant DNA molecule, construct, cassette or sequence for expression of a non-coding RNA molecule, mRNA and/or protein in the plant. A transgenic plant includes an $R_0$ plant developed or regenerated from an originally transformed plant cell(s) as well as progeny transgenic plants in later generations or crosses from the $R_0$ transgenic plant that comprise the recombinant DNA molecule, construct, cassette or sequence. A plant having an integrated or inserted recombinant DNA molecule, construct, cassette or sequence is considered a transgenic plant even if the plant also has other mutation(s) or edit(s) that would not themselves be considered transgenic.

As used herein, the term "heterologous" can refer broadly to a combination of two or more DNA molecules or sequences, such as a promoter and an associated transcribable DNA sequence, coding sequence, or gene, when such a combination is man-made and not normally found in nature. The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence. For example, a transcribable DNA sequence encoding a non-coding RNA molecule that targets one or more GA oxidase gene(s) for suppression can be operably linked to a heterologous plant-expressible promoter.

As used herein, the term "expression" refers to the process for converting the genetic information of a gene into a functional unit (without being limiting, for example, a mRNA and/or protein or a non-coding RNA molecule).

As used herein, the term "suppression" refers to a lowering, reduction or elimination of the expression level of a mRNA and/or protein encoded by a gene in a plant, plant cell, or plant tissue at one or more stage(s) of plant development, as compared to the expression level of such mRNA and/or protein in a wild-type or control plant, cell, or tissue at the same stage(s) of plant development. In an aspect, a polynucleotide provided herein can suppress the expression of a complementary target gene. In another aspect, a non-coding RNA molecule can suppress the expression of a complementary target gene.

As used herein, a "mutation" refers to an insertion, deletion, substitution, duplication, or inversion of one or more nucleotides and/or encoded amino acids as compared to a reference or wild-type nucleotide and/or amino acid sequence, which can be introduced by any suitable mutagenesis or gene editing technique.

Without being limited by any theory, it is presently proposed that the productivity and yield of commercial corn seed production can be increased by using certain combinations of male and female plants. Typically for commercial corn seed production, one inbred line is used as a male corn plant and another inbred line is used as a female corn plant. By placing or juxtaposing one or more (e.g., a population or row(s)) of male inbred plants next to or near one or more (e.g., a population or row(s)) of female inbred plants in an environment (e.g., the field), the male plants can contribute their genetic material (pollen) to the silk of the ears of the female plants to pollinate and fertilize the ears to produce seed (kernels). Since corn plants have both male and female reproductive structures or flowers, plants can be made "female" by removing, detasseling and/or sterilizing the male reproductive structures, flowers or tassels, such that the genetic contribution of pollen from the female plant is minimized or eliminated and the genetic contribution from pollen can be exclusively or nearly exclusively from the "male" plants. By selectively fertilizing the female ears with pollen from the male plants, hybrid corn seed can be produced if the male and female corn plants are different inbred lines. As well known in the art, corn plants grown from hybrid corn seed have increased yield for growers due to heterosis, or hybrid vigor. To improve agronomic practices with corn seed production, the male and female plants can each be planted in groups or rows. The rows of corn plants can be arranged in a regular or irregular pattern. Furthermore, more female corn plants than male corn plants can be planted to increase yield since corn ears and seeds are harvested from the female corn plants.

One limitation on increasing the number of female corn plants to increase seed production, such as by increasing the number of rows of female corn plants and thus the number of harvested ears, is that there needs to be a sufficient number of male plants to fully pollinate the female corn ears. There is a limit to how far pollen can flow or be distributed by wind, etc., with a decreasing amount or concentration of pollen at increasing distances from the male pollen donor. Thus, corn seed production can be effectively achieved with 4:1, 5:2 or 6:2 row arrangements of female and male plants, respectively (e.g., four female rows, followed by one male row, followed by four female rows, etc., or six female rows, followed by two male rows, followed by six female rows, etc.). Without being limited by any theory, greater numbers of female rows may lead to reduced pollination, fertilization, and/or yield, especially for females in the more interior or distant rows relative to the male plants. Other factors can interfere with pollen flow to female corn plants, such as obstruction by neighboring plants. If the female plants have the same or similar height as the male plant, then the neighboring plants themselves can obstruct air and pollen flow to more interior or distant female rows, even after detasseling of the female plants.

Without being limited by any theory, it is presently proposed, however, that pollen flow could be improved and increased to more interior or distant females or female rows if the female corn plants or rows could be made shorter in height relative to the male plants or rows to not obstruct, or lessen the obstruction of, the flow of pollen to the more interior or distant female corn plants. Indeed, it has been observed that the middle two rows of females in a 4:1 configuration in the field of females to males can have a small yield reduction relative to the other two rows of females. Without being limited by any theory, if pollen flow and/or pollen load could be improved or increased, not only could ear pollination and fertilization rates be increased, leading to larger ears and/or reduced ear tip void, but the number of female corn plants and/or rows, relative to the number of male plants, could be increased to increase the number of ears/seeds harvested due to the ability to pollinate and/or fertilize the more interior or distant female corn plants. Thus, alternative row arrangements of female and male plants, such as 5:1 or 6:1, and potentially 7:1, 8:1, 7:2, 8:2, etc., female to male rows, respectively, can be made more effective and productive with improved pollination and/or fertilization of the more interior or distant female corn plants. If the male and female plants are planted in a regular pattern of rows, the male plants may be planted in rows with equal or similar spacing to the other (female) rows, or male plants may alternatively be inter-planted between female rows.

Even though detasseling can reduce the effective plant height of females (to some extent) at the time of pollination, females having a shorter plant height prior to detasseling should allow for improved pollen flow relative female plants having a more normal height due to the greater height differences between the male and female plants and lower obstruction of pollen flow with the shorter females. This benefit can be additionally useful for female plants having male reproductive structures or tassels that are sterilized by chemical treatment without a reduction in plant height due to detasseling. As a result of the improved pollen flow and/or pollen load, the process of seed production could be made more environmentally sustainable due to the ability to produce as much or more seed on a smaller footprint of fewer acres.

Without being limited by any theory, it is further proposed that shorter plant heights of females may decrease light shading of neighboring male plants, and with reduced shading the male plants may have a reduced or eliminated tassel skeletonization (TSK) in comparison to male plants next to female plants having the same or similar plant height. With reduced tassel skeletonization, pollen production or load by or from the male corn plants can be increased. In some prior cases, row arrangements, such as 4:3, 3:2, and 2:2 females to males, have been used to increased pollen load. However, the present system and method can help overcome these hurdles by reducing tassel skeletonization and permitting fewer numbers of male plants or rows of male plants used for seed production due to the higher pollen load produced per male plant. Therefore, without being limited by theory, it is proposed that corn seed production can be increased with shorter females not only by improving pollen flow, but also by increasing pollen load due to reduced tassel skeletonization of the male plants.

According to another aspect of the present disclosure, it is proposed that corn seed production can be increased with shorter females because shorter female plants can exhibit less root and stalk lodging and/or increased standability at or after the normal time of harvest, which may allow for more flexibility in how long corn is left in the field after drying down and/or allow for direct harvesting of hybrid seeds in a production field. These benefits may further enhance the yield and/or efficiency of corn seed production fields in addition to improved pollen flow, reduced skeletonization and higher number of females in the field. In an aspect, hybrid seeds produced here are collected via direct harvesting. In another aspect, shorter female corn plants are left in a corn field post maturity and can afford a much longer time period for harvesting seeds without jeopardizing the eventual seed yield. As used herein, “direct harvesting” refers to the harvesting of crop seeds from plants with a combine harvester in the field with little or no further drying or other processing or desiccation steps prior to seed storage. As used herein, “standability” refers to the ability of a plant to stand upright in a position that enables it to be harvested by standard farm equipment (e.g., a combine harvester). Corn plants with better standability, such as dwarf corn plants, semi-dwarf corn plants, and brachytic corn plants, are resistant to lodging. As used herein, “lodging” can refer to either “stalk lodging” or “root lodging.” Stalk lodging occurs when the corn plant stalk is severely bent or broken below the ear. Root lodging occurs when the corn plant is leaning at an angle (e.g., greater than or equal to 45° relative to perpendicular from the ground, or at an angle less than 45° relative to the ground).

According to some embodiments, it is proposed that pollen flow could be further improved or increased by optionally using a fan, blower or other device that increases or directs air flow (collectively, “air flow device”). Such an air flow device(s) could be placed at one or more predetermined distance(s) from a male corn plant(s), such as a row(s) of male corn plants, on one side of such male corn plant(s) and/or row or rows of male corn plants, wherein the female corn plant(s), such as a row(s) of female corn plants, are on the other (or opposite) side of such male corn plant(s) and/or row or rows of male corn plants relative to the air flow device(s). Such an air flow device could be fixed (i.e., stationary) or mobile. For example, a mobile or moveable air flow device may move along or parallel to a row of male plants. According to another embodiment, a pollinating device or vehicle may be used to promote or enhance the efficient release, distribution or spreading of pollen from male plants to female plants. See, e.g., PCT Application Publication No. WO 2018/129302, the entire contents and disclosure of which are incorporated herein by reference.

There are various ways in which a corn plant can be made to have a shorter semi-dwarf plant height. According to many aspects, a corn plant can be made shorter or semi-dwarf relative to a control plant by lowering the level(s) of active GAs in one or more tissue(s) of the plant, such as by suppressing, mutating or editing one or more GA oxidase gene(s) in the corn plant. According to other aspects, a corn plant or plurality of corn plants provided herein can have a mutation or edit in an auxin, brassinosteroid, jasmonic acid, cell cycle regulation, and/or other pathway gene(s) that are known to affect plant height. According to yet other aspects, a female corn plant or plurality of female corn plants provided herein can be made shorter by application of one or more chemistries, such as GA inhibitors, known to affect plant height. Additional information regarding chemistries, such as GA inhibitors, can be found in WO 2017/011791 and U.S. Patent Application Publication Nos. 2019/0014730 and 2019/0014731, which are incorporated herein by reference in their entireties. According to another aspect, a corn plant or plurality of corn plants provided herein can comprise a mutation or mutant allele in one or more loci or genes that have been associated with a short stature phenotype in corn, such as one or more of the following: anther ear 1 (An1), brachytic 1 (Br1), *brevis* plant 1 (Bv1) or brachytic 3 (br3), crinkly 4 (Cr4), compact plant 2 (Ct2), dwarf plant 1 (d1), dwarf plant 8 (d8), dwarf plant 9 (d9), nana plant 1 (Na1), nana plant 2 (Na2), non-chromosomal stripe 3 (Nsc3), narrow leaf dwarf 1 (Nld1), reduced plant 1 (Rd1), semi-dwarf/(Sdw1), semi-dwarf 2 (Sdw2), tangled/(Tan1), terminal ear 1 (Tel), and vanishing tassel 2 (Vt2).

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, have not been realized through manipulation of the GA pathway. Corn or maize is unique among the grain-producing grasses in that it forms separate male (tassel) and female (ear) inflorescences, and mutations in the GA pathway in corn have been shown to negatively impact reproductive development. Indeed, some mutations in the GA pathway genes in corn have been associated with various off-types that are incompatible with yield, which has led researchers away from finding semi-dwarf, high-yielding corn varieties via manipulation of the GA pathway.

Despite these prior difficulties in achieving higher grain yields in corn through manipulation of the GA pathway, PCT Application No. PCT/US2017/047405 describes a way to manipulate active GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants with reduced GA levels can also have one or more additional yield and/or stress tolerance traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that incomplete suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, can be sufficient to produce a short-stature plant with increased lodging resistance, but without significant off-types in reproductive tissues. Expression of a GA20 or GA3 oxidase suppression element in a tissue-specific or tissue-preferred manner can be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) can be targeted for suppression using a vascular promoter, such as a rice tungro bacilliform virus (RTBV) promoter, which drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant that produce active GAs can reduce plant height and increase lodging resistance, and off-types can be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Without being limited by theory, it is further proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, it was surprisingly found that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), may be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this can be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types.

In an aspect, a corn plant or plurality of corn plants provided herein can each comprise a recombinant DNA construct or polynucleotide sequence, where the recombinant DNA construct or polynucleotide sequence comprises a transcribable DNA sequence encoding a non-coding RNA molecule that targets at least one endogenous GA20 or GA3 oxidase gene for suppression. In another aspect, a corn plant provided herein can comprise suppressed GA3 oxidase gene expression in one or more tissues as compared to a wild-type control plant. In another aspect, a corn plant provided herein can comprise suppressed GA20 oxidase gene expression in one or more tissues as compared to a wild-type control plant. In another aspect, a corn plant provided herein can comprise a mutation at or near an endogenous GA oxidase gene, where the expression level of the endogenous GA oxidase gene is reduced or eliminated in the corn plant, and where the corn plant has a shorter plant height as compared to a wild-type control plant. In an aspect, a corn plant provided herein can comprise a recombinant polynucleotide capable of suppressing expression of one or more GA20 oxidase and/or GA3 oxidase gene(s) and/or mRNA(s) transcribed therefrom. Alternatively, a corn plant provided herein can comprise one or more mutation(s) or edit(s) in one or more GA20 oxidase and/or GA3 oxidase gene(s). In an aspect, a female corn plant provided herein can comprise a mutation in a GA20 oxidase locus or gene as compared to a wildtype GA20 oxidase locus or gene. In an aspect, a corn plant provided herein is homozygous (or biallelic) for a mutation or an edit in one or more GA20 oxidase loci or genes as compared to a wildtype GA20 oxidase locus or gene. In another aspect, a corn plant provided herein is heterozygous for a mutation or an edit in one or more GA20 oxidase loci or genes as compared to a wildtype GA20 oxidase locus or gene. In another aspect, a corn plant provided herein can comprise a mutation in a GA3 oxidase locus or gene as compared to a wildtype GA3 oxidase locus or gene. In an aspect, a corn plant provided herein is homozygous (or biallelic) for a mutation or an edit in one or more GA3 oxidase loci or genes as compared to a wildtype GA3 oxidase locus or gene. In another aspect, a corn plant provided herein is heterozygous for a mutation or an edit in a one or more GA3 oxidase loci or genes as compared to a wildtype GA3 oxidase locus or gene. In another aspect, a corn plant provided herein can comprise a heterologous polynucleotide capable of suppressing expression of a GA20 oxidase gene or an mRNA transcribed therefrom.

By targeting a subset of one or more endogenous GA3 or GA20 oxidase genes for suppression within a plant, a more pervasive pattern of expression (e.g., with a constitutive promoter) can be used to produce semi-dwarf plants without significant reproductive off-types and/or other undesirable traits in the plant, even with expression of the suppression construct in reproductive tissue(s). Indeed, suppression elements and constructs are provided herein that selectively target the GA20 oxidase_3 and/or GA20 oxidase_5 genes for suppression, which can be operably linked to a vascular, leaf and/or constitutive promoter.

As introduced above, instead of suppressing one or more GA oxidase gene(s), active GA levels can also be reduced in a corn plant by mutation or editing of one or more GA20 and/or GA3 oxidase gene(s).

Corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

In an aspect, a corn plant provided herein is homozygous (or biallelic) for a mutation or an edit in a GA20 oxidase_5 locus or gene as compared to a wildtype GA20 oxidase_5 locus or gene and homozygous (or biallelic) for a mutation or an edit in a GA20 oxidase_3 locus or gene as compared to a wildtype GA20 oxidase_3 locus or gene. In an aspect, a corn plant provided herein is homozygous (or biallelic) for a mutation or an edit in a GA20 oxidase_5 locus or gene as compared to a wildtype GA20 oxidase_5 locus or gene and heterozygous for a mutation or an edit in a GA20 oxidase_3 locus or gene as compared to a wildtype GA20 oxidase_3 locus or gene. In an aspect, a corn plant provided herein is heterozygous for a mutation or an edit in a GA20 oxidase_5 locus or gene as compared to a wildtype GA20 oxidase_5 locus or gene and homozygous (or biallelic) for a mutation or an edit in a GA20 oxidase_3 locus or gene as compared to a wildtype GA20 oxidase_3 locus or gene. See, e.g., U.S. Provisional Patent Application Nos. 62/631,412; 62/631,416; and 62/710,302; the contents and disclosures of which are incorporated herein by reference in their entireties.

TABLE 1

DNA and protein sequences by sequence identifier for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
|---|---|---|---|
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

The genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

In addition to phenotypic observations with targeting the GA20 oxidase_3 and/or GA20 oxidase_5 gene(s), or the GA3 oxidase_1 and/or GA3 oxidase_2 gene(s), for suppression, a semi-dwarf phenotype is also observed with suppression of the GA20 oxidase_4 gene. The genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

In an aspect, the present disclosure provides a corn plant or plurality of corn plants each comprising a recombinant DNA construct or polynucleotide sequence comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or corn cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, and/or 33, and wherein the transcribable DNA sequence is operably linked to a plant-expressible promoter, which can be heterologous with respect to the transcribable DNA sequence and/or the corn plant.

Recombinant DNA constructs and transgenic corn plants are provided herein comprising a GA20 or GA3 oxidase suppression element or sequence operably linked to a plant expressible promoter, which can be a constitutive or tissue-specific or tissue-preferred promoter. Such a tissue-specific or tissue-preferred promoter can drive expression of its associated GA oxidase suppression element or sequence in one or more active GA-producing tissue(s) of the plant to suppress or reduce the level of active GAs produced in those tissue(s). Such a tissue-specific or tissue-preferred promoter can drive expression of its associated GA oxidase suppression construct or transgene during one or more vegetative stage(s) of development. Such a tissue-specific or tissue-preferred promoter can also have little or no expression in one or more cell(s) or tissue(s) of the developing female organ or ear of the plant to avoid the possibility of off-types in those reproductive tissues.

As used herein, a "plant-expressible promoter" refers to a promoter that drives, causes, or initiates expression of a transcribable DNA sequence or transgene operably linked to such promoter in one or more plant cells or tissues, such as one or more cells or tissues of a corn plant. In an aspect, a plant-expressible promoter is a constitutive promoter. In another aspect, a plant-expressible promoter is a vascular promoter. As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) can comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters. In another aspect, a plant-expressible promoter is a leaf promoter. As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

Promoters that drive enhanced expression in certain tissues of the plant relative to other plant tissues are referred to as "tissue-enhanced" or "tissue-preferred" promoters. Thus, a "tissue-preferred" promoter causes relatively higher or preferential or predominant expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters.

A non-limiting exemplary plant-expressible promoter is the RTBV promoter. In an aspect, a plant-expressible promoter is an RTBV promoter. In another aspect, a plant expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 39, SEQ ID NO: 40, or a functional portion thereof.

Non-limiting exemplary vascular promoters include a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, and a rice yellow stripe 2 (OsYSL2) promoter. In an aspect, a vascular promoter is selected from the group consisting of a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, a rice yellow stripe 2 (OsYSL2) promoter, and functional portions thereof. In an aspect, a vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 41, SEQ ID NO: 42, SEQ ID NO: 43, SEQ ID NO: 44, SEQ ID NO: 45, or a functional portion thereof.

Non-limiting exemplary leaf promoters include a RuBisCO promoter, a PPDK promoter, a FDA promoter, a Nadh-Gogat promoter, a chlorophyll a/b binding protein gene promoter, a phosphoenolpyruvate carboxylase (PEPC) promoter, and a Myb gene promoter. In an aspect, a leaf promoter is selected from the group consisting of a RuBisCO promoter, a PPDK promoter, a FDA promoter, a Nadh-Gogat promoter, a chlorophyll a/b binding protein gene promoter, a phosphoenolpyruvate carboxylase (PEPC) promoter, a Myb gene promoter, and functional portions thereof. In an aspect, a leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 46, SEQ ID NO: 47, SEQ ID NO: 48, or a functional portion thereof.

Non-limiting exemplary constitutive promoters include an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, and a maize alcohol dehydrogenase. In an aspect, a constitutive promoter is selected from the group consisting of an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, a maize alcohol dehydrogenase, or functional portions thereof. In an aspect, a constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, or a functional portion thereof.

In another aspect, the present disclosure provides a corn plant or plurality of corn plants each comprising a recombinant DNA construct or polynucleotide sequence comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase gene having at least 80%, at least 85%, at least 90%, at least 95%, at least 96%, at least 97%, at least 98%, at least 99%, at least 99.5%, or 100% identical to SEQ ID NO: 9, 12, 15, 30, and/or 33, and wherein the transcribable DNA sequence is operably linked to a plant-expressible promoter, which can be heterologous with respect to the transcribable DNA sequence and/or the corn plant.

As provided above, a corn plant or plant part can comprise a first expression cassette comprising a first sequence encoding a non-coding RNA molecule that targets one or more GA20 or GA3 oxidase gene(s) for suppression. In an aspect, the non-coding RNA molecule can target one or more GA20 oxidase gene(s) for suppression, such as a GA20 oxidase_3 gene, a GA20 oxidase_4 gene, a GA20 oxidase_5 gene, or any combination thereof. According to some embodiments, the first expression cassette comprises a first transcribable DNA sequence encoding a non-coding RNA targeting a GA20 oxidase_3 gene for suppression. According to other embodiments, the first expression cassette comprises a first transcribable DNA sequence encoding a non-coding RNA targeting a GA20 oxidase_5 gene for suppression. According to yet further embodiments, the first expression cassette comprises a first transcribable DNA sequence encoding a non-coding RNA that targets both the GA20 oxidase_3 gene and the GA20 oxidase_5 gene for suppression. In addition to targeting a mature mRNA sequence (including either or both of the untranslated or exonic sequences), a non-coding RNA molecule can also target the intronic sequences of a GA20 oxidase gene or transcript.

For suppression of a GA20 oxidase_3 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 7, SEQ ID NO: 8, and SEQ ID NO: 34.

For suppression of a GA20 oxidase_4 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 10, SEQ ID NO: 11, and SEQ ID NO: 38.

For suppression of a GA20 oxidase_5 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 13, SEQ ID NO: 14, and SEQ ID NO: 35.

For suppression of a GA20 oxidase_3 gene and a GA20 oxidase_5 gene, a transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 7, SEQ ID NO: 8, and SEQ ID NO: 34; and the transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 13, SEQ ID NO: 14, and SEQ ID NO: 35.

In another aspect, a first expression cassette comprises a first transcribable DNA sequence encoding a non-coding RNA targeting a GA3 oxidase gene(s) for suppression in corn, such as a GA3 oxidase_1 gene or a GA3 oxidase_2 gene. In another aspect, a first transcribable DNA sequence encoding a non-coding RNA targets both the GA3 oxidase_1 gene and the GA3 oxidase_2 gene for suppression. In addition to targeting a mature mRNA sequence (including either or both of the untranslated or exonic sequences), a non-coding RNA molecule can also target the intronic sequences of a GA3 oxidase gene or transcript.

For suppression of a GA3 oxidase_1 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 28, SEQ ID NO: 29, and SEQ ID NO: 36.

For suppression of a GA3 oxidase_2 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 31, SEQ ID NO: 32, and SEQ ID NO: 37.

For suppression of a GA3 oxidase_1 gene and a GA3 oxidase_2 gene, a transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 28, SEQ ID NO: 29, and SEQ ID NO: 36; and the transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 31, SEQ ID NO: 32 and SEQ ID NO: 37.

Any method known in the art for suppression of a target gene can be used to suppress GA oxidase gene(s) according to aspects of the present disclosure including expression of antisense RNAs, double stranded RNAs (dsRNAs) or inverted repeat RNA sequences, or via co-suppression or RNA interference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules can be used that target the non-coding genomic sequences or regions within or near a gene to cause silencing of the gene. Accordingly, any of these methods can be used for the targeted suppression of an endogenous GA oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

In an aspect, an expression level(s) of one or more endogenous GA20 oxidase and/or GA3 oxidase gene(s) is/are reduced or eliminated in the corn plant, thereby suppressing the endogenous GA20 oxidase and/or GA3 oxidase gene(s).

According to an aspect, a corn plant is provided having the expression level(s) of one or more GA20 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control corn plant.

According to an aspect, a corn plant is provided having the expression level(s) of one or more GA3 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control corn plant.

According to an aspect, a corn plant is provided having the expression level(s) of one or more GA20 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control corn plant.

According to an aspect, a corn plant is provided having the expression level(s) of one or more GA3 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control corn plant.

According to an aspect, the at least one tissue of a corn plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In an aspect, suppression of an endogenous GA20 oxidase gene or a GA3 oxidase gene is tissue-specific (e.g., only in leaf and/or vascular tissue). Suppression of a GA20 oxidase gene can be constitutive and/or vascular or leaf tissue specific or preferred. In other aspects, suppression of a GA20 oxidase gene or a GA3 oxidase gene is constitutive and not tissue-specific. According to an aspect, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

Certain mutations of brachytic genes have been shown to result in a short stature, semi-dwarf phenotype. In an aspect of the present disclosure, a female corn plant is provided having a non-silent mutation or edit in a brachytic gene. See, e.g., PCT Application No. PCT/US2016/029492 and PCT/US2017/067888, the entire contents and disclosures of which are incorporated herein by reference. Thus, a shorter female corn plant can comprise a mutation (or edit) in a brachytic gene, and can be homozygous (or biallelic) for a mutation (or edit) in a brachytic gene. As used herein, a "brachytic mutant plant" refers to a plant having a short semi-dwarf height and stature relative to a control plant (e.g., a wild-type sibling plant comprising all other traits except the brachytic trait) due to a shortening of the average internode length. Such a brachytic mutant plant can have a short semi-dwarf height and stature due to a shortening of the average internode length. As used herein, a "brachytic gene", "BR gene" or "br gene", or "Br gene" refers to any brachytic gene in a corn plant that when mutated or edited to reduce its expression or function can result in a shorter, semi-dwarf corn plant and phenotype. In an aspect, a female inbred corn plant or plurality of female inbred corn plants provided herein each has a non-silent mutation or edit in a brachytic gene. In an aspect, the brachytic gene is a br1 mutant gene. In another aspect, the brachytic gene is a br2 mutant gene. In yet another aspect, the brachytic gene is a br3 mutant gene.

In maize, brachytic mutants have a short stature due to a shortening of the internode length without a corresponding reduction in the number of internodes or the number and size of other organs, including the leaves, ear and tassel. See Kempton *J. Hered.* 11:111-115(1920); Pilu et al., *Molecular Breeding,* 20:83-91(2007). Three brachytic mutants have been isolated in maize to date: brachytic1 (br1), brachytic2 (br2) and brachytic3 (br3). Both br1 and br3 mutations cause a reduction in corn plant height, which has been thought too severe for commercial exploitation due to potential impacts on yield. In contrast, the br2 mutant has particular agronomic potential because of shortening of the internodes of the lower stalk without an obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with gibberellins, auxins, brassinosteroids and cytokinins, suggesting that the biosynthesis of these hormones is not modified by the br2 mutation. Multani et al. identified the genomic sequence of the br2 gene (SEQ ID NO: 58) and deposited it under GenBank Accession No. AY366085. See Multani et al., *Science,* 302(5642) 81-84 (2003). br2 was annotated to encode a putative protein similar to adenosine triphosphate (ATP)-binding cassette transporters of the multidrug resistant (MDR) class of P-glycoproteins (PGPs). Pilu et al. reported a br2-23 allele having an 8-bp deletion in the 3' end of the br2 gene and claimed a direct relationship between this deletion and the brachytic phenotype in their br2-23 plants. See Pilu et al., *Molecular Breeding,* 20:83-91(2007). Nevertheless, the use of brachytic mutations in corn has not been exploited commercially partly because of the severity of the available brachytic mutant alleles.

As used herein, a "brachytic allele" is an allele at a particular genomic locus that confers, or contributes to, a brachytic or semi-dwarf phenotype, such as an allele of a brachytic gene that causes a brachytic or semi-dwarf phenotype, or alternatively, is an allele that allows for the identification of plants that comprise a brachytic phenotype or plants that can give rise to progenies with a brachytic phenotype. For example, a brachytic allele of a marker can be a marker allele that segregates with a brachytic phenotype.

In some aspects, a brachytic, dwarf, or semi-dwarf corn plant comprises a reduced level of br2 mRNA and/or protein, as compared to a control corn plant not having the brachytic allele. In other aspects, the corn plants or seeds comprise reduced br2 protein activity compared to a control plant not having the brachytic allele. In some aspects, the height of a brachytic, dwarf, or semi-dwarf plant comprising a brachytic allele at maturity is reduced by at least 10%, at least 20%, at least 30%, at least 40%, at least 50%, at least 60%, or at least 70% compared to a control plant not having a brachytic allele. In another aspect, the yield of a brachytic, dwarf, or semi-dwarf corn plant comprising a brachytic allele is equal to or more than the yield of a control plant not having the brachytic allele. In an aspect, a brachytic, dwarf, or semi-dwarf corn plant comprising a brachytic allele requires about 5%, 10%, 15%, 20%, or 25% fewer heat units than a control plant not having the brachytic allele to reach anthesis. In an aspect, a brachytic, dwarf, or semi-dwarf corn plant is homozygous for a brachytic allele. In another aspect, a brachytic, dwarf, or semi-dwarf corn plant is heterozygous for a brachytic allele. In another aspect, a brachytic, dwarf, or semi-dwarf corn plant is a hybrid. In another aspect, a brachytic, dwarf, or semi-dwarf corn plant is an inbred, such as a female inbred.

In an aspect, this disclosure provides brachytic, dwarf, or semi-dwarf corn plants comprising a brachytic allele comprising one or more sequences selected from the group consisting of SEQ ID Nos: 59-85. In another aspect, a brachytic, dwarf, or semi-dwarf corn plant comprises a single gene conversion of the br2 genomic region.

In an aspect, a brachytic, dwarf, or semi-dwarf corn plant comprises a brachytic allele at a polymorphic locus, wherein the polymorphic locus is associated with, or linked to, a marker selected from the group consisting of SEQ ID NOs: 86-131. In another aspect, a brachytic allele at a polymorphic locus is within 20 cM (centimorgans), within 10 cM, within 5 cM, within 1 cM, or within 0.5 cM of a marker selected from the group consisting of SEQ ID NOs: 86-131. In another aspect, a brachytic allele is at a polymorphic locus within 20 cM, within 10 cM, within 5 cM, within 1 cM, or within 0.5 cM of a marker selected from the group consisting of SEQ ID NOs: 90-117. In another aspect, a brachytic allele is at a polymorphic locus within 20 cM, within 10 cM, within 5 cM, within 1 cM, or within 0.5 cM of a marker selected from the group consisting of SEQ ID NOs: 92 and 117.

In an aspect, a corn plant or plurality of corn plants provided herein, such as a female corn plant or inbred or a plurality or population of female corn plants, can comprise at least one non-natural brachytic mutation, where the corn plant exhibits a semi-dwarf phenotype compared to a control corn plant not comprising the at least one non-natural brachytic mutation when grown under comparable conditions. In another aspect, a corn plant provided herein can comprise at least one non-natural brachytic mutation. In another aspect, a corn plant provided herein can comprise at least one non-natural brachytic mutant allele. In another aspect, a corn plant provided herein can comprise at least one non-natural brachytic mutation and exhibits a semi-dwarf phenotype. In another aspect, a corn plant provided herein can comprise at least one non-natural brachytic mutant allele and exhibit a semi-dwarf phenotype. In another aspect, a corn plant provided herein can comprise a non-naturally occurring mutation in a br gene reducing the activity of the br gene, where the mutation is not introduced via a transposon. In another aspect, a corn plant provided herein can comprise a mutation in a br2 locus or gene as compared to a wildtype br2 locus or gene. In an aspect, a corn plant provided herein is homozygous (or biallelic) for a mutation in a br2 locus or gene as compared to a wildtype br2 locus or gene. In another aspect, a corn plant provided herein is heterozygous for a mutation in a br2 locus or gene as compared to a wildtype br2 locus or gene. In another aspect, a corn plant provided herein can comprise a modified br2 gene with reduced activity, where the corn plant does not comprise a br2-23 brachytic allele or SNP5259. In another aspect, a corn plant provided herein can comprise a synthetic mutation in a br gene, reducing the activity of the br gene.

In an aspect, a corn plant or plurality of corn plants provided herein, such as a female corn plant or inbred or a plurality or population of female corn plants, can each comprise a non-transgene or non-transposon mediated mutation in a br gene reducing the activity of the br gene. In another aspect, a corn plant provided herein can comprise a recessive, non-transgenic br mutant allele. In another aspect, a corn plant provided herein can comprise a heterologous polynucleotide capable of suppressing expression of a br gene or an mRNA transcribed therefrom. In another aspect, a corn plant provided herein can comprise a heterologous polynucleotide capable of suppressing expression of a br1 gene or an mRNA transcribed therefrom. In another aspect, a corn plant provided herein can comprise a heterologous polynucleotide capable of suppressing expression of a br2 gene or an mRNA transcribed therefrom. In another aspect, a corn plant provided herein can comprise a heterologous polynucleotide capable of suppressing expression of a br3 gene or an mRNA transcribed therefrom. Additional details about altering the expression of br genes can be found in PCT Application No. PCT/US2016/029492 and PCT/US2017/067888, the entire contents and disclosure of which are incorporated herein by reference.

Corn leaves consist of four main anatomical parts: a proximal sheath, a ligule, an auricle, and a distal blade. The sheath wraps around the stem and younger leaves, while the blade is flattened in the mediolateral axis (midrib to margin). The ligule and auricle are found at the blade/sheath boundary; the ligule is an adaxial (upper) membranous structure that acts as a collar around the stem, and the auricle is a projection on the lower surface of the blade base that connects the blade to the sheath. Stages of corn plant growth are divided into vegetative (V) stages and reproductive (R) stages. Upon germination, a corn plant is in the VE stage (emergence). Once the first leaf collar (e.g., the ligule) is visible, the corn plant is in the V1 stage. The emergence of the second leaf collar signifies V2 stage; the emergence of the third leaf collar signifies the V3 stage; and so on until the tassel emerges. For example, if twelve leaf collars are visible, the plant is a V12 stage plant. Once the bottom-most branch of the tassel emerges the plant is in VT stage, which is the final vegetative stage. The reproductive stage of growth occurs after the vegetative stage. The number of vegetative stages prior to VT stage can vary by environment and corn line. The first reproductive stage (R1; silking stage) occurs when silk is visible outside the husk leaves surrounding an ear of corn. R2 (blistering stage) occurs when corn kernels are white on the outside and are filled with a clear liquid inside. R3 (milk stage) occurs when the kernels are yellow on the outside and are filled with a milky white fluid inside. R4 (dough stage) occurs when the kernels are filled with a thick, or pasty, fluid. In some corn lines the cob will also turn pink or red at this stage. R5 (dent stage) occurs when a majority of the kernels are at least partially dented. The final reproductive stage, R6 (physiological maturity), occurs when the kernels have attained their maximum dry weight.

The height of a corn plant can be measured using a variety of methods known in the art. The height of a corn plant can also be determined based on a variety of anatomical locations on a corn plant. In an aspect, the height of a corn plant is measured as the distance between the soil or ground and the ligule of the uppermost fully-expanded leaf of the corn plant. As used herein, a "fully-expanded leaf" is a leaf where the leaf blade is exposed and both the ligule and auricle are visible at the blade/sheath boundary. In another aspect, the height of a corn plant is measured as the distance between the soil or ground and the upper leaf surface of the leaf farthest from the soil. In another aspect, the height of a corn plant is measured as the distance between the soil or ground and the arch of the highest corn leaf that is at least 50% developed. As used herein, an "arch of the highest corn leaf" is the highest point of the arch of the uppermost leaf of the corn plant that is curving downward. In another aspect, the height of a corn plant is measured at the first reproductive (R1) stage. Exemplary, non-limiting methods of measuring plant height include comparing photographs of corn plants to a height reference, or physically measuring individual corn plants with a suitable ruler.

As used herein, the term "ground" or "ground level" used in relation to a corn plant, such as to measure plant height, refers to the top or uppermost surface of the growth medium or soil (e.g., earth) from which the corn plant grows.

Corn plant height varies depending on the line or variety grown, whether the plant is a hybrid or inbred, and environmental conditions. Although hybrid corn plants can reach a height of over 3.6 meters tall by maturity, a height of around 2.0-2.5 meters by maturity for hybrid plants is more common. Inbred corn lines tend to be shorter than hybrids and can commonly have an average plant height ranging from about 1.75 meters to about 2.25 meters, or from about 1.85 meters to about 2.25 meters, or from about 1.95 meters to about 2.25 meters, or from about 2.05 meters to about 2.25 meters, or from about 1.85 to about 2.35 meters, or from about 1.95 meters to about 2.35 meters, or from about 2.05 meters to about 2.35 meters, or from about 2.15 meters to about 2.35 meters, or from about 1.8 meters to about 2.0 meters, or from about 1.8 meters to about 2.1 meters, or from about 1.8 meters to about 2.2 meters, or from about 1.8 meters to about 2.3 meters, or from about 1.9 meters to about 2.1 meters, or from about 1.9 meters to about 2.2 meters, or from about 1.9 meters to about 2.3 meters, or from about 2.0 meters to 2.2 meters, or from about 2.0 meters to 2.3 meters, or from about 1.75 meters to about 2.35 meters. According to some embodiments, a corn line or variety, or transgenic, mutated or edited corn plant, or a plurality or population of such a line, variety, transgenic, mutated, or edited corn plant, is provided having a reduced average plant height at maturity relative to a control plant of about 2.3 meters or less, about 2.2 meters or less, about 2.1 meters or less, about 2.0 meters or less, about 1.9 meters or less, about 1.8 meters or less, about 1.7 meters or less, about 1.6 meters or less, or about 1.5 meters or less.

The "average height" of a group of corn plants is the height obtained by dividing the sum of the heights of all plants within the group by the total number of plants within the group. For clarity, an "average height" for one plant is simply the height of that plant (i.e., its height divided by "1" equals its height).

In an aspect, the average height of the female inbred corn plants provided herein is at least 2% less or lower than the height (or average height) of at least one male inbred corn plant(s) (or the average plant height of male inbred corn plants) provided herein. In an aspect, the average height of the female inbred corn plants provided herein is at least 2.5% less or lower than the height (or average height) of at least one male inbred corn plant(s) (or the average plant height of male inbred corn plants) provided herein. In an aspect, the average height of the female inbred corn plants provided herein is at least 3% less or lower than the height (or average height) of at least one male inbred corn plant(s) (or the average plant height of male inbred corn plants) provided herein. In an aspect, the average height of the female inbred corn plants provided herein is at least 4% less or lower than the height (or average height) of at least one male inbred corn plant(s) (or the average plant height of male inbred corn plants) provided herein. In an aspect, the average height of the female inbred corn plants provided herein is at least 5% less or lower than the height (or average height) of at least one male inbred corn plant(s) provided herein. In an aspect, the average height of the female inbred corn plants provided herein is at least 10% less or lower than the height (or average height) of at least one male inbred corn plant(s) provided herein. In another aspect, the average height of the female inbred corn plants provided herein is at least 15% less or lower than the height (or average height) of at least one male inbred corn plant(s) provided herein. In another aspect, the average height of the female inbred corn plants provided herein is at least 20% less or lower than the height (or average height) of at least one male inbred corn plant(s) provided herein. In another aspect, the average height of the female inbred corn plants provided herein is at least 25% less or lower than the height (or average height) of at least one male inbred corn plant provided herein. In another aspect, the average height of the female inbred corn plants provided herein is at least 30% less or lower than the height (or average height) of at least one male inbred corn plant(s) provided herein. In another aspect, the average height of the female inbred corn plants provided herein is at least 35% less or lower than the height (or average height) of at least one male inbred corn plant(s) provided herein. In another aspect, the average height of the female inbred corn plants provided herein is at least 40% less or lower than the height (or average height) of at least one male inbred corn plant(s) provided herein. In another aspect, the average height of the female inbred corn plants provided herein is at least 45% less or lower than the height (or average height) of at least one male inbred corn plant(s) provided herein. In another aspect, the average height of the female inbred corn plants provided herein is at least 50% less or lower than the height (or average height) of at least one male inbred corn plant(s) provided herein. In another aspect, the average height of the female inbred corn plants provided herein is at least 55% less or lower than the height (or average height) of at least one male inbred corn plant(s) provided herein. In another aspect, the average height of the female inbred corn plants provided herein is at least 60% less or lower than the height (or average height) of at least one male inbred corn plant(s) provided herein. In another aspect, the average height of the female inbred corn plants provided herein is at least 65% less or lower than the height (or average height) of at least one male inbred corn plant(s) provided herein. In another aspect, the average height of the female inbred corn plants provided herein is at least 70% less or lower than the height (or average height) of at least one male inbred corn plant(s) provided herein. In another aspect, the average height of the female inbred corn plants provided herein is at least 75% less or lower than the height (or average height) of at least one male inbred corn plant(s) provided herein.

Corn plant height can be measured according to two different methods. According to one method, corn plant height is measured from the ground or soil to the ligule (or collar) of the uppermost fully expanded leaf—i.e., from the ground or soil to the base of the uppermost collared leaf. According to another method, corn plant height is measured from the ground or soil to the uppermost leaf surface of the leaf farthest from the soil. This latter method will typically give a higher plant height than the former method due to measuring a feature of the plant that is further from the ground. According to another method for measuring the height of a corn plant during and after VT stage, plant height can be measured from the ground or soil to the tops of the tassel. Relative plant heights and percentage differences in plant height as provided herein may be applied to each of these methods. For purposes of clarity, however, if the method for measuring plant height is not expressly stated herein, then the plant height is measured as the distance between the ground or soil and the ligule (or collar) of the uppermost fully expanded leaf—i.e., from the ground or soil to the base of the uppermost collared leaf.

According to embodiments of the present disclosure, corn plant heights, average corn plant heights, male-to-female or female-to-male corn plant height differences, male-to-female or female-to-male average corn plant height differences, male-to-female average plant height ratios, female-to-male average plant height ratios, male-to-female plant height ratios, and female-to-male plant height ratios as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the corn plant height(s), average corn plant height(s), male-to-female or female-to-male corn plant height difference(s), male-to-female plant height ratio(s), and/or female-to-male plant height ratio(s) as described herein is at R1 stage. According to present embodiments, corn developmental stages are defined according to the Iowa State University (ISU) method. See, e.g., Ritchie, S. W. et al., How a corn plant develops. Special Report No. 48, Iowa State University, CES, Ames, IA, reprinted 1996, the entire contents and disclosure of which are incorporated herein by reference.

In an aspect, the female inbred corn plants provided herein comprise an average height that is between 2% and 30% less or lower than the height (or average height) of at least one male inbred corn plant(s) (or the average plant height of male inbred corn plants) provided herein. In an aspect, the female inbred corn plants provided herein comprise an average height that is between 2% and 25% less or lower than the height (or average height) of at least one male inbred corn plant(s) (or the average plant height of male inbred corn plants) provided herein. In an aspect, the female inbred corn plants provided herein comprise an average height that is between 2% and 20% less or lower than the height (or average height) of at least one male inbred corn plant(s) (or the average plant height of male inbred corn plants) provided herein. In an aspect, the female inbred corn plants provided herein comprise an average height that is between 2% and 15% less or lower than the height (or average height) of at least one male inbred corn plant(s) (or the average plant height of male inbred corn plants) provided herein. In an aspect, the female inbred corn plants provided herein comprise an average height that is between 2% and 10% less or lower than the height (or average height) of at least one male inbred corn plant(s) (or the average plant height of male inbred corn plants) provided herein. In an aspect, the female inbred corn plants provided herein comprise an average height that is between 2% and 5% less or lower than the height (or average height) of at least one male inbred corn plant(s) (or the average plant height of male inbred corn plants) provided herein. In an aspect, the female inbred corn plants provided herein comprise an average height that is between 2.5% and 30% less or lower than the height (or average height) of at least one male inbred corn plant(s) (or the average plant height of male inbred corn plants) provided herein. In an aspect, the female inbred corn plants provided herein comprise an average height that is between 2.5% and 25% less or lower than the height of at least one male inbred corn plant(s) (or the average plant height of male inbred corn plants) provided herein. In an aspect, the female inbred corn plants provided herein comprise an average height that is between 2.5% and 20% less or lower than the height of at least one male inbred corn plant(s) (or the average plant height of male inbred corn plants) provided herein. In an aspect, the female inbred corn plants provided herein comprise an average height that is between 2.5% and 15% less or lower than the height of at least one male inbred corn plant(s) (or the average plant height of male inbred corn plants) provided herein. In an aspect, the female inbred corn plants provided herein comprise an average height that is between 2.5% and 10% less or lower than the height (or average height) of at least one male inbred corn plant(s) (or the average plant height of male inbred corn plants) provided herein. In an aspect, the female inbred corn plants provided herein comprise an average height that is between 2.5% and 5% less or lower than the height (or average height) of at least one male inbred corn plant(s) (or the average plant height of male inbred corn plants) provided herein.

In an aspect, the female inbred corn plants provided herein comprise an average height that is between 5% and 50% less or lower than the height (or average height) of at least one male inbred corn plant(s) (or the average plant height of male inbred corn plants) provided herein. In an aspect, the female inbred corn plants provided herein comprise an average height that is between 5% and 40% less or lower than the height (or average height) of at least one male inbred corn plant(s) (or the average plant height of male inbred corn plants) provided herein. In an aspect, the female inbred corn plants provided herein comprise an average height that is between 5% and 30% less or lower than the height (or average height) of at least one male inbred corn plant(s) (or the average plant height of male inbred corn plants) provided herein. In an aspect, the female inbred corn plants provided herein comprise an average height that is between 5% and 25% less or lower than the height (or average height) of at least one male inbred corn plant(s) (or the average plant height of male inbred corn plants) provided herein. In an aspect, the female inbred corn plants provided herein comprise an average height that is between 5% and 20% less or lower than the height of at least one male inbred corn plant(s) (or the average plant height of male inbred corn plants) provided herein. In an aspect, the female inbred corn plants provided herein comprise an average height that is between 5% and 15% less or lower than the height of at least one male inbred corn plant(s) (or the average plant height of male inbred corn plants) provided herein. In an aspect, the female inbred corn plants provided herein comprise an average height that is between 5% and 10% less or lower than the height of at least one male inbred corn plant(s) (or the average plant height of male inbred corn plants) provided herein.

In an aspect, the female inbred corn plants provided herein comprise an average height that is between 10% and 50% less or lower than the height (or average height) of at least one male inbred corn plant(s) (or the average plant height of male inbred corn plants) provided herein. In an aspect, the female inbred corn plants provided herein comprise an average height that is between 10% and 40% less or lower than the height (or average height) of at least one male inbred corn plant(s) (or the average plant height of male inbred corn plants) provided herein. In an aspect, the female inbred corn plants provided herein comprise an average height that is between 10% and 30% less or lower than the height (or average height) of at least one male inbred corn plant(s) (or the average plant height of male inbred corn plants) provided herein. In an aspect, the female inbred corn plants provided herein comprise an average height that is between 10% and 25% less or lower than the height (or average height) of at least one male inbred corn plant(s) (or the average plant height of male inbred corn plants) provided herein. In an aspect, the female inbred corn plants provided herein comprise an average height that is between 10% and 20% less or lower than the height (or average height) of at least one male inbred corn plant(s) (or the average plant height of male inbred corn plants) provided herein. In an aspect, the female inbred corn plants provided herein comprise an average height that is between 10% and 15% less or lower than the height (or average height) of at least one male inbred corn plant(s) (or the average plant height of male inbred corn plants) provided herein.

In another aspect, the female inbred corn plants provided herein comprise an average height that is between 15% and 60% less or lower than the height (or average height) of at least one male inbred corn plant(s) (or the average plant height of male inbred corn plants) provided herein. In another aspect, the female inbred corn plants provided herein comprise an average height that is between 15% and 50% less or lower than the height (or average height) of at least one male inbred corn plant(s) (or the average plant height of male inbred corn plants) provided herein. In another aspect, the female inbred corn plants provided herein comprise an average height that is between 15% and 40% less or lower than the height (or average height) of at least one male inbred corn plant(s) (or the average plant height of male inbred corn plants) provided herein. In another aspect, the female inbred corn plants provided herein comprise an average height that is between 15% and 30% less or lower than the height (or average height) of at least one male inbred corn plant(s) (or the average plant height of male inbred corn plants) provided herein. In another aspect, the female inbred corn plants provided herein comprise an average height that is between 15% and 25% less or lower than the height (or average height) of at least one male inbred corn plant(s) (or the average plant height of male inbred corn plants) provided herein. In another aspect, the female inbred corn plants provided herein comprise an average height that is between 15% and 20% less or lower than the height (or average height) of at least one male inbred corn plant(s) (or the average plant height of male inbred corn plants) provided herein.

In another aspect, the female inbred corn plants provided herein comprise an average height that is between 20% and 70% less or lower than the height (or average height) of at least one male inbred corn plant(s) (or the average plant height of male inbred corn plants) provided herein. In another aspect, the female inbred corn plants provided herein comprise an average height that is between 20% and 60% less or lower than the height (or average height) of at least one male inbred corn plant(s) (or the average plant height of male inbred corn plants) provided herein. In another aspect, the female inbred corn plants provided herein comprise an average height that is between 20% and 50% less or lower than the height (or average height) of at least one male inbred corn plant(s) (or the average plant height of male inbred corn plants) provided herein. In another aspect, the female inbred corn plants provided herein comprise an average height that is between 20% and 40% less or lower than the height (or average height) of at least one male inbred corn plant(s) (or the average plant height of male inbred corn plants) provided herein. In another aspect, the female inbred corn plants provided herein comprise an average height that is between 20% and 30% less or lower than the height (or average height) of at least one male inbred corn plant(s) (or the average plant height of male inbred corn plants) provided herein.

In an aspect, the average height of the female inbred corn plants provided herein is at least 0.05 meters less or lower than the height (or average height) of at least one male inbred corn plant(s) (or the average plant height of male inbred corn plants) provided herein. In an aspect, the average height of the female inbred corn plants provided herein is at least 0.06 meters less or lower than the height (or average height) of at least one male inbred corn plant(s) (or the average plant height of male inbred corn plants) provided herein. In an aspect, the average height of the female inbred corn plants provided herein is at least 0.07 meters less or lower than the height (or average height) of at least one male inbred corn plant(s) (or the average plant height of male inbred corn plants) provided herein. In an aspect, the average height of the female inbred corn plants provided herein is at least 0.08 meters less or lower than the height (or average height) of at least one male inbred corn plant(s) (or the average plant height of male inbred corn plants) provided herein. In an aspect, the average height of the female inbred corn plants provided herein is at least 0.09 meters less or lower than the height (or average height) of at least one male inbred corn plant(s) (or the average plant height of male inbred corn plants) provided herein. In an aspect, the average height of the female inbred corn plants provided herein is at least 0.1 meters less or lower than the height (or average height) of at least one male inbred corn plant(s) (or the average plant height of male inbred corn plants) provided herein. In another aspect, the average height of the female inbred corn plants provided herein is at least 0.2 meters less or lower than the height (or average height) of at least one male inbred corn plant(s) (or the average plant height of male inbred corn plants) provided herein. In another aspect, the average height of the female inbred corn plants provided herein is at least 0.3 meters less or lower than the height (or average height) of at least one male inbred corn plant(s) (or the average plant height of male inbred corn plants) provided herein. In another aspect, the average height of the female inbred corn plants provided herein is at least 0.4 meters less or lower than the height (or average height) of at least one male inbred corn plant(s) (or the average plant height of male inbred corn plants) provided herein. In another aspect, the average height of the female inbred corn plants provided herein is at least 0.5 meters less or lower than the height (or average height) of at least one male inbred corn plant(s) (or the average plant height of male inbred corn plants) provided herein. In another aspect, the average height of the female inbred corn plants provided herein is at least 0.6 meters less or lower than the height (or average height) of at least one male inbred corn plant(s) (or the average plant height of male inbred corn plants) provided herein. In another aspect, the average height of the female inbred corn plants provided herein is at least 0.7 meters less or lower than the height (or average height) of at least one male inbred corn plant(s) (or the average plant height of male inbred corn plants) provided herein. In another aspect, the average height of the female inbred corn plants provided herein is at least 0.8 meters less or lower than the height (or average height) of at least one male inbred corn plant(s) (or the average plant height of male inbred corn plants) provided herein. In another aspect, the average height of the female inbred corn plants provided herein is at least 0.9 meters less or lower than the height (or average height) of at least one male inbred corn plant(s) (or the average plant height of male inbred corn plants) provided herein. In another aspect, the average height of the female inbred corn plants provided herein is at least 1.0 meters less or lower than the height (or average height) of at least one male inbred corn plant(s) (or the average plant height of male inbred corn plants) provided herein. In another aspect, the average height of the female inbred corn plants provided herein is at least 1.2 meters less or lower than the height (or average height) of at least one male inbred corn plant(s) (or the average plant height of male inbred corn plants) provided herein. In another aspect, the average height of the female inbred corn plants provided herein is at least 1.4 meters less or lower than the height (or average height) of at least one male inbred corn plant(s) (or the average plant height of male inbred corn plants) provided herein. In another aspect, the average height of the female inbred corn plants provided herein is at least 1.6 meters less or lower than the height (or average height) of at least one male inbred corn plant(s) (or the average plant height of male inbred corn plants) provided herein. In another aspect, the average height of the female inbred corn plants provided herein is at least 1.8 meters less or lower than the height (or average height) of at least one male inbred corn plant(s) (or the average plant height of male inbred corn plants) provided herein. In another aspect, the average height of the female inbred corn plants provided herein is at least 2.0 meters less or lower than the height (or average height) of at least one male inbred corn plant(s) (or the average plant height of male inbred corn plants) provided herein. In another aspect, the average height of the female inbred corn plants provided herein is at least 2.2 meters less or lower than the height (or average height) of at least one male inbred corn plant(s) (or the average plant height of male inbred corn plants) provided herein.

In an aspect, the female inbred corn plants provided herein comprise an average height that is between 0.05 and 1.0 meters less or lower than the height (or average height) of at least one male inbred corn plant(s) (or the average plant height of male inbred corn plants) provided herein. In an aspect, the female inbred corn plants provided herein comprise an average height that is between 0.05 and 0.9 meters less or lower than the height (or average height) of at least one male inbred corn plant(s) (or the average plant height of male inbred corn plants) provided herein. In an aspect, the female inbred corn plants provided herein comprise an average height that is between 0.05 and 0.8 meters less or lower than the height (or average height) of at least one male inbred corn plant(s) (or the average plant height of male inbred corn plants) provided herein. In an aspect, the female inbred corn plants provided herein comprise an average height that is between 0.05 and 0.7 meters less or lower than the height (or average height) of at least one male inbred corn plant(s) (or the average plant height of male inbred corn plants) provided herein. In an aspect, the female inbred corn plants provided herein comprise an average height that is between 0.05 and 0.6 meters less or lower than the height (or average height) of at least one male inbred corn plant(s) (or the average plant height of male inbred corn plants) provided herein. In an aspect, the female inbred corn plants provided herein comprise an average height that is between 0.05 and 0.5 meters less or lower than the height (or average height) of at least one male inbred corn plant(s) (or the average plant height of male inbred corn plants) provided herein. In an aspect, the female inbred corn plants provided herein comprise an average height that is between 0.05 and 0.4 meters less or lower than the height (or average height) of at least one male inbred corn plant(s) (or the average plant height of male inbred corn plants) provided herein. In an aspect, the female inbred corn plants provided herein comprise an average height that is between 0.05 and 0.3 meters less or lower than the height (or average height) of at least one male inbred corn plant(s) (or the average plant height of male inbred corn plants) provided herein. In an aspect, the female inbred corn plants provided herein comprise an average height that is between 0.05 and 0.2 meters less or lower than the height (or average height) of at least one male inbred corn plant(s) (or the average plant height of male inbred corn plants) provided herein. In an aspect, the female inbred corn plants provided herein comprise an average height that is between 0.05 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.06 and 1.0 meters less or lower than the height (or average height) of at least one male inbred corn plant(s) (or the average plant height of male inbred corn plants) provided herein. In an aspect, the female inbred corn plants provided herein comprise an average height that is between 0.06 and 0.9 meters less or lower than the height (or average height) of at least one male inbred corn plant(s) (or the average plant height of male inbred corn plants) provided herein. In an aspect, the female inbred corn plants provided herein comprise an average height that is between 0.06 and 0.8 meters less or lower than the height (or average height) of at least one male inbred corn plant(s) (or the average plant height of male inbred corn plants) provided herein. In an aspect, the female inbred corn plants provided herein comprise an average height that is between 0.06 and 0.7 meters less or lower than the height (or average height) of at least one male inbred corn plant(s) (or the average plant height of male inbred corn plants) provided herein. In an aspect, the female inbred corn plants provided herein comprise an average height that is between 0.06 and 0.6 meters less or lower than the height (or average height) of at least one male inbred corn plant(s) (or the average plant height of male inbred corn plants) provided herein. In an aspect, the female inbred corn plants provided herein comprise an average height that is between 0.06 and 0.5 meters less or lower than the height (or average height) of at least one male inbred corn plant(s) (or the average plant height of male inbred corn plants) provided herein. In an aspect, the female inbred corn plants provided herein comprise an average height that is between 0.06 and 0.4 meters less or lower than the height (or average height) of at least one male inbred corn plant(s) (or the average plant height of male inbred corn plants) provided herein. In an aspect, the female inbred corn plants provided herein comprise an average height that is between 0.06 and 0.3 meters less or lower than the height (or average height) of at least one male inbred corn plant(s) (or the average plant height of male inbred corn plants) provided herein. In an aspect, the female inbred corn plants provided herein comprise an average height that is between 0.06 and 0.2 meters less or lower than the height (or average height) of at least one male inbred corn plant(s) (or the average plant height of male inbred corn plants) provided herein. In an aspect, the female inbred corn plants provided herein comprise an average height that is between 0.06 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.07 and 1.0 meters less or lower than the height (or average height) of at least one male inbred corn plant(s) (or the average plant height of male inbred corn plants) provided herein. In an aspect, the female inbred corn plants provided herein comprise an average height that is between 0.07 and 0.9 meters less or lower than the height (or average height) of at least one male inbred corn plant(s) (or the average plant height of male inbred corn plants) provided herein. In an aspect, the female inbred corn plants provided herein comprise an average height that is between 0.07 and 0.8 meters less or lower than the height (or average height) of at least one male inbred corn plant(s) (or the average plant height of male inbred corn plants) provided herein. In an aspect, the female inbred corn plants provided herein comprise an average height that is between 0.07 and 0.7 meters less or lower than the height (or average height) of at least one male inbred corn plant(s) (or the average plant height of male inbred corn plants) provided herein. In an aspect, the female inbred corn plants provided herein comprise an average height that is between 0.07 and 0.6 meters less or lower than the height (or average height) of at least one male inbred corn plant(s) (or the average plant height of male inbred corn plants) provided herein. In an aspect, the female inbred corn plants provided herein comprise an average height that is between 0.07 and 0.5 meters less or lower than the height (or average height) of at least one male inbred corn plant(s) (or the average plant height of male inbred corn plants) provided herein. In an aspect, the female inbred corn plants provided herein comprise an average height that is between 0.07 and 0.4 meters less or lower than the height (or average height) of at least one male inbred corn plant(s) (or the average plant height of male inbred corn plants) provided herein. In an aspect, the female inbred corn plants provided herein comprise an average height that is between 0.07 and 0.3 meters less or lower than the height (or average height) of at least one male inbred corn plant(s) (or the average plant height of male inbred corn plants) provided herein. In an aspect, the female inbred corn plants provided herein comprise an average height that is between 0.07 and 0.2 meters less or lower than the height (or average height) of at least one male inbred corn plant(s) (or the average plant height of male inbred corn plants) provided herein. In an aspect, the female inbred corn plants provided herein comprise an average height that is between 0.07 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.08 and 1.0 meters less or lower than the height (or average height) of at least one male inbred corn plant(s) (or the average plant height of male inbred corn plants) provided herein. In an aspect, the female inbred corn plants provided herein comprise an average height that is between 0.08 and 0.9 meters less or lower than the height (or average height) of at least one male inbred corn plant(s) (or the average plant height of male inbred corn plants) provided herein. In an aspect, the female inbred corn plants provided herein comprise an average height that is between 0.08 and 0.8 meters less or lower than the height (or average height) of at least one male inbred corn plant(s) (or the average plant height of male inbred corn plants) provided herein. In an aspect, the female inbred corn plants provided herein comprise an average height that is between 0.08 and 0.7 meters less or lower than the height (or average height) of at least one male inbred corn plant(s) (or the average plant height of male inbred corn plants) provided herein. In an aspect, the female inbred corn plants provided herein comprise an average height that is between 0.08 and 0.6 meters less or lower than the height (or average height) of at least one male inbred corn plant(s) (or the average plant height of male inbred corn plants) provided herein. In an aspect, the female inbred corn plants provided herein comprise an average height that is between 0.08 and 0.5 meters less or lower than the height (or average height) of at least one male inbred corn plant(s) (or the average plant height of male inbred corn plants) provided herein. In an aspect, the female inbred corn plants provided herein comprise an average height that is between 0.08 and 0.4 meters less or lower than the height (or average height) of at least one male inbred corn plant(s) (or the average plant height of male inbred corn plants) provided herein. In an aspect, the female inbred corn plants provided herein comprise an average height that is between 0.08 and 0.3 meters less or lower than the height (or average height) of at least one male inbred corn plant(s) (or the average plant height of male inbred corn plants) provided herein. In an aspect, the female inbred corn plants provided herein comprise an average height that is between 0.08 and 0.2 meters less or lower than the height (or average height) of at least one male inbred corn plant(s) (or the average plant height of male inbred corn plants) provided herein. In an aspect, the female inbred corn plants provided herein comprise an average height that is between 0.08 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.09 and 1.0 meters less or lower than the height (or average height) of at least one male inbred corn plant(s) (or the average plant height of male inbred corn plants) provided herein. In an aspect, the female inbred corn plants provided herein comprise an average height that is between 0.09 and 0.9 meters less or lower than the height (or average height) of at least one male inbred corn plant(s) (or the average plant height of male inbred corn plants) provided herein. In an aspect, the female inbred corn plants provided herein comprise an average height that is between 0.09 and 0.8 meters less or lower than the height (or average height) of at least one male inbred corn plant(s) (or the average plant height of male inbred corn plants) provided herein. In an aspect, the female inbred corn plants provided herein comprise an average height that is between 0.09 and 0.7 meters less or lower than the height (or average height) of at least one male inbred corn plant(s) (or the average plant height of male inbred corn plants) provided herein. In an aspect, the female inbred corn plants provided herein comprise an average height that is between 0.09 and 0.6 meters less or lower than the height (or average height) of at least one male inbred corn plant(s) (or the average plant height of male inbred corn plants) provided herein. In an aspect, the female inbred corn plants provided herein comprise an average height that is between 0.09 and 0.5 meters less or lower than the height (or average height) of at least one male inbred corn plant(s) (or the average plant height of male inbred corn plants) provided herein. In an aspect, the female inbred corn plants provided herein comprise an average height that is between 0.09 and 0.4 meters less or lower than the height (or average height) of at least one male inbred corn plant(s) (or the average plant height of male inbred corn plants) provided herein. In an aspect, the female inbred corn plants provided herein comprise an average height that is between 0.09 and 0.3 meters less or lower than the height (or average height) of at least one male inbred corn plant(s) (or the average plant height of male inbred corn plants) provided herein. In an aspect, the female inbred corn plants provided herein comprise an average height that is between 0.09 and 0.2 meters less or lower than the height (or average height) of at least one male inbred corn plant(s) (or the average plant height of male inbred corn plants) provided herein. In an aspect, the female inbred corn plants provided herein comprise an average height that is between 0.09 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.1 and 1.5 meters less or lower than the height (or average height) of at least one male inbred corn plant(s) (or the average plant height of male inbred corn plants) provided herein. In an aspect, the female inbred corn plants provided herein comprise an average height that is between 0.1 and 1.4 meters less or lower than the height (or average height) of at least one male inbred corn plant(s) (or the average plant height of male inbred corn plants) provided herein. In an aspect, the female inbred corn plants provided herein comprise an average height that is between 0.1 and 1.3 meters less or lower than the height (or average height) of at least one male inbred corn plant(s) (or the average plant height of male inbred corn plants) provided herein. In an aspect, the female inbred corn plants provided herein comprise an average height that is between 0.1 and 1.2 meters less or lower than the height (or average height) of at least one male inbred corn plant(s) (or the average plant height of male inbred corn plants) provided herein. In an aspect, the female inbred corn plants provided herein comprise an average height that is between 0.1 and 1.1 meters less or lower than the height (or average height) of at least one male inbred corn plant(s) (or the average plant height of male inbred corn plants) provided herein. In an aspect, the female inbred corn plants provided herein comprise an average height that is between 0.1 and 1.0 meters less or lower than the height (or average height) of at least one male inbred corn plant(s) (or the average plant height of male inbred corn plants) provided herein. In an aspect, the female inbred corn plants provided herein comprise an average height that is between 0.1 and 0.9 meters less or lower than the height (or average height) of at least one male inbred corn plant(s) (or the average plant height of male inbred corn plants) provided herein. In an aspect, the female inbred corn plants provided herein comprise an average height that is between 0.1 and 0.8 meters less or lower than the height (or average height) of at least one male inbred corn plant(s) (or the average plant height of male inbred corn plants) provided herein. In an aspect, the female inbred corn plants provided herein comprise an average height that is between 0.1 and 0.7 meters less or lower than the height (or average height) of at least one male inbred corn plant(s) (or the average plant height of male inbred corn plants) provided herein. In an aspect, the female inbred corn plants provided herein comprise an average height that is between 0.1 and 0.6 meters less or lower than the height (or average height) of at least one male inbred corn plant(s) (or the average plant height of male inbred corn plants) provided herein. In an aspect, the female inbred corn plants provided herein comprise an average height that is between 0.1 and 0.5 meters less or lower than the height (or average height) of at least one male inbred corn plant(s) (or the average plant height of male inbred corn plants) provided herein. In an aspect, the female inbred corn plants provided herein comprise an average height that is between 0.1 and 0.4 meters less or lower than the height (or average height) of at least one male inbred corn plant(s) (or the average plant height of male inbred corn plants) provided herein. In an aspect, the female inbred corn plants provided herein comprise an average height that is between 0.1 and 0.3 meters less or lower than the height (or average height) of at least one male inbred corn plant(s) (or the average plant height of male inbred corn plants) provided herein. In an aspect, the female inbred corn plants provided herein comprise an average height that is between 0.1 and 0.2 meters less or lower than the height (or average height) of at least one male inbred corn plant(s) (or the average plant height of male inbred corn plants) provided herein.

In another aspect, the female inbred corn plants provided herein comprise an average height that is between 0.2 and 1.5 meters less or lower than the height (or average height) of at least one male inbred corn plant(s) (or the average plant height of male inbred corn plants) provided herein. In another aspect, the female inbred corn plants provided herein comprise an average height that is between 0.2 and 1.4 meters less or lower than the height (or average height) of at least one male inbred corn plant(s) (or the average plant height of male inbred corn plants) provided herein. In another aspect, the female inbred corn plants provided herein comprise an average height that is between 0.2 and 1.3 meters less or lower than the height (or average height) of at least one male inbred corn plant(s) (or the average plant height of male inbred corn plants) provided herein. In another aspect, the female inbred corn plants provided herein comprise an average height that is between 0.2 and 1.2 meters less or lower than the height (or average height) of at least one male inbred corn plant(s) (or the average plant height of male inbred corn plants) provided herein. In another aspect, the female inbred corn plants provided herein comprise an average height that is between 0.2 and 1.1 meters less or lower than the height (or average height) of at least one male inbred corn plant(s) (or the average plant height of male inbred corn plants) provided herein. In another aspect, the female inbred corn plants provided herein comprise an average height that is between 0.2 and 1.0 meters less or lower than the height (or average height) of at least one male inbred corn plant(s) (or the average plant height of male inbred corn plants) provided herein. In another aspect, the female inbred corn plants provided herein comprise an average height that is between 0.2 and 0.9 meters less or lower than the height (or average height) of at least one male inbred corn plant(s) (or the average plant height of male inbred corn plants) provided herein. In another aspect, the female inbred corn plants provided herein comprise an average height that is between 0.2 and 0.8 meters less or lower than the height (or average height) of at least one male inbred corn plant(s) (or the average plant height of male inbred corn plants) provided herein. In another aspect, the female inbred corn plants provided herein comprise an average height that is between 0.2 and 0.7 meters less or lower than the height (or average height) of at least one male inbred corn plant(s) (or the average plant height of male inbred corn plants) provided herein. In another aspect, the female inbred corn plants provided herein comprise an average height that is between 0.2 and 0.6 meters less or lower than the height (or average height) of at least one male inbred corn plant(s) (or the average plant height of male inbred corn plants) provided herein. In another aspect, the female inbred corn plants provided herein comprise an average height that is between 0.2 and 0.5 meters less or lower than the height (or average height) of at least one male inbred corn plant(s) (or the average plant height of male inbred corn plants) provided herein. In another aspect, the female inbred corn plants provided herein comprise an average height that is between 0.2 and 0.4 meters less or lower than the height (or average height) of at least one male inbred corn plant(s) (or the average plant height of male inbred corn plants) provided herein. In another aspect, the female inbred corn plants provided herein comprise an average height that is between 0.2 and 0.3 meters less or lower than the height (or average height) of at least one male inbred corn plant(s) (or the average plant height of male inbred corn plants) provided herein.

In another aspect, the female inbred corn plants provided herein comprise an average height that is between 0.3 and 1.5 meters less or lower than the height (or average height) of at least one male inbred corn plant(s) (or the average plant height of male inbred corn plants) provided herein. In another aspect, the female inbred corn plants provided herein comprise an average height that is between 0.3 and 1.4 meters less or lower than the height (or average height) of at least one male inbred corn plant(s) (or the average plant height of male inbred corn plants) provided herein. In another aspect, the female inbred corn plants provided herein comprise an average height that is between 0.3 and 1.3 meters less or lower than the height (or average height) of at least one male inbred corn plant(s) (or the average plant height of male inbred corn plants) provided herein. In another aspect, the female inbred corn plants provided herein comprise an average height that is between 0.3 and 1.2 meters less or lower than the height (or average height) of at least one male inbred corn plant(s) (or the average plant height of male inbred corn plants) provided herein. In another aspect, the female inbred corn plants provided herein comprise an average height that is between 0.3 and 1.1 meters less or lower than the height (or average height) of at least one male inbred corn plant(s) (or the average plant height of male inbred corn plants) provided herein. In another aspect, the female inbred corn plants provided herein comprise an average height that is between 0.3 and 1.0 meters less or lower than the height (or average height) of at least one male inbred corn plant(s) (or the average plant height of male inbred corn plants) provided herein. In another aspect, the female inbred corn plants provided herein comprise an average height that is between 0.3 and 0.9 meters less or lower than the height (or average height) of at least one male inbred corn plant(s) (or the average plant height of male inbred corn plants) provided herein. In another aspect, the female inbred corn plants provided herein comprise an average height that is between 0.3 and 0.8 meters less or lower than the height (or average height) of at least one male inbred corn plant(s) (or the average plant height of male inbred corn plants) provided herein. In another aspect, the female inbred corn plants provided herein comprise an average height that is between 0.3 and 0.7 meters less or lower than the height (or average height) of at least one male inbred corn plant(s) (or the average plant height of male inbred corn plants) provided herein. In another aspect, the female inbred corn plants provided herein comprise an average height that is between 0.3 and 0.6 meters less or lower than the height (or average height) of at least one male inbred corn plant(s) (or the average plant height of male inbred corn plants) provided herein. In another aspect, the female inbred corn plants provided herein comprise an average height that is between 0.3 and 0.5 meters less or lower than the height (or average height) of at least one male inbred corn plant(s) (or the average plant height of male inbred corn plants) provided herein. In another aspect, the female inbred corn plants provided herein comprise an average height that is between 0.3 and 0.4 meters less or lower than the height (or average height) of at least one male inbred corn plant(s) (or the average plant height of male inbred corn plants) provided herein.

In another aspect, the female inbred corn plants provided herein comprise an average height that is between 0.4 and 2.0 meters less or lower than the height (or average height) of at least one male inbred corn plant(s) (or the average plant height of male inbred corn plants) provided herein. In another aspect, the female inbred corn plants provided herein comprise an average height that is between 0.4 and 1.9 meters less or lower than the height (or average height) of at least one male inbred corn plant(s) (or the average plant height of male inbred corn plants) provided herein. In another aspect, the female inbred corn plants provided herein comprise an average height that is between 0.4 and 1.8 meters less or lower than the height (or average height) of at least one male inbred corn plant(s) (or the average plant height of male inbred corn plants) provided herein. In another aspect, the female inbred corn plants provided herein comprise an average height that is between 0.4 and 1.7 meters less or lower than the height (or average height) of at least one male inbred corn plant(s) (or the average plant height of male inbred corn plants) provided herein. In another aspect, the female inbred corn plants provided herein comprise an average height that is between 0.4 and 1.6 meters less or lower than the height (or average height)

of at least one male inbred corn plant(s) (or the average plant height of male inbred corn plants) provided herein. In another aspect, the female inbred corn plants provided herein comprise an average height that is between 0.4 and 1.5 meters less or lower than the height (or average height) of at least one male inbred corn plant(s) (or the average plant height of male inbred corn plants) provided herein. In another aspect, the female inbred corn plants provided herein comprise an average height that is between 0.4 and 1.4 meters less or lower than the height (or average height) of at least one male inbred corn plant(s) (or the average plant height of male inbred corn plants) provided herein. In another aspect, the female inbred corn plants provided herein comprise an average height that is between 0.4 and 1.3 meters less or lower than the height (or average height) of at least one male inbred corn plant(s) (or the average plant height of male inbred corn plants) provided herein. In another aspect, the female inbred corn plants provided herein comprise an average height that is between 0.4 and 1.2 meters less or lower than the height (or average height) of at least one male inbred corn plant(s) (or the average plant height of male inbred corn plants) provided herein. In another aspect, the female inbred corn plants provided herein comprise an average height that is between 0.4 and 1.1 meters less or lower than the height (or average height) of at least one male inbred corn plant(s) (or the average plant height of male inbred corn plants) provided herein. In another aspect, the female inbred corn plants provided herein comprise an average height that is between 0.4 and 1.0 meters less or lower than the height (or average height) of at least one male inbred corn plant(s) (or the average plant height of male inbred corn plants) provided herein. In another aspect, the female inbred corn plants provided herein comprise an average height that is between 0.4 and 0.9 meters less or lower than the height (or average height) of at least one male inbred corn plant(s) (or the average plant height of male inbred corn plants) provided herein. In another aspect, the female inbred corn plants provided herein comprise an average height that is between 0.4 and 0.8 meters less or lower than the height (or average height) of at least one male inbred corn plant(s) (or the average plant height of male inbred corn plants) provided herein. In another aspect, the female inbred corn plants provided herein comprise an average height that is between 0.4 and 0.7 meters less or lower than the height (or average height) of at least one male inbred corn plant(s) (or the average plant height of male inbred corn plants) provided herein. In another aspect, the female inbred corn plants provided herein comprise an average height that is between 0.4 and 0.6 meters less or lower than the height (or average height) of at least one male inbred corn plant(s) (or the average plant height of male inbred corn plants) provided herein. In another aspect, the female inbred corn plants provided herein comprise an average height that is between 0.4 and 0.5 meters less or lower than the height (or average height) of at least one male inbred corn plant(s) (or the average plant height of male inbred corn plants) provided herein.

In another aspect, the female inbred corn plants provided herein comprise an average height that is between 0.5 and 2.0 meters less or lower than the height (or average height) of at least one male inbred corn plant(s) (or the average plant height of male inbred corn plants) provided herein. In another aspect, the female inbred corn plants provided herein comprise an average height that is between 0.5 and 1.9 meters less or lower than the height (or average height) of at least one male inbred corn plant(s) (or the average plant height of male inbred corn plants) provided herein. In another aspect, the female inbred corn plants provided herein comprise an average height that is between 0.5 and 1.8 meters less or lower than the height (or average height) of at least one male inbred corn plant(s) (or the average plant height of male inbred corn plants) provided herein. In another aspect, the female inbred corn plants provided herein comprise an average height that is between 0.5 and 1.7 meters less or lower than the height (or average height) of at least one male inbred corn plant(s) (or the average plant height of male inbred corn plants) provided herein. In another aspect, the female inbred corn plants provided herein comprise an average height that is between 0.5 and 1.6 meters less or lower than the height (or average height) of at least one male inbred corn plant(s) (or the average plant height of male inbred corn plants) provided herein. In another aspect, the female inbred corn plants provided herein comprise an average height that is between 0.5 and 1.5 meters less or lower than the height (or average height) of at least one male inbred corn plant(s) (or the average plant height of male inbred corn plants) provided herein. In another aspect, the female inbred corn plants provided herein comprise an average height that is between 0.5 and 1.4 meters less or lower than the height (or average height) of at least one male inbred corn plant(s) (or the average plant height of male inbred corn plants) provided herein. In another aspect, the female inbred corn plants provided herein comprise an average height that is between 0.5 and 1.3 meters less or lower than the height (or average height) of at least one male inbred corn plant(s) (or the average plant height of male inbred corn plants) provided herein. In another aspect, the female inbred corn plants provided herein comprise an average height that is between 0.5 and 1.2 meters less or lower than the height (or average height) of at least one male inbred corn plant(s) (or the average plant height of male inbred corn plants) provided herein. In another aspect, the female inbred corn plants provided herein comprise an average height that is between 0.5 and 1.1 meters less or lower than the height (or average height) of at least one male inbred corn plant(s) (or the average plant height of male inbred corn plants) provided herein. In another aspect, the female inbred corn plants provided herein comprise an average height that is between 0.5 and 1.0 meters less or lower than the height (or average height) of at least one male inbred corn plant(s) (or the average plant height of male inbred corn plants) provided herein. In another aspect, the female inbred corn plants provided herein comprise an average height that is between 0.5 and 0.9 meters less or lower than the height (or average height) of at least one male inbred corn plant(s) (or the average plant height of male inbred corn plants) provided herein. In another aspect, the female inbred corn plants provided herein comprise an average height that is between 0.5 and 0.8 meters less or lower than the height (or average height) of at least one male inbred corn plant(s) (or the average plant height of male inbred corn plants) provided herein. In another aspect, the female inbred corn plants provided herein comprise an average height that is between 0.5 and 0.7 meters less or lower than the height (or average height) of at least one male inbred corn plant(s) (or the average plant height of male inbred corn plants) provided herein. In another aspect, the female inbred corn plants provided herein comprise an average height that is between 0.5 and 0.6 meters less or lower than the height (or average height) of at least one male inbred corn plant(s) (or the average plant height of male inbred corn plants) provided herein.

In another aspect, the female inbred corn plants provided herein comprise an average height that is between 0.6 and 2.2 meters less or lower than the height (or average height) of at least one male inbred corn plant(s) (or the average plant height of male inbred corn plants) provided herein. In another aspect, the female inbred corn plants provided herein comprise an average height that is between 0.6 and 2.1 meters less or lower than the height (or average height) of at least one male inbred corn plant(s) (or the average plant height of male inbred corn plants) provided herein. In another aspect, the female inbred corn plants provided herein comprise an average height that is between 0.6 and 2.0 meters less or lower than the height (or average height) of at least one male inbred corn plant(s) (or the average plant height of male inbred corn plants) provided herein. In another aspect, the female inbred corn plants provided herein comprise an average height that is between 0.6 and 1.9 meters less or lower than the height (or average height) of at least one male inbred corn plant(s) (or the average plant height of male inbred corn plants) provided herein. In another aspect, the female inbred corn plants provided herein comprise an average height that is between 0.6 and 1.8 meters less or lower than the height (or average height) of at least one male inbred corn plant(s) (or the average plant height of male inbred corn plants) provided herein. In another aspect, the female inbred corn plants provided herein comprise an average height that is between 0.6 and 1.7 meters less or lower than the height (or average height) of at least one male inbred corn plant(s) (or the average plant height of male inbred corn plants) provided herein. In another aspect, the female inbred corn plants provided herein comprise an average height that is between 0.6 and 1.6 meters less or lower than the height (or average height) of at least one male inbred corn plant(s) (or the average plant height of male inbred corn plants) provided herein. In another aspect, the female inbred corn plants provided herein comprise an average height that is between 0.6 and 1.5 meters less or lower than the height (or average height) of at least one male inbred corn plant(s) (or the average plant height of male inbred corn plants) provided herein. In another aspect, the female inbred corn plants provided herein comprise an average height that is between 0.6 and 1.4 meters less or lower than the height (or average height) of at least one male inbred corn plant(s) (or the average plant height of male inbred corn plants) provided herein. In another aspect, the female inbred corn plants provided herein comprise an average height that is between 0.6 and 1.3 meters less or lower than the height (or average height) of at least one male inbred corn plant(s) (or the average plant height of male inbred corn plants) provided herein. In another aspect, the female inbred corn plants provided herein comprise an average height that is between 0.6 and 1.2 meters less or lower than the height (or average height) of at least one male inbred corn plant(s) (or the average plant height of male inbred corn plants) provided herein. In another aspect, the female inbred corn plants provided herein comprise an average height that is between 0.6 and 1.1 meters less or lower than the height (or average height) of at least one male inbred corn plant(s) (or the average plant height of male inbred corn plants) provided herein. In another aspect, the female inbred corn plants provided herein comprise an average height that is between 0.6 and 1.0 meters less or lower than the height (or average height) of at least one male inbred corn plant(s) (or the average plant height of male inbred corn plants) provided herein. In another aspect, the female inbred corn plants provided herein comprise an average height that is between 0.6 and 0.9 meters less or lower than the height (or average height) of at least one male inbred corn plant(s) (or the average plant height of male inbred corn plants) provided herein. In another aspect, the female inbred corn plants provided herein comprise an average height that is between 0.6 and 0.8 meters less or lower than the height (or average height) of at least one male inbred corn plant(s) (or the average plant height of male inbred corn plants) provided herein. In another aspect, the female inbred corn plants provided herein comprise an average height that is between 0.6 and 0.7 meters less or lower than the height (or average height) of at least one male inbred corn plant(s) (or the average plant height of male inbred corn plants) provided herein.

In another aspect, the female inbred corn plants provided herein comprise an average height that is between 0.7 and 2.2 meters less or lower than the height (or average height) of at least one male inbred corn plant(s) (or the average plant height of male inbred corn plants) provided herein. In another aspect, the female inbred corn plants provided herein comprise an average height that is between 0.7 and 2.1 meters less or lower than the height (or average height) of at least one male inbred corn plant(s) (or the average plant height of male inbred corn plants) provided herein. In another aspect, the female inbred corn plants provided herein comprise an average height that is between 0.7 and 2.0 meters less or lower than the height (or average height) of at least one male inbred corn plant(s) (or the average plant height of male inbred corn plants) provided herein. In another aspect, the female inbred corn plants provided herein comprise an average height that is between 0.7 and 1.9 meters less or lower than the height (or average height) of at least one male inbred corn plant(s) (or the average plant height of male inbred corn plants) provided herein. In another aspect, the female inbred corn plants provided herein comprise an average height that is between 0.7 and 1.8 meters less or lower than the height (or average height) of at least one male inbred corn plant(s) (or the average plant height of male inbred corn plants) provided herein. In another aspect, the female inbred corn plants provided herein comprise an average height that is between 0.7 and 1.7 meters less or lower than the height (or average height) of at least one male inbred corn plant(s) (or the average plant height of male inbred corn plants) provided herein. In another aspect, the female inbred corn plants provided herein comprise an average height that is between 0.7 and 1.6 meters less or lower than the height (or average height) of at least one male inbred corn plant(s) (or the average plant height of male inbred corn plants) provided herein. In another aspect, the female inbred corn plants provided herein comprise an average height that is between 0.7 and 1.5 meters less or lower than the height (or average height) of at least one male inbred corn plant(s) (or the average plant height of male inbred corn plants) provided herein. In another aspect, the female inbred corn plants provided herein comprise an average height that is between 0.7 and 1.4 meters less or lower than the height (or average height) of at least one male inbred corn plant(s) (or the average plant height of male inbred corn plants) provided herein. In another aspect, the female inbred corn plants provided herein comprise an average height that is between 0.7 and 1.3 meters less or lower than the height (or average height) of at least one male inbred corn plant(s) (or the average plant height of male inbred corn plants) provided herein. In another aspect, the female inbred corn plants provided herein comprise an average height that is between 0.7 and 1.2 meters less or lower than the height (or average height) of at least one male inbred corn plant(s) (or the average plant height of male inbred corn plants) provided herein. In another aspect, the female inbred corn plants provided herein comprise an average height that is between 0.7 and 1.1 meters less or lower than the height (or average height) of at least one male inbred corn plant(s) (or the average plant height of male inbred corn plants) provided herein. In another aspect, the female inbred corn plants provided herein comprise an average height that is between 0.7 and 1.0 meters less or lower than the height (or average height) of at least one male inbred corn plant(s) (or the average plant height of male inbred corn plants) provided herein. In another aspect, the female inbred corn plants provided herein comprise an average height that is between 0.7 and 0.9 meters less or lower than the height (or average height) of at least one male inbred corn plant(s) (or the average plant height of male inbred corn plants) provided herein. In another aspect, the female inbred corn plants provided herein comprise an average height that is between 0.7 and 0.8 meters less or lower than the height (or average height) of at least one male inbred corn plant(s) (or the average plant height of male inbred corn plants) provided herein.

In another aspect, the female inbred corn plants provided herein comprise an average height that is between 0.8 and 2.4 meters less or lower than the height (or average height) of at least one male inbred corn plant(s) (or the average plant height of male inbred corn plants) provided herein. In another aspect, the female inbred corn plants provided herein comprise an average height that is between 0.8 and 2.3 meters less or lower than the height (or average height) of at least one male inbred corn plant(s) (or the average plant height of male inbred corn plants) provided herein. In another aspect, the female inbred corn plants provided herein comprise an average height that is between 0.8 and 2.2 meters less or lower than the height (or average height) of at least one male inbred corn plant(s) (or the average plant height of male inbred corn plants) provided herein. In another aspect, the female inbred corn plants provided herein comprise an average height that is between 0.8 and 2.1 meters less or lower than the height (or average height) of at least one male inbred corn plant(s) (or the average plant height of male inbred corn plants) provided herein. In another aspect, the female inbred corn plants provided herein comprise an average height that is between 0.8 and 2.0 meters less or lower than the height (or average height) of at least one male inbred corn plant(s) (or the average plant height of male inbred corn plants) provided herein. In another aspect, the female inbred corn plants provided herein comprise an average height that is between 0.8 and 1.9 meters less or lower than the height (or average height) of at least one male inbred corn plant(s) (or the average plant height of male inbred corn plants) provided herein. In another aspect, the female inbred corn plants provided herein comprise an average height that is between 0.8 and 1.8 meters less or lower than the height (or average height) of at least one male inbred corn plant(s) (or the average plant height of male inbred corn plants) provided herein. In another aspect, the female inbred corn plants provided herein comprise an average height that is between 0.8 and 1.7 meters less or lower than the height (or average height) of at least one male inbred corn plant(s) (or the average plant height of male inbred corn plants) provided herein. In another aspect, the female inbred corn plants provided herein comprise an average height that is between 0.8 and 1.6 meters less or lower than the height (or average height) of at least one male inbred corn plant(s) (or the average plant height of male inbred corn plants) provided herein. In another aspect, the female inbred corn plants provided herein comprise an average height that is between 0.8 and 1.5 meters less or lower than the height (or average height) of at least one male inbred corn plant(s) (or the average plant height of male inbred corn plants) provided herein. In another aspect, the female inbred corn plants provided herein comprise an average height that is between 0.8 and 1.4 meters less or lower than the height (or average height) of at least one male inbred corn plant(s) (or the average plant height of male inbred corn plants) provided herein. In another aspect, the female inbred corn plants provided herein comprise an average height that is between 0.8 and 1.3 meters less or lower than the height (or average height) of at least one male inbred corn plant(s) (or the average plant height of male inbred corn plants) provided herein. In another aspect, the female inbred corn plants provided herein comprise an average height that is between 0.8 and 1.2 meters less or lower than the height (or average height) of at least one male inbred corn plant(s) (or the average plant height of male inbred corn plants) provided herein. In another aspect, the female inbred corn plants provided herein comprise an average height that is between 0.8 and 1.1 meters less or lower than the height (or average height) of at least one male inbred corn plant(s) (or the average plant height of male inbred corn plants) provided herein. In another aspect, the female inbred corn plants provided herein comprise an average height that is between 0.8 and 1.0 meters less or lower than the height (or average height) of at least one male inbred corn plant(s) (or the average plant height of male inbred corn plants) provided herein. In another aspect, the female inbred corn plants provided herein comprise an average height that is between 0.8 and 0.9 meters less or lower than the height of at least one male inbred corn plant (or the average plant height of male inbred corn plants) provided herein.

In another aspect, the female inbred corn plants provided herein comprise an average height that is between 0.9 and 2.4 meters less or lower than the height (or average height) of at least one male inbred corn plant(s) (or the average plant height of male inbred corn plants) provided herein. In another aspect, the female inbred corn plants provided herein comprise an average height that is between 0.9 and 2.3 meters less or lower than the height (or average height) of at least one male inbred corn plant(s) (or the average plant height of male inbred corn plants) provided herein. In another aspect, the female inbred corn plants provided herein comprise an average height that is between 0.9 and 2.2 meters less or lower than the height (or average height) of at least one male inbred corn plant(s) (or the average plant height of male inbred corn plants) provided herein. In another aspect, the female inbred corn plants provided herein comprise an average height that is between 0.9 and 2.1 meters less or lower than the height (or average height) of at least one male inbred corn plant(s) (or the average plant height of male inbred corn plants) provided herein. In another aspect, the female inbred corn plants provided herein comprise an average height that is between 0.9 and 2.0 meters less or lower than the height (or average height) of at least one male inbred corn plant(s) (or the average plant height of male inbred corn plants) provided herein. In another aspect, the female inbred corn plants provided herein comprise an average height that is between 0.9 and 1.9 meters less or lower than the height (or average height) of at least one male inbred corn plant(s) (or the average plant height of male inbred corn plants) provided herein. In another aspect, the female inbred corn plants provided herein comprise an average height that is between 0.9 and 1.8 meters less or lower than the height (or average height) of at least one male inbred corn plant(s) (or the average plant height of male inbred corn plants) provided herein. In another aspect, the female inbred corn plants provided herein comprise an average height that is between 0.9 and 1.7 meters less or lower than the height (or average height) of at least one male inbred corn plant(s) (or the average plant height of male inbred corn plants) provided herein. In another aspect, the female inbred corn plants provided herein comprise an average height that is between 0.9 and 1.6 meters less or lower than the height (or average height) of at least one male inbred corn plant(s) (or the average plant height of male inbred corn plants) provided herein. In another aspect, the female inbred corn plants provided herein comprise an average height that is between 0.9 and 1.5 meters less or lower than the height (or average height) of at least one male inbred corn plant(s) (or the average plant height of male inbred corn plants) provided herein. In another aspect, the female inbred corn plants provided herein comprise an average height that is between 0.9 and 1.4 meters less or lower than the height (or average height) of at least one male inbred corn plant(s) (or the average plant height of male inbred corn plants) provided herein. In another aspect, the female inbred corn plants provided herein comprise an average height that is between 0.9 and 1.3 meters less or lower than the height (or average height) of at least one male inbred corn plant(s) (or the average plant height of male inbred corn plants) provided herein. In another aspect, the female inbred corn plants provided herein comprise an average height that is between 0.9 and 1.2 meters less or lower than the height (or average height) of at least one male inbred corn plant(s) (or the average plant height of male inbred corn plants) provided herein. In another aspect, the female inbred corn plants provided herein comprise an average height that is between 0.9 and 1.1 meters less or lower than the height (or average height) of at least one male inbred corn plant(s) (or the average plant height of male inbred corn plants) provided herein. In another aspect, the female inbred corn plants provided herein comprise an average height that is between 0.9 and 1.0 meters less or lower than the height of at least one male inbred corn plant (or the average plant height of male inbred corn plants) provided herein.

In another aspect, the female inbred corn plants provided herein comprise an average height that is between 1.0 and 2.5 meters less or lower than the height (or average height) of at least one male inbred corn plant(s) (or the average plant height of male inbred corn plants) provided herein. In another aspect, the female inbred corn plants provided herein comprise an average height that is between 1.0 and 2.4 meters less or lower than the height (or average height) of at least one male inbred corn plant(s) (or the average plant height of male inbred corn plants) provided herein. In another aspect, the female inbred corn plants provided herein comprise an average height that is between 1.0 and 2.3 meters less or lower than the height (or average height) of at least one male inbred corn plant(s) (or the average plant height of male inbred corn plants) provided herein. In another aspect, the female inbred corn plants provided herein comprise an average height that is between 1.0 and 2.2 meters less or lower than the height (or average height) of at least one male inbred corn plant(s) (or the average plant height of male inbred corn plants) provided herein. In another aspect, the female inbred corn plants provided herein comprise an average height that is between 1.0 and 2.1 meters less or lower than the height (or average height) of at least one male inbred corn plant(s) (or the average plant height of male inbred corn plants) provided herein. In another aspect, the female inbred corn plants provided herein comprise an average height that is between 1.0 and 2.0 meters less or lower than the height (or average height) of at least one male inbred corn plant(s) (or the average plant height of male inbred corn plants) provided herein. In another aspect, the female inbred corn plants provided herein comprise an average height that is between 1.0 and 1.9 meters less or lower than the height (or average height) of at least one male inbred corn plant(s) (or the average plant height of male inbred corn plants) provided herein. In another aspect, the female inbred corn plants provided herein comprise an average height that is between 1.0 and 1.8 meters less or lower than the height (or average height) of at least one male inbred corn plant(s) (or the average plant height of male inbred corn plants) provided herein. In another aspect, the female inbred corn plants provided herein comprise an average height that is between 1.0 and 1.7 meters less or lower than the height (or average height) of at least one male inbred corn plant(s) (or the average plant height of male inbred corn plants) provided herein. In another aspect, the female inbred corn plants provided herein comprise an average height that is between 1.0 and 1.6 meters less or lower than the height (or average height) of at least one male inbred corn plant(s) (or the average plant height of male inbred corn plants) provided herein. In another aspect, the female inbred corn plants provided herein comprise an average height that is between 1.0 and 1.5 meters less or lower than the height (or average height) of at least one male inbred corn plant(s) (or the average plant height of male inbred corn plants) provided herein. In another aspect, the female inbred corn plants provided herein comprise an average height that is between 1.0 and 1.4 meters less or lower than the height (or average height) of at least one male inbred corn plant(s) (or the average plant height of male inbred corn plants) provided herein. In another aspect, the female inbred corn plants provided herein comprise an average height that is between 1.0 and 1.3 meters less or lower than the height (or average height) of at least one male inbred corn plant(s) (or the average plant height of male inbred corn plants) provided herein. In another aspect, the female inbred corn plants provided herein comprise an average height that is between 1.0 and 1.2 meters less or lower than the height (or average height) of at least one male inbred corn plant(s) (or the average plant height of male inbred corn plants) provided herein. In another aspect, the female inbred corn plants provided herein comprise an average height that is between 1.0 and 1.1 meters less or lower than the height (or average height) of at least one male inbred corn plant(s) (or the average plant height of male inbred corn plants) provided herein.

In another aspect, the female inbred corn plants provided herein comprise an average height that is between 1.2 and 2.5 meters less or lower than the height (or average height) of at least one male inbred corn plant(s) (or the average plant height of male inbred corn plants) provided herein. In another aspect, the female inbred corn plants provided herein comprise an average height that is between 1.2 and 2.4 meters less or lower than the height (or average height) of at least one male inbred corn plant(s) (or the average plant height of male inbred corn plants) provided herein. In another aspect, the female inbred corn plants provided herein comprise an average height that is between 1.2 and 2.3 meters less or lower than the height (or average height) of at least one male inbred corn plant(s) (or the average plant height of male inbred corn plants) provided herein. In another aspect, the female inbred corn plants provided herein comprise an average height that is between 1.2 and 2.2 meters less or lower than the height (or average height) of at least one male inbred corn plant(s) (or the average plant height of male inbred corn plants) provided herein. In another aspect, the female inbred corn plants provided herein comprise an average height that is between 1.2 and 2.1 meters less or lower than the height (or average height) of at least one male inbred corn plant(s) (or the average plant height of male inbred corn plants) provided herein. In another aspect, the female inbred corn plants provided herein comprise an average height that is between 1.2 and 2.0 meters less or lower than the height (or average height) of at least one male inbred corn plant(s) (or the average plant height of male inbred corn plants) provided herein. In another aspect, the female inbred corn plants provided herein comprise an average height that is between 1.2 and 1.9 meters less or lower than the height (or average height) of at least one male inbred corn plant(s) (or the average plant height of male inbred corn plants) provided herein. In another aspect, the female inbred corn plants provided herein comprise an average height that is between 1.2 and 1.8 meters less or lower than the height (or average height) of at least one male inbred corn plant(s) (or the average plant height of male inbred corn plants) provided herein. In another aspect, the female inbred corn plants provided herein comprise an average height that is between 1.2 and 1.7 meters less or lower than the height (or average height) of at least one male inbred corn plant(s) (or the average plant height of male inbred corn plants) provided herein. In another aspect, the female inbred corn plants provided herein comprise an average height that is between 1.2 and 1.6 meters less or lower than the height (or average height) of at least one male inbred corn plant(s) (or the average plant height of male inbred corn plants) provided herein. In another aspect, the female inbred corn plants provided herein comprise an average height that is between 1.2 and 1.5 meters less or lower than the height (or average height) of at least one male inbred corn plant(s) (or the average plant height of male inbred corn plants) provided herein. In another aspect, the female inbred corn plants provided herein comprise an average height that is between 1.2 and 1.4 meters less or lower than the height (or average height) of at least one male inbred corn plant(s) (or the average plant height of male inbred corn plants) provided herein. In another aspect, the female inbred corn plants provided herein comprise an average height that is between 1.2 and 1.3 meters less or lower than the height (or average height) of at least one male inbred corn plant(s) (or the average plant height of male inbred corn plants) provided herein.

In another aspect, the female inbred corn plants provided herein comprise an average height that is between 1.4 and 2.5 meters less or lower than the height (or average height) of at least one male inbred corn plant(s) (or the average plant height of male inbred corn plants) provided herein. In another aspect, the female inbred corn plants provided herein comprise an average height that is between 1.4 and 2.4 meters less or lower than the height (or average height) of at least one male inbred corn plant(s) (or the average plant height of male inbred corn plants) provided herein. In another aspect, the female inbred corn plants provided herein comprise an average height that is between 1.4 and 2.3 meters less or lower than the height (or average height) of at least one male inbred corn plant(s) (or the average plant height of male inbred corn plants) provided herein. In another aspect, the female inbred corn plants provided herein comprise an average height that is between 1.4 and 2.2 meters less or lower than the height (or average height) of at least one male inbred corn plant(s) (or the average plant height of male inbred corn plants) provided herein. In another aspect, the female inbred corn plants provided herein comprise an average height that is between 1.4 and 2.1 meters less or lower than the height (or average height) of at least one male inbred corn plant(s) (or the average plant height of male inbred corn plants) provided herein. In another aspect, the female inbred corn plants provided herein comprise an average height that is between 1.4 and 2.0 meters less or lower than the height (or average height) of at least one male inbred corn plant(s) (or the average plant height of male inbred corn plants) provided herein. In another aspect, the female inbred corn plants provided herein comprise an average height that is between 1.4 and 1.9 meters less or lower than the height (or average height) of at least one male inbred corn plant(s) (or the average plant height of male inbred corn plants) provided herein. In another aspect, the female inbred corn plants provided herein comprise an average height that is between 1.4 and 1.8 meters less or lower than the height (or average height) of at least one male inbred corn plant(s) (or the average plant height of male inbred corn plants) provided herein. In another aspect, the female inbred corn plants provided herein comprise an average height that is between 1.4 and 1.7 meters less or lower than the height (or average height) of at least one male inbred corn plant(s) (or the average plant height of male inbred corn plants) provided herein. In another aspect, the female inbred corn plants provided herein comprise an average height that is between 1.4 and 1.6 meters less or lower than the height (or average height) of at least one male inbred corn plant(s) (or the average plant height of male inbred corn plants) provided herein. In another aspect, the female inbred corn plants provided herein comprise an average height that is between 1.4 and 1.5 meters less or lower than the height (or average height) of at least one male inbred corn plant(s) (or the average plant height of male inbred corn plants) provided herein.

In another aspect, the female inbred corn plants provided herein comprise an average height that is between 1.6 and 2.5 meters less or lower than the height (or average height) of at least one male inbred corn plant(s) (or the average plant height of male inbred corn plants) provided herein. In another aspect, the female inbred corn plants provided herein comprise an average height that is between 1.6 and 2.4 meters less or lower than the height (or average height) of at least one male inbred corn plant(s) (or the average plant height of male inbred corn plants) provided herein. In another aspect, the female inbred corn plants provided herein comprise an average height that is between 1.6 and 2.3 meters less or lower than the height (or average height) of at least one male inbred corn plant(s) (or the average plant height of male inbred corn plants) provided herein. In another aspect, the female inbred corn plants provided herein comprise an average height that is between 1.6 and 2.2 meters less or lower than the height (or average height) of at least one male inbred corn plant(s) (or the average plant height of male inbred corn plants) provided herein. In another aspect, the female inbred corn plants provided herein comprise an average height that is between 1.6 and 2.1 meters less or lower than the height (or average height) of at least one male inbred corn plant(s) (or the average plant height of male inbred corn plants) provided herein. In another aspect, the female inbred corn plants provided herein comprise an average height that is between 1.6 and 2.0 meters less or lower than the height (or average height) of at least one male inbred corn plant(s) (or the average plant height of male inbred corn plants) provided herein. In another aspect, the female inbred corn plants provided herein comprise an average height that is between 1.6 and 1.9 meters less or lower than the height (or average height)

of at least one male inbred corn plant(s) (or the average plant height of male inbred corn plants) provided herein. In another aspect, the female inbred corn plants provided herein comprise an average height that is between 1.6 and 1.8 meters less or lower than the height of at least one male inbred corn plant (or the average plant height of male inbred corn plants) provided herein.

In another aspect, the female inbred corn plants provided herein comprise an average height that is between 1.8 and 2.5 meters less or lower than the height (or average height) of at least one male inbred corn plant(s) (or the average plant height of male inbred corn plants) provided herein. In another aspect, the female inbred corn plants provided herein comprise an average height that is between 1.8 and 2.4 meters less or lower than the height (or average height) of at least one male inbred corn plant(s) (or the average plant height of male inbred corn plants) provided herein. In another aspect, the female inbred corn plants provided herein comprise an average height that is between 1.8 and 2.3 meters less or lower than the height (or average height) of at least one male inbred corn plant(s) (or the average plant height of male inbred corn plants) provided herein. In another aspect, the female inbred corn plants provided herein comprise an average height that is between 1.8 and 2.2 meters less or lower than the height (or average height) of at least one male inbred corn plant(s) (or the average plant height of male inbred corn plants) provided herein. In another aspect, the female inbred corn plants provided herein comprise an average height that is between 1.8 and 2.1 meters less or lower than the height (or average height) of at least one male inbred corn plant(s) (or the average plant height of male inbred corn plants) provided herein. In another aspect, the female inbred corn plants provided herein comprise an average height that is between 1.8 and 2.0 meters less or lower than the height of at least one male inbred corn plant (or the average plant height of male inbred corn plants) provided herein.

In an aspect, a female corn plant provided herein comprises one or more ears at least 14 inches above ground level. In another aspect, a female corn plant provided herein comprises one or more ears at least 15 inches above ground level. In another aspect, a female corn plant provided herein comprises one or more ears at least 16 inches above ground level. In another aspect, a female corn plant provided herein comprises one or more ears at least 17 inches above ground level. In another aspect, a female corn plant provided herein comprises one or more ears at least 18 inches above ground level. In another aspect, a female corn plant provided herein comprises one or more ears at least 19 inches above ground level. In another aspect, a female corn plant provided herein comprises one or more ears at least 20 inches above ground level. In another aspect, a female corn plant provided herein comprises one or more ears at least 21 inches above ground level. In another aspect, a female corn plant provided herein comprises one or more ears at least 22 inches above ground level. In another aspect, a female corn plant provided herein comprises one or more ears at least 23 inches above ground level. In another aspect, a female corn plant provided herein comprises one or more ears at least 24 inches above ground level. In another aspect, a female corn plant provided herein comprises one or more ears at least 25 inches above ground level. In another aspect, a female corn plant provided herein comprises one or more ears at least 26 inches above ground level. In another aspect, a female corn plant provided herein comprises one or more ears at least 27 inches above ground level. In another aspect, a female corn plant provided herein comprises one or more ears at least 28 inches above ground level. In another aspect, a female corn plant provided herein comprises one or more ears at least 29 inches above ground level. In another aspect, a female corn plant provided herein comprises one or more ears at least 30 inches above ground level.

According to embodiments of the present disclosure, corn ear heights or average corn ear height of (or on) female corn plants as described herein (e.g., in a corn production field) may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the corn ear height(s) and/or average corn ear height(s) of (or on) female corn plants as described herein is at R1 stage.

In an aspect, at least one female corn plant provided herein comprises at least one ear or an average ear height that is at least 14 inches above ground level. In another aspect, at least one female corn plant provided herein comprises at least one ear or an average ear height that is at least 15 inches above ground level. In another aspect, at least one female corn plant provided herein comprises at least one ear that is at least 16 inches above ground level. In another aspect, at least one female corn plant provided herein comprises at least one ear or an average ear height that is at least 17 inches above ground level. In another aspect, at least one female corn plant provided herein comprises at least one ear that is at least 18 inches above ground level. In another aspect, at least one female corn plant provided herein comprises at least one ear or an average ear height that is at least 19 inches above ground level. In another aspect, at least one female corn plant provided herein comprises at least one ear that is at least 20 inches above ground level. In another aspect, at least one female corn plant provided herein comprises at least one ear or an average ear height that is at least 21 inches above ground level. In another aspect, at least one female corn plant provided herein comprises at least one ear or an average ear height that is at least 22 inches above ground level. In another aspect, at least one female corn plant provided herein comprises at least one ear that is at least 23 inches above ground level. In another aspect, at least one female corn plant provided herein comprises at least one ear or an average ear height that is at least 24 inches above ground level. In another aspect, at least one female corn plant provided herein comprises at least one ear or an average ear height that is at least 25 inches above ground level. In another aspect, at least one female corn plant provided herein comprises at least one ear or an average ear height that is at least 26 inches above ground level. In another aspect, at least one female corn plant provided herein comprises at least one ear or an average ear height that is at least 27 inches above ground level. In another aspect, at least one female corn plant provided herein comprises at least one ear or an average ear height that is at least 28 inches above ground level. In another aspect, at least one female corn plant provided herein comprises at least one ear or an average ear height that is at least 29 inches above ground level. In another aspect, at least one female corn plant provided herein comprises at least one ear or an average ear height that is at least 30 inches above ground level.

In an aspect, at least one female corn plant provided herein comprises at least one ear or an average ear height between 14 and 40 inches above ground level. In an aspect, at least one female corn plant provided herein comprises at least one ear or an average ear height between 14 and 35 inches above ground level. In an aspect, at least one female corn plant provided herein comprises at least one ear or an average ear height between 14 and 30 inches above ground level. In an aspect, at least one female corn plant provided herein comprises at least one ear or an average ear height between 14 and 25 inches above ground level. In an aspect, at least one female corn plant provided herein comprises at least one ear or an average ear height between 14 and 20 inches above ground level. In an aspect, at least one female corn plant provided herein comprises at least one ear or an average ear height between 14 and 18 inches above ground level. In an aspect, at least one female corn plant provided herein comprises at least one ear or an average ear height between 14 and 16 inches above ground level.

In an aspect, at least one female corn plant provided herein comprises at least one ear or an average ear height between 16 and 40 inches above ground level. In an aspect, at least one female corn plant provided herein comprises at least one ear or an average ear height between 16 and 35 inches above ground level. In an aspect, at least one female corn plant provided herein comprises at least one ear or an average ear height between 16 and 30 inches above ground level. In an aspect, at least one female corn plant provided herein comprises at least one ear or an average ear height between 16 and 25 inches above ground level. In an aspect, at least one female corn plant provided herein comprises at least one ear or an average ear height between 16 and 20 inches above ground level. In another aspect, at least one female corn plant provided herein comprises at least one ear or an average ear height between 16 and 18 inches above ground level.

In an aspect, at least one female corn plant provided herein comprises at least one ear or an average ear height between 18 and 40 inches above ground level. In an aspect, at least one female corn plant provided herein comprises at least one ear or an average ear height between 18 and 35 inches above ground level. In an aspect, at least one female corn plant provided herein comprises at least one ear or an average ear height between 18 and 30 inches above ground level. In an aspect, at least one female corn plant provided herein comprises at least one ear or an average ear height between 18 and 25 inches above ground level. In an aspect, at least one female corn plant provided herein comprises at least one ear or an average ear height between 18 and 22 inches above ground level. In another aspect, at least one female corn plant provided herein comprises at least one ear or an average ear height between 18 and 20 inches above ground level.

In an aspect, at least one female corn plant provided herein comprises at least one ear or an average ear height between 20 and 40 inches above ground level. In an aspect, at least one female corn plant provided herein comprises at least one ear or an average ear height between 20 and 35 inches above ground level. In an aspect, at least one female corn plant provided herein comprises at least one ear or an average ear height between 20 and 30 inches above ground level. In an aspect, at least one female corn plant provided herein comprises at least one ear or an average ear height between 20 and 25 inches above ground level. In another aspect, at least one female corn plant provided herein comprises at least one ear or an average ear height between 20 and 22 inches above ground level.

The description above for a female corn plant having at least one ear at or above a height, or within a height range, can also be applied to a plurality, row(s) or population of female corn plants used for seed production.

As used herein, the term "pollination" refers to the transfer of pollen from a male corn plant, or male floret, to a receptive structure of a female corn plant, or female floret. An example of a receptive structure of a female corn plant is a silk. It is appreciated in the art that a corn plant can pollinate itself (e.g., it is capable of self-pollination) if not detasseled, etc. In an aspect, a corn plant provided herein is not capable of self-pollination.

As used herein, the term "fertilization" refers to the union of a male gamete and a female gamete to produce a kernel, or fertilized egg, following pollination. In an aspect, fertilization is performed by wind. In another aspect, fertilization is performed by human intervention. In another aspect, fertilization is performed by an animal or insect.

As used herein, the term "crossing" refers to the deliberate mating of two plants. The two types of plants can be distantly related, closely related, or identical. In an aspect, crossing comprises pollination and/or fertilization of a plurality or population of female inbred corn plants with pollen from at least one male inbred corn plant. In another aspect, crossing comprises pollination and/or fertilization of a plurality or population of female corn plants with pollen from at least one male corn plant. In another aspect, crossing comprises pollination and/or fertilization of a female corn plant or inbred with pollen from at least one male corn plant.

As used herein, a male corn plant and a female corn plant are in "proximity" or "near" to one other if they are physically separated by a distance short enough to allow cross-pollination to occur.

As used herein, a "hybrid corn seed" is considered to be a seed which is produced by the fertilization of a female corn plant of a first variety, line, or cultivar with the pollen of a male corn plant of a different variety, line, or cultivar (i.e., a seed produced by a hybrid corn plant).

As used herein, a "field" or a "corn field" refers to an outdoor location that is suitable for growing corn. The location can be irrigated or non-irrigated. A corn field can comprise a land area planted with corn seed and/or at least one corn plant or a plurality of corn plants, which can be at one or more stages of development. In an aspect, a corn plant provided herein is planted in a field. In another aspect, a corn plant provided herein is planted indoors, such as in a greenhouse, and/or in a container holding a growth medium or soil.

In an aspect, a field comprises a single plot. In another aspect, a field comprises multiple plots. In another aspect, one or more edges of a field are bordered by a fence. In another aspect, one or more edges of a field are unfenced. In another aspect, one or more edges of a field are bordered by hedges. In an aspect, a field comprises a physically contiguous space. In another aspect, the field comprises a physically non-contiguous space. In still another aspect, the field comprises a biologically contiguous space. As used herein, a "biologically contiguous space" refers to a space or field wherein the pollen can move from one section of the space or field to another section of the space or field. In an aspect, a biologically contiguous field is physically contiguous. In another aspect, a biologically contiguous field is physically non-contiguous (e.g., plots within the field or a single plot within the field can be separated by one or more structures, such as, without being limiting, a road, creek, irrigation ditch, trail, hedgerow, fence, irrigation pipes, fallow field, empty field, non-corn plants).

In an aspect, a field comprises at least 0.5 acres. In an aspect, a field comprises at least 1 acre. In another aspect, a field comprises at least 5 acres. In another aspect, a field comprises at least 10 acres. In another aspect, a field comprises at least 15 acres. In another aspect, a field comprises at least 20 acres. In another aspect, a field comprises at least 25 acres. In another aspect, a field comprises at least 30 acres. In another aspect, a field comprises at least 35 acres. In another aspect, a field comprises at least 40 acres. In another aspect, a field comprises at least 45 acres. In another aspect, a field comprises at least 50 acres. In another aspect, a field comprises at least 75 acres. In another aspect, a field comprises at least 100 acres. In another aspect, a field comprises at least 150 acres. In another aspect, a field comprises at least 200 acres. In another aspect, a field comprises at least 250 acres. In another aspect, a field comprises at least 300 acres. In another aspect, a field comprises at least 350 acres. In another aspect, a field comprises at least 400 acres. In another aspect, a field comprises at least 450 acres. In another aspect, a field comprises at least 500 acres. In another aspect, a field comprises at least 750 acres. In another aspect, a field comprises at least 1000 acres. In another aspect, a field comprises at least 1500 acres. In another aspect, a field comprises at least 2000 acres. In another aspect, a field comprises at least 2500 acres. In another aspect, a field comprises at least 3000 acres. In another aspect, a field comprises at least 4000 acres. In another aspect, a field comprises at least 5000 acres. In another aspect, a field comprises at least 10,000 acres.

In an aspect, a field comprises between 0.5 acres and 10,000 acres. In another aspect, a field comprises between 1 acre and 10,000 acres. In another aspect, a field comprises between 5 acres and 10,000 acres. In another aspect, a field comprises between 10 acres and 10,000 acres. In another aspect, a field comprises between 15 acres and 10,000 acres. In another aspect, a field comprises between 20 acres and 10,000 acres. In another aspect, a field comprises between 25 acres and 10,000 acres. In another aspect, a field comprises between 30 acres and 10,000 acres. In another aspect, a field comprises between 35 acres and 10,000 acres. In another aspect, a field comprises between 40 acres and 10,000 acres. In another aspect, a field comprises between 45 acres and 10,000 acres. In another aspect, a field comprises between 50 acres and 10,000 acres. In another aspect, a field comprises between 75 acres and 10,000 acres. In another aspect, a field comprises between 100 acres and 10,000 acres. In another aspect, a field comprises between 150 acres and 10,000 acres. In another aspect, a field comprises between 200 acres and 10,000 acres. In another aspect, a field comprises between 250 acres and 10,000 acres. In another aspect, a field comprises between 300 acres and 10,000 acres. In another aspect, a field comprises between 350 acres and 10,000 acres. In another aspect, a field comprises between 400 acres and 10,000 acres. In another aspect, a field comprises between 450 acres and 10,000 acres. In another aspect, a field comprises between 500 acres and 10,000 acres. In another aspect, a field comprises between 750 acres and 10,000 acres. In another aspect, a field comprises between 1000 acres and 10,000 acres. In another aspect, a field comprises between 1500 acres and 10,000 acres. In another aspect, a field comprises between 2000 acres and 10,000 acres. In another aspect, a field comprises between 2500 acres and 10,000 acres. In another aspect, a field comprises between 3000 acres and 10,000 acres. In another aspect, a field comprises between 4000 acres and 10,000 acres. In another aspect, a field comprises between 5000 acres and 10,000 acres. In another aspect, a field comprises between 1 acre and 5000 acres. In another aspect, a field comprises between 1 acre and 2500 acres. In another aspect, a field comprises between 1 acre and 1000 acres. In another aspect, a field comprises between 1 acre and 500 acres. In another aspect, a field comprises between 1 acre and 250 acres. In another aspect, a field comprises between 1 acre and 100 acres. In another aspect, a field comprises between 1 acre and 75 acres. In another aspect, a field comprises between 1 acre and 50 acres. In another aspect, a field comprises between 1 acre and 25 acres. In another aspect, a field comprises between 1 acre and 10 acres.

In an aspect, the corn plants provided herein are grown in a field. According to aspects of the present disclosure, a field may comprise male and female corn plants of different inbreds or varieties for hybrid corn seed production. In another aspect, the female inbred corn plants and at least one male inbred corn plant provided herein are grown in a field. In another aspect, the corn plants provided herein are grown in a greenhouse. In another aspect, the female inbred corn plants and at least one male inbred corn plant provided herein are grown in a greenhouse. According to some aspects, a corn field can comprise two or more pluralities of corn plants with the pluralities of corn plants being planted with different corn varieties, at different times, at different densities, in different arrangements (e.g., in rows or scattered or random placement), and/or at different row spacings and/or row lengths, such that the pluralities of corn plants have different heights, spacings, etc., at different time points during the growing season, although each plurality of corn plants can be relatively uniform with respect to plant height and other growth metrics. Typically, corn plants are planted in rows of approximately equal spacing, which may comprise male and female rows for corn seed production. The female and male rows may be present in a regular or repeating pattern or in an irregular or non-repeating pattern, and/or male plants may be interplanted between female rows. As yet another alternative, the female and male plants may be planted randomly or not in rows.

In an aspect, a corn field can further comprise plants other than corn plants including, without being limiting, cotton, alfalfa, sunflowers, sorghum, wheat, barley, oat, rice, rye, soybean, vegetables (e.g., potato, tomato, carrot), grass (e.g., bluegrass, Triticale), and weeds. In another aspect, a greenhouse and/or in a container holding a growth medium or soil can further comprise plants other than corn plants including, without being limiting, cotton, alfalfa, sunflowers, sorghum, wheat, barley, oat, rice, rye, soybean, vegetables (e.g., potato, tomato, carrot), grass (e.g., bluegrass, Triticale), and weeds.

In an aspect, a corn field comprises at least two corn plants. In another aspect, a corn field comprises at least 10 corn plants. In another aspect, a corn field comprises at least 100 corn plants. In another aspect, a corn field comprises at least 200 corn plants. In another aspect, a corn field comprises at least 500 corn plants. In another aspect, a corn field comprises at least 1,000 corn plants. In another aspect, a corn field comprises at least 2,000 corn plants. In another aspect, a corn field comprises at least 5,000 corn plants. In another aspect, a corn field comprises at least 10,000 corn plants. In another aspect, a corn field comprises at least 20,000 corn plants. In another aspect, a corn field comprises at least 50,000 corn plants. In another aspect, a corn field comprises at least 100,000 corn plants. In another aspect, a corn field comprises at least 200,000 corn plants. In another aspect, a corn field comprises at least 500,000 corn plants. In another aspect, a corn field comprises at least 1,000,000 corn plants. In another aspect, a corn field comprises at least 2,000,000 corn plants. In another aspect, a corn field comprises at least 5,000,000 corn plants. In another aspect, a corn field comprises at least 10,000,000 corn plants.

In an aspect, a corn field comprises between 1 and 10 corn plants. In another aspect, a corn field comprises between 1 and 100 corn plants. In another aspect, a corn field comprises between 1 and 200 corn plants. In another aspect, a corn field comprises between 1 and 500 corn plants. In another aspect, a corn field comprises between 1 and 1,000 corn plants. In another aspect, a corn field comprises between 1 and 2,000 corn plants. In another aspect, a corn field comprises between 1 and 5,000 corn plants. In another aspect, a corn field comprises between 1 and 10,000 corn plants. In another aspect, a corn field comprises between 1 and 20,000 corn plants. In another aspect, a corn field comprises between 1 and 50,000 corn plants. In another aspect, a corn field comprises between 1 and 100,000 corn plants. In another aspect, a corn field comprises between 1 and 200,000 corn plants. In another aspect, a corn field comprises between 1 and 500,000 corn plants. In another aspect, a corn field comprises between 1 and 1,000,000 corn plants. In another aspect, a corn field comprises between 1 and 2,000,000 corn plants. In another aspect, a corn field comprises between 1 and 5,000,000 corn plants. In another aspect, a corn field comprises between 1 and 10,000,000 corn plants. In another aspect, a corn field comprises between 10 and 10,000,000 corn plants. In another aspect, a corn field comprises between 100 and 10,000,000 corn plants. In another aspect, a corn field comprises between 200 and 10,000,000 corn plants. In another aspect, a corn field comprises between 500 and 10,000,000 corn plants. In another aspect, a corn field comprises between 1,000 and 10,000,000 corn plants. In another aspect, a corn field comprises between 2,000 and 10,000,000 corn plants. In another aspect, a corn field comprises between 5,000 and 10,000,000 corn plants. In another aspect, a corn field comprises between 10,000 and 10,000,000 corn plants. In another aspect, a corn field comprises between 20,000 and 10,000,000 corn plants. In another aspect, a corn field comprises between 50,000 and 10,000,000 corn plants. In another aspect, a corn field comprises between 100,000 and 10,000,000 corn plants. In another aspect, a corn field comprises between 200,000 and 10,000,000 corn plants. In another aspect, a corn field comprises between 500,000 and 10,000,000 corn plants. In another aspect, a corn field comprises between 1,000,000 and 10,000,000 corn plants. In another aspect, a corn field comprises between 2,000,000 and 10,000,000 corn plants. In another aspect, a corn field comprises between 5,000,000 and 10,000,000 corn plants. In another aspect, a corn field comprises between 1,000 and 10,000 corn plants. In another aspect, a corn field comprises between 1,000 and 100,000 corn plants. In another aspect, a corn field comprises between 10,000 and 50,000 corn plants. In another aspect, a corn field comprises between 10,000 and 100,000 corn plants. In another aspect, a corn field comprises between 10,000 and 1,000,000 corn plants. In another aspect, a corn field comprises between 100,000 and 1,000,000 corn plants. In another aspect, a corn field comprises between 100,000 and 2,000,000 corn plants. In another aspect, a corn field comprises between 100,000 and 5,000,000 corn plants. In another aspect, a corn field comprises between 1,000,000 and 2,000,000 corn plants. In another aspect, a corn field comprises between 1,000,000 and 5,000,000 corn plants. In another aspect, a corn field comprises between 2,000,000 and 5,000,000 corn plants.

As used herein, a "row" comprises at least one corn plant. In an aspect, a row comprises at least two corn plants. Without being limiting, a row of corn plants is planted in a line or in a generally or approximately linear arrangement, and if a corn field comprises two or more rows, they are typically planted parallel or nearly parallel to each other. A corn field can comprise one or more rows of corn plants where the rows are of the same or different lengths. Without being limiting, a corn field can comprise at least 1 row of corn plants. In another aspect, a corn field comprises at least 10 rows of corn plants. In another aspect, a corn field comprises at least 50 rows of corn plants. In another aspect, a corn field comprises at least 500 rows of corn plants. In another aspect, a corn field comprises at least 1,000 rows of corn plants. In another aspect, a corn field comprises at least 5,000 rows of corn plants. In another aspect, a corn field comprises at least 10,000 rows of corn plants.

In an aspect, a corn field comprises rows that are spaced at least 5 inches apart. In another aspect, a corn field comprises rows that are spaced at least 10 inches apart. In another aspect, a corn field comprises rows that are spaced at least 15 inches apart. In another aspect, a corn field comprises rows of corn plants that are spaced at least 20 inches apart. In another aspect, a corn field comprises rows of corn that are spaced at least 25 inches apart. In another aspect, a corn field comprises rows of corn that are spaced at least 30 inches apart. In another aspect, a corn field comprises rows of corn that are spaced at least 35 inches apart. In another aspect, a corn field comprises rows of corn that are spaced at least 40 inches apart.

As used herein, the term "density" refers to the number of individual plants that occur within a given unit area. In an aspect, a corn field comprises a density of at least 9,000 corn plants per acre. In another aspect, a corn field comprises a density of at least 12,000 corn plants per acre. In another aspect, a corn field comprises a density of at least 15,000 corn plants per acre. In another aspect, a corn field comprises a density of at least 18,000 corn plants per acre. In another aspect, a corn field comprises a density of at least 21,000 corn plants per acre. In another aspect, a corn field comprises a density of at least 24,000 corn plants per acre. In another aspect, a corn field comprises a density of at least 27,000 corn plants per acre. In another aspect, a corn field comprises a density of at least 30,000 corn plants per acre. In another aspect, a corn field comprises a density of at least 33,000 corn plants per acre. In another aspect, a corn field comprises a density of at least 36,000 corn plants per acre. In another aspect, a corn field comprises a density of at least 39,000 corn plants per acre. In another aspect, a corn field comprises a density of at least 42,000 corn plants per acre. In another aspect, a corn field comprises a density of at least 45,000 corn plants per acre. In another aspect, a corn field comprises a density of at least 48,000 corn plants per acre. In another aspect, a corn field comprises a density of at least 51,000 corn plants per acre. In another aspect, a corn field comprises a density of at least 54,000 corn plants per acre. In another aspect, a corn field comprises a density of at least 57,000 corn plants per acre. In another aspect, a corn field comprises a density of at least 60,000 corn plants per acre. In another aspect, a corn field comprises a density of at least 63,000 corn plants per acre. In another aspect, a corn field comprises a density of at least 66,000 corn plants per acre. In another aspect, a corn field comprises a density of at least 69,000 corn plants per acre. In another aspect, a corn field comprises a density of at least 72,000 corn plants per acre. In another aspect, a corn field comprises a density of at least 75,000 corn plants per acre.

In an aspect, a corn field comprises a density of between 20,000 corn plants and 60,000 corn plants per acre. In another aspect, a corn field comprises a density of between 20,000 corn plants and 55,000 corn plants per acre. In another aspect, a corn field comprises a density of between 20,000 corn plants and 50,000 corn plants per acre. In another aspect, a corn field comprises a density of between 20,000 corn plants and 45,000 corn plants per acre. In another aspect, a corn field comprises a density of between 20,000 corn plants and 40,000 corn plants per acre. In another aspect, a corn field comprises a density of between 20,000 corn plants and 35,000 corn plants per acre. In another aspect, a corn field comprises a density of between 20,000 corn plants and 30,000 corn plants per acre. In another aspect, a corn field comprises a density of between 24,000 corn plants and 58,000 corn plants per acre. In another aspect, a corn field comprises a density of between 38,000 corn plants and 60,000 corn plants per acre. In another aspect, a corn field comprises a density of between 38,000 corn plants and 50,000 corn plants per acre. In an aspect, a corn field comprises a density of less than 10,000 corn plants per acre. In another aspect, a corn field comprises a density of less than 20,000 corn plants per acre. In another aspect, a corn field comprises a density of less than 30,000 corn plants per acre.

In an aspect, a corn field comprises at least one corn plant and further comprises a density of at least 9,000 corn plants per acre. In another aspect, a corn field comprises at least one corn plant and further comprises a density of at least 12,000 corn plants per acre. In another aspect, a corn field comprises at least one corn plant and further comprises a density of at least 15,000 corn plants per acre. In another aspect, a corn field comprises at least one corn plant and further comprises a density of at least 18,000 corn plants per acre. In another aspect, a corn field comprises at least one corn plant and further comprises a density of at least 21,000 corn plants per acre. In another aspect, a corn field comprises at least one corn plant and further comprises a density of at least 24,000 corn plants per acre. In another aspect, a corn field comprises at least one corn plant and further comprises a density of at least 27,000 corn plants per acre. In another aspect, a corn field comprises at least one corn plant and further comprises a density of at least 30,000 corn plants per acre. In another aspect, a corn field comprises at least one corn plant and further comprises a density of at least 33,000 corn plants per acre. In another aspect, a corn field comprises at least one corn plant and further comprises a density of at least 36,000 corn plants per acre. In another aspect, a corn field comprises at least one corn plant and further comprises a density of at least one corn plant per acre. In another aspect, a corn field comprises at least one corn plant and further comprises a density of at least 42,000 corn plants per acre. In another aspect, a corn field comprises at least one corn plant and further comprises a density of at least 45,000 corn plants per acre. In another aspect, a corn field comprises at least one corn plant and further comprises a density of at least 48,000 corn plants per acre. In another aspect, a corn field comprises at least one corn plant and further comprises a density of at least 51,000 corn plants per acre. In another aspect, a corn field comprises at least one corn plant and further comprises a density of at least 54,000 corn plants per acre. In another aspect, a corn field comprises at least one corn plant and further comprises a density of at least 57,000 corn plants per acre. In another aspect, a corn field comprises at least one corn plant and further comprises a density of at least 60,000 corn plants per acre. In another aspect, a corn field comprises at least one corn plant and further comprises a density of at least 63,000 corn plants per acre. In another aspect, a corn field comprises at least one corn plant and further comprises a density of at least 66,000 corn plants per acre. In another aspect, a corn field comprises at least one corn plant and further comprises a density of at least 69,000 corn plants per acre. In another aspect, a corn field comprises at least one corn plant and further comprises a density of at least 72,000 corn plants per acre. In another aspect, a corn field comprises at least one corn plant and further comprises a density of at least 75,000 corn plants per acre.

In an aspect, a corn field comprises at least 1,000 corn plants and further comprises a density of at least 9,000 corn plants per acre. In another aspect, a corn field comprises at least 1,000 corn plants and further comprises a density of at least 12,000 corn plants per acre. In another aspect, a corn field comprises at least 1,000 corn plants and further comprises a density of at least 15,000 corn plants per acre. In another aspect, a corn field comprises at least 1,000 corn plants and further comprises a density of at least 18,000 corn plants per acre. In another aspect, a corn field comprises at least 1,000 corn plants and further comprises a density of at least 21,000 corn plants per acre. In another aspect, a corn field comprises at least 1,000 corn plants and further comprises a density of at least 24,000 corn plants per acre. In another aspect, a corn field comprises at least 1,000 corn plants and further comprises a density of at least 27,000 corn plants per acre. In another aspect, a corn field comprises at least 1,000 corn plants and further comprises a density of at least 30,000 corn plants per acre. In another aspect, a corn field comprises at least 1,000 corn plants and further comprises a density of at least 33,000 corn plants per acre. In another aspect, a corn field comprises at least 1,000 corn plants and further comprises a density of at least 36,000 corn plants per acre. In another aspect, a corn field comprises at least 1,000 corn plants and further comprises a density of at least 39,000 corn plants per acre. In another aspect, a corn field comprises at least 1,000 corn plants and further comprises a density of at least 42,000 corn plants per acre. In another aspect, a corn field comprises at least 1,000 corn plants and further comprises a density of at least 45,000 corn plants per acre. In another aspect, a corn field comprises at least 1,000 corn plants and further comprises a density of at least 48,000 corn plants per acre. In another aspect, a corn field comprises at least 1,000 corn plants and further comprises a density of at least 51,000 corn plants per acre. In another aspect, a corn field comprises at least 1,000 corn plants and further comprises a density of at least 54,000 corn plants per acre. In another aspect, a corn field comprises at least 1,000 corn plants and further comprises a density of at least 57,000 corn plants per acre. In another aspect, a corn field comprises at least 1,000 corn plants and further comprises a density of at least 60,000 corn plants per acre. In another aspect, a corn field comprises at least 1,000 corn plants and further comprises a density of at least 63,000 corn plants per acre. In another aspect, a corn field comprises at least 1,000 corn plants and further comprises a density of at least 66,000 corn plants per acre. In another aspect, a corn field comprises at least 1,000 corn plants and further comprises a density of at least 69,000 corn plants per acre. In another aspect, a corn field comprises at least 1,000 corn plants and further comprises a density of at least 72,000 corn plants per acre. In another aspect, a corn field comprises at least 1,000 corn plants and further comprises a density of at least 75,000 corn plants per acre.

In an aspect, a corn field comprises at least 10,000 corn plants and further comprises a density of at least 9,000 corn plants per acre. In another aspect, a corn field comprises at least 10,000 corn plants and further comprises a density of at least 12,000 corn plants per acre. In another aspect, a corn field comprises at least 10,000 corn plants and further comprises a density of at least 15,000 corn plants per acre. In another aspect, a corn field comprises at least 10,000 corn plants and further comprises a density of at least 18,000 corn plants per acre. In another aspect, a corn field comprises at least 10,000 corn plants and further comprises a density of at least 21,000 corn plants per acre. In another aspect, a corn field comprises at least 10,000 corn plants and further comprises a density of at least 24,000 corn plants per acre. In another aspect, a corn field comprises at least 10,000 corn plants and further comprises a density of at least 27,000 corn plants per acre. In another aspect, a corn field comprises at least 10,000 corn plants and further comprises a density of at least 30,000 corn plants per acre. In another aspect, a corn field comprises at least 10,000 corn plants and further comprises a density of at least 33,000 corn plants per acre. In another aspect, a corn field comprises at least 10,000 corn plants and further comprises a density of at least 36,000 corn plants per acre. In another aspect, a corn field comprises at least 10,000 corn plants and further comprises a density of at least 39,000 corn plants per acre. In another aspect, a corn field comprises at least 10,000 corn plants and further comprises a density of at least 42,000 corn plants per acre. In another aspect, a corn field comprises at least 10,000 corn plants and further comprises a density of at least 45,000 corn plants per acre. In another aspect, a corn field comprises at least 10,000 corn plants and further comprises a density of at least 48,000 corn plants per acre. In another aspect, a corn field comprises at least 10,000 corn plants and further comprises a density of at least 51,000 corn plants per acre. In another aspect, a corn field comprises at least 10,000 corn plants and further comprises a density of at least 54,000 corn plants per acre. In another aspect, a corn field comprises at least 10,000 corn plants and further comprises a density of at least 57,000 corn plants per acre. In another aspect, a corn field comprises at least 10,000 corn plants and further comprises a density of at least 60,000 corn plants per acre. In another aspect, a corn field comprises at least 10,000 corn plants and further comprises a density of at least 63,000 corn plants per acre. In another aspect, a corn field comprises at least 10,000 corn plants and further comprises a density of at least 66,000 corn plants per acre. In another aspect, a corn field comprises at least 10,000 corn plants and further comprises a density of at least 69,000 corn plants per acre. In another aspect, a corn field comprises at least 10,000 corn plants and further comprises a density of at least 72,000 corn plants per acre. In another aspect, a corn field comprises at least 10,000 corn plants and further comprises a density of at least 75,000 corn plants per acre.

In an aspect, a corn field comprises at least 100,000 corn plants and further comprises a density of at least 9,000 corn plants per acre. In another aspect, a corn field comprises at least 100,000 corn plants and further comprises a density of at least 12,000 corn plants per acre. In another aspect, a corn field comprises at least 100,000 corn plants and further comprises a density of at least 15,000 corn plants per acre. In another aspect, a corn field comprises at least 100,000 corn plants and further comprises a density of at least 18,000 corn plants per acre. In another aspect, a corn field comprises at least 100,000 corn plants and further comprises a density of at least 21,000 corn plants per acre. In another aspect, a corn field comprises at least 100,000 corn plants and further comprises a density of at least 24,000 corn plants per acre. In another aspect, a corn field comprises at least 100,000 corn plants and further comprises a density of at least 27,000 corn plants per acre. In another aspect, a corn field comprises at least 100,000 corn plants and further comprises a density of at least 30,000 corn plants per acre. In another aspect, a corn field comprises at least 100,000 corn plants and further comprises a density of at least 33,000 corn plants per acre. In another aspect, a corn field comprises at least 100,000 corn plants and further comprises a density of at least 36,000 corn plants per acre. In another aspect, a corn field comprises at least 100,000 corn plants and further comprises a density of at least 39,000 corn plants per acre. In another aspect, a corn field comprises at least 100,000 corn plants and further comprises a density of at least 42,000 corn plants per acre. In another aspect, a corn field comprises at least 100,000 corn plants and further comprises a density of at least 45,000 corn plants per acre. In another aspect, a corn field comprises at least 100,000 corn plants and further comprises a density of at least 48,000 corn plants per acre. In another aspect, a corn field comprises at least 100,000 corn plants and further comprises a density of at least 51,000 corn plants per acre. In another aspect, a corn field comprises at least 100,000 corn plants and further comprises a density of at least 54,000 corn plants per acre. In another aspect, a corn field comprises at least 100,000 corn plants and further comprises a density of at least 57,000 corn plants per acre. In another aspect, a corn field comprises at least 100,000 corn plants and further comprises a density of at least 60,000 corn plants per acre. In another aspect, a corn field comprises at least 100,000 corn plants and further comprises a density of at least 63,000 corn plants per acre. In another aspect, a corn field comprises at least 100,000 corn plants and further comprises a density of at least 66,000 corn plants per acre. In another aspect, a corn field comprises at least 100,000 corn plants and further comprises a density of at least 69,000 corn plants per acre. In another aspect, a corn field comprises at least 100,000 corn plants and further comprises a density of at least 72,000 corn plants per acre. In another aspect, a corn field comprises at least 100,000 corn plants and further comprises a density of at least 75,000 corn plants per acre.

In an aspect, a corn field comprises at least 1,000,000 corn plants and further comprises a density of at least 9,000 corn plants per acre. In another aspect, a corn field comprises at least 1,000,000 corn plants and further comprises a density of at least 12,000 corn plants per acre. In another aspect, a corn field comprises at least 1,000,000 corn plants and further comprises a density of at least 15,000 corn plants per acre. In another aspect, a corn field comprises at least 1,000,000 corn plants and further comprises a density of at least 18,000 corn plants per acre. In another aspect, a corn field comprises at least 1,000,000 corn plants and further comprises a density of at least 21,000 corn plants per acre. In another aspect, a corn field comprises at least 1,000,000 corn plants and further comprises a density of at least 24,000 corn plants per acre. In another aspect, a corn field comprises at least 1,000,000 corn plants and further comprises a density of at least 27,000 corn plants per acre. In another aspect, a corn field comprises at least 1,000,000 corn plants and further comprises a density of at least 30,000 corn plants per acre. In another aspect, a corn field comprises at least 1,000,000 corn plants and further comprises a density of at least 33,000 corn plants per acre. In another aspect, a corn field comprises at least 1,000,000 corn plants and further comprises a density of at least 36,000 corn plants per acre. In another aspect, a corn field comprises at least 1,000,000 corn plants and further comprises a density of at least 39,000 corn plants per acre. In another aspect, a corn field comprises at least 1,000,000 corn plants and further comprises a density of at least 42,000 corn plants per acre. In another aspect, a corn field comprises at least 1,000,000 corn plants and further comprises a density of at least 45,000 corn plants per acre. In another aspect, a corn field comprises at least 1,000,000 corn plants and further comprises a density of at least 48,000 corn plants per acre. In another aspect, a corn field comprises at least 1,000,000 corn plants and further comprises a density of at least 51,000 corn plants per acre. In another aspect, a corn field comprises at least 1,000,000 corn plants and further comprises a density of at least 54,000 corn plants per acre. In another aspect, a corn field comprises at least 1,000,000 corn plants and further comprises a density of at least 57,000 corn plants per acre. In another aspect, a corn field comprises at least 1,000,000 corn plants and further comprises a density of at least 60,000 corn plants per acre. In another aspect, a corn field comprises at least 1,000,000 corn plants and further comprises a density of at least 63,000 corn plants per acre. In another aspect, a corn field comprises at least 1,000,000 corn plants and further comprises a density of at least 66,000 corn plants per acre. In another aspect, a corn field comprises at least 1,000,000 corn plants and further comprises a density of at least 69,000 corn plants per acre. In another aspect, a corn field comprises at least 1,000,000 corn plants and further comprises a density of at least 72,000 corn plants per acre. In another aspect, a corn field comprises at least 1,000,000 corn plants and further comprises a density of at least 75,000 corn plants per acre.

In an aspect, a corn field comprises at least 10,000,000 corn plants and further comprises a density of at least 9,000 corn plants per acre. In another aspect, a corn field comprises at least 10,000,000 corn plants and further comprises a density of at least 12,000 corn plants per acre. In another aspect, a corn field comprises at least 10,000,000 corn plants and further comprises a density of at least 15,000 corn plants per acre. In another aspect, a corn field comprises at least 10,000,000 corn plants and further comprises a density of at least 18,000 corn plants per acre. In another aspect, a corn field comprises at least 10,000,000 corn plants and further comprises a density of at least 21,000 corn plants per acre. In another aspect, a corn field comprises at least 10,000,000 corn plants and further comprises a density of at least 24,000 corn plants per acre. In another aspect, a corn field comprises at least 10,000,000 corn plants and further comprises a density of at least 27,000 corn plants per acre. In another aspect, a corn field comprises at least 10,000,000 corn plants and further comprises a density of at least 30,000 corn plants per acre. In another aspect, a corn field comprises at least 10,000,000 corn plants and further comprises a density of at least 33,000 corn plants per acre. In another aspect, a corn field comprises at least 10,000,000 corn plants and further comprises a density of at least 36,000 corn plants per acre. In another aspect, a corn field comprises at least 10,000,000 corn plants and further comprises a density of at least 39,000 corn plants per acre. In another aspect, a corn field comprises at least 10,000,000 corn plants and further comprises a density of at least 42,000 corn plants per acre. In another aspect, a corn field comprises at least 10,000,000 corn plants and further comprises a density of at least 45,000 corn plants per acre. In another aspect, a corn field comprises at least 10,000,000 corn plants and further comprises a density of at least 48,000 corn plants per acre. In another aspect, a corn field comprises at least 10,000,000 corn plants and further comprises a density of at least 51,000 corn plants per acre. In another aspect, a corn field comprises at least 10,000,000 corn plants and further comprises a density of at least 54,000 corn plants per acre. In another aspect, a corn field comprises at least 10,000,000 corn plants and further comprises a density of at least 57,000 corn plants per acre. In another aspect, a corn field comprises at least 10,000,000 corn plants and further comprises a density of at least 60,000 corn plants per acre. In another aspect, a corn field comprises at least 10,000,000 corn plants and further comprises a density of at least 63,000 corn plants per acre. In another aspect, a corn field comprises at least 10,000,000 corn plants and further comprises a density of at least 66,000 corn plants per acre. In another aspect, a corn field comprises at least 10,000,000 corn plants and further comprises a density of at least 69,000 corn plants per acre. In another aspect, a corn field comprises at least 10,000,000 corn plants and further comprises a density of at least 72,000 corn plants per acre. In another aspect, a corn field comprises at least 10,000,000 corn plants and further comprises a density of at least 75,000 corn plants per acre.

In an aspect, a corn field comprises at least one corn plant and further comprises a density of between 20,000 corn plants and 55,000 corn plants per acre. In another aspect, a corn field comprises at least one corn plant and further comprises a density of between 20,000 corn plants and 50,000 corn plants per acre. In another aspect, a corn field comprises at least one corn plant and further comprises a density of between 20,000 corn plants and 45,000 corn plants per acre. In another aspect, a corn field comprises at least one corn plant and further comprises a density of between 20,000 corn plants and 40,000 corn plants per acre. In another aspect, a corn field comprises at least one corn plant and further comprises a density of between 20,000 corn plants and 35,000 corn plants per acre. In another aspect, a corn field comprises at least one corn plant and further comprises a density of between 20,000 corn plants and 30,000 corn plants per acre. In another aspect, a corn field comprises at least one corn plant and further comprises a density of between 24,000 corn plants and 58,000 corn plants per acre. In another aspect, a corn field comprises at least one corn plant and further comprises a density of between 38,000 corn plants and 60,000 corn plants per acre. In another aspect, a corn field comprises at least one corn plant and further comprises a density of between 38,000 corn plants and 50,000 corn plants per acre. In another aspect, a corn field comprises at least one corn plant and further comprises a density of less than 10,000 corn plants per acre. In another aspect, a corn field comprises at least one corn plant and further comprises a density of less than 20,000 corn plants per acre. In another aspect, a corn field comprises at least one corn plant and further comprises a density of less than 30,000 corn plants per acre.

In an aspect, a corn field comprises at least 1,000 corn plants and further comprises a density of between 20,000 corn plants and 55,000 corn plants per acre. In another aspect, a corn field comprises at least 1,000 corn plants and further comprises a density of between 20,000 corn plants and 50,000 corn plants per acre. In another aspect, a corn field comprises at least 1,000 corn plants and further comprises a density of between 20,000 corn plants and 45,000 corn plants per acre. In another aspect, a corn field comprises at least 1,000 corn plants and further comprises a density of between 20,000 corn plants and 40,000 corn plants per acre. In another aspect, a corn field comprises at least 1,000 corn plants and further comprises a density of between 20,000 corn plants and 35,000 corn plants per acre. In another aspect, a corn field comprises at least 1,000 corn plants and further comprises a density of between 20,000 corn plants and 30,000 corn plants per acre. In another aspect, a corn field comprises at least 1,000 corn plants and further comprises a density of between 24,000 corn plants and 58,000 corn plants per acre. In another aspect, a corn field comprises at least 1,000 corn plants and further comprises a density of between 38,000 corn plants and 60,000 corn plants per acre.

In another aspect, a corn field comprises at least 1,000 corn plants and further comprises a density of between 38,000 corn plants and 50,000 corn plants per acre. In another aspect, a corn field comprises at least 1,000 corn plants and further comprises a density of less than 10,000 corn plants per acre. In another aspect, a corn field comprises at least 1,000 corn plants and further comprises a density of less than 20,000 corn plants per acre. In another aspect, a corn field comprises at least 1,000 corn plants and further comprises a density of less than 30,000 corn plants per acre.

In an aspect, a corn field comprises at least 10,000 corn plants and further comprises a density of between 20,000 corn plants and 55,000 corn plants per acre. In another aspect, a corn field comprises at least 10,000 corn plants and further comprises a density of between 20,000 corn plants and 50,000 corn plants per acre. In another aspect, a corn field comprises at least 10,000 corn plants and further comprises a density of between 20,000 corn plants and 45,000 corn plants per acre. In another aspect, a corn field comprises at least 10,000 corn plants and further comprises a density of between 20,000 corn plants and 40,000 corn plants per acre. In another aspect, a corn field comprises at least 10,000 corn plants and further comprises a density of between 20,000 corn plants and 35,000 corn plants per acre. In another aspect, a corn field comprises at least 10,000 corn plants and further comprises a density of between 20,000 corn plants and 30,000 corn plants per acre. In another aspect, a corn field comprises at least 10,000 corn plants and further comprises a density of between 24,000 corn plants and 58,000 corn plants per acre. In another aspect, a corn field comprises at least 10,000 corn plants and further comprises a density of between 38,000 corn plants and 60,000 corn plants per acre. In another aspect, a corn field comprises at least 10,000 corn plants and further comprises a density of between 38,000 corn plants and 50,000 corn plants per acre. In another aspect, a corn field comprises at least 10,000 corn plants and further comprises a density of less than 10,000 corn plants per acre. In another aspect, a corn field comprises at least 10,000 corn plants and further comprises a density of less than 20,000 corn plants per acre. In another aspect, a corn field comprises at least 10,000 corn plants and further comprises a density of less than 30,000 corn plants per acre.

In an aspect, a corn field comprises at least 100,000 corn plants and further comprises a density of between 20,000 corn plants and 55,000 corn plants per acre. In another aspect, a corn field comprises at least 100,000 corn plants and further comprises a density of between 20,000 corn plants and 50,000 corn plants per acre. In another aspect, a corn field comprises at least 100,000 corn plants and further comprises a density of between 20,000 corn plants and 45,000 corn plants per acre. In another aspect, a corn field comprises at least 100,000 corn plants and further comprises a density of between 20,000 corn plants and 40,000 corn plants per acre. In another aspect, a corn field comprises at least 100,000 corn plants and further comprises a density of between 20,000 corn plants and 35,000 corn plants per acre. In another aspect, a corn field comprises at least 100,000 corn plants and further comprises a density of between 20,000 corn plants and 30,000 corn plants per acre. In another aspect, a corn field comprises at least 100,000 corn plants and further comprises a density of between 24,000 corn plants and 58,000 corn plants per acre. In another aspect, a corn field comprises at least 100,000 corn plants and further comprises a density of between 38,000 corn plants and 60,000 corn plants per acre. In another aspect, a corn field comprises at least 100,000 corn plants and further comprises a density of between 38,000 corn plants and 50,000 corn plants per acre. In another aspect, a corn field comprises at least 100,000 corn plants and further comprises a density of less than 10,000 corn plants per acre. In another aspect, a corn field comprises at least 100,000 corn plants and further comprises a density of less than 20,000 corn plants per acre. In another aspect, a corn field comprises at least 100,000 corn plants and further comprises a density of less than 30,000 corn plants per acre.

In an aspect, a corn field comprises at least 1,000,000 corn plants and further comprises a density of between 20,000 corn plants and 55,000 corn plants per acre. In another aspect, a corn field comprises at least 1,000,000 corn plants and further comprises a density of between 20,000 corn plants and 50,000 corn plants per acre. In another aspect, a corn field comprises at least 1,000,000 corn plants and further comprises a density of between 20,000 corn plants and 45,000 corn plants per acre. In another aspect, a corn field comprises at least 1,000,000 corn plants and further comprises a density of between 20,000 corn plants and 40,000 corn plants per acre. In another aspect, a corn field comprises at least 1,000,000 corn plants and further comprises a density of between 20,000 corn plants and 35,000 corn plants per acre. In another aspect, a corn field comprises at least 1,000,000 corn plants and further comprises a density of between 20,000 corn plants and 30,000 corn plants per acre. In another aspect, a corn field comprises at least 1,000,000 corn plants and further comprises a density of between 24,000 corn plants and 58,000 corn plants per acre. In another aspect, a corn field comprises at least 1,000,000 corn plants and further comprises a density of between 38,000 corn plants and 60,000 corn plants per acre. In another aspect, a corn field comprises at least 1,000,000 corn plants and further comprises a density of between 38,000 corn plants and 50,000 corn plants per acre. In another aspect, a corn field comprises at least 1,000,000 corn plants and further comprises a density of less than 10,000 corn plants per acre. In another aspect, a corn field comprises at least 1,000,000 corn plants and further comprises a density of less than 20,000 corn plants per acre. In another aspect, a corn field comprises at least 1,000,000 corn plants and further comprises a density of less than 30,000 corn plants per acre.

In an aspect, a corn field comprises at least 10,000,000 corn plants and further comprises a density of between 20,000 corn plants and 55,000 corn plants per acre. In another aspect, a corn field comprises at least 10,000,000 corn plants and further comprises a density of between 20,000 corn plants and 50,000 corn plants per acre. In another aspect, a corn field comprises at least 10,000,000 corn plants and further comprises a density of between 20,000 corn plants and 45,000 corn plants per acre. In another aspect, a corn field comprises at least 10,000,000 corn plants and further comprises a density of between 20,000 corn plants and 40,000 corn plants per acre. In another aspect, a corn field comprises at least 10,000,000 corn plants and further comprises a density of between 20,000 corn plants and 35,000 corn plants per acre. In another aspect, a corn field comprises at least 10,000,000 corn plants and further comprises a density of between 20,000 corn plants and 30,000 corn plants per acre. In another aspect, a corn field comprises at least 10,000,000 corn plants and further comprises a density of between 24,000 corn plants and 58,000 corn plants per acre. In another aspect, a corn field comprises at least 10,000,000 corn plants and further comprises a density of between 38,000 corn plants and 60,000 corn plants per acre. In another aspect, a corn field comprises at least 10,000,000 corn plants and further comprises a density of between 38,000 corn plants and 50,000 corn plants per acre. In another aspect, a corn field comprises at least 10,000,000 corn plants and further comprises a density of less than 10,000 corn plants per acre. In another aspect, a corn field comprises at least 10,000,000 corn plants and further comprises a density of less than 20,000 corn plants per acre. In another aspect, a corn field comprises at least 10,000,000 corn plants and further comprises a density of less than 30,000 corn plants per acre.

In an aspect, a corn field comprises between one and 1,000 corn plants and further comprises a density of at least 9,000 corn plants per acre. In another aspect, a corn field comprises between one and 1,000 corn plants and further comprises a density of at least 12,000 corn plants per acre. In another aspect, a corn field comprises between one and 1,000 corn plants and further comprises a density of at least 15,000 corn plants per acre. In another aspect, a corn field comprises between one and 1,000 corn plants and further comprises a density of at least 18,000 corn plants per acre. In another aspect, a corn field comprises between one and 1,000 corn plants and further comprises a density of at least 21,000 corn plants per acre. In another aspect, a corn field comprises between one and 1,000 corn plants and further comprises a density of at least 24,000 corn plants per acre. In another aspect, a corn field comprises between one and 1,000 corn plants and further comprises a density of at least 27,000 corn plants per acre. In another aspect, a corn field comprises between one and 1,000 corn plants and further comprises a density of at least 30,000 corn plants per acre. In another aspect, a corn field comprises between one and 1,000 corn plants and further comprises a density of at least 33,000 corn plants per acre. In another aspect, a corn field comprises between one and 1,000 corn plants and further comprises a density of at least 36,000 corn plants per acre. In another aspect, a corn field comprises between one and 1,000 corn plants and further comprises a density of at least 39,000 corn plants per acre. In another aspect, a corn field comprises between one and 1,000 corn plants and further comprises a density of at least 42,000 corn plants per acre. In another aspect, a corn field comprises between one and 1,000 corn plants and further comprises a density of at least 45,000 corn plants per acre. In another aspect, a corn field comprises between one and 1,000 corn plants and further comprises a density of at least 48,000 corn plants per acre. In another aspect, a corn field comprises between one and 1,000 corn plants and further comprises a density of at least 51,000 corn plants per acre. In another aspect, a corn field comprises between one and 1,000 corn plants and further comprises a density of at least 54,000 corn plants per acre. In another aspect, a corn field comprises between one and 1,000 corn plants and further comprises a density of at least 57,000 corn plants per acre. In another aspect, a corn field comprises between one and 1,000 corn plants and further comprises a density of at least 60,000 corn plants per acre. In another aspect, a corn field comprises between one and 1,000 corn plants and further comprises a density of at least 63,000 corn plants per acre. In another aspect, a corn field comprises between one and 1,000 corn plants and further comprises a density of at least 66,000 corn plants per acre. In another aspect, a corn field comprises between one and 1,000 corn plants and further comprises a density of at least 69,000 corn plants per acre. In another aspect, a corn field comprises between one and 1,000 corn plants and further comprises a density of at least 72,000 corn plants per acre. In another aspect, a corn field comprises between one and 1,000 corn plants and further comprises a density of at least 75,000 corn plants per acre.

In an aspect, a corn field comprises between 1,000 and 10,000 corn plants and further comprises a density of at least 9,000 corn plants per acre. In another aspect, a corn field comprises between 1,000 and 10,000 corn plants and further comprises a density of at least 12,000 corn plants per acre. In another aspect, a corn field comprises between 1,000 and 10,000 corn plants and further comprises a density of at least 15,000 corn plants per acre. In another aspect, a corn field comprises between 1,000 and 10,000 corn plants and further comprises a density of at least 18,000 corn plants per acre. In another aspect, a corn field comprises between 1,000 and 10,000 corn plants and further comprises a density of at least 21,000 corn plants per acre. In another aspect, a corn field comprises between 1,000 and 10,000 corn plants and further comprises a density of at least 24,000 corn plants per acre. In another aspect, a corn field comprises between 1,000 and 10,000 corn plants and further comprises a density of at least 27,000 corn plants per acre. In another aspect, a corn field comprises between 1,000 and 10,000 corn plants and further comprises a density of at least 30,000 corn plants per acre. In another aspect, a corn field comprises between 1,000 and 10,000 corn plants and further comprises a density of at least 33,000 corn plants per acre. In another aspect, a corn field comprises between 1,000 and 10,000 corn plants and further comprises a density of at least 36,000 corn plants per acre. In another aspect, a corn field comprises between 1,000 and 10,000 corn plants and further comprises a density of at least 39,000 corn plants per acre. In another aspect, a corn field comprises between 1,000 and 10,000 corn plants and further comprises a density of at least 42,000 corn plants per acre. In another aspect, a corn field comprises between 1,000 and 10,000 corn plants and further comprises a density of at least 45,000 corn plants per acre. In another aspect, a corn field comprises between 1,000 and 10,000 corn plants and further comprises a density of at least 48,000 corn plants per acre. In another aspect, a corn field comprises between 1,000 and 10,000 corn plants and further comprises a density of at least 51,000 corn plants per acre. In another aspect, a corn field comprises between 1,000 and 10,000 corn plants and further comprises a density of at least 54,000 corn plants per acre. In another aspect, a corn field comprises between 1,000 and 10,000 corn plants and further comprises a density of at least 57,000 corn plants per acre. In another aspect, a corn field comprises between 1,000 and 10,000 corn plants and further comprises a density of at least 60,000 corn plants per acre. In another aspect, a corn field comprises between 1,000 and 10,000 corn plants and further comprises a density of at least 63,000 corn plants per acre. In another aspect, a corn field comprises between 1,000 and 10,000 corn plants and further comprises a density of at least 66,000 corn plants per acre. In another aspect, a corn field comprises between 1,000 and 10,000 corn plants and further comprises a density of at least 69,000 corn plants per acre. In another aspect, a corn field comprises between 1,000 and 10,000 corn plants and further comprises a density of at least 72,000 corn plants per acre. In another aspect, a corn field comprises between 1,000 and 10,000 corn plants and further comprises a density of at least 75,000 corn plants per acre.

In an aspect, a corn field comprises between 10,000 and 100,000 corn plants and further comprises a density of at least 9,000 corn plants per acre. In another aspect, a corn field comprises between 10,000 and 100,000 corn plants and further comprises a density of at least 12,000 corn plants per acre. In another aspect, a corn field comprises between 10,000 and 100,000 corn plants and further comprises a density of at least 15,000 corn plants per acre. In another aspect, a corn field comprises between 10,000 and 100,000 corn plants and further comprises a density of at least 18,000 corn plants per acre. In another aspect, a corn field comprises between 10,000 and 100,000 corn plants and further comprises a density of at least 21,000 corn plants per acre. In another aspect, a corn field comprises between 10,000 and 100,000 corn plants and further comprises a density of at least 24,000 corn plants per acre. In another aspect, a corn field comprises between 10,000 and 100,000 corn plants and further comprises a density of at least 27,000 corn plants per acre. In another aspect, a corn field comprises between 10,000 and 100,000 corn plants and further comprises a density of at least 30,000 corn plants per acre. In another aspect, a corn field comprises between 10,000 and 100,000 corn plants and further comprises a density of at least 33,000 corn plants per acre. In another aspect, a corn field comprises between 10,000 and 100,000 corn plants and further comprises a density of at least 36,000 corn plants per acre. In another aspect, a corn field comprises between 10,000 and 100,000 corn plants and further comprises a density of at least 39,000 corn plants per acre. In another aspect, a corn field comprises between 10,000 and 100,000 corn plants and further comprises a density of at least 42,000 corn plants per acre. In another aspect, a corn field comprises between 10,000 and 100,000 corn plants and further comprises a density of at least 45,000 corn plants per acre. In another aspect, a corn field comprises between 10,000 and 100,000 corn plants and further comprises a density of at least 48,000 corn plants per acre. In another aspect, a corn field comprises between 10,000 and 100,000 corn plants and further comprises a density of at least 51,000 corn plants per acre. In another aspect, a corn field comprises between 10,000 and 100,000 corn plants and further comprises a density of at least 54,000 corn plants per acre. In another aspect, a corn field comprises between 10,000 and 100,000 corn plants and further comprises a density of at least 57,000 corn plants per acre. In another aspect, a corn field comprises between 10,000 and 100,000 corn plants and further comprises a density of at least 60,000 corn plants per acre. In another aspect, a corn field comprises between 10,000 and 100,000 corn plants and further comprises a density of at least 63,000 corn plants per acre. In another aspect, a corn field comprises between 10,000 and 100,000 corn plants and further comprises a density of at least 66,000 corn plants per acre. In another aspect, a corn field comprises between 10,000 and 100,000 corn plants and further comprises a density of at least 69,000 corn plants per acre. In another aspect, a corn field comprises between 10,000 and 100,000 corn plants and further comprises a density of at least 72,000 corn plants per acre. In another aspect, a corn field comprises between 10,000 and 100,000 corn plants and further comprises a density of at least 75,000 corn plants per acre.

In an aspect, a corn field comprises between 100,000 and 1,000,000 corn plants and further comprises a density of at least 9,000 corn plants per acre. In another aspect, a corn field comprises between 100,000 and 1,000,000 corn plants and further comprises a density of at least 12,000 corn plants per acre. In another aspect, a corn field comprises between 100,000 and 1,000,000 corn plants and further comprises a density of at least 15,000 corn plants per acre. In another aspect, a corn field comprises between 100,000 and 1,000,000 corn plants and further comprises a density of at least 18,000 corn plants per acre. In another aspect, a corn field comprises between 100,000 and 1,000,000 corn plants and further comprises a density of at least 21,000 corn plants per acre. In another aspect, a corn field comprises between 100,000 and 1,000,000 corn plants and further comprises a density of at least 24,000 corn plants per acre. In another aspect, a corn field comprises between 100,000 and 1,000,000 corn plants and further comprises a density of at least 27,000 corn plants per acre. In another aspect, a corn field comprises between 100,000 and 1,000,000 corn plants and further comprises a density of at least 30,000 corn plants per acre. In another aspect, a corn field comprises between 100,000 and 1,000,000 corn plants and further comprises a density of at least 33,000 corn plants per acre. In another aspect, a corn field comprises between 100,000 and 1,000,000 corn plants and further comprises a density of at least 36,000 corn plants per acre. In another aspect, a corn field comprises between 100,000 and 1,000,000 corn plants and further comprises a density of at least 39,000 corn plants per acre. In another aspect, a corn field comprises between 100,000 and 1,000,000 corn plants and further comprises a density of at least 42,000 corn plants per acre. In another aspect, a corn field comprises between 100,000 and 1,000,000 corn plants and further comprises a density of at least 45,000 corn plants per acre. In another aspect, a corn field comprises between 100,000 and 1,000,000 corn plants and further comprises a density of at least 48,000 corn plants per acre. In another aspect, a corn field comprises between 100,000 and 1,000,000 corn plants and further comprises a density of at least 51,000 corn plants per acre. In another aspect, a corn field comprises between 100,000 and 1,000,000 corn plants and further comprises a density of at least 54,000 corn plants per acre. In another aspect, a corn field comprises between 100,000 and 1,000,000 corn plants and further comprises a density of at least 57,000 corn plants per acre. In another aspect, a corn field comprises between 100,000 and 1,000,000 corn plants and further comprises a density of at least 60,000 corn plants per acre. In another aspect, a corn field comprises between 100,000 and 1,000,000 corn plants and further comprises a density of at least 63,000 corn plants per acre. In another aspect, a corn field comprises between 100,000 and 1,000,000 corn plants and further comprises a density of at least 66,000 corn plants per acre. In another aspect, a corn field comprises between 100,000 and 1,000,000 corn plants and further comprises a density of at least 69,000 corn plants per acre. In another aspect, a corn field comprises between 100,000 and 1,000,000 corn plants and further comprises a density of at least 72,000 corn plants per acre. In another aspect, a corn field comprises between 100,000 and 1,000,000 corn plants and further comprises a density of at least 75,000 corn plants per acre.

In an aspect, a corn field comprises between 1,000,000 and 10,000,000 corn plants and further comprises a density of at least 9,000 corn plants per acre. In another aspect, a corn field comprises between 1,000,000 and 10,000,000 corn plants and further comprises a density of at least 12,000 corn plants per acre. In another aspect, a corn field comprises between 1,000,000 and 10,000,000 corn plants and further comprises a density of at least 15,000 corn plants per acre. In another aspect, a corn field comprises between 1,000,000 and 10,000,000 corn plants and further comprises a density of at least 18,000 corn plants per acre. In another aspect, a corn field comprises between 1,000,000 and 10,000,000 corn plants and further comprises a density of at least 21,000 corn plants per acre. In another aspect, a corn field comprises between 1,000,000 and 10,000,000 corn plants and further comprises a density of at least 24,000 corn plants per acre. In another aspect, a corn field comprises between 1,000,000 and 10,000,000 corn plants and further comprises a density of at least 27,000 corn plants per acre. In another aspect, a corn field comprises between 1,000,000 and 10,000,000 corn plants and further comprises a density of at least 30,000 corn plants per acre. In another aspect, a corn field comprises between 1,000,000 and 10,000,000 corn plants and further comprises a density of at least 33,000 corn plants per acre. In another aspect, a corn field comprises between 1,000,000 and 10,000,000 corn plants and further comprises a density of at least 36,000 corn plants per acre. In another aspect, a corn field comprises between 1,000,000 and 10,000,000 corn plants and further comprises a density of at least 39,000 corn plants per acre. In another aspect, a corn field comprises between 1,000,000 and 10,000,000 corn plants and further comprises a density of at least 42,000 corn plants per acre. In another aspect, a corn field comprises between 1,000,000 and 10,000,000 corn plants and further comprises a density of at least 45,000 corn plants per acre. In another aspect, a corn field comprises between 1,000,000 and 10,000,000 corn plants and further comprises a density of at least 48,000 corn plants per acre. In another aspect, a corn field comprises between 1,000,000 and 10,000,000 corn plants and further comprises a density of at least 51,000 corn plants per acre. In another aspect, a corn field comprises between 1,000,000 and 10,000,000 corn plants and further comprises a density of at least 54,000 corn plants per acre. In another aspect, a corn field comprises between 1,000,000 and 10,000,000 corn plants and further comprises a density of at least 57,000 corn plants per acre. In another aspect, a corn field comprises between 1,000,000 and 10,000,000 corn plants and further comprises a density of at least 60,000 corn plants per acre. In another aspect, a corn field comprises between 1,000,000 and 10,000,000 corn plants and further comprises a density of at least 63,000 corn plants per acre. In another aspect, a corn field comprises between 1,000,000 and 10,000,000 corn plants and further comprises a density of at least 66,000 corn plants per acre. In another aspect, a corn field comprises between 1,000,000 and 10,000,000 corn plants and further comprises a density of at least 69,000 corn plants per acre. In another aspect, a corn field comprises between 1,000,000 and 10,000,000 corn plants and further comprises a density of at least 72,000 corn plants per acre. In another aspect, a corn field comprises between 1,000,000 and 10,000,000 corn plants and further comprises a density of at least 75,000 corn plants per acre.

In an aspect, a corn field comprises between one and 1,000 corn plants and further comprises a density of between 20,000 corn plants and 55,000 corn plants per acre. In another aspect, a corn field comprises between one and 1,000 corn plants and further comprises a density of between 20,000 corn plants and 50,000 corn plants per acre. In another aspect, a corn field comprises between one and 1,000 corn plants and further comprises a density of between 20,000 corn plants and 45,000 corn plants per acre. In another aspect, a corn field comprises between one and 1,000 corn plants and further comprises a density of between 20,000 corn plants and 40,000 corn plants per acre. In another aspect, a corn field comprises between one and 1,000 corn plants and further comprises a density of between 20,000 corn plants and 35,000 corn plants per acre. In another aspect, a corn field comprises between one and 1,000 corn plants and further comprises a density of between 20,000 corn plants and 30,000 corn plants per acre. In another aspect, a corn field comprises between one and 1,000 corn plants and further comprises a density of between 24,000 corn plants and 58,000 corn plants per acre. In another aspect, a corn field comprises between one and 1,000 corn plants and further comprises a density of between 38,000 corn plants and 60,000 corn plants per acre. In another aspect, a corn field comprises between one and 1,000 corn plants and further comprises a density of between 38,000 corn plants and 50,000 corn plants per acre. In another aspect, a corn field comprises between one and 1,000 corn plants and further comprises a density of less than 10,000 corn plants per acre. In another aspect, a corn field comprises between one and 1,000 corn plants and further comprises a density of less than 20,000 corn plants per acre. In another aspect, a corn field comprises between one and 1,000 corn plants and further comprises a density of less than 30,000 corn plants per acre.

In an aspect, a corn field comprises between 1,000 and 10,000 corn plants and further comprises a density of between 20,000 corn plants and 55,000 corn plants per acre. In another aspect, a corn field comprises between 1,000 and 10,000 corn plants and further comprises a density of between 20,000 corn plants and 50,000 corn plants per acre. In another aspect, a corn field comprises between 1,000 and 10,000 corn plants and further comprises a density of between 20,000 corn plants and 45,000 corn plants per acre. In another aspect, a corn field comprises between 1,000 and 10,000 corn plants and further comprises a density of between 20,000 corn plants and 40,000 corn plants per acre. In another aspect, a corn field comprises between 1,000 and 10,000 corn plants and further comprises a density of between 20,000 corn plants and 35,000 corn plants per acre. In another aspect, a corn field comprises between 1,000 and 10,000 corn plants and further comprises a density of between 20,000 corn plants and 30,000 corn plants per acre. In another aspect, a corn field comprises between 1,000 and 10,000 corn plants and further comprises a density of between 24,000 corn plants and 58,000 corn plants per acre. In another aspect, a corn field comprises between 1,000 and 10,000 corn plants and further comprises a density of between 38,000 corn plants and 60,000 corn plants per acre. In another aspect, a corn field comprises between 1,000 and 10,000 corn plants and further comprises a density of between 38,000 corn plants and 50,000 corn plants per acre. In another aspect, a corn field comprises between 1,000 and 10,000 corn plants and further comprises a density of less than 10,000 corn plants per acre. In another aspect, a corn field comprises between 1,000 and 10,000 corn plants and further comprises a density of less than 20,000 corn plants per acre. In another aspect, a corn field comprises between 1,000 and 10,000 corn plants and further comprises a density of less than 30,000 corn plants per acre.

In an aspect, a corn field comprises between 10,000 and 100,000 corn plants and further comprises a density of between 20,000 corn plants and 55,000 corn plants per acre. In another aspect, a corn field comprises between 10,000 and 100,000 corn plants and further comprises a density of between 20,000 corn plants and 50,000 corn plants per acre. In another aspect, a corn field comprises between 10,000 and 100,000 corn plants and further comprises a density of between 20,000 corn plants and 45,000 corn plants per acre. In another aspect, a corn field comprises between 10,000 and 100,000 corn plants and further comprises a density of between 20,000 corn plants and 40,000 corn plants per acre. In another aspect, a corn field comprises between 10,000 and 100,000 corn plants and further comprises a density of between 20,000 corn plants and 35,000 corn plants per acre. In another aspect, a corn field comprises between 10,000 and 100,000 corn plants and further comprises a density of between 20,000 corn plants and 30,000 corn plants per acre. In another aspect, a corn field comprises between 10,000 and 100,000 corn plants and further comprises a density of between 24,000 corn plants and 58,000 corn plants per acre. In another aspect, a corn field comprises between 10,000 and 100,000 corn plants and further comprises a density of between 38,000 corn plants and 60,000 corn plants per acre. In another aspect, a corn field comprises between 10,000 and 100,000 corn plants and further comprises a density of between 38,000 corn plants and 50,000 corn plants per acre. In another aspect, a corn field comprises between 10,000 and 100,000 corn plants and further comprises a density of less than 10,000 corn plants per acre. In another aspect, a corn field comprises between 10,000 and 100,000 corn plants and further comprises a density of less than 20,000 corn plants per acre. In another aspect, a corn field comprises between 10,000 and 100,000 corn plants and further comprises a density of less than 30,000 corn plants per acre.

In an aspect, a corn field comprises between 100,000 and 1,000,000 corn plants and further comprises a density of between 20,000 corn plants and 55,000 corn plants per acre. In another aspect, a corn field comprises between 100,000 and 1,000,000 corn plants and further comprises a density of between 20,000 corn plants and 50,000 corn plants per acre. In another aspect, a corn field comprises between 100,000 and 1,000,000 corn plants and further comprises a density of between 20,000 corn plants and 45,000 corn plants per acre. In another aspect, a corn field comprises between 100,000 and 1,000,000 corn plants and further comprises a density of between 20,000 corn plants and 40,000 corn plants per acre. In another aspect, a corn field comprises between 100,000 and 1,000,000 corn plants and further comprises a density of between 20,000 corn plants and 35,000 corn plants per acre. In another aspect, a corn field comprises between 100,000 and 1,000,000 corn plants and further comprises a density of between 20,000 corn plants and 30,000 corn plants per acre. In another aspect, a corn field comprises between 100,000 and 1,000,000 corn plants and further comprises a density of between 24,000 corn plants and 58,000 corn plants per acre. In another aspect, a corn field comprises between 100,000 and 1,000,000 corn plants and further comprises a density of between 38,000 corn plants and 60,000 corn plants per acre. In another aspect, a corn field comprises between 100,000 and 1,000,000 corn plants and further comprises a density of between 38,000 corn plants and 50,000 corn plants per acre. In another aspect, a corn field comprises between 100,000 and 1,000,000 corn plants and further comprises a density of less than 10,000 corn plants per acre. In another aspect, a corn field comprises between 100,000 and 1,000,000 corn plants and further comprises a density of less than 20,000 corn plants per acre. In another aspect, a corn field comprises between 100,000 and 1,000,000 corn plants and further comprises a density of less than 30,000 corn plants per acre.

In an aspect, a corn field comprises between 1,000,000 and 10,000,000 corn plants and further comprises a density of between 20,000 corn plants and 55,000 corn plants per acre. In another aspect, a corn field comprises between 1,000,000 and 10,000,000 corn plants and further comprises a density of between 20,000 corn plants and 50,000 corn plants per acre. In another aspect, a corn field comprises between 1,000,000 and 10,000,000 corn plants and further comprises a density of between 20,000 corn plants and 45,000 corn plants per acre. In another aspect, a corn field comprises between 1,000,000 and 10,000,000 corn plants and further comprises a density of between 20,000 corn plants and 40,000 corn plants per acre. In another aspect, a corn field comprises between 1,000,000 and 10,000,000 corn plants and further comprises a density of between 20,000 corn plants and 35,000 corn plants per acre. In another aspect, a corn field comprises between 1,000,000 and 10,000,000 corn plants and further comprises a density of between 20,000 corn plants and 30,000 corn plants per acre. In another aspect, a corn field comprises between 1,000,000 and 10,000,000 corn plants and further comprises a density of between 24,000 corn plants and 58,000 corn plants per acre. In another aspect, a corn field comprises between 1,000,000 and 10,000,000 corn plants and further comprises a density of between 38,000 corn plants and 60,000 corn plants per acre. In another aspect, a corn field comprises between 1,000,000 and 10,000,000 corn plants and further comprises a density of between 38,000 corn plants and 50,000 corn plants per acre. In another aspect, a corn field comprises between 1,000,000 and 10,000,000 corn plants and further comprises a density of less than 10,000 corn plants per acre. In another aspect, a corn field comprises between 1,000,000 and 10,000,000 corn plants and further comprises a density of less than 20,000 corn plants per acre. In another aspect, a corn field comprises between 1,000,000 and 10,000,000 corn plants and further comprises a density of less than 30,000 corn plants per acre.

As used herein, the term "planting pattern" refers to the spatial arrangement of corn plants within a field. In an aspect, the planting pattern within a field is described as the ratio of female plants to male plants. In an aspect, the planting pattern of plants in a field within a field is random. In another aspect, the planting pattern of plants in a field are arranged in rows of male plants and rows of female plants, and the planting pattern is described as the ratio of male plant rows to female plant rows, or vice versa, within the field. In another aspect, the planting pattern within a field is described by the spacing between rows of plants. In another aspect, the planting pattern within a field is described by the spacing between plants within a given row. In an aspect, the planting pattern of plants in a field are arranged in a regular and repeating pattern of rows, which may comprise one or more rows of male plants or two or more contiguous rows of male plants separated by two or more contiguous rows of female plants, three or more contiguous rows of female plants, four or more contiguous rows of female plants, five or more contiguous rows of female plants, six or more contiguous rows of female plants, seven or more contiguous rows of female plants, eight or more contiguous rows of female plants, nine or more contiguous rows of female plants, or ten or more contiguous rows of female plants, wherein the rows of female and/or male plants are separated by equal (or approximately equal) spacing. In another aspect, the planting pattern of plants in a field are arranged in an irregular and non-repeating pattern of rows. In another aspect, the planting pattern within a field is described by a combination of two or more of the arrangements described above.

In an aspect, a corn field provided herein comprises a ratio of at least 1 female inbred corn plant for every male inbred corn plant. In another aspect, a corn field provided herein comprises a ratio of at least 2 female inbred corn plants for every male inbred corn plant. In another aspect, a corn field provided herein comprises a ratio of at least 3 female inbred corn plants for every male inbred corn plant. In another aspect, a corn field provided herein comprises a ratio of at least 4 female corn inbred plants for every male inbred corn plant. In another aspect, a corn field provided herein comprises a ratio of at least 5 female inbred corn plants for every male inbred corn plant. In another aspect, a corn field provided herein comprises a ratio of at least 6 female inbred corn plants for every male inbred corn plant. In another aspect, a corn field provided herein comprises a ratio of at least 7 female inbred corn plants for every male inbred corn plant. In another aspect, a corn field provided herein comprises a ratio of at least 8 female inbred corn plants for every male inbred corn plant. In another aspect, a corn field provided herein comprises a ratio of at least 9 female inbred corn plants for every male inbred corn plant. In another aspect, a corn field provided herein comprises a ratio of at least 10 female inbred corn plants for every male inbred corn plant. In another aspect, a corn field provided herein comprises a ratio of at least 15 female inbred corn plants for every male inbred corn plant. In another aspect, a corn field provided herein comprises a ratio of at least 20 female inbred corn plants for every male inbred corn plant. In another aspect, a corn field provided herein comprises a ratio of at least 25 female inbred corn plants for every male inbred corn plant. In another aspect, a corn field provided herein comprises a ratio of at least 30 female inbred corn plants for every male inbred corn plant. In another aspect, a corn field provided herein comprises a ratio of at least 35 female inbred corn plants for every male inbred corn plant. In another aspect, a corn field provided herein comprises a ratio of at least 40 female inbred corn plants for every male inbred corn plant. In another aspect, a corn field provided herein comprises a ratio of at least 45 female inbred corn plants for every male inbred corn plant. In another aspect, a corn field provided herein comprises a ratio of at least 50 female inbred corn plants for every male inbred corn plant. In another aspect, a corn field provided herein comprises a ratio of at least 55 female inbred corn plants for every male inbred corn plant. In another aspect, a corn field provided herein comprises a ratio of at least 60 female inbred corn plants for every male inbred corn plant. In another aspect, a corn field provided herein comprises a ratio of at least 65 female inbred corn plants for every male inbred corn plant. In another aspect, a corn field provided herein comprises a ratio of at least 70 female inbred corn plants for every male inbred corn plant. In another aspect, a corn field provided herein comprises a ratio of at least 75 female inbred corn plants for every male inbred corn plant. In another aspect, a corn field provided herein comprises a ratio of at least 80 female inbred corn plants for every male inbred corn plant. In another aspect, a corn field provided herein comprises a ratio of at least 85 female inbred corn plants for every male inbred corn plant. In another aspect, a corn field provided herein comprises a ratio of at least 90 female inbred corn plants for every male inbred corn plant. In another aspect, a corn field provided herein comprises a ratio of at least 95 female inbred corn plants for every male inbred corn plant. In another aspect, a corn field provided herein comprises a ratio of at least 100 female inbred corn plants for every male inbred corn plant. In another aspect, a corn field provided herein comprises a ratio of at least 105 female inbred corn plants for every male inbred corn plant. In another aspect, a corn field provided herein comprises a ratio of at least 110 female inbred corn plants for every male inbred corn plant. In another aspect, a corn field provided herein comprises a ratio of at least 115 female inbred corn plants for every male inbred corn plant. In another aspect, a corn field provided herein comprises a ratio of at least 120 female inbred corn plants for every male inbred corn plant.

In an aspect, a corn field provided herein comprises between 1 and 10 female inbred corn plants for every male inbred corn plant. In another aspect, a corn field provided herein comprises between 5 and 10 female inbred corn plants for every male inbred corn plant. In another aspect, a corn field provided herein comprises between 1 and 20 female inbred corn plants for every male inbred corn plant. In another aspect, a corn field provided herein comprises between 5 and 20 female inbred corn plants for every male inbred corn plant. In another aspect, a corn field provided herein comprises between 5 and 15 female inbred corn plants for every male inbred corn plant. In another aspect, a corn field provided herein comprises between 5 and 10 female inbred corn plants for every two male inbred corn plants. In another aspect, a corn field provided herein comprises between 5 and 20 female inbred corn plants for every two male inbred corn plants. In another aspect, a corn field provided herein comprises between 5 and 15 female inbred corn plants for every two male inbred corn plants. In another aspect, a corn field provided herein comprises between 1 and 30 female inbred corn plants for every male inbred corn plant. In another aspect, a corn field provided herein comprises between 1 and 40 female inbred corn plants for every male inbred corn plant. In another aspect, a corn field provided herein comprises between 1 and 50 female inbred corn plants for every male inbred corn plant. In another aspect, a corn field provided herein comprises between 1 and 60 female inbred corn plants for every male inbred corn plant. In another aspect, a corn field provided herein comprises between 1 and 80 female inbred corn plants for every male inbred corn plant. In another aspect, a corn field provided herein comprises between 1 and 100 female inbred corn plants for every male inbred corn plant. In another aspect, a corn field provided herein comprises between 1 and 120 female inbred corn plants for every male inbred corn plant. In another aspect, a corn field provided herein comprises between 10 and 20 female inbred corn plants for every male inbred corn plant. In another aspect, a corn field provided herein comprises between 20 and 30 female inbred corn plants for every male inbred corn plant. In another aspect, a corn field provided herein comprises between 30 and 40 female inbred corn plants for every male inbred corn plant. In another aspect, a corn field provided herein comprises between 40 and 50 female inbred corn plants for every male inbred corn plant. In another aspect, a corn field provided herein comprises between 50 and 60 female inbred corn plants for every male inbred corn plant. In another aspect, a corn field provided herein comprises between 60 and 70 female inbred corn plants for every male inbred corn plant. In another aspect, a corn field provided herein comprises between 70 and 80 female inbred corn plants for every male inbred corn plant. In another aspect, a corn field provided herein comprises between 80 and 90 female inbred corn plants for every male inbred corn plant. In another aspect, a corn field provided herein comprises between 90 and 100 female inbred corn plants for every male inbred corn plant. In another aspect, a corn field provided herein comprises between 100 and 110 female inbred corn plants for every male inbred corn plant. In another aspect, a corn field provided herein comprises between 110 and 120 female inbred corn plants for every male inbred corn plant. In another aspect, a corn field provided herein comprises between 20 and 40 female inbred corn plants for every male inbred corn plant. In another aspect, a corn field provided herein comprises between 40 and 60 female inbred corn plants for every male inbred corn plant. In another aspect, a corn field provided herein comprises between 60 and 80 female inbred corn plants for every male inbred corn plant. In another aspect, a corn field provided herein comprises between 80 and 100 female inbred corn plants for every male inbred corn plant. In another aspect, a corn field provided herein comprises between 100 and 120 female inbred corn plants for every male inbred corn plant. In another aspect, a corn field provided herein comprises between 20 and 80 female inbred corn plants for every male inbred corn plant. In another aspect, a corn field provided herein comprises between 40 and 100 female inbred corn plants for every male inbred corn plant. In another aspect, a corn field provided herein comprises between 60 and 120 female inbred corn plants for every male inbred corn plant.

In an aspect, a corn field provided herein comprises a ratio of at least 1 female corn plant for every male corn plant. In another aspect, a corn field provided herein comprises a ratio of at least 2 female corn plants for every male corn plant. In another aspect, a corn field provided herein comprises a ratio of at least 3 female corn plants for every male corn plant. In another aspect, a corn field provided herein comprises a ratio of at least 4 female corn plants for every male corn plant. In another aspect, a corn field provided herein comprises a ratio of at least 5 female corn plants for every male corn plant. In another aspect, a corn field provided herein comprises a ratio of at least 6 female corn plants for every male corn plant. In another aspect, a corn field provided herein comprises a ratio of at least 7 female corn plants for every male corn plant. In another aspect, a corn field provided herein comprises a ratio of at least 8 female corn plants for every male corn plant. In another aspect, a corn field provided herein comprises a ratio of at least 9 female corn plants for every male corn plant. In another aspect, a corn field provided herein comprises a ratio of at least 10 female corn plants for every male corn plant. In another aspect, a corn field provided herein comprises a ratio of at least 15 female corn plants for every male corn plant. In another aspect, a corn field provided herein comprises a ratio of at least 20 female corn plants for every male corn plant. In another aspect, a corn field provided herein comprises a ratio of at least 25 female corn plants for every male corn plant. In another aspect, a corn field provided herein comprises a ratio of at least 30 female corn plants for every male corn plant. In another aspect, a corn field provided herein comprises a ratio of at least 35 female corn plants for every male corn plant. In another aspect, a corn field provided herein comprises a ratio of at least 40 female corn plants for every male corn plant. In another aspect, a corn field provided herein comprises a ratio of at least 45 female corn plants for every male corn plant. In another aspect, a corn field provided herein comprises a ratio of at least 50 female corn plants for every male corn plant. In another aspect, a corn field provided herein comprises a ratio of at least 55 female corn plants for every male corn plant. In another aspect, a corn field provided herein comprises a ratio of at least 60 female corn plants for every male corn plant. In another aspect, a corn field provided herein comprises a ratio of at least 65 female corn plants for every male corn plant. In another aspect, a corn field provided herein comprises a ratio of at least 70 female corn plants for every male corn plant. In another aspect, a corn field provided herein comprises a ratio of at least 75 female corn plants for every male corn plant. In another aspect, a corn field provided herein comprises a ratio of at least 80 female corn plants for every male corn plant. In another aspect, a corn field provided herein comprises a ratio of at least 85 female corn plants for every male corn plant. In another aspect, a corn field provided herein comprises a ratio of at least 90 female corn plants for every male corn plant. In another aspect, a corn field provided herein comprises a ratio of at least 95 female corn plants for every male corn plant. In another aspect, a corn field provided herein comprises a ratio of at least 100 female corn plants for every male corn plant. In another aspect, a corn field provided herein comprises a ratio of at least 105 female corn plants for every male corn plant. In another aspect, a corn field provided herein comprises a ratio of at least 110 female corn plants for every male corn plant. In another aspect, a corn field provided herein comprises a ratio of at least 115 female corn plants for every male corn plant. In another aspect, a corn field provided herein comprises a ratio of at least 120 female corn plants for every male corn plant.

In an aspect, a corn field provided herein comprises between 1 and 10 female corn plants for every male corn plant. In another aspect, a corn field provided herein comprises between 5 and 10 female corn plants for every male corn plant. In another aspect, a corn field provided herein comprises between 1 and 20 female corn plants for every male corn plant. In another aspect, a corn field provided herein comprises between 5 and 20 female corn plants for every male corn plant. In another aspect, a corn field provided herein comprises between 5 and 15 female corn plants for every male corn plant. In another aspect, a corn field provided herein comprises between 5 and 10 female corn plants for every two male corn plants. In another aspect, a corn field provided herein comprises between 5 and 20 female corn plants for every two male corn plants. In another aspect, a corn field provided herein comprises between 5 and 15 female corn plants for every two male corn plants. In another aspect, a corn field provided herein comprises between 1 and 30 female corn plants for every male corn plant. In another aspect, a corn field provided herein comprises between 1 and 40 female corn plants for every male corn plant. In another aspect, a corn field provided herein comprises between 1 and 50 female corn plants for every male corn plant. In another aspect, a corn field provided herein comprises between 1 and 60 female corn plants for every male corn plant. In another aspect, a corn field provided herein comprises between 1 and 80 female corn plants for every male corn plant. In another aspect, a corn field provided herein comprises between 1 and 100 female corn plants for every male corn plant. In another aspect, a corn field provided herein comprises between 1 and 120 female corn plants for every male corn plant. In another aspect, a corn field provided herein comprises between 10 and 20 female corn plants for every male corn plant. In another aspect, a corn field provided herein comprises between 20 and 30 female corn plants for every male corn plant. In another aspect, a corn field provided herein comprises between 30 and 40 female corn plants for every male corn plant. In another aspect, a corn field provided herein comprises between 40 and 50 female corn plants for every male corn plant. In another aspect, a corn field provided herein comprises between 50 and 60 female corn plants for every male corn plant. In another aspect, a corn field provided herein comprises between 60 and 70 female corn plants for every male corn plant. In another aspect, a corn field provided herein comprises between 70 and 80 female corn plants for every male corn plant. In another aspect, a corn field provided herein comprises between 80 and 90 female corn plants for every male corn plant. In another aspect, a corn field provided herein comprises between 90 and 100 female corn plants for every male corn plant. In another aspect, a corn field provided herein comprises between 100 and 110 female corn plants for every male corn plant. In another aspect, a corn field provided herein comprises between 110 and 120 female corn plants for every male corn plant. In another aspect, a corn field provided herein comprises between 20 and 40 female corn plants for every male corn plant. In another aspect, a corn field provided herein comprises between 40 and 60 female corn plants for every male corn plant. In another aspect, a corn field provided herein comprises between 60 and 80 female corn plants for every male corn plant. In another aspect, a corn field provided herein comprises between 80 and 100 female corn plants for every male corn plant. In another aspect, a corn field provided herein comprises between 100 and 120 female corn plants for every male corn plant. In another aspect, a corn field provided herein comprises between 20 and 80 female corn plants for every male corn plant. In another aspect, a corn field provided herein comprises between 40 and 100 female corn plants for every male corn plant. In another aspect, a corn field provided herein comprises between 60 and 120 female corn plants for every male corn plant.

In an aspect, a corn field provided herein comprises at least one row of female inbred corn plants and at least one row of male inbred corn plants. In another aspect, a corn field provided herein comprises multiple rows of female inbred corn plants and at least one row of male inbred corn plants. In another aspect, a corn field provided herein comprises multiple rows of female inbred corn plants and multiple rows of male inbred corn plants.

In an aspect, a corn field provided herein comprises at least one row of female corn plants and at least one row of male corn plants. In another aspect, a corn field provided herein comprises multiple rows of female corn plants and at least one row of male corn plants. In another aspect, a corn field provided herein comprises multiple rows of female corn plants and multiple rows of male corn plants.

In an aspect, a corn field provided herein comprises rows of female inbred corn plants and rows of male inbred corn plants where the overall female-to-male corn plant ratio (or the ratio of female-to-male corn plant rows) within the field is 2:2. In another aspect, a corn field provided herein comprises rows of female inbred corn plants and rows of male inbred corm plants where the overall female-to-male corn plant ratio (or the ratio of female-to-male corn plant rows) within the field is 3:1. In another aspect, a corn field provided herein comprises rows of female inbred corn plants and rows of male inbred corm plants where the overall female-to-male corn plant ratio (or the ratio of female-to-male corn plant rows) within the field is 3:2. In another aspect, a corn field provided herein comprises rows of female inbred corn plants and rows of male inbred corm plants where the overall female-to-male corn plant ratio (or the ratio of female-to-male corn plant rows) within the field is 4:1. In another aspect, a corn field provided herein comprises rows of female inbred corn plants and rows of male inbred corm plants where the overall female-to-male corn plant ratio (or the ratio of female-to-male corn plant rows) within the field is 4:2. In another aspect, a corn field provided herein comprises rows of female inbred corn plants and rows of male inbred corm plants where the overall female-to-male corn plant ratio (or the ratio of female-to-male corn plant rows) within the field is 4:3. In another aspect, a corn field provided herein comprises rows of female inbred corn plants and rows of male inbred corm plants where the overall female-to-male corn plant ratio (or the ratio of female-to-male corn plant rows) within the field is 5:1. In another aspect, a corn field provided herein comprises rows of female inbred corn plants and rows of male inbred corm plants where the overall female-to-male corn plant ratio (or the ratio of female-to-male corn plant rows) within the field is 5:2. In another aspect, a corn field provided herein comprises rows of female inbred corn plants and rows of male inbred corm plants where the overall female-to-male corn plant ratio (or the ratio of female-to-male corn plant rows) within the field is 6:1. In another aspect, a corn field provided herein comprises rows of female inbred corn plants and rows of male inbred corm plants where the overall female-to-male corn plant ratio (or the ratio of female-to-male corn plant rows) within the field is 6:2. In another aspect, a corn field provided herein comprises rows of female inbred corn plants and rows of male inbred corm plants where the overall female-to-male corn plant ratio (or the ratio of female-to-male corn plant rows) within the field is 7:1. In another aspect, a corn field provided herein comprises rows of female inbred corn plants and rows of male inbred corm plants where the overall female-to-male corn plant ratio (or the ratio of female-to-male corn plant rows) within the field is 7:2. In another aspect, a corn field provided herein comprises rows of female inbred corn plants and rows of male inbred corm plants where the overall female-to-male corn plant ratio (or the ratio of female-to-male corn plant rows) within the field is 8:1. In another aspect, a corn field provided herein comprises rows of female inbred corn plants and rows of male inbred corm plants where the overall female-to-male corn plant ratio (or the ratio of female-to-male corn plant rows) within the field is 8:2.

In an aspect, a corn field provided herein comprises rows of female corn plants and rows of male corn plants where the overall female-to-male corn plant ratio (or the ratio of female-to-male corn plant rows) within the field is 2:2. In another aspect, a corn field provided herein comprises rows of female inbred corn plants and rows of male inbred corm plants where the overall female-to-male corn plant ratio (or the ratio of female-to-male corn plant rows) within the field is 3:1. In another aspect, a corn field provided herein comprises rows of female corn plants and rows of male corm plants where the overall female-to-male corn plant ratio (or the ratio of female-to-male corn plant rows) within the field is 3:2. In another aspect, a corn field provided herein comprises rows of female corn plants and rows of male corm plants where the overall female-to-male corn plant ratio (or the ratio of female-to-male corn plant rows) within the field is 4:1. In another aspect, a corn field provided herein comprises rows of female corn plants and rows of male corm plants where the overall female-to-male corn plant ratio (or the ratio of female-to-male corn plant rows) within the field is 4:2. In another aspect, a corn field provided herein comprises rows of female corn plants and rows of male corm plants where the overall female-to-male corn plant ratio (or the ratio of female-to-male corn plant rows) within the field is 4:3. In another aspect, a corn field provided herein comprises rows of female corn plants and rows of male corm plants where the overall female-to-male corn plant ratio (or the ratio of female-to-male corn plant rows) within the field is 5:1. In another aspect, a corn field provided herein comprises rows of female corn plants and rows of male corm plants where the overall female-to-male corn plant ratio (or the ratio of female-to-male corn plant rows) within the field is 5:2. In another aspect, a corn field provided herein comprises rows of female corn plants and rows of male corm plants where the overall female-to-male corn plant ratio (or the ratio of female-to-male corn plant rows) within the field is 6:1. In another aspect, a corn field provided herein comprises rows of female corn plants and rows of male corm plants where the overall female-to-male corn plant ratio (or the ratio of female-to-male corn plant rows) within the field is 6:2. In another aspect, a corn field provided herein comprises rows of female corn plants and rows of male corm plants where the overall female-to-male corn plant ratio (or the ratio of female-to-male corn plant rows) within the field is 7:1. In another aspect, a corn field provided herein comprises rows of female corn plants and rows of male corm plants where the overall female-to-male corn plant ratio (or the ratio of female-to-male corn plant rows) within the field is 7:2. In another aspect, a corn field provided herein comprises rows of female corn plants and rows of male corm plants where the overall female-to-male corn plant ratio (or the ratio of female-to-male corn plant rows) within the field is 8:1. In another aspect, a corn field provided herein comprises rows of female corn plants and rows of male corm plants where the overall female-to-male corn plant ratio (or the ratio of female-to-male corn plant rows) within the field is 8:2.

In an aspect, a corn field provided herein comprises at least 1 female corn plant row for every male corn plant row. In another aspect, a corn field provided herein comprises at least 2 female corn plant rows for every male corn plant row. In another aspect, a corn field provided herein comprises at least 3 female corn plant rows for every male corn plant row. In another aspect, a corn field provided herein comprises at least 4 female corn plant rows for every male corn plant row. In another aspect, a corn field provided herein comprises at least 5 female corn plant rows for every male corn plant row. In another aspect, a corn field provided herein comprises at least 6 female corn plant rows for every male corn plant row. In another aspect, a corn field provided herein comprises at least 7 female corn plant rows for every male corn plant row. In another aspect, a corn field provided herein comprises at least 8 female corn plant rows for every male corn plant row. In another aspect, a corn field provided herein comprises at least 9 female corn plant rows for every male corn plant row. In another aspect, a corn field provided herein comprises at least 10 female corn plant rows for every male corn plant row. In another aspect, a corn field provided herein comprises at least 11 female corn plant rows for every male corn plant row. In another aspect, a corn field provided herein comprises at least 12 female corn plant rows for every male corn plant row.

In an aspect, a corn field provided herein comprises between 1 female row and 2 female rows for every male row. In another aspect, a corn field provided herein comprises between 2 female rows and 3 female rows for every male row. In another aspect, a corn field provided herein comprises between 3 female rows and 4 female rows for every male row. In another aspect, a corn field provided herein comprises between 4 female rows and 5 female rows for every male row. In another aspect, a corn field provided herein comprises between 5 female rows and 6 female rows for every male row. In another aspect, a corn field provided herein comprises between 6 female rows and 7 female rows for every male row. In another aspect, a corn field provided herein comprises between 7 female rows and 8 female rows for every male row. In another aspect, a corn field provided herein comprises between 8 female rows and 9 female rows for every male row. In another aspect, a corn field provided herein comprises between 9 female rows and 10 female rows for every male row. In another aspect, a corn field provided herein comprises between 10 female rows and 11 female rows for every male row. In another aspect, a corn field provided herein comprises between 11 female rows and 12 female rows for every male row. In another aspect, a corn field provided herein comprises between 1 female row and 4 female rows for every male row. In another aspect, a corn field provided herein comprises between 4 female rows and 8 female rows for every male row. In another aspect, a corn field provided herein comprises between 8 female rows and 12 female rows for every male row. In another aspect, a corn field provided herein comprises between 1 female row and 10 female rows for every male row. In another aspect, a corn field provided herein comprises between 1 female row and 12 female rows for every male row.

In an aspect, a corn field provided herein comprises a regular and repeating pattern of two contiguous rows of female corn plants followed by two contiguous rows of male corn plants. In an aspect, a corn field provided herein comprises a regular and repeating pattern of three contiguous rows of female corn plants followed by one row of male corn plants. In an aspect, a corn field provided herein comprises a regular and repeating pattern of three contiguous rows of female corn plants followed by two rows of male corn plants. In an aspect, a corn field provided herein comprises a regular and repeating pattern of four contiguous rows of female corn plants followed by one row of male corn plants. In an aspect, a corn field provided herein comprises a regular and repeating pattern of four contiguous rows of female corn plants followed by two contiguous rows of male corn plants. In an aspect, a corn field provided herein comprises a regular and repeating pattern of four contiguous rows of female corn plants followed by three contiguous rows of male corn plants. In an aspect, a corn field provided herein comprises a regular and repeating pattern of five contiguous rows of female corn plants followed by one row of male corn plants. In an aspect, a corn field provided herein comprises a regular and repeating pattern of five contiguous rows of female corn plants followed by two contiguous rows of male corn plants. In an aspect, a corn field provided herein comprises a regular and repeating pattern of six contiguous rows of female corn plants followed by one row of male corn plants. In an aspect, a corn field provided herein comprises a regular and repeating pattern of six contiguous rows of female corn plants followed by two contiguous rows of male corn plants. In an aspect, a corn field provided herein comprises a regular and repeating pattern of seven contiguous rows of female corn plants followed by one row of male corn plants. In an aspect, a corn field provided herein comprises a regular and repeating pattern of seven contiguous rows of female corn plants followed by two contiguous rows of male corn plants. In an aspect, a corn field provided herein comprises a regular and repeating pattern of eight contiguous rows of female corn plants followed by one row of male corn plants. In an aspect, a corn field provided herein comprises a regular and repeating pattern of eight contiguous rows of female corn plants followed by two contiguous rows of male corn plants.

In an aspect, a corn field provided herein comprises at least two rows of corn plants, where any two adjacent rows are spaced at least 10 inches apart. In another aspect, a corn field provided herein comprises at least two rows of corn plants, where any two adjacent rows are spaced at least 12 inches apart. In another aspect, a corn field provided herein comprises at least two rows of corn plants, where any two adjacent rows are spaced at least 14 inches apart. In another aspect, a corn field provided herein comprises at least two rows of corn plants, where any two adjacent rows are spaced at least 16 inches apart. In another aspect, a corn field provided herein comprises at least two rows of corn plants, where any two adjacent rows are spaced at least 18 inches apart. In another aspect, a corn field provided herein comprises at least two rows of corn plants, where any two adjacent rows are spaced at least 20 inches apart. In another aspect, a corn field provided herein comprises at least two rows of corn plants, where any two adjacent rows are spaced at least 22 inches apart. In another aspect, a corn field provided herein comprises at least two rows of corn plants, where any two adjacent rows are spaced at least 24 inches apart. In another aspect, a corn field provided herein comprises at least two rows of corn plants, where any two adjacent rows are spaced at least 26 inches apart. In another aspect, a corn field provided herein comprises at least two rows of corn plants, where any two adjacent rows are spaced at least 28 inches apart. In another aspect, a corn field provided herein comprises at least two rows of corn plants, where any two adjacent rows are spaced at least 30 inches apart. In another aspect, a corn field provided herein comprises at least two rows of corn plants, where any two adjacent rows are spaced at least 32 inches apart. In another aspect, a corn field provided herein comprises at least two rows of corn plants, where any two adjacent rows are spaced at least 34 inches apart. In another aspect, a corn field provided herein comprises at least two rows of corn plants, where any two adjacent rows are spaced at least 36 inches apart. In another aspect, a corn field provided herein comprises at least two rows of corn plants, where any two adjacent rows are spaced at least 38 inches apart. In another aspect, a corn field provided herein comprises at least two rows of corn plants, where any two adjacent rows are spaced at least 40 inches apart. In another aspect, a corn field provided herein comprises at least two rows of corn plants, where different adjacent rows of the corn field have variable and/or irregular spacing.

In an aspect, a corn field provided herein comprises an average of at least 10 inches between adjacent rows of corn plants. In an aspect, a corn field provided herein comprises an average of at least 12 inches between adjacent rows of corn plants. In an aspect, a corn field provided herein comprises an average of at least 14 inches between adjacent rows of corn plants. In an aspect, a corn field provided herein comprises an average of at least 16 inches between adjacent rows of corn plants. In an aspect, a corn field provided herein comprises an average of at least 18 inches between adjacent rows of corn plants. In an aspect, a corn field provided herein comprises an average of at least 20 inches between adjacent rows of corn plants. In an aspect, a corn field provided herein comprises an average of at least 22 inches between adjacent rows of corn plants. In an aspect, a corn field provided herein comprises an average of at least 24 inches between adjacent rows of corn plants. In an aspect, a corn field provided herein comprises an average of at least 26 inches between adjacent rows of corn plants. In an aspect, a corn field provided herein comprises an average of at least 28 inches between adjacent rows of corn plants. In an aspect, a corn field provided herein comprises an average of at least 30 inches between adjacent rows of corn plants. In an aspect, a corn field provided herein comprises an average of at least 32 inches between adjacent rows of corn plants. In an aspect, a corn field provided herein comprises an average of at least 34 inches between adjacent rows of corn plants. In an aspect, a corn field provided herein comprises an average of at least 36 inches between adjacent rows of corn plants. In an aspect, a corn field provided herein comprises an average of at least 38 inches between adjacent rows of corn plants. In an aspect, a corn field provided herein comprises an average of at least 40 inches between adjacent rows of corn plants.

In an aspect, a corn field provided herein comprises at least two rows of corn plants, where any two adjacent rows are spaced between 10 and 12 inches apart. In another aspect, a corn field provided herein comprises at least two rows of corn plants, where any two adjacent rows are spaced between 12 and 14 inches apart. In another aspect, a corn field provided herein comprises at least two rows of corn plants, where any two adjacent rows are spaced between 14 and 16 inches apart. In another aspect, a corn field provided herein comprises at least two rows of corn plants, where any two adjacent rows are spaced between 16 and 18 inches apart. In another aspect, a corn field provided herein comprises at least two rows of corn plants, where any two adjacent rows are spaced between 18 and 20 inches apart. In another aspect, a corn field provided herein comprises at least two rows of corn plants, where any two adjacent rows are spaced between 20 and 22 inches apart. In another aspect, a corn field provided herein comprises at least two rows of corn plants, where any two adjacent rows are spaced between 22 and 24 inches apart. In another aspect, a corn field provided herein comprises at least two rows of corn plants, where any two adjacent rows are spaced between 24 and 26 inches apart. In another aspect, a corn field provided herein comprises at least two rows of corn plants, where any two adjacent rows are spaced between 26 and 28 inches apart. In another aspect, a corn field provided herein comprises at least two rows of corn plants, where any two adjacent rows are spaced between 28 and 30 inches apart. In another aspect, a corn field provided herein comprises at least two rows of corn plants, where any two adjacent rows are spaced between 30 and 32 inches apart. In another aspect, a corn field provided herein comprises at least two rows of corn plants, where any two adjacent rows are spaced between 32 and 34 inches apart. In another aspect, a corn field provided herein comprises at least two rows of corn plants, where any two adjacent rows are spaced between 34 and 36 inches apart. In another aspect, a corn field provided herein comprises at least two rows of corn plants, where any two adjacent rows are spaced between 36 and 38 inches apart. In another aspect, a corn field provided herein comprises at least two rows of corn plants, where any two adjacent rows are spaced between 38 and 40 inches apart. In another aspect, a corn field provided herein comprises at least two rows of corn plants, where any two adjacent rows are spaced between 10 and 15 inches apart. In another aspect, a corn field provided herein comprises at least two rows of corn plants, where any two adjacent rows are spaced between 15 and 20 inches apart. In another aspect, a corn field provided herein comprises at least two rows of corn plants, where any two adjacent rows are spaced between 20 and 25 inches apart. In another aspect, a corn field provided herein comprises at least two rows of corn plants, where any two adjacent rows are spaced between 25 and 30 inches apart. In another aspect, a corn field provided herein comprises at least two rows of corn plants, where any two adjacent rows are spaced between 30 and 35 inches apart. In another aspect, a corn field provided herein comprises at least two rows of corn plants, where any two adjacent rows are spaced between 35 and 40 inches apart. In another aspect, a corn field provided herein comprises at least two rows of corn plants, where any two adjacent rows are spaced between 12 and 24 inches apart. In another aspect, a corn field provided herein comprises at least two rows of corn plants, where any two adjacent rows are spaced between 24 and 36 inches apart. In another aspect, a corn field provided herein comprises at least two rows of corn plants, where any two adjacent rows are spaced between 12 and 36 inches apart. In another aspect, a corn field provided herein comprises at least two rows of corn plants, where any two adjacent rows are spaced between 10 and 40 inches apart.

In an aspect, a corn field provided herein comprises an average of between 10 and 12 inches between adjacent rows of corn plants. In an aspect, a corn field provided herein comprises an average of between 10 and 14 inches between adjacent rows of corn plants. In an aspect, a corn field provided herein comprises an average of between 10 and 16 inches between adjacent rows of corn plants. In an aspect, a corn field provided herein comprises an average of between 10 and 18 inches between adjacent rows of corn plants. In an aspect, a corn field provided herein comprises an average of between 10 and 20 inches between adjacent rows of corn plants. In an aspect, a corn field provided herein comprises an average of between 10 and 22 inches between adjacent rows of corn plants. In an aspect, a corn field provided herein comprises an average of between 10 and 24 inches between adjacent rows of corn plants. In an aspect, a corn field provided herein comprises an average of between 10 and 26 inches between adjacent rows of corn plants. In an aspect, a corn field provided herein comprises an average of between 10 and 28 inches between adjacent rows of corn plants. In an aspect, a corn field provided herein comprises an average of between 10 and 30 inches between adjacent rows of corn plants. In an aspect, a corn field provided herein comprises an average of between 10 and 32 inches between adjacent rows of corn plants. In an aspect, a corn field provided herein comprises an average of between 10 and 34 inches between adjacent rows of corn plants. In an aspect, a corn field provided herein comprises an average of between 10 and 36 inches between adjacent rows of corn plants. In an aspect, a corn field provided herein comprises an average of between 10 and 38 inches between adjacent rows of corn plants. In an aspect, a corn field provided herein comprises an average of between 10 and 40 inches between adjacent rows of corn plants. In an aspect, a corn field provided herein comprises an average of between 12 and 18 inches between adjacent rows of corn plants. In an aspect, a corn field provided herein comprises an average of between 12 and 20 inches between adjacent rows of corn plants. In an aspect, a corn field provided herein comprises an average of between 12 and 22 inches between adjacent rows of corn plants. In an aspect, a corn field provided herein comprises an average of between 12 and 24 inches between adjacent rows of corn plants. In an aspect, a corn field provided herein comprises an average of between 12 and 36 inches between adjacent rows of corn plants. In an aspect, a corn field provided herein comprises an average of between 18 and 24 inches between adjacent rows of corn plants. In an aspect, a corn field provided herein comprises an average of between 18 and 36 inches between adjacent rows of corn plants.

As used herein, the term "harvesting" refers to the process of removing or gathering at least one ear of corn from a corn plant. A corn field is considered to be "harvested" when at least one ear has been removed from at least 50% of the corn plants in the corn field. As such, an "unharvested" corn plant has not had any ears purposely removed. In an aspect, a corn field provided herein is an unharvested corn field. In another aspect, at least 50% of the corn plants in a corn field provided herein are unharvested. In another aspect, at least 60% of the corn plants in a corn field provided herein are unharvested. In another aspect, at least 70% of the inbred corn plants in a corn field provided herein are unharvested. In another aspect, at least 80% of the corn plants in a corn field provided herein are unharvested. In another aspect, at least 90% of the corn plants in a corn field provided herein are unharvested. In another aspect, 100% of the corn plants in a corn field provided herein are unharvested.

As used herein, the term "yield" refers to the amount of harvested plant material, such as kernels or seeds, per harvested field or cultivated area. In an aspect, yield is measured in bushels per acre. Yield can be dependent on average kernel weight and the average number of kernels per ear. As used herein, "seed yield" refers to the number of seeds or kernels harvested per harvested field or cultivated area. In an aspect, seed yield is measured in Standard Seed Units (SSU) per acre. One SSU for corn is equivalent to 80,000 corn seed kernels. In an aspect, seed yield is measured in terms of the average number of kernels or seeds per ear. The number of Standard Seed Units (SSUs) or the average number of kernels per ear is/are appropriate for seed production since they quantify the number of seeds or kernels that can be produced, harvested or collected from a seed production field or from female corn plant(s), and thus the number of hybrid corn seeds or kernels that can potentially be sold and planted from the quantity of seeds or kernels produced, whereas yield takes into account both seed number and seed size.

In an aspect, the yield of hybrid corn seed provided herein comprises an average of at least 60 bushels per acre. In an aspect, the yield of hybrid corn seed provided herein comprises an average of at least 80 bushels per acre. In an aspect, the yield of hybrid corn seed provided herein comprises an average of at least 100 bushels per acre. In another aspect, the yield of hybrid corn seed provided herein comprises an average of at least 120 bushels per acre. In another aspect, the yield of hybrid corn seed provided herein comprises an average of at least 140 bushels per acre. In another aspect, the yield of hybrid corn seed provided herein comprises an average of at least 160 bushels per acre. In another aspect, the yield of hybrid corn seed provided herein comprises an average of at least 180 bushels per acre. In another aspect, the yield of hybrid corn seed provided herein comprises an average of at least 200 bushels per acre. In another aspect, the yield of hybrid corn seed provided herein comprises an average of at least 220 bushels per acre. In another aspect, the yield of hybrid corn seed provided herein comprises an average of at least 240 bushels per acre. In another aspect, the yield of hybrid corn seed provided herein comprises an average of at least 260 bushels per acre. In another aspect, the yield of hybrid corn seed provided herein comprises an average of at least 300 bushels per acre. In another aspect, the yield of hybrid corn seed provided herein comprises an average of at least 400 bushels per acre. In another aspect, the yield of hybrid corn seed provided herein comprises an average of at least 500 bushels per acre.

In an aspect, the yield of hybrid corn seed provided herein comprises an average of between 100 and 120 bushels per acre. In another aspect, the yield of hybrid corn seed provided herein comprises an average of between 120 and 140 bushels per acre. In another aspect, the yield of hybrid corn seed provided herein comprises an average of between 140 and 160 bushels per acre. In another aspect, the yield of hybrid corn seed provided herein comprises an average of between 160 and 180 bushels per acre. In another aspect, the yield of hybrid corn seed provided herein comprises an average of between 180 and 200 bushels per acre. In another aspect, the yield of hybrid corn seed provided herein comprises an average of between 200 and 220 bushels per acre. In another aspect, the yield of hybrid corn seed provided herein comprises an average of between 220 and 240 bushels per acre. In another aspect, the yield of hybrid corn seed provided herein comprises an average of between 240 and 260 bushels per acre. In another aspect, the yield of hybrid corn seed provided herein comprises an average of between 100 and 140 bushels per acre. In another aspect, the yield of hybrid corn seed provided herein comprises an average of between 140 and 180 bushels per acre. In another aspect, the yield of hybrid corn seed provided herein comprises an average of between 180 and 220 bushels per acre. In another aspect, the yield of hybrid corn seed provided herein comprises an average of between 220 and 260 bushels per acre. In another aspect, the yield of hybrid corn seed provided herein comprises an average of between 100 and 180 bushels per acre. In another aspect, the yield of hybrid corn seed provided herein comprises an average of between 180 and 260 bushels per acre. In another aspect, the yield of hybrid corn seed provided herein comprises an average of between 100 and 500 bushels per acre. In another aspect, the yield of hybrid corn seed provided herein comprises an average of between 100 and 400 bushels per acre. In another aspect, the yield of hybrid corn seed provided herein comprises an average of between 100 and 350 bushels per acre. In another aspect, the yield of hybrid corn seed provided herein comprises an average of between 100 and 300 bushels per acre. In another aspect, the yield of hybrid corn seed provided herein comprises an average of between 100 and 260 bushels per acre. In another aspect, the yield of hybrid corn seed provided herein comprises an average of between 100 and 200 bushels per acre.

In an aspect, the yield of hybrid corn seed provided herein comprises at least 100 bushels per acre. In another aspect, the yield of hybrid corn seed provided herein comprises at least 120 bushels per acre. In another aspect, the yield of hybrid corn seed provided herein comprises at least 140 bushels per acre. In another aspect, the yield of hybrid corn seed provided herein comprises at least 160 bushels per acre. In another aspect, the yield of hybrid corn seed provided herein comprises at least 180 bushels per acre. In another aspect, the yield of hybrid corn seed provided herein comprises at least 200 bushels per acre. In another aspect, the yield of hybrid corn seed provided herein comprises at least 220 bushels per acre. In another aspect, the yield of hybrid corn seed provided herein comprises at least 240 bushels per acre. In another aspect, the yield of hybrid corn seed provided herein comprises at least 260 bushels per acre. In another aspect, the yield of hybrid corn seed provided herein comprises at least 300 bushels per acre. In another aspect, the yield of hybrid corn seed provided herein comprises at least 350 bushels per acre. In another aspect, the yield of hybrid corn seed provided herein comprises at least 400 bushels per acre. In another aspect, the yield of hybrid corn seed provided herein comprises at least 450 bushels per acre. In another aspect, the yield of hybrid corn seed provided herein comprises at least 500 bushels per acre.

In an aspect, the yield of hybrid corn seed provided herein comprises between 100 and 120 bushels per acre. In another aspect, the yield of hybrid corn seed provided herein comprises between 120 and 140 bushels per acre. In another aspect, the yield of hybrid corn seed provided herein comprises between 140 and 160 bushels per acre. In another aspect, the yield of hybrid corn seed provided herein comprises between 160 and 180 bushels per acre. In another aspect, the yield of hybrid corn seed provided herein comprises between 180 and 200 bushels per acre. In another aspect, the yield of hybrid corn seed provided herein comprises between 200 and 220 bushels per acre. In another aspect, the yield of hybrid corn seed provided herein comprises between 220 and 240 bushels per acre. In another aspect, the yield of hybrid corn seed provided herein comprises between 240 and 260 bushels per acre. In another aspect, the yield of hybrid corn seed provided herein comprises between 100 and 140 bushels per acre. In another aspect, the yield of hybrid corn seed provided herein comprises between 140 and 180 bushels per acre. In another aspect, the yield of hybrid corn seed provided herein comprises between 180 and 220 bushels per acre. In another aspect, the yield of hybrid corn seed provided herein comprises between 220 and 260 bushels per acre. In another aspect, the yield of hybrid corn seed provided herein comprises between 100 and 180 bushels per acre. In another aspect, the yield of hybrid corn seed provided herein comprises between 180 and 260 bushels per acre. In another aspect, the yield of hybrid corn seed provided herein comprises between 100 and 500 bushels per acre. In another aspect, the yield of hybrid corn seed provided herein comprises between 100 and 450 bushels per acre. In another aspect, the yield of hybrid corn seed provided herein comprises between 100 and 400 bushels per acre. In another aspect, the yield of hybrid corn seed provided herein comprises between 100 and 350 bushels per acre. In another aspect, the yield of hybrid corn seed provided herein comprises between 100 and 300 bushels per acre. In another aspect, the yield of hybrid corn seed provided herein comprises between 100 and 260 bushels per acre. In another aspect, the yield of hybrid corn seed provided herein comprises between 100 and 200 bushels per acre.

In an aspect, the hybrid corn seed yield provided herein comprises an average of at least 200 kernels per ear. In another aspect, the hybrid corn seed yield provided herein comprises an average of at least 300 kernels per ear. In another aspect, the hybrid corn seed yield provided herein comprises an average of at least 400 kernels per ear. In another aspect, the hybrid corn seed yield provided herein comprises an average of at least 500 kernels per ear. In another aspect, the hybrid corn seed yield provided herein comprises an average of at least 600 kernels per ear. In another aspect, the hybrid corn seed yield provided herein comprises an average of at least 700 kernels per ear. In another aspect, the hybrid corn seed yield provided herein comprises an average of at least 800 kernels per ear. In another aspect, the hybrid corn seed yield provided herein comprises an average of at least 900 kernels per ear. In another aspect, the hybrid corn seed yield provided herein comprises an average of at least 1,000 kernels per ear. In another aspect, the hybrid corn seed yield provided herein comprises an average of at least 1,100 kernels per ear. In another aspect, the hybrid corn seed yield provided herein comprises an average of at least 1,200 kernels per ear. In another aspect, the hybrid corn seed yield provided herein comprises an average of at least 1,300 kernels per ear. In another aspect, the hybrid corn seed yield provided herein comprises an average of at least 1,400 kernels per ear. In another aspect, the hybrid corn seed yield provided herein comprises an average of at least 1,500 kernels per ear.

In an aspect, the hybrid corn seed yield provided herein comprises an average of between 200 and 300 kernels per ear. In another aspect, the hybrid corn seed yield provided herein comprises an average of between 300 and 400 kernels per ear. In another aspect, the hybrid corn seed yield provided herein comprises an average of between 400 and 500 kernels per ear. In another aspect, the hybrid corn seed yield provided herein comprises an average of between 500 and 600 kernels per ear. In another aspect, the hybrid corn seed yield provided herein comprises an average of between 600 and 700 kernels per ear. In another aspect, the hybrid corn seed yield provided herein comprises an average of between 700 and 800 kernels per ear. In another aspect, the hybrid corn seed yield provided herein comprises an average of between 800 and 900 kernels per ear. In another aspect, the hybrid corn seed yield provided herein comprises an average of between 900 and 1,000 kernels per ear. In another aspect, the hybrid corn seed yield provided herein comprises an average of between 1,000 and 1,100 kernels per ear. In another aspect, the hybrid corn seed yield provided herein comprises an average of between 1,100 and 1,200 kernels per ear. In another aspect, the hybrid corn seed yield provided herein comprises an average of between 200 and 400 kernels per ear. In another aspect, the hybrid corn seed yield provided herein comprises an average of between 400 and 600 kernels per ear. In another aspect, the hybrid corn seed yield provided herein comprises an average of between 600 and 800 kernels per ear. In another aspect, the hybrid corn seed yield provided herein comprises an average of between 800 and 1,000 kernels per ear. In another aspect, the hybrid corn seed yield provided herein comprises an average of between 1,000 and 1,200 kernels per ear. In another aspect, the hybrid corn seed yield provided herein comprises an average of between 200 and 700 kernels per ear. In another aspect, the hybrid corn seed yield provided herein comprises an average of between 700 and 1,200 kernels per ear. In another aspect, the hybrid corn seed yield provided herein comprises an average of between 200 and 1,500 kernels per ear. In another aspect, the hybrid corn seed yield provided herein comprises an average of between 200 and 1,400 kernels per ear. In another aspect, the hybrid corn seed yield provided herein comprises an average of between 200 and 1,300 kernels per ear. In another aspect, the hybrid corn seed yield provided herein comprises an average of between 200 and 1,200 kernels per ear.

In an aspect, the hybrid corn seed yield provided herein comprises at least 200 kernels per ear. In another aspect, the hybrid corn seed yield provided herein comprises at least 300 kernels per ear. In another aspect, the hybrid corn seed yield provided herein comprises at least 400 kernels per ear. In another aspect, the hybrid corn seed yield provided herein comprises at least 500 kernels per ear. In another aspect, the hybrid corn seed yield provided herein comprises at least 600 kernels per ear. In another aspect, the hybrid corn seed yield provided herein comprises at least 700 kernels per ear. In another aspect, the hybrid corn seed yield provided herein comprises at least 800 kernels per ear. In another aspect, the hybrid corn seed yield provided herein comprises at least 900 kernels per ear. In another aspect, the hybrid corn seed yield provided herein comprises at least 1,000 kernels per ear. In another aspect, the hybrid corn seed yield provided herein comprises at least 1,100 kernels per ear. In another aspect, the hybrid corn seed yield provided herein comprises at least 1,200 kernels per ear. In another aspect, the hybrid corn seed yield provided herein comprises at least 1,300 kernels per ear. In another aspect, the hybrid corn seed yield provided herein comprises at least 1,400 kernels per ear. In another aspect, the hybrid corn seed yield provided herein comprises at least 1,500 kernels per ear.

In an aspect, the hybrid corn seed yield provided herein comprises between 200 and 300 kernels per ear. In another aspect, the hybrid corn seed yield provided herein comprises between 300 and 400 kernels per ear. In another aspect, the hybrid corn seed yield provided herein comprises between 400 and 500 kernels per ear. In another aspect, the hybrid corn seed yield provided herein comprises between 500 and 600 kernels per ear. In another aspect, the hybrid corn seed yield provided herein comprises between 600 and 700 kernels per ear. In another aspect, the hybrid corn seed yield provided herein comprises between 700 and 800 kernels per ear. In another aspect, the hybrid corn seed yield provided herein comprises between 800 and 900 kernels per ear. In another aspect, the hybrid corn seed yield provided herein comprises between 900 and 1,000 kernels per ear. In another aspect, the hybrid corn seed yield provided herein comprises between 1,000 and 1,100 kernels per ear. In another aspect, the hybrid corn seed yield provided herein comprises between 1,100 and 1,200 kernels per ear. In another aspect, the hybrid corn seed yield provided herein comprises between 200 and 400 kernels per ear. In another aspect, the hybrid corn seed yield provided herein comprises between 400 and 600 kernels per ear. In another aspect, the hybrid corn seed yield provided herein comprises between 600 and 800 kernels per ear. In another aspect, the hybrid corn seed yield provided herein comprises between 800 and 1,000 kernels per ear. In another aspect, the hybrid corn seed yield provided herein comprises between 1,000 and 1,200 kernels per ear. In another aspect, the hybrid corn seed yield provided herein comprises between 200 and 700 kernels per ear. In another aspect, the hybrid corn seed yield provided herein comprises between 700 and 1,200 kernels per ear. In another aspect, the hybrid corn seed yield provided herein comprises between 200 and 1,200 kernels per ear.

In an aspect, the hybrid corn seed provided herein comprises an average of at least 0.2 grams per dry kernel. In another aspect, the hybrid corn seed provided herein comprises an average of at least 0.25 grams per dry kernel. In another aspect, the hybrid corn seed provided herein comprises an average of at least 0.3 grams per dry kernel. In another aspect, the hybrid corn seed provided herein comprises an average of at least 0.35 grams per dry kernel. In another aspect, the hybrid corn seed provided herein comprises an average of at least 0.4 grams per dry kernel. In another aspect, the hybrid corn seed provided herein comprises an average of at least 0.45 grams per dry kernel. In another aspect, the hybrid corn seed provided herein comprises an average of at least 0.5 grams per dry kernel. In another aspect, the hybrid corn seed provided herein comprises an average of at least 0.55 grams per dry kernel. In another aspect, the hybrid corn seed provided herein comprises an average of at least 0.6 grams per dry kernel.

In an aspect, the hybrid corn seed provided herein comprises an average of between 0.2 and 0.25 grams per dry kernel. In another aspect, the hybrid corn seed provided herein comprises an average of between 0.25 and 0.3 grams per dry kernel. In another aspect, the hybrid corn seed provided herein comprises an average of between 0.3 and 0.35 grams per dry kernel. In another aspect, the hybrid corn seed provided herein comprises an average of between 0.35 and 0.4 grams per dry kernel. In another aspect, the hybrid corn seed provided herein comprises an average of between 0.4 and 0.45 grams per dry kernel. In another aspect, the hybrid corn seed provided herein comprises an average of between 0.45 and 0.5 grams per dry kernel. In another aspect, the hybrid corn seed provided herein comprises an average of between 0.5 and 0.55 grams per dry kernel. In another aspect, the hybrid corn seed provided herein comprises an average of between 0.55 and 0.6 grams per dry kernel. In another aspect, the hybrid corn seed provided herein comprises an average of between 0.2 and 0.3 grams per dry kernel. In another aspect, the hybrid corn seed provided herein comprises an average of between 0.3 and 0.4 grams per dry kernel. In another aspect, the hybrid corn seed provided herein comprises an average of between 0.4 and 0.5 grams per dry kernel. In another aspect, the hybrid corn seed provided herein comprises an average of between 0.5 and 0.6 grams per dry kernel. In another aspect, the hybrid corn seed provided herein comprises an average of between 0.2 and 0.4 grams per dry kernel. In another aspect, the hybrid corn seed provided herein comprises an average of between 0.4 and 0.6 grams per dry kernel. In another aspect, the hybrid corn seed provided herein comprises an average of between 0.2 and 0.6 grams per dry kernel.

In an aspect, the hybrid corn seed provided herein comprises at least 0.2 grams per dry kernel. In another aspect, the hybrid corn seed provided herein comprises at least 0.25 grams per dry kernel. In another aspect, the hybrid corn seed provided herein comprises at least 0.3 grams per dry kernel. In another aspect, the hybrid corn seed provided herein comprises at least 0.35 grams per dry kernel. In another aspect, the yield corn seed provided herein comprises at least 0.4 grams per dry kernel. In another aspect, the hybrid corn seed provided herein comprises at least 0.45 grams per dry kernel. In another aspect, the hybrid corn seed provided herein comprises at least 0.5 grams per dry kernel. In another aspect, the hybrid corn seed provided herein comprises at least 0.55 grams per dry kernel. In another aspect, the hybrid corn seed provided herein comprises at least 0.6 grams per dry kernel.

In an aspect, the hybrid corn seed provided herein comprises between 0.2 and 0.25 grams per dry kernel. In another aspect, the hybrid corn seed provided herein comprises between 0.25 and 0.3 grams per dry kernel. In another aspect, the hybrid corn seed provided herein comprises between 0.3 and 0.35 grams per dry kernel. In another aspect, the hybrid corn seed provided herein comprises between 0.35 and 0.4 grams per dry kernel. In another aspect, the hybrid corn seed provided herein comprises between 0.4 and 0.45 grams per dry kernel. In another aspect, the hybrid corn seed provided herein comprises between 0.45 and 0.5 grams per dry kernel. In another aspect, the hybrid corn seed provided herein comprises between 0.5 and 0.55 grams per dry kernel. In another aspect, the hybrid corn seed provided herein comprises between 0.55 and 0.6 grams per dry kernel. In another aspect, the hybrid corn seed provided herein comprises between 0.2 and 0.3 grams per dry kernel. In another aspect, the hybrid corn seed provided herein comprises between 0.3 and 0.4 grams per dry kernel. In another aspect, the hybrid corn seed provided herein comprises between 0.4 and 0.5 grams per dry kernel. In another aspect, the hybrid corn seed provided herein comprises between 0.5 and 0.6 grams per dry kernel. In another aspect, the hybrid corn seed provided herein comprises between 0.2 and 0.4 grams per dry kernel. In another aspect, the hybrid corn seed provided herein comprises between 0.4 and 0.6 grams per dry kernel. In another aspect, the hybrid corn seed provided herein comprises between 0.2 and 0.6 grams per dry kernel.

In an aspect, the yield of hybrid corn seed provided herein comprises at least 80 SSUs per acre. In an aspect, the yield of hybrid corn seed provided herein comprises at least 90 SSUs per acre. In an aspect, the yield of hybrid corn seed provided herein comprises at least 100 SSUs per acre. In an aspect, the yield of hybrid corn seed provided herein comprises at least 105 SSUs per acre. In an aspect, the yield of hybrid corn seed provided herein comprises at least 110 SSUs per acre. In an aspect, the yield of hybrid corn seed provided herein comprises at least 115 SSUs per acre. In an aspect, the yield of hybrid corn seed provided herein comprises at least 120 SSUs per acre. In an aspect, the yield of hybrid corn seed provided herein comprises at least 125 SSUs per acre. In an aspect, the yield of hybrid corn seed provided herein comprises at least 130 SSUs per acre. In an aspect, the yield of hybrid corn seed provided herein comprises at least 135 SSUs per acre. In an aspect, the yield of hybrid corn seed provided herein comprises at least 140 SSUs per acre. In an aspect, the yield of hybrid corn seed provided herein comprises at least 145 SSUs per acre. In an aspect, the yield of hybrid corn seed provided herein comprises at least 150 SSUs per acre. In an aspect, the yield of hybrid corn seed provided herein comprises at least 155 SSUs per acre. In an aspect, the yield of hybrid corn seed provided herein comprises at least 160 SSUs per acre. In an aspect, the yield of hybrid corn seed provided herein comprises at least 170 SSUs per acre. In an aspect, the yield of hybrid corn seed provided herein comprises at least 180 SSUs per acre. In an aspect, the yield of hybrid corn seed provided herein comprises at least 190 SSUs per acre. In an aspect, the yield of hybrid corn seed provided herein comprises at least 200 SSUs per acre.

In an aspect, the hybrid corn seed yield provided herein comprises between 80 SSUs per acre and 200 SSUs per acre. In an aspect, the hybrid corn seed yield provided herein comprises between 80 SSUs per acre and 190 SSUs per acre. In an aspect, the hybrid corn seed yield provided herein comprises between 80 SSUs per acre and 180 SSUs per acre. In an aspect, the hybrid corn seed yield provided herein comprises between 80 SSUs per acre and 170 SSUs per acre. In an aspect, the hybrid corn seed yield provided herein comprises between 80 SSUs per acre and 160 SSUs per acre. In an aspect, the hybrid corn seed yield provided herein comprises between 80 SSUs per acre and 150 SSUs per acre. In an aspect, the hybrid corn seed yield provided herein comprises between 80 SSUs per acre and 140 SSUs per acre. In an aspect, the hybrid corn seed yield provided herein comprises between 80 SSUs per acre and 130 SSUs per acre. In an aspect, the hybrid corn seed yield provided herein comprises between 80 SSUs per acre and 120 SSUs per acre. In an aspect, the hybrid corn seed yield provided herein comprises between 80 SSUs per acre and 110 SSUs per acre. In an aspect, the hybrid corn seed yield provided herein comprises between 80 SSUs per acre and 100 SSUs per acre. In an aspect, the hybrid corn seed yield provided herein comprises between 80 SSUs per acre and 90 SSUs per acre.

In an aspect, the hybrid corn seed yield provided herein comprises between 90 SSUs per acre and 200 SSUs per acre. In an aspect, the hybrid corn seed yield provided herein comprises between 90 SSUs per acre and 190 SSUs per acre. In an aspect, the hybrid corn seed yield provided herein comprises between 90 SSUs per acre and 180 SSUs per acre. In an aspect, the hybrid corn seed yield provided herein comprises between 90 SSUs per acre and 170 SSUs per acre. In an aspect, the hybrid corn seed yield provided herein comprises between 90 SSUs per acre and 160 SSUs per acre. In an aspect, the hybrid corn seed yield provided herein comprises between 90 SSUs per acre and 150 SSUs per acre. In an aspect, the hybrid corn seed yield provided herein comprises between 90 SSUs per acre and 140 SSUs per acre. In an aspect, the hybrid corn seed yield provided herein comprises between 90 SSUs per acre and 130 SSUs per acre. In an aspect, the hybrid corn seed yield provided herein comprises between 90 SSUs per acre and 120 SSUs per acre. In an aspect, the hybrid corn seed yield provided herein comprises between 90 SSUs per acre and 110 SSUs per acre. In an aspect, the hybrid corn seed yield provided herein comprises between 90 SSUs per acre and 100 SSUs per acre.

In an aspect, the hybrid corn seed yield provided herein comprises between 100 SSUs per acre and 200 SSUs per acre. In an aspect, the hybrid corn seed yield provided herein comprises between 100 SSUs per acre and 190 SSUs per acre. In an aspect, the hybrid corn seed yield provided herein comprises between 100 SSUs per acre and 180 SSUs per acre. In an aspect, the hybrid corn seed yield provided herein comprises between 100 SSUs per acre and 170 SSUs per acre. In an aspect, the hybrid corn seed yield provided herein comprises between 100 SSUs per acre and 160 SSUs per acre. In an aspect, the hybrid corn seed yield provided herein comprises between 100 SSUs per acre and 150 SSUs per acre. In an aspect, the hybrid corn seed yield provided herein comprises between 100 SSUs per acre and 140 SSUs per acre. In an aspect, the hybrid corn seed yield provided herein comprises between 100 SSUs per acre and 130 SSUs per acre. In an aspect, the hybrid corn seed yield provided herein comprises between 100 SSUs per acre and 120 SSUs per acre. In an aspect, the hybrid corn seed yield provided herein comprises between 100 SSUs per acre and 110 SSUs per acre.

In an aspect, the hybrid corn seed yield provided herein comprises between 110 SSUs per acre and 200 SSUs per acre. In an aspect, the hybrid corn seed yield provided herein comprises between 110 SSUs per acre and 190 SSUs per acre. In an aspect, the hybrid corn seed yield provided herein comprises between 110 SSUs per acre and 180 SSUs per acre. In an aspect, the hybrid corn seed yield provided herein comprises between 110 SSUs per acre and 170 SSUs per acre. In an aspect, the hybrid corn seed yield provided herein comprises between 110 SSUs per acre and 160 SSUs per acre. In an aspect, the hybrid corn seed yield provided herein comprises between 110 SSUs per acre and 150 SSUs per acre. In an aspect, the hybrid corn seed yield provided herein comprises between 110 SSUs per acre and 140 SSUs per acre. In an aspect, the hybrid corn seed yield provided herein comprises between 110 SSUs per acre and 130 SSUs per acre. In an aspect, the hybrid corn seed yield provided herein comprises between 110 SSUs per acre and 120 SSUs per acre.

In an aspect, the hybrid corn seed yield provided herein comprises between 120 SSUs per acre and 200 SSUs per acre. In an aspect, the hybrid corn seed yield provided herein comprises between 120 SSUs per acre and 190 SSUs per acre. In an aspect, the hybrid corn seed yield provided herein comprises between 120 SSUs per acre and 180 SSUs per acre. In an aspect, the hybrid corn seed yield provided herein comprises between 120 SSUs per acre and 170 SSUs per acre. In an aspect, the hybrid corn seed yield provided herein comprises between 120 SSUs per acre and 160 SSUs per acre. In an aspect, the hybrid corn seed yield provided herein comprises between 120 SSUs per acre and 150 SSUs per acre. In an aspect, the hybrid corn seed yield provided herein comprises between 120 SSUs per acre and 140 SSUs per acre. In an aspect, the hybrid corn seed yield provided herein comprises between 120 SSUs per acre and 130 SSUs per acre.

In an aspect, the hybrid corn seed yield provided herein comprises between 130 SSUs per acre and 200 SSUs per acre. In an aspect, the hybrid corn seed yield provided herein comprises between 130 SSUs per acre and 190 SSUs per acre. In an aspect, the hybrid corn seed yield provided herein comprises between 130 SSUs per acre and 180 SSUs per acre. In an aspect, the hybrid corn seed yield provided herein comprises between 130 SSUs per acre and 170 SSUs per acre. In an aspect, the hybrid corn seed yield provided herein comprises between 130 SSUs per acre and 160 SSUs per acre. In an aspect, the hybrid corn seed yield provided herein comprises between 130 SSUs per acre and 150 SSUs per acre. In an aspect, the hybrid corn seed yield provided herein comprises between 130 SSUs per acre and 140 SSUs per acre.

In an aspect, the hybrid corn seed yield provided herein comprises between 140 SSUs per acre and 200 SSUs per acre. In an aspect, the hybrid corn seed yield provided herein comprises between 140 SSUs per acre and 190 SSUs per acre. In an aspect, the hybrid corn seed yield provided herein comprises between 140 SSUs per acre and 180 SSUs per acre. In an aspect, the hybrid corn seed yield provided herein comprises between 140 SSUs per acre and 170 SSUs per acre. In an aspect, the hybrid corn seed yield provided herein comprises between 140 SSUs per acre and 160 SSUs per acre. In an aspect, the hybrid corn seed yield provided herein comprises between 140 SSUs per acre and 150 SSUs per acre.

In an aspect, the hybrid corn seed yield provided herein comprises between 150 SSUs per acre and 200 SSUs per acre. In an aspect, the hybrid corn seed yield provided herein comprises between 150 SSUs per acre and 190 SSUs per acre. In an aspect, the hybrid corn seed yield provided herein comprises between 150 SSUs per acre and 180 SSUs per acre. In an aspect, the hybrid corn seed yield provided herein comprises between 150 SSUs per acre and 170 SSUs per acre. In an aspect, the hybrid corn seed yield provided herein comprises between 150 SSUs per acre and 160 SSUs per acre.

In an aspect, the hybrid corn seed yield provided herein comprises between 160 SSUs per acre and 200 SSUs per acre. In an aspect, the hybrid corn seed yield provided herein comprises between 160 SSUs per acre and 190 SSUs per acre. In an aspect, the hybrid corn seed yield provided herein comprises between 160 SSUs per acre and 180 SSUs per acre. In an aspect, the hybrid corn seed yield provided herein comprises between 160 SSUs per acre and 170 SSUs per acre. In an aspect, the hybrid corn seed yield provided herein comprises between 170 SSUs per acre and 200 SSUs per acre. In an aspect, the hybrid corn seed yield provided herein comprises between 170 SSUs per acre and 190 SSUs per acre. In an aspect, the hybrid corn seed yield provided herein comprises between 170 SSUs per acre and 180 SSUs per acre. In an aspect, the hybrid corn seed yield provided herein comprises between 180 SSUs per acre and 200 SSUs per acre. In an aspect, the hybrid corn seed yield provided herein comprises between 180 SSUs per acre and 190 SSUs per acre.

In an aspect, the yield of hybrid corn seed provided herein comprises between 190 SSUs per acre and 200 SSUs per acre.

As used herein, "detasseled" corn refers to corn where the pollen-producing flowers, or tassels, have been removed. Detasseling is typically performed before the tassel can shed pollen. Detasseling can be accomplished via machine detasseling, manual detasseling, or a combination of both machine and manual detasseling. Detasseling often removes the uppermost leaves of the corn plant along with the developing tassel. Detasseled corn plants retain their female flowers, which eventually produce kernels on the ear. In an aspect, a corn plant provided herein is a detasseled corn plant.

In an aspect, the female corn plants provided herein have been detasseled. In another aspect, at least 50% of the female corn plants provided herein have been detasseled. In another aspect, at least 60% of the female corn plants provided herein have been detasseled. In another aspect, at least 70% of the female corn plants provided herein have been detasseled. In another aspect, at least 80% of the female corn plants provided herein have been detasseled. In another aspect, at least 90% of the female corn plants provided herein have been detasseled. In another aspect, at least 95% of the female corn plants provided herein have been detasseled. In another aspect, 99% of the female corn plants provided herein have been detasseled. In another aspect, 100% of the female corn plants provided herein have been detasseled.

As an alternative to detasseling, the female corn plants can have sterility through genetic crosses and inheritance and/or use of an inducible system. One system that can be employed to induce male sterility in female corn plants is the Roundup® hybridization system (RHS), wherein the male reproductive tissues or tassels are unable to produce pollen following treatment with glyphosate during an appropriate window of plant development. In one RHS system, corn plants (or female corn plants) in a seed production field have a Roundup® or glyphosate resistant 5-enolpyruvylshikimate-3-phosphate synthase (EPSPS) transgene, but due to the combination expression elements, the expression of the transgene in male reproductive tissues is low. As a result, when these corn plants (or female corn plants) are treated with glyphosate, their male reproductive structures or tassels do not develop to produce pollen. In a second generation RHS system (RHS2), the corn plants (or female corn plants) in a seed production field have a Roundup® or glyphosate resistant 5-enolpyruvylshikimate-3-phosphate synthase (EPSPS) transgene that further contains in its 3' untranslated region (UTR) a target site for an endogenous small interfering RNA (siRNA) expressed specifically in male tissues. Thus, expression of the transgene is suppressed in the male reproductive tissues to render those tissues susceptible to Roundup® or glyphosate treatment. Accordingly, corn plants (or female corn plants) containing this transgene can be made male sterile and unable to produce pollen by Roundup® or glyphosate treatment. According to some embodiments, corn plants (or female corn plants) comprise a RHS event, such as MON 87427 (see, e.g., U.S. Application Pub. No. 2011/0126310, the entire contents and disclosure of which are incorporated herein by reference) or MON 87429 (see, e.g., U.S. Provisional App. No. 62/625,537, the entire contents and disclosure of which are incorporated herein by reference). In addition to the RHS system, other chemical hybridizing agents (CHAs) known in the art could be used to make corn plants male sterile.

As an alternative to chemical treatment, corn plants (or female corn plants) can be made male sterile through genetic crosses and inheritance causing cytoplasmic male sterility. As used herein, the term "cytoplasmic male sterility" or "CMS" refers to a condition where a corn plant is partially or fully incapable of producing functional pollen. As known in the art, cytoplasmic male sterility is a maternally inherited trait that is commonly associated with unusual open reading frames within the mitochondrial genome which cause cytoplasmic dysfunction. In an aspect, a corn plant or female corn plant provided herein is a cytoplasmic male sterile corn plant.

The shorter plant heights of female corn plants in a production field as provided herein are more accessible for over-the-top treatment with a chemical hybridizing agent or glyphosate (or Roundup®) treatment with standard farming equipment without damaging the female corn plants. In an aspect, methods are provided for planting and treating shorter female corn plants in a seed production field as described herein with a chemical hybridizing agent or glyphosate (or Roundup®) to induce male sterility. In another aspect, shorter female corn plants in a seed production field as described herein further have cytoplasmic male sterility.

In an aspect, the female corn plants provided herein exhibit cytoplasmic male sterility. In another aspect, at least 60% of the female corn plants in a corn field provided herein exhibit cytoplasmic male sterility. In another aspect, at least 70% of the female corn plants in a corn field provided herein exhibit cytoplasmic male sterility. In another aspect, at least 80% of the female corn plants in a corn field provided herein exhibit cytoplasmic male sterility. In another aspect, at least 90% of the female corn plants in a corn field provided herein exhibit cytoplasmic male sterility. In another aspect, 100% of the female corn plants in a corn field provided herein exhibit cytoplasmic male sterility.

In an aspect, this disclosure provides a method of fertilizing at least one female inbred corn plant with pollen from at least one male inbred corn plant, where the at least one female inbred corn plant has an average height that is at least 2.5% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants have the same or similar average height or do not differ in average height by more than 1%. In an aspect, this disclosure provides a method of fertilizing at least one female inbred corn plant with pollen from at least one male inbred corn plant, where the at least one female inbred corn plant has an average height that is at least 5% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants have the same or similar average height or do not differ in average height by more than 1% or 2.5%. In an aspect, this disclosure provides a method of fertilizing at least one female inbred corn plant with pollen from at least one male inbred corn plant, where the at least one female inbred corn plant has an average height that is at least 10% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants have the same or similar average height or do not differ in average height by more than 1%, 2.5% or 5%. In another aspect, this disclosure provides a method of fertilizing a plurality of female inbred corn plants with pollen from at least one male inbred corn plant, where the female inbred corn plants have an average height that is at least 10% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 15% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 20% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 25% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 30% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%.

In another aspect, this disclosure provides a method of fertilizing a plurality of female inbred corn plants with pollen from at least one male inbred corn plant, where the female inbred corn plants have an average height that is at least 10% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 15% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 20% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 25% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 30% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%.

In an aspect, this disclosure provides a method of fertilizing at least one female inbred corn plant with pollen from at least one male inbred corn plant, where the at least one female inbred corn plant has an average height that is at least 15% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants do not differ in average height by more than 10%. In another aspect, this disclosure provides a method of fertilizing a plurality of female inbred corn plants with pollen from at least one male inbred corn plant, where the female inbred corn plants have an average height that is at least 15% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%. In an aspect, this disclosure provides a method of fertilizing a plurality of female inbred corn plants with pollen from at least one male inbred corn plant, where the female inbred corn plants have an average height that is at least 20% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%. In an aspect, this disclosure provides a method of fertilizing a plurality of female inbred corn plants with pollen from at least one male inbred corn plant, where the female inbred corn plants have an average height that is at least 25% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%. In an aspect, this disclosure provides a method of fertilizing a plurality of female inbred corn plants with pollen from at least one male inbred corn plant, where the female inbred corn plants have an average height that is at least 30% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%.

In an aspect, this disclosure provides a method of fertilizing at least one female inbred corn plant with pollen from at least one male inbred corn plant, where the female-to-male plant height ratio is 0.98:1 or less, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one male control inbred corn plant, where the female-to-male control plant height ratio is about 1:1. In an aspect, this disclosure provides a method of fertilizing at least one female inbred corn plant with pollen from at least one male inbred corn plant, where the female-to-male plant height ratio is 0.97:1 or less, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one male control inbred corn plant, where the female-to-male control plant height ratio is about 1:1. In an aspect, this disclosure provides a method of fertilizing at least one female inbred corn plant with pollen from at least one male inbred corn plant, where the female-to-male plant height ratio is 0.96:1 or less, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one male control inbred corn plant, where the female-to-male control plant height ratio is about 1:1. In another aspect, this disclosure provides a method of fertilizing a plurality of female inbred corn plants with pollen from at least one male inbred corn plant, where the female-to-male plant height ratio is 0.95:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1. In an aspect, this disclosure provides a method of fertilizing at least one female inbred corn plant with pollen from at least one male inbred corn plant, where the female-to-male plant height ratio is 0.9:1 or less, and then harvesting the hybrid corn seeds produced by the at least one female inbred corn plant, where the yield, seed yield or SSUs of harvested hybrid corn seeds is greater than the yield or SSUs that is obtained by fertilizing at least one control female inbred corn plant with pollen from at least one male control inbred corn plant, where the female-to-male control plant height ratio is about 1:1 or between 0.95:1 and 1:1. In another aspect, this disclosure provides a method of fertilizing a plurality of female inbred corn plants with pollen from at least one male inbred corn plant, where the female-to-male plant height ratio is 0.9:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In another aspect, this disclosure provides a method of fertilizing a plurality of female inbred corn plants with pollen from at least one male inbred corn plant, where the female-to-male plant height ratio is 0.85:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.8:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.75:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.7:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.6:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1.

In an aspect, this disclosure provides a method of fertilizing a plurality of female inbred corn plants with pollen from at least one male inbred corn plant, where the female-to-male plant height ratio is between 0.6:1 and 0.95:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is between 0.7:1 and 0.95:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is between 0.8:1 and 0.95:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1.

In an aspect, this disclosure provides a method of fertilizing a plurality of female inbred corn plants with pollen from at least one male inbred corn plant, where the female-to-male plant height ratio is 0.85:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.8:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.75:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.7:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.6:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is between 0.6:1 and 0.9:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1.

In an aspect, this disclosure provides a method of fertilizing at least one female inbred corn plant with pollen from at least one male inbred corn plant, where the at least one female-inbred corn plant has a height (or average height) that is at least 2.0 meters shorter, at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter than the height (or average height) of the at least one male inbred corn plant, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one control male inbred corn plant, where the female control plant height is no more than 0.25 meters shorter than the height of the at least one male control plant. In an aspect, this disclosure provides a method of fertilizing a plurality of female inbred corn plants with pollen from at least one male inbred corn plant, where the average female-inbred corn plant height is at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter, or at least 0.2 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one control male inbred corn plant, where the average female control plant height is about the same as, or is no more than 0.2 meters shorter than, the height of the at least one male control plant. In an aspect, this disclosure provides a method of fertilizing a plurality of female inbred corn plants with pollen from at least one male inbred corn plant, where the average female-inbred corn plant height is at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter, at least 0.2 meters shorter, or at least 0.1 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one control male inbred corn plant, where the average female control plant height is about the same as, or is no more than 0.15 meters shorter than, the height of the at least one male control plant. In an aspect, this disclosure provides a method of fertilizing a plurality of female inbred corn plants with pollen from at least one male inbred corn plant, where the average female-inbred corn plant height is at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter, at least 0.2 meters shorter, or at least 0.1 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one control male inbred corn plant, where the average female control plant height is about the same as, or is no more than 0.1 meters shorter than the height of the at least one male control plant.

In an aspect, this disclosure provides a method of fertilizing a plurality of female inbred corn plants with pollen from at least one male inbred corn plant, where the average female inbred corn plant height is between 0.1 and 1.0 meters shorter, between 0.2 and 1.0 meters shorter, or between 0.2 and 0.5 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In an aspect, this disclosure provides a method of fertilizing a plurality of female inbred corn plants with pollen from at least one male inbred corn plant, where the average female-inbred corn plant height is between 0.5 and 1.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 1.0 and 1.5 meters shorter than the height (or average height) of the male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 1.5 and 2.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the male control plant. In another aspect, this disclosure provides a method of fertilizing a plurality of female inbred corn plants with pollen from at least one male inbred corn plant, where the average female-inbred corn plant height is between 0.5 and 1.5 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 1.0 and 2.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 0.5 and 2.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant.

In an aspect, the yield, seed yield or SSUs of hybrid corn seed is increased by at least 1.0%. In an aspect, the yield, seed yield or SSUs of hybrid corn seed is increased by at least 1.5%. In an aspect, the yield, seed yield or SSUs of hybrid corn seed is increased by at least 2.0%. In an aspect, the yield, seed yield or SSUs of hybrid corn seed is increased by at least 2.5%. In an aspect, the yield, seed yield or SSUs of hybrid corn seed is increased by at least 3.0%. In another aspect, the yield, seed yield or SSUs of hybrid corn seed is increased by at least 3.5%. In another aspect, the yield, seed yield or SSUs of hybrid corn seed is increased by at least 4.0%. In another aspect, the yield, seed yield or SSUs of hybrid corn seed is increased by at least 4.5%. In another aspect, the yield, seed yield or SSUs of hybrid corn seed is increased by at least 5.0%. In another aspect, the yield, seed yield or SSUs of hybrid corn seed is increased by at least 5.5%. In another aspect, the yield, seed yield or SSUs of hybrid corn seed is increased by at least 6.0%. In another aspect, the yield, seed yield or SSUs of hybrid corn seed is increased by at least 6.5%. In another aspect, the yield, seed yield or SSUs of hybrid corn seed is increased by at least 7.0%. In another aspect, the yield, seed yield or SSUs of hybrid corn seed is increased by at least 7.5%. In another aspect, the yield, seed yield or SSUs of hybrid corn seed is increased by at least 8.0%. In another aspect, the yield, seed yield or SSUs of hybrid corn seed is increased by at least 8.5%. In another aspect, the yield, seed yield or SSUs of hybrid corn seed is increased by at least 9.0%. In another aspect, the yield, seed yield or SSUs of hybrid corn seed is increased by at least 9.5%. In another aspect, the yield, seed yield or SSUs of hybrid corn seed is increased by at least 10%. In another aspect, the yield, seed yield of hybrid corn seed is increased by at least 11%. In another aspect, the yield, seed yield or SSUs of hybrid corn seed is increased by at least 12%. In another aspect, the yield, seed yield or SSUs of hybrid corn seed is increased by at least 13%. In another aspect, the yield, seed yield or SSUs of hybrid corn seed is increased by at least 14%. In another aspect, the yield, seed yield or SSUs of hybrid corn seed is increased by at least 15%. In another aspect, the yield, seed yield or SSUs of hybrid corn seed is increased by at least 16%. In another aspect, the yield, seed yield or SSUs of hybrid corn seed is increased by at least 17%. In another aspect, the yield, seed yield or SSUs of hybrid corn seed is increased by at least 18%. In another aspect, the yield, seed yield or SSUs of hybrid corn seed is increased by at least 19%. In another aspect, the yield, seed yield or SSUs of hybrid corn seed is increased by at least 20%.

In another aspect, the yield, seed yield or SSUs of hybrid corn seed is increased by between 1% and 20%. In another aspect, the yield, seed yield or SSUs of hybrid corn seed is increased by between 1% and 15%. In another aspect, the yield, seed yield or SSUs of hybrid corn seed is increased by between 1% and 10%. In another aspect, the yield, seed yield or SSUs of hybrid corn seed is increased by between 1% and 5%. In another aspect, the yield, seed yield or SSUs of hybrid corn seed is increased by between 3% and 6%. In another aspect, the yield, seed yield or SSUs of hybrid corn seed is increased by between 6% and 9%. In another aspect, the yield, seed yield or SSUs of hybrid corn seed is increased by between 9% and 12%. In another aspect, the yield, seed yield or SSUs of hybrid corn seed is increased by between 12% and 15%. In another aspect, the yield, seed yield or SSUs of hybrid corn seed is increased by between 15% and 18%. In another aspect, the yield, seed yield or SSUs of hybrid corn seed is increased by between 18% and 20%. In another aspect, the yield, seed yield or SSUs of hybrid corn seed is increased by between 3% and 12%. In another aspect, the yield, seed yield or SSUs of hybrid corn seed is increased by between 12% and 20%. In another aspect, the yield, seed yield or SSUs of hybrid corn seed is increased by between 3% and 20%. Any other range of increased yield, seed yield or SSUs of hybrid corn seed above 1% is contemplated herein.

In an aspect, this disclosure provides a method of crossing at least one male inbred corn plant with at least one female inbred corn plant to produce hybrid corn seeds, where the at least one female inbred corn plant has an average height that is at least 2.5% lower than the height (or average height) of the at least one male inbred corn plant, and then harvesting the hybrid corn seeds produced by the at least one female inbred corn plant. In an aspect, this disclosure provides a method of crossing at least one male inbred corn plant with at least one female inbred corn plant to produce hybrid corn seeds, where the at least one female inbred corn plant has an average height that is at least 5% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 7.5% lower than the height (or average height) of the at least one male inbred corn plant, and then harvesting the hybrid corn seeds produced by the at least one female inbred corn plant. In an aspect, this disclosure provides a method of crossing at least one male inbred corn plant with at least one female inbred corn plant to produce hybrid corn seeds, where the at least one female inbred corn plants has an average height that is at least 10% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 12.5% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 15% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 17.5% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 20% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 25% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant have an average height that is at least 30% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant have an average height that is at least 35% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 40% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 45% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 50% lower than the height (or average height) of the at least one male inbred corn plant, and then harvesting the hybrid corn seeds produced by one or more of the female inbred corn plants.

In an aspect, this disclosure provides a method of crossing at least one male inbred corn plant with at least one female inbred corn plant to produce hybrid corn seeds, where the female-to-male plant height ratio is 0.95:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.95:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.9:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.9:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.85:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.85:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.8:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.8:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.75:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.75:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.7:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.7:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.65:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.65:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.6:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.6:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.55:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.55:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.5:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.5:1 or less, and then harvesting the hybrid corn seeds produced by one or more of the female inbred corn plants.

In an aspect, this disclosure provides a method of crossing at least one male inbred corn plant with at least one female inbred corn plant to produce hybrid corn seeds, where the at least one female inbred corn plant has a height that is at least 0.1 meters shorter or at least 0.2 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.1 meters shorter or at least 0.2 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 0.3 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.3 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 0.4 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.4 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 0.5 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.5 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 1.0 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 1.0 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 1.5 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 1.5 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 2.0 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to a plurality of female inbred corn plants to produce hybrid corn seeds, where the female inbred corn plants have an average height that is between 0.1 and 0.5 meters or between 0.2 and 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds, where the female inbred corn plants have an average height that is between 1.0 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds, where the female inbred corn plants have an average height that is between 1.5 and 2.0 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds, where the female inbred corn plants have an average height that is between 0.5 and 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to at least one female inbred corn plant to produce hybrid corn seeds, where the at least one female inbred corn plant has an average height that is at least 2.5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 2.5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 10% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 10% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 12.5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 12.5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 15% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 15% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 17.5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 17.5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 20% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 20% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 25% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 25% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 30% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 30% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 35% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 35% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 40% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 40% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 45% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 45% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 50% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 50% lower than the height of the at least one male inbred corn plant, and then harvesting the hybrid corn seeds produced by one or more of the female inbred corn plants.

In an aspect, this disclosure provides a method of planting at least one male inbred corn plant in proximity to at least one female inbred corn plant to produce hybrid corn seeds, where the female-to-male plant height ratio is 0.98:1 or less, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female-to-male plant height ratio is 0.98:1 or less, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the female-to-male plant height ratio is 0.95:1 or less, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female-to-male plant height ratio is 0.95:1 or less, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the female-to-male plant height ratio is 0.9:1 or less, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female-to-male plant height ratio is 0.9:1 or less, and then harvesting the hybrid corn seeds produced by one or more of the female inbred corn plants. In another aspect, this disclosure provides a method of planting at least one male inbred corn plant in proximity to a plurality of female inbred corn plants to produce hybrid corn seeds, where the female-to-male plant height ratio is 0.85:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.8:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.75:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.7:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.65:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.6:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.55:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.5:1 or less, and then harvesting the hybrid corn seeds produced by one or more of the female inbred corn plants.

In an aspect, this disclosure provides a method of planting at least one male inbred corn plant in proximity to at least one female inbred corn plant to produce hybrid corn seeds, where the at least one female inbred corn plant has a height that is at least 0.1 meters or at least 0.2 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.1 meters or at least 0.2 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has a height that is at least 0.3 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.3 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has a height that is at least 0.4 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.4 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has a height that is at least 0.5 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is at least 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is at least 1.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is at least 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to a plurality of female inbred corn plants to produce hybrid corn seeds, where the female inbred corn plants have an average height that is between 0.1 and 0.5 meters or between 0.2 and 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 1.0 and 1.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 1.5 and 2.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 2.0 meters shorter than the height of the at least one male inbred corn plant, and then harvesting the hybrid corn seeds produced by one or more of the female inbred corn plants. According to some of these aspect, the at least one male inbred corn plant and the plurality of female inbred corn plants may be planted in rows as provided herein.

In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 2.5% lower than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 2.5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 5% lower than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 10% lower than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 10% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 12.5% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 12.5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 15% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 15% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 17.5% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 17.5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 20% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 20% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 25% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 25% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 30% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 30% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 35% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 35% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 40% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 40% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 45% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 45% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 50% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 50% lower than the height of the at least one male inbred corn plant, and then harvesting the hybrid corn seeds produced by one or more of the female inbred corn plants.

In an aspect, this disclosure provides a method of crossing at least one male inbred corn plant with at least one female inbred corn plant to produce hybrid corn seeds by fertilizing the at least one female inbred corn plant with pollen from the at least one male corn plant, where the female-to-male plant height ratio is 0.98:1 or less, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.98:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the female-to-male plant height ratio is 0.95:1 or less, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.95:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the female-to-male plant height ratio is 0.9:1 or less, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.9:1 or less, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.85:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.8:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.75:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.7:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.65:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.6:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.55:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.5:1 or less, and then harvesting the hybrid corn seeds produced by one or more of the female inbred corn plants.

In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.1 meters or at least 0.2 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.1 meters or at least 0.2 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.3 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.3 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.4 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.4 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.5 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the female inbred corn plants with pollen from the at least one male corn plant, where the plurality of female inbred corn plants have an average height that is at least 1.0 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 1.0 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 1.5 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 1.5 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to a plurality of female inbred corn plants to produce hybrid corn seeds, where the female inbred corn plants have an average height that is between 0.1 and 0.5 meters or between 0.2 and 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is between 1.0 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is between 1.5 and 2.0 meters shorter than the height of the at least one male inbred corn plant by fertilizing the plurality of female inbred corn plants with pollen from the at least one male corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is between 0.5 and 2.0 meters shorter than the height of the at least one male inbred corn plant, and then harvesting the hybrid corn seeds produced by one or more of the female inbred corn plants.

As used herein, the term "tassel skeletonization" (TSK) refers to under-developed male tassels or spikelets that become "skeletonized" by producing little to no pollen. Tassel skeletonization can result in fewer if any anthers developing on the affected parts of the tassel. Tassel skeletonization negatively impacts crop productivity and yield as the reproductive capacity of male corn plants to produce pollen is curtailed or eliminated. If the pollen shed is reduced from male plants, then fertilization of females and seed production will likely be reduced. In an aspect, TSK can be measured by the percentage of anthers that undergo dehiscence. As used herein, "dehiscence" refers to the release of pollen from an anther.

In an aspect, at least one male corn plant provided herein comprises at least 5% greater anther dehiscence as compared to a control male corn plant. In another aspect, a male corn plant provided herein comprises at least 10% greater anther dehiscence as compared to a control male corn plant. In another aspect, at least one male corn plant provided herein comprises at least 15% greater anther dehiscence as compared to a control male corn plant. In another aspect, at least one male corn plant provided herein comprises at least 20% greater anther dehiscence as compared to a control male corn plant. In another aspect, at least one male corn plant provided herein comprises at least 25% greater anther dehiscence as compared to a control male corn plant. In another aspect, at least one male corn plant provided herein comprises at least 30% greater anther dehiscence as compared to a control male corn plant. In another aspect, at least one male corn plant provided herein comprises at least 35% greater anther dehiscence as compared to a control male corn plant. In another aspect, at least one male corn plant provided herein comprises at least 40% greater anther dehiscence as compared to a control male corn plant. In another aspect, at least one male corn plant provided herein comprises at least 45% greater anther dehiscence as compared to a control male corn plant. In another aspect, at least one male corn plant provided herein comprises at least 50% greater anther dehiscence as compared to a control male corn plant. In another aspect, at least one male corn plant provided herein comprises at least 60% greater anther dehiscence as compared to a control male corn plant. In another aspect, at least one male corn plant provided herein comprises at least 70% greater anther dehiscence as compared to a control male corn plant. In another aspect, at least one male corn plant provided herein comprises at least 80% greater anther dehiscence as compared to a control male corn plant. In another aspect, at least one male corn plant provided herein comprises at least 90% greater anther dehiscence as compared to a control male corn plant. In another aspect, at least one male corn plant provided herein comprises at least 100% greater anther dehiscence as compared to a control male corn plant. In another aspect, at least one male corn plant provided herein comprises at least 150% greater anther dehiscence as compared to a control male corn plant. In another aspect, at least one male corn plant provided herein comprises at least 200% greater anther dehiscence as compared to a control male corn plant. In another aspect, at least one male corn plant provided herein comprises at least 250% greater anther dehiscence as compared to a control male corn plant. In another aspect, at least one male corn plant provided herein comprises at least 300% greater anther dehiscence as compared to a control male corn plant. In another aspect, at least one male corn plant provided herein comprises at least 400% greater anther dehiscence as compared to a control male corn plant. In another aspect, at least one male corn plant provided herein comprises at least 500% greater anther dehiscence as compared to a control male corn plant.

According to embodiments of the present disclosure, the anther dehiscence of a male corn plant and the average anther dehiscence of male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the anther dehiscence of a male corn plant or the average anther dehiscence of male corn plants is at R1 stage.

In an aspect, TSK can be measured by the total number of anthers present on the tassel. In an aspect, at least one male corn plant provided herein comprises at least 5% more anthers as compared to a control male corn plant. In another aspect, at least one male corn plant provided herein comprises at least 10% more anthers as compared to a control male corn plant. In another aspect, at least one male corn plant provided herein comprises at least 15% more anthers as compared to a control male corn plant. In another aspect, at least one male corn plant provided herein comprises at least 20% more anthers as compared to a control male corn plant. In another aspect, at least one male corn plant provided herein comprises at least 25% more anthers as compared to a control male corn plant. In another aspect, at least one male corn plant provided herein comprises at least 30% more anthers as compared to a control male corn plant. In another aspect, at least one male corn plant provided herein comprises at least 35% more anthers as compared to a control male corn plant. In another aspect, at least one male corn plant provided herein comprises at least 40% more anthers as compared to a control male corn plant. In another aspect, at least one male corn plant provided herein comprises at least 45% more anthers as compared to a control male corn plant. In another aspect, at least one male corn plant provided herein comprises at least 50% more anthers as compared to a control male corn plant. In another aspect, at least one male corn plant provided herein comprises at least 60% more anthers as compared to a control male corn plant. In another aspect, at least one male corn plant provided herein comprises at least 70% more anthers as compared to a control male corn plant. In another aspect, at least one male corn plant provided herein comprises at least 80% more anthers as compared to a control male corn plant. In another aspect, at least one male corn plant provided herein comprises at least 90% more anthers as compared to a control male corn plant. In another aspect, at least one male corn plant provided herein comprises at least 100% more anthers as compared to a control male corn plant. In another aspect, at least one male corn plant provided herein comprises at least 150% more anthers as compared to a control male corn plant. In another aspect, at least one male corn plant provided herein comprises at least 200% more anthers as compared to a control male corn plant. In another aspect, at least one male corn plant provided herein comprises at least 250% more anthers as compared to a control male corn plant. In another aspect, at least one male corn plant provided herein comprises at least 300% more anthers as compared to a control male corn plant. In another aspect, at least one male corn plant provided herein comprises at least 400% more anthers as compared to a control male corn plant. In another aspect, at least one male corn plant provided herein comprises at least 500% more anthers as compared to a control male corn plant.

According to embodiments of the present disclosure, the number of anthers of (or on) a male corn plant and the average number of anthers of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the number of anthers of (or on) a male corn plant or the average number of anthers of (or on) male corn plants is at R1 stage.

Tassel skeletonization can result in a reduced number of tassel branches. In an aspect, TSK can be measured by the total number of tassel branches. In an aspect, at least one male corn plant provided herein comprises at least 5% more tassel branches as compared to a control male corn plant. In another aspect, at least one male corn plant provided herein comprises at least 10% more tassel branches as compared to a control male corn plant. In another aspect, at least one male corn plant provided herein comprises at least 15% more tassel branches as compared to a control male corn plant. In another aspect, at least one male corn plant provided herein comprises at least 20% more tassel branches as compared to a control male corn plant. In another aspect, at least one male corn plant provided herein comprises at least 25% more tassel branches as compared to a control male corn plant. In another aspect, at least one male corn plant provided herein comprises at least 30% more tassel branches as compared to a control male corn plant. In another aspect, at least one male corn plant provided herein comprises at least 35% more tassel branches as compared to a control male corn plant. In another aspect, at least one male corn plant provided herein comprises at least 40% more tassel branches as compared to a control male corn plant. In another aspect, at least one male corn plant provided herein comprises at least 45% more tassel branches as compared to a control male corn plant. In another aspect, at least one male corn plant provided herein comprises at least 50% more tassel branches as compared to a control male corn plant. In another aspect, at least one male corn plant provided herein comprises at least 60% more tassel branches as compared to a control male corn plant. In another aspect, at least one male corn plant provided herein comprises at least 70% more tassel branches as compared to a control male corn plant. In another aspect, at least one male corn plant provided herein comprises at least 80% more tassel branches as compared to a control male corn plant. In another aspect, at least one male corn plant provided herein comprises at least 90% more tassel branches as compared to a control male corn plant. In another aspect, at least one male corn plant provided herein comprises at least 100% more tassel branches as compared to a control male corn plant. In another aspect, at least one male corn plant provided herein comprises at least 150% more tassel branches as compared to a control male corn plant. In another aspect, at least one male corn plant provided herein comprises at least 200% more tassel branches as compared to a control male corn plant. In another aspect, at least one male corn plant provided herein comprises at least 250% more tassel branches as compared to a control male corn plant. In another aspect, at least one male corn plant provided herein comprises at least 300% more tassel branches as compared to a control male corn plant. In another aspect, at least one male corn plant provided herein comprises at least 400% more tassel branches as compared to a control male corn plant. In another aspect, at least one male corn plant provided herein comprises at least 500% more tassel branches as compared to a control male corn plant.

According to embodiments of the present disclosure, the number of tassel branches of (or on) a male corn plant and the average number of tassel branches of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the number of tassel branches of (or on) a male corn plant or the average number of tassel branches of (or on) male corn plants is at R1 stage.

Tassel skeletonization can result in a reduction of tassel branch length. In an aspect, TSK can be measured by the average length of tassel branches. In an aspect, at least one male corn plant provided herein comprises at least 5% longer tassel branches as compared to a control male corn plant. In another aspect, at least one male corn plant provided herein comprises at least 10% longer tassel branches as compared to a control male corn plant. In another aspect, at least one male corn plant provided herein comprises at least 15% longer tassel branches compared to a control male corn plant. In another aspect, at least one male corn plant provided herein comprises at least 20% longer tassel branches as compared to a control male corn plant. In another aspect, at least one male corn plant provided herein comprises at least 25% longer tassel branches as compared to a control male corn plant. In another aspect, at least one male corn plant provided herein comprises at least 30% longer tassel branches as compared to a control male corn plant. In another aspect, at least one male corn plant provided herein comprises at least 35% longer tassel branches as compared to a control male corn plant. In another aspect, at least one male corn plant provided herein comprises at least 40% longer tassel branches as compared to a control male corn plant. In another aspect, at least one male corn plant provided herein comprises at least 45% longer tassel branches as compared to a control male corn plant. In another aspect, at least one male corn plant provided herein comprises at least 50% longer tassel branches as compared to a control male corn plant. In another aspect, at least one male corn plant provided herein comprises at least 60% longer tassel branches as compared to a control male corn plant. In another aspect, at least one male corn plant provided herein comprises at least 70% longer tassel branches as compared to a control male corn plant. In another aspect, at least one male corn plant provided herein comprises at least 80% longer tassel branches as compared to a control male corn plant. In another aspect, at least one male corn plant provided herein comprises at least 90% longer tassel branches as compared to a control male corn plant. In another aspect, at least one male corn plant provided herein comprises at least 100% longer tassel branches as compared to a control male corn plant. In another aspect, at least one male corn plant provided herein comprises at least 150% longer tassel branches as compared to a control male corn plant. In another aspect, at least one male corn plant provided herein comprises at least 200% longer tassel branches as compared to a control male corn plant. In another aspect, at least one male corn plant provided herein comprises at least 250% longer tassel branches as compared to a control male corn plant. In another aspect, at least one male corn plant provided herein comprises at least 300% longer tassel branches as compared to a control male corn plant. In another aspect, at least one male corn plant provided herein comprises at least 400% longer tassel branches as compared to a control male corn plant. In another aspect, at least one male corn plant provided herein comprises at least 500% longer tassel branches as compared to a control male corn plant.

According to embodiments of the present disclosure, the length of tassel branches of (or on) a male corn plant and the average length of tassel branches of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the length of tassel branches of (or on) a male corn plant or the average length of tassel branches of (or on) male corn plants is at R1 stage.

In an aspect, TSK can be measured using a "TSK scoring guide," which scores corn plants on a 1-10 scale based on the percentage of tassels on the plant that are skeletonized (e.g., a corn plant with less than or equal to 10% of its tassels being skeletonized is given a score of 1, a plant with approximately 50% of its tassels being skeletonized is given a score of 5, a plant with about 90% of its tassels being skeletonized is given a score of 9, etc.). In an aspect, at least one male corn plant that is planted near one or more female corn plants of a lesser height as provided herein has a TSK score that is improved (decreased) by at least 1 unit according to the TSK scoring guide, in comparison to at least one male control corn plant (i.e., at least one male corn plant of the same inbred line that is planted at the same density next to, and surrounded by, other corn plants of the same or similar height). In an aspect, at least one male corn plant provided herein has a TSK score that is improved (decreased) by at least 2 units as measured by using the TSK scoring guide in comparison to a control plant. In an aspect, at least one male corn plant provided herein has a TSK score that is improved (decreased) by at least 3 units as measured by using the TSK scoring guide in comparison to a control plant. In an aspect, at least one male corn plant provided herein has a TSK score that is improved (decreased) by at least 4 units as measured by using the TSK scoring guide in comparison to a control plant. In an aspect, at least one male corn plant provided herein has a TSK score that is improved (decreased) by at least 5 units as measured by using the TSK scoring guide in comparison to a control plant. In an aspect, at least one male corn plant provided herein has a TSK score that is improved (decreased) by at least 6 units as measured by using the TSK scoring guide in comparison to a control plant. In an aspect, at least one male corn plant provided herein has a TSK score that is improved (decreased) by at least 7 units as measured by using the TSK scoring guide in comparison to a control plant. In an aspect, at least one male corn plant provided herein has a TSK score that is improved (decreased) by at least 8 units as measured by using the TSK scoring guide in comparison to a control plant. In an aspect, at least one male corn plant provided herein has a TSK score that is improved (decreased) by at least 9 units as measured by using the TSK scoring guide in comparison to a control plant.

According to embodiments of the present disclosure, the TSK score of (or on) a male corn plant and the average TSK score of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the TSK score of (or on) a male corn plant or the average TSK score of (or on) male corn plants is at R1 stage.

In an aspect, this disclosure provides a corn field comprising at least two male inbred corn plants and at least two female inbred corn plants, where the female inbred corn plants are at least 10% shorter in average height than the male inbred corn plants, and further where the male inbred corn plants exhibit at least 10% less tassel skeletonization as compared to the tassel skeletonization exhibited by control male inbred corn plants in a corn field comprising at least two control male inbred corn plants and at least two control female inbred corn plants where the control male and female inbred corn plants do not differ in height by more than 5%. In an aspect, male inbred corn plants provided herein exhibit at least 12.5% less tassel skeletonization as compared to control male inbred corn plants. In an aspect, male inbred corn plants provided herein exhibit at least 15% less tassel skeletonization as compared to control male inbred corn plants. In an aspect, male inbred corn plants provided herein exhibit at least 17.5% less tassel skeletonization as compared to control male inbred corn plants. In an aspect, male inbred corn plants provided herein exhibit at least 20% less tassel skeletonization as compared to control male inbred corn plants. In an aspect, male inbred corn plants provided herein exhibit at least 25% less tassel skeletonization as compared to control male inbred corn plants. In an aspect, male inbred corn plants provided herein exhibit at least 30% less tassel skeletonization as compared to control male inbred corn plants. In an aspect, male inbred corn plants provided herein exhibit at least 35% less tassel skeletonization as compared to control male inbred corn plants. In an aspect, male inbred corn plants provided herein exhibit at least 40% less tassel skeletonization as compared to control male inbred corn plants. In an aspect, male inbred corn plants provided herein exhibit at least 45% less tassel skeletonization as compared to control male inbred corn plants. In an aspect, male inbred corn plants provided herein exhibit at least 50% less tassel skeletonization as compared to control male inbred corn plants. In an aspect, male inbred corn plants provided herein exhibit at least 55% less tassel skeletonization as compared to control male inbred corn plants. In an aspect, male inbred corn plants provided herein exhibit at least 60% less tassel skeletonization as compared to control male inbred corn plants. In an aspect, male inbred corn plants provided herein exhibit at least 65% less tassel skeletonization as compared to control male inbred corn plants. In an aspect, male inbred corn plants provided herein exhibit at least 70% less tassel skeletonization as compared to control male inbred corn plants. In an aspect, male inbred corn plants provided herein exhibit at least 75% less tassel skeletonization as compared to control male inbred corn plants. In an aspect, male inbred corn plants provided herein exhibit at least 80% less tassel skeletonization as compared to control male inbred corn plants. In an aspect, male inbred corn plants provided herein exhibit at least 85% less tassel skeletonization as compared to control male inbred corn plants. In an aspect, male inbred corn plants provided herein exhibit at least 90% less tassel skeletonization as compared to control male inbred corn plants. In an aspect, male inbred corn plants provided herein exhibit at least 95% less tassel skeletonization as compared to control male inbred corn plants. In an aspect, male inbred corn plants provided herein exhibit 100% less tassel skeletonization as compared to control male inbred corn plants.

According to embodiments of the present disclosure, the tassel skeletonization of (or on) a male corn plant and the average tassel skeletonization of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the tassel skeletonization of (or on) a male corn plant or the average tassel skeletonization of (or on) male corn plants is at R1 stage.

In an aspect, this disclosure provides a method of reducing tassel skeletonization by providing a corn field comprising at least two male inbred corn plants and at least two female inbred corn plants, where the female inbred corn plants are 10% shorter in average height than the male inbred corn plants, and further where the male inbred corn plants exhibit between 10% and 20% less tassel skeletonization as compared to the tassel skeletonization exhibited by control male inbred corn plants in a corn field comprising control male inbred corn plants and control female inbred corn plants where the control male and female inbred corn plants do not differ in height by more than 5%. In an aspect, male inbred corn plants provided herein exhibit between 10% and 30% less tassel skeletonization as compared to control male inbred corn plants. In an aspect, male inbred corn plants provided herein exhibit between 10% and 40% less tassel skeletonization as compared to control male inbred corn plants. In an aspect, male inbred corn plants provided herein exhibit between 10% and 50% less tassel skeletonization as compared to control male inbred corn plants. In an aspect, male inbred corn plants provided herein exhibit between 10% and 60% less tassel skeletonization as compared to control male inbred corn plants. In an aspect, male inbred corn plants provided herein exhibit between 10% and 70% less tassel skeletonization as compared to control male inbred corn plants. In an aspect, male inbred corn plants provided herein exhibit between 10% and 80% less tassel skeletonization as compared to control male inbred corn plants. In an aspect, male inbred corn plants provided herein exhibit between 10% and 90% less tassel skeletonization as compared to control male inbred corn plants. In an aspect, male inbred corn plants provided herein exhibit between 10% and 100% less tassel skeletonization as compared to control male inbred corn plants. In an aspect, male inbred corn plants provided herein exhibit between 20% and 30% less tassel skeletonization as compared to control male inbred corn plants. In an aspect, male inbred corn plants provided herein exhibit between 20% and 40% less tassel skeletonization as compared to control male inbred corn plants. In an aspect, male inbred corn plants provided herein exhibit between 20% and 50% less tassel skeletonization as compared to control male inbred corn plants. In an aspect, male inbred corn plants provided herein exhibit between 20% and 60% less tassel skeletonization as compared to control male inbred corn plants. In an aspect, male inbred corn plants provided herein exhibit between 20% and 70% less tassel skeletonization as compared to control male inbred corn plants. In an aspect, male inbred corn plants provided herein exhibit between 20% and 80% less tassel skeletonization as compared to control male inbred corn plants. In an aspect, male inbred corn plants provided herein exhibit between 20% and 90% less tassel skeletonization as compared to control male inbred corn plants. In an aspect, male inbred corn plants provided herein exhibits between 20% and 100% less tassel skeletonization as compared to control male inbred corn plants. In an aspect, male inbred corn plants provided herein exhibit between 30% and 50% less tassel skeletonization as compared to control male inbred corn plants. In an aspect, male inbred corn plants provided herein exhibit between 30% and 80% less tassel skeletonization as compared to control male inbred corn plants. In an aspect, male inbred corn plants provided herein exhibit between 30% and 100% less tassel skeletonization as compared to control male inbred corn plants. In an aspect, male inbred corn plants provided herein exhibit between 50% and 70% less tassel skeletonization as compared to control male inbred corn plants. In an aspect, male inbred corn plants provided herein exhibit between 60% and 80% less tassel skeletonization as compared to control male inbred corn plants. In an aspect, male inbred corn plants provided herein exhibit between 70% and 90% less tassel skeletonization as compared to control male inbred corn plants. In an aspect, male inbred corn plants provided herein exhibit between 50% and 100% less tassel skeletonization as compared to control male inbred corn plants.

According to an aspect of the present disclosure, one or more male corn plants can be made "taller" or higher by raising the male plants (or base of the male plants) relative to the female corn plants. This could be done regardless of whether the female plants are shorter than the male plants—i.e., the female plants may be taller or shorter than, or about the same height as, the male plants when the male plants have not been raised, but the top(s) of the male plants would be higher than the tops of the female plants when the male plants are raised relative to the surrounding soil or ground. For example, male plants may be planted in ground, earth or soil that is mounded or raised relative to the ground, earth or soil in which the female plants are planted, such that the tassels of the male plants are higher than the tops of the female plants. As another example, male plants may be planted in pots or containers to raise their height relative to the female plants. Conversely, a similar effect could be achieved if the female corn plant(s) are lowered relative to the male corn plant(s). For example, the female corn plants may be planted in furrows or valleys or at lower elevations or downslope relative to the male corn plants.

According to these embodiments, when a male plant(s) is/are raised relative to one or more female plants, the effective height(s) or effective average height(s) of the male plants is/are calculated and defined as including the raised height relative to the top surface of the surrounding soil or ground in addition to the actual height of the male plant(s). Likewise, if female corn plants are lowered relative to one or more male plants, the effective height(s) or effective average height(s) of the female plants is/are calculated and defined by subtracting from the actual height of the female plant, the lowered height of the female plant(s) relative to the top surface of the surrounding soil or ground (e.g., the surrounding soil or ground where the male plants are located or planted). For example, if the actual height of a corn plant is 3 meters, but the corn plant is raised 0.5 meters above the top surface of the surrounding soil or ground, then the effective height of the corn plant is 3.5 meters, but if such a plant is not raised relative to the top surface of the surrounding soil or ground, then the effective height of the plant is equal to its actual height. As another example, if the actual height of a corn plant is 3 meters, but the corn plant is lowered 0.5 meters below the top surface of the surrounding soil or ground, then the effective height of the corn plant is 2.5 meters. According to present embodiments, all of the description provided herein in reference to individual or average plant height(s), and relative plant height(s) of male and female corn plants, shall be equally and fully applicable to the effective plant height(s) or average effective plant height(s) of raised or lowered plants.

According to some aspects, the difference in plant height and/or placement (or average plant height and/or placement) between the male and female corn plants may be described as the difference in height or elevation of a particular structural or anatomical feature. In terms of placement, the relative height or elevation of the particular structural or anatomical feature, such as the ligule or collar or uppermost leaf surface, may provide an alternative or additional basis to describe the effective height of a plant that is raised or lowered relative to other plants. In an aspect, the average height of the ligule or collar of the uppermost fully expanded leaf and/or the uppermost leaf surface of the female inbred corn plants is at least 2% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 2.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 3% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 3.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 4% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 4.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 7.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 10% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 15% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 20% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 25% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 30% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 35% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 40% less or lower than the height (or average height) of the ligule or collar of at least one male inbred corn plant(s) (or the average plant height of male inbred corn plants).

The following are non-limiting exemplary embodiments of the present disclosure:

1. A method comprising: (a) fertilizing a plurality of female inbred corn plants with pollen from at least one male inbred corn plant to produce hybrid corn seeds, wherein the female inbred corn plants have an average height that is at least 2.5% lower than the average height of the at least one male inbred corn plant.
2. A method comprising: (a) crossing at least one male inbred corn plant with a plurality of female inbred corn plants to produce hybrid corn seeds, wherein the plurality of female inbred corn plants have an average height that is at least 2.5% lower than the height or average height of the at least one male inbred corn plant; and (b) harvesting said hybrid corn seeds from one or more of the female inbred corn plants.
3. A method comprising: (a) planting at least one male inbred corn plant in proximity to a plurality of female inbred corn plants to produce hybrid corn seeds, wherein the female inbred corn plants have an average height that is at least 2.5% lower than the height of the at least one male inbred corn plant; and (b) harvesting said hybrid corn seeds from one or more of the female inbred corn plants.
4. The method of embodiment 1, wherein the yield or seed yield of hybrid corn seeds produced in step (b) is greater than the yield or seed yield of control hybrid corn seeds obtained from fertilizing a plurality of control female inbred corn plants with pollen from at least one control male inbred corn plant and harvesting said control hybrid corn seeds from one or more of said control female inbred corn plants, wherein said control hybrid corn seeds are harvested from the same number of female inbred corn plants as in step (b), and wherein the average height of said plurality of control female inbred corn plants is the same or similar to the average height of said at least one control male inbred corn plants.
5. The method of any one of embodiments 1-4, wherein said female inbred corn plants have an average height that is at least 5%, at least 10%, at least 15%, at least 20%, at least 25%, at least 30%, at least 35%, at least 40%, at least 45%, at least 50%, at least 55%, at least 60%, or at least 70% shorter than said at least one male inbred corn plant.
6. The method of any one of the embodiments 1-5, wherein said female inbred corn plants have an average height that is between 2.5% and 50% shorter than said at least one male inbred corn plant.
7. The method of any one of the embodiments 1-6, wherein said female inbred corn plants are dwarf corn plants, semi-dwarf corn plants, or brachytic mutant corn plant.
8. The method of any one of the embodiments 1-7, wherein said female inbred corn plants comprise one or more ears at least 18 inches, at least 19 inches, at least 20 inches, at least 21 inches, at least 22 inches, at least 23 inches, or at least 24 inches above ground level.
9. The method of any one of the embodiments 1-8, wherein said female inbred corn plants comprise at least one ear that is at least 18 inches above ground level.
10. The method of any one of the embodiments 1-9, wherein said female inbred corn plants comprise at least one ear that is at least 24 inches above ground level.
11. The method of any one of the embodiments 1-10, wherein said female inbred corn plants comprise a mutation in a brachytic2 (br2) locus as compared to a wildtype br2 locus.
12. The method of any one of the embodiments 1-11, wherein said female inbred corn plants comprise a heterologous polynucleotide encoding an RNA molecule that suppresses expression of a brachytic2 (br2) gene or an mRNA transcribed therefrom.
13. The method of any one of the embodiments 1-12, wherein said female inbred corn plants comprise a mutation in a GA20 oxidase locus as compared to a wildtype GA20 oxidase locus.
14. The method of any one of the embodiments 1-13, wherein said female inbred corn plants comprise a heterologous polynucleotide encoding an RNA molecule that suppresses expression of a GA20 oxidase gene or an mRNA transcribed therefrom.
15. The method of embodiment 4, wherein the yield and/or seed yield is increased by at least 3.0%, at least 3.5%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10%, at least 11%, at least 12%, at least 13%, at least 14%, at least 15%, at least 16%, at least 17%, at least 18%, at least 19%, or at least 20% relative to the yield of hybrid corn seeds obtained from fertilizing a plurality of control female inbred corn plants with pollen from at least one control male inbred corn plant, wherein the female and male control plants do not differ in average height by more than 5%.
16. The method of embodiments 4 or 15, wherein the yield and/or seed yield said hybrid corn seeds is increased by between 3% and 20% relative to the yield of hybrid corn seeds obtained from fertilizing a plurality of control female inbred corn plants with pollen from at least one control male inbred corn plant, wherein the female and male control plants do not differ in average height by more than 5%.
17. The method of any one of the embodiments 1-16, wherein said female inbred corn plants and said at least one male inbred corn plant are grown in a corn field.
18. The method of any one of the embodiments 1-16, wherein said female inbred corn plants and said at least one male inbred corn plant are grown in a greenhouse.
19. The method of any one of the embodiments 1-18, wherein said female inbred corn plants are detasseled.
20. The method of any one of the embodiments 1-19, wherein said female inbred corn plants have cytoplasmic male sterility.

21. The method of any one of the embodiments 1-20, wherein the heights of said female inbred corn plants and said at least one male inbred corn plant are measured as the distance between the soil and the ligule of the uppermost fully-expanded leaf.
22. The method of any one of the embodiments 1-20, wherein the heights of said female inbred corn plants and said at least one male inbred corn plant are measured as the distance between the soil and the upper leaf surface of the leaf farthest from the soil.
23. The method of any one of the embodiments 1-20, wherein the heights of said female inbred corn plants and said at least one male inbred corn plant are measured as the distance between the soil and the arch of the highest corn leaf that is at least 50% developed.
24. The method of any one of the embodiments 1-23, wherein the heights of said female inbred corn plants and said at least one male inbred corn plant are measured at R1 stage.
25. The method of any one of the embodiments 4, 15, or 16, wherein the yield is measured in bushels per acre.
26. The method of any one of the embodiments 4, 15, 16, or 25, wherein the yield is at least 100 bushels per acre, at least 120 bushels per acre, at least 140 bushels per acre, at least 160 bushels per acre, at least 180 bushels per acre, at least 200 bushels per acre, at least 220 bushels per acre, at least 240 bushels per acre, or at least 260 bushels per acre.
27. The method of any one of the embodiments 4, 15, 16, 25, or 26, wherein the yield is between 100 and 260 bushels per acre.
28. The method of any one of the embodiments, 4, 15, or 16, wherein the seed yield is measured in standard seed units (SSUs) per acre.
29. The method of any one of the embodiments 4, 15, 16, or 28, wherein the seed yield is at least 80 SSUs per acre, at least 90 SSUs per acre, at least 100 SSUs per acre, at least 110 SSUs per acre, at least 120 SSUs per acre, at least 130 SSUs per acre, at least 140 SSUs per acre, at least 150 SSUs per acre, at least 160 SSUs per acre, at least 170 SSUs per acre, at least 180 SSUs per acre, at least 190 SSUs per acre, or at least 200 SSUs per acre.
30. The method of any one of the embodiments 4, 15, or 16, wherein the seed yield is measured in average number of kernels per ear.
31. The method of any one of the embodiments 4, 15, 16, or 30, wherein the seed yield is at least 200 kernels per ear, at least 300 kernels per ear, at least 400 kernels per ear, at least 500 kernels per ear, at least 600 kernels per ear, at least 700 kernels per ear, at least 800 kernels per ear, at least 900 kernels per ear, at least 1,000 kernels per ear, at least 1100 kernels per ear, or at least 1,200 kernels per ear.
32. The method of any one of the embodiments 4, 15, 16, 30, or 31, wherein the yield is between 200 and 1,200 kernels per ear.
33. The method of any one of the embodiments 4, 15, or 16, wherein the seed yield is measured in dry weight of kernels.
34. The method of any one of the embodiments 4, 15, 16, or 33, wherein the seed yield is at least 0.2 grams per dry kernel, at least 0.25 grams per dry kernel, at least 0.3 grams per dry kernel, at least 0.35 grams per dry kernel, at least 0.4 grams per dry kernel, at least 0.45 grams per dry kernel, at least 0.5 grams per dry kernel, at least 0.55 grams per dry kernel, or at least 0.6 grams per dry kernel.
35. The method of any one of the embodiments 4, 15, 16, 33, or 34, wherein the seed yield is between 0.2 and 0.6 grams per dry kernel.
36. The method of embodiment 17, wherein the field comprises at least one row of female inbred corn plants and at least one row of male inbred corn plants.
37. The method of embodiments 17 or 36, wherein the field comprises multiple rows of female inbred corn plants and at least one row of male inbred corn plants.
38. The method of any one of the embodiments 17, 36, or 37, wherein the field comprises multiple rows of female inbred corn plants and multiple rows of male inbred corn plants.
39. The method of any one of the embodiments 36-38, wherein the ratio of female inbred corn plant rows to male inbred corn plant rows is selected from the group consisting of 2:2, 3:2, 4:1, 4:2, 4:3, 6:1, and 6:2.
40. The method of any one of the embodiments 36-39, wherein the corn field comprises between 1 female row and 10 female rows for every male row.
41. The method of any one of the embodiments 36-40, wherein the corn field comprises at least 1, at least 2, at least 3, at least 4, at least 5, at least 6, at least 7, at least 8, at least 9, or at least 10 female rows for every male row.
42. The method of any one of the embodiments 17 or 36-41, wherein the corn field further comprises at least two rows of inbred corn plants, and wherein said at least two rows of inbred corn plants are spaced at least 12 inches, at least 14 inches, at least 16 inches, at least 18 inches, at least 20 inches, at least 22 inches, at least 24 inches, at least 26 inches, at least 28 inches, at least 30 inches, at least 32 inches, at least 34 inches, or at least 36 inches apart.
43. The method of any one of the embodiments 17 or 36-42, wherein the corn field further comprises at least two rows of inbred corn plants, and wherein said at least two rows are spaced between 12 and 36 inches apart.
44. The method of any one of the embodiments 17 or 36-43, wherein the corn field comprises a ratio of at least 1 female inbred corn plant, at least 2 female inbred corn plants, at least 3 female inbred corn plants, at least 4 female inbred corn plants, at least 5 female inbred corn plants, at least 6 female inbred corn plants, at least 7 female inbred corn plants, at least 8 female inbred corn plants, at least 9 female inbred corn plants, at least 10 female inbred corn plants, at least 15 female inbred corn plants, at least 20 female inbred corn plants, at least 25 female inbred corn plants, at least 30 female inbred corn plants, at least 35 female inbred corn plants, at least 40 female inbred corn plants, at least 45 female inbred corn plants, at least 50 female inbred corn plants, at least 60 female inbred corn plants, at least 70 female inbred corn plants, at least 80 female inbred corn plants, at least 90 female inbred corn plants, or at least 100 female inbred corn plants for every male inbred corn plant.
45. The method of any one of the embodiments 17 or 36-44, wherein the corn field comprises between 1 female inbred corn plant and 100 female inbred corn plants for every male inbred corn plant.
46. The method of any one of the embodiments 17 or 36-45, wherein the corn field comprises a planting density of at least 12,000 corn plants per acre, at least 15,000 corn plants per acre, at least 18,000 corn plants per acre, at least 21,000 corn plants per acre, at least 24,000 corn plants per acre, at least 27,000 corn plants per acre, at least 30,000 corn plants per acre, at least 33,000 corn plants per acre, at least 36,000 corn plants per acre, at least 39,000 corn plants per acre, at least 42,000 corn plants per acre, at least 45,000 corn plants per acre, at least 48,000 corn plants per acre, at least 51,000 corn plants per acre, at least 54,000 corn plants per acre, at least 57,000 corn plants per acre, or at least 60,000 corn plants per acre.

47. The method of any one of the embodiments 17 or 36-46, wherein the corn field comprises a planting density of between 12,000 and 60,000 corn plants per acre.

48. The method of any one of the embodiments 17 or 36-47, wherein the corn field comprises at least two male inbred corn plants and at least two female inbred corn plants, wherein said female inbred corn plants comprise an average height that is at least 10% shorter than the average height of said male inbred corn plants, and wherein said male inbred corn plants exhibit at least 2.5% less tassel skeletonization as compared to a control corn field comprising at least two control male inbred corn plants and at least two control female inbred corn plants, wherein said male and female control plants have the same or similar plant heights.

49. The method of embodiment 48, wherein tassel skeletonization is measured based on the percentage of tassels that are skeletonized.

50. The method of embodiments 48 or 49, wherein said male inbred corn plants exhibit at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less tassel skeletonization.

51. The method of embodiment 2, wherein the crossing comprises fertilization of said plurality of female inbred corn plants with pollen from said at least one male inbred corn plant.

EXAMPLES

Example 1. Comparison of Corn Seed Yield Distribution, as Grouped by Height of Female Parental Line Relative to Male, for Varying Hybrid Combinations To understand the effects on corn seed yield due to the relative height differences of male and female parental inbred lines, over 400 hybrid combinations of varying parental plant heights were studied. The study comprised US hybrid seed production from different parental inbred combinations in diverse growth environments from 2008-2016. Although each of the 400 hybrid combinations may not be equally represented across all testing years and environments, the large data set provides a good indication of yield trends across all female rows in the field in relation to the relative male/female plant heights. Seed yield is defined by Standard Seed Units (SSU) per acre. One SSU for corn is equivalent to 80,000 corn seed kernels.

In this experiment, the yield data (expressed in total SSU's per acre) was separated into two groups: (a) Shorter Female Bucket (where the female parent line comprised a height at least 10% shorter than that of the male line), and (b) Taller Female Bucket (comprising the remainder of the crosses). Three hundred seventy-nine hybrid combinations were grouped into the Taller Female Bucket, and 36 hybrid combinations were grouped in the Shorter Female Bucket. The height difference between each male/female parent pair does not take into account the effect of detasseling the female plants, which was typically done in these fields over this time period. Although the effective female plant height at pollination was shortened after detasseling, the yield data is still meaningful in that relative height differences between female plants should still be present after detasseling.

The seed yield in this analysis (expressed in total SSUs per acre) was measured for each hybrid combination in the study and grouped into the Taller Female or Shorter Female buckets or groups as described above. The distribution of seed yields per acre for the Taller and Shorter Female Buckets is shown in the box and whisker plots in FIG. 1. Each whisker marks the first point outside the box that is larger or smaller than 1.5 times the inner quartile range (IQR), where the IQR is the middle 50% of the data. The 75th percentile and the 25th percentile of the data are marked by the upper and lower ends of the box, respectively, with the median indicated by the dividing line of the box in between the two ends of the box. Most of the data points are expected to fall between the whisker boundaries, although a few additional data points are shown above and below the upper and lower whiskers, respectively.

This data shows that seed yield in the Shorter Female Bucket was less variable than that of the Taller Female Bucket. As shown in FIG. 1, if the female parent line is at least 10% shorter than the pairing male parent line, hybrid seed production stability was significantly improved as demonstrated by a decrease in variation.

Example 2. Distribution of Corn Seed Yield by Height Ratio of Male/Female Parental Lines for Hybrid Combinations of a Single Female Parental Line Corn seed yield is primarily determined by the female parental line in hybrid seed production. To control for variation in genetic potential with corn seed yields, the female parental line in this example was held constant and the male parental lines were varied. The effects of the relative plant heights of the male and female parental lines upon corn seed yield were studied by leveraging the normal variation of plant heights of various male parental lines. Twenty-five different hybrid combinations using various male parental lines for each female line were analyzed in this study.

Figure 2:
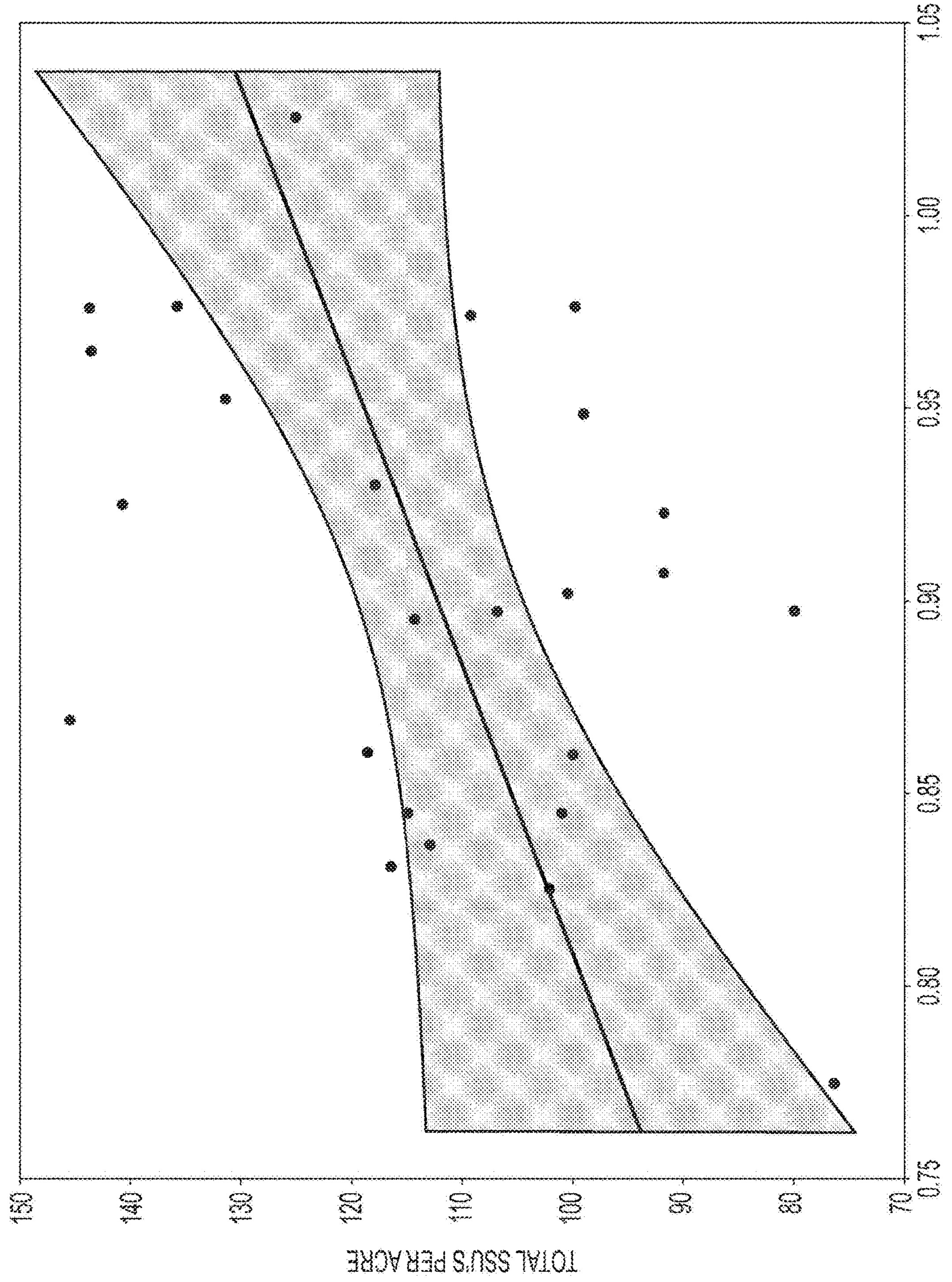
FIG. 2 is a plot comparing male-to-female (M/F) parent corn plant height ratio (x-axis) to hybrid corn seed yield (y-axis, measured in Standard Seed Units (SSUs)) for 25 different hybrid corn combinations.

Although the height difference between each pair of male/female parents does not take into account the effect of detasseling the female plants, which was employed in most of the production practice, the relative plant heights should still be present after detasseling. The seed yield in this analysis (total SSUs per acre) measures the overall seed yield over all female rows. The data presented in FIG. 2 compares corn seed yield, expressed as total SSUs per acre, to the ratio of characteristic heights of male/female parental lines (M/F). Each data point is the average seed yield for each male/female hybrid combination. The linear regression line is shown. The shaded area covers 95% confidence for the regression line.

While seed yield varies significantly for individual male/female hybrid combinations, FIG. 2 shows an overall trend of higher corn seed yield when the female parental line is shorter relative to the male parental line. In this example, seed yield is an average over the field, and does not distinguished between different rows of females, although it is expected that the more interior female rows further away from the male plants would most benefit from the shorter plant height and improved pollen flow as discussed herein.

Example 3. Short Female Parental Lines Allow for Improved Seed Yield and More Efficient Use of Planting Area Approximately 19% of the male inbreds used in commercial corn production today are considered high risk males due to their tendency for tassel skeletonization and/or reduced pollen load relative to other male lines. Indeed, tassel skeletonization (TSK) can cause male inbred corn plants to have a reduced pollen load. TSK is one of the phenotypes that is taken into account during male risk assessment and selection of male lines for commercial seed production. One of the major inducers of TSK can be shading of male plants by neighboring females.

Figure 3:
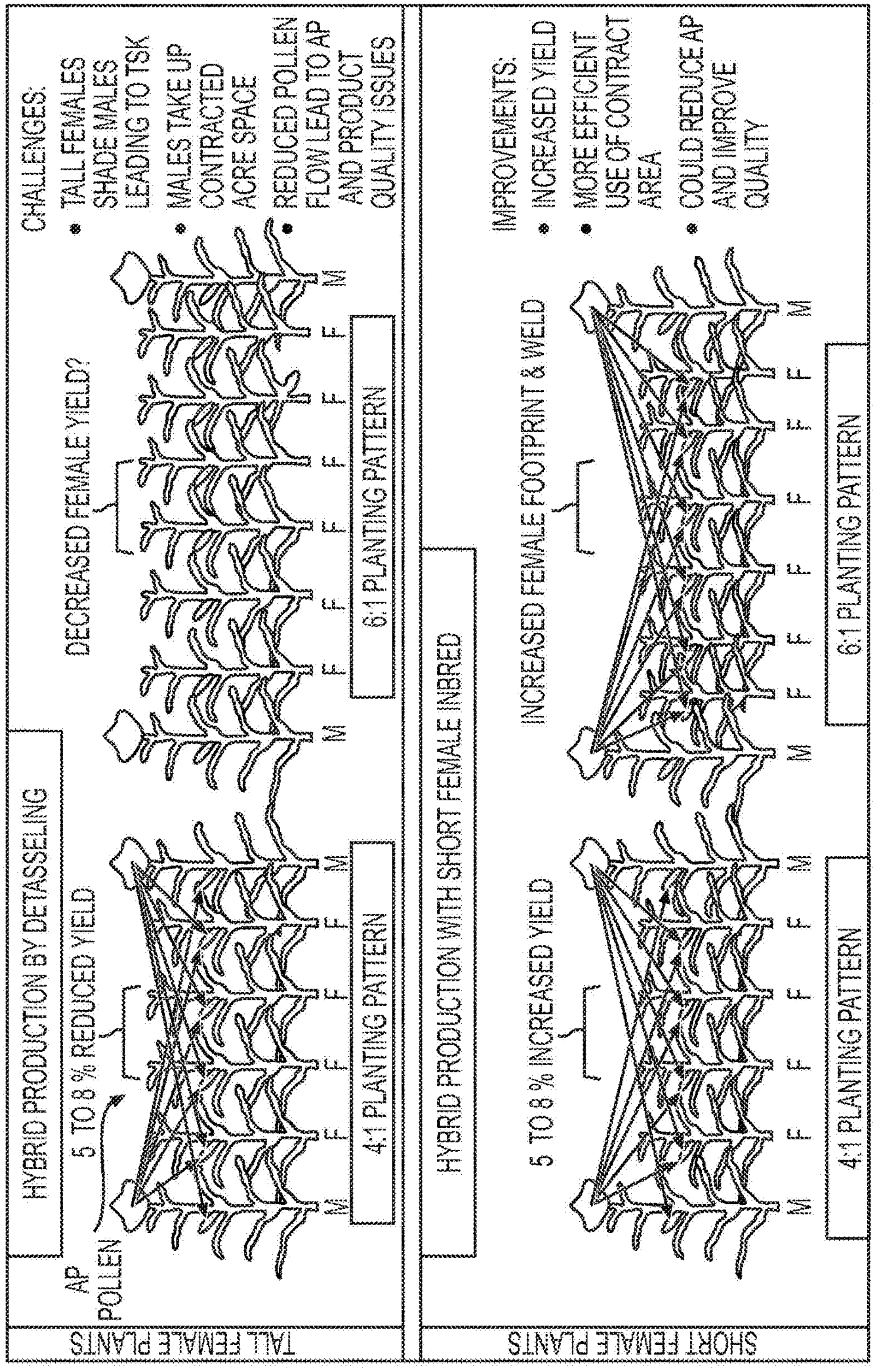
FIG. 3 is a visual representation of two common planting patterns (4:1 and 6:1) incorporating rows of either tall female inbred corn plants (upper panel) or short female inbred plants (lower panel). Abbreviations: TSK: tassel skeletonization; AP: adventitious presence; M: male; F: female.

As introduced above, by reducing the shading of adjacent male plants, shorter female plants reduce the risk of TSK in males and could thereby improve overall seed yield. Historically, the middle two rows in a 4:1 female-to-male row configuration exhibit a 5% to 8% reduction in seed yield relative to the two outer rows due to poor pollen distribution and/or a lack of pollen availability to these rows. In addition to improving yield in the center panels of female rows, shorter female inbred plants could also enable an increase in the ratio of female-to-male rows to 6:1 or some other higher ratio of female-to-male rows than is used currently, which may improve seed yield per acre and/or reduce the overall field production footprint. Having an improved pollen flow with shorter female inbreds can also help ensure that the females are pollinated by the male plants, thus reducing the possibility and/or occurrence rate of adventitious presence (AP) of unwanted transgenes or genetics due to unintended pollination and fertilization events from other pollen sources. A diagram of how shorter female plants can improve pollen flow in a 6:1 and 4:1 arrangement ratio of female-to-male rows is shown in FIG. 3, relative to male and female plants of a similar height.

Example 4. Improved Seed Yield with Short Female Parental Line

Field trials are described in this example demonstrating improved seed yield in hybrid corn seed production by utilizing a shorter female parental line. These corn seed production field trials were conducted over one growing season at two field sites in Illinois, U.S.A., which are approximately 100 miles away from each other, with one of the two sites (first field site) being further north than the other (second) field site. The two sites have similar soil conditions, but the second site received less rainfall than the other (first) site during the trial season.

To produce hybrid corn seeds, a tall inbred male parental line was used with a shorter inbred (transgenic) female parental line. A corresponding tall inbred (non-transgenic) female line was used as a control. The inbred lines were planted with two ratio arrangements of females to males: one with 4:1 female/male row configuration and 30-inch row spacing, and another with 6:1 female/male row configuration and 20-inch row spacing. Each arrangement of female-to-male row ratio had a medium planting density of 34,400 plants/acre for 20-inch row field or 27,200 plants/acre for 30-inch row field, and a high planting density of 39,560 plants/acre for 20-inch row field or 32,000 plants/acres for 30-inch row field. The tall and short female plants were planted with approximately equal spacing along each row. Mature corn ears were hand harvested in these trials, and results were collected from 5 interior plants of each 17.5-inch plot row, with 24 replicates for the 30-inch row spacing plots, and 36 replicates for the 20-inch row spacing plots, respectively. Seed yield was measured as the number of SSUs per acre where the number of acres took into account only the area of female plants. One Standard Seed Unit (SSU) is defined as 80,000 corn seed kernels.

Figure 4:
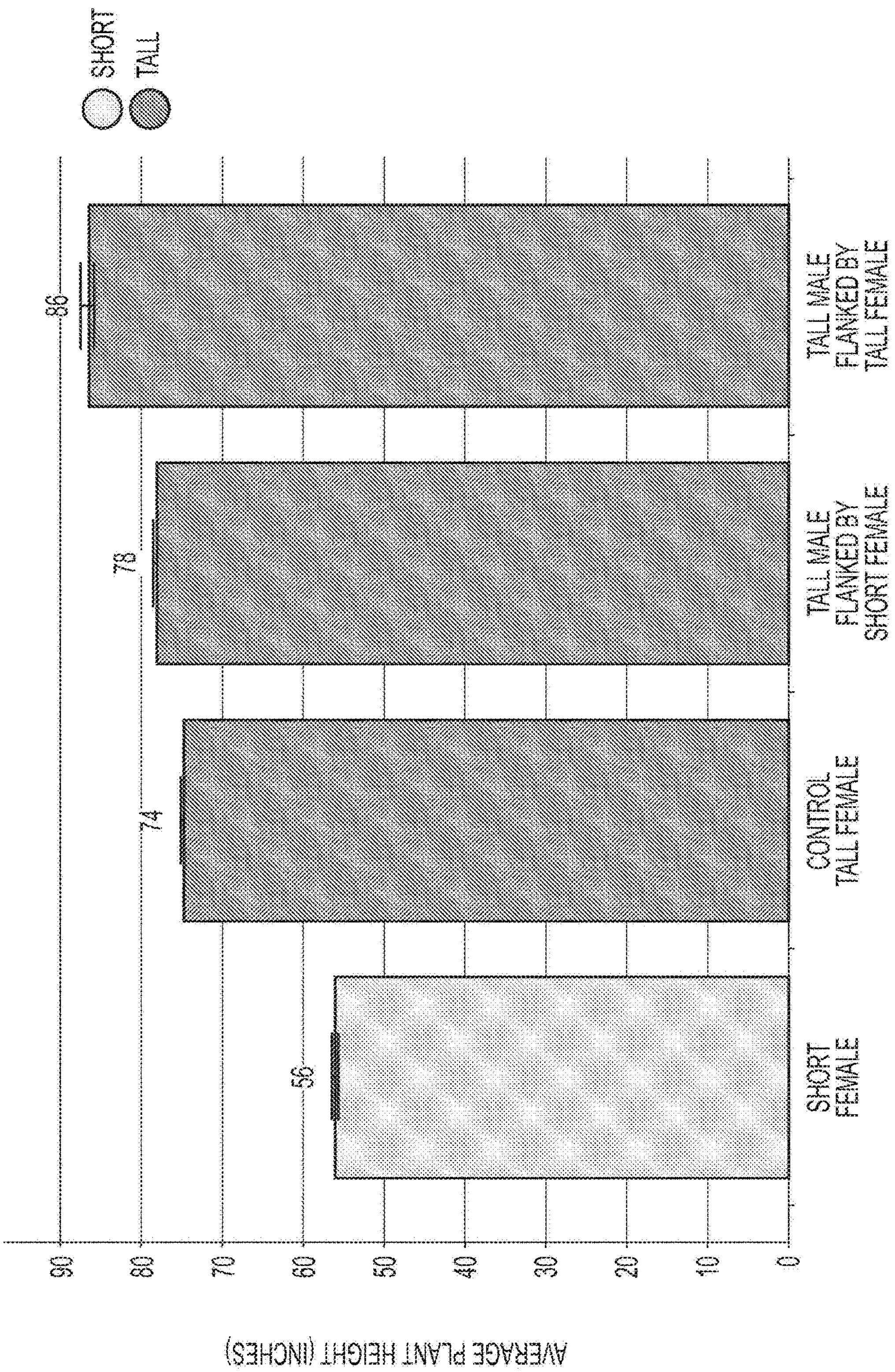
FIG. 4 shows the average plant height (PHT) of the inbred corn plants grown in the present field trials: (1) short female, (2) the control tall female, (3) tall male flanked by short female, and (4) tall male flanked by tall female.

FIG. 4 shows the average plant height (PHT) of the inbred corn plants grown in the present field trials: (1) short female, (2) the control tall female, (3) tall male flanked by short female, and (4) tall male flanked by tall female. In this experiment, the plant height is measured from the ground to the base of the uppermost collared leaf. The vertical error bars indicate the standard errors for PHT. Note that for the same inbred male line, the heights of the male plants flanked by shorter female plants are significantly reduced relative to those flanked by the control tall female plants. Without being bound by theory, the reduced male plant height may result from having less need for competitive vertical growth due to the surrounding female plants being shorter. The reduced vertical growth may improve male corn plant robustness, lodging resistance and stability, as well as male tassel formation and pollen shed.

Figure 5:
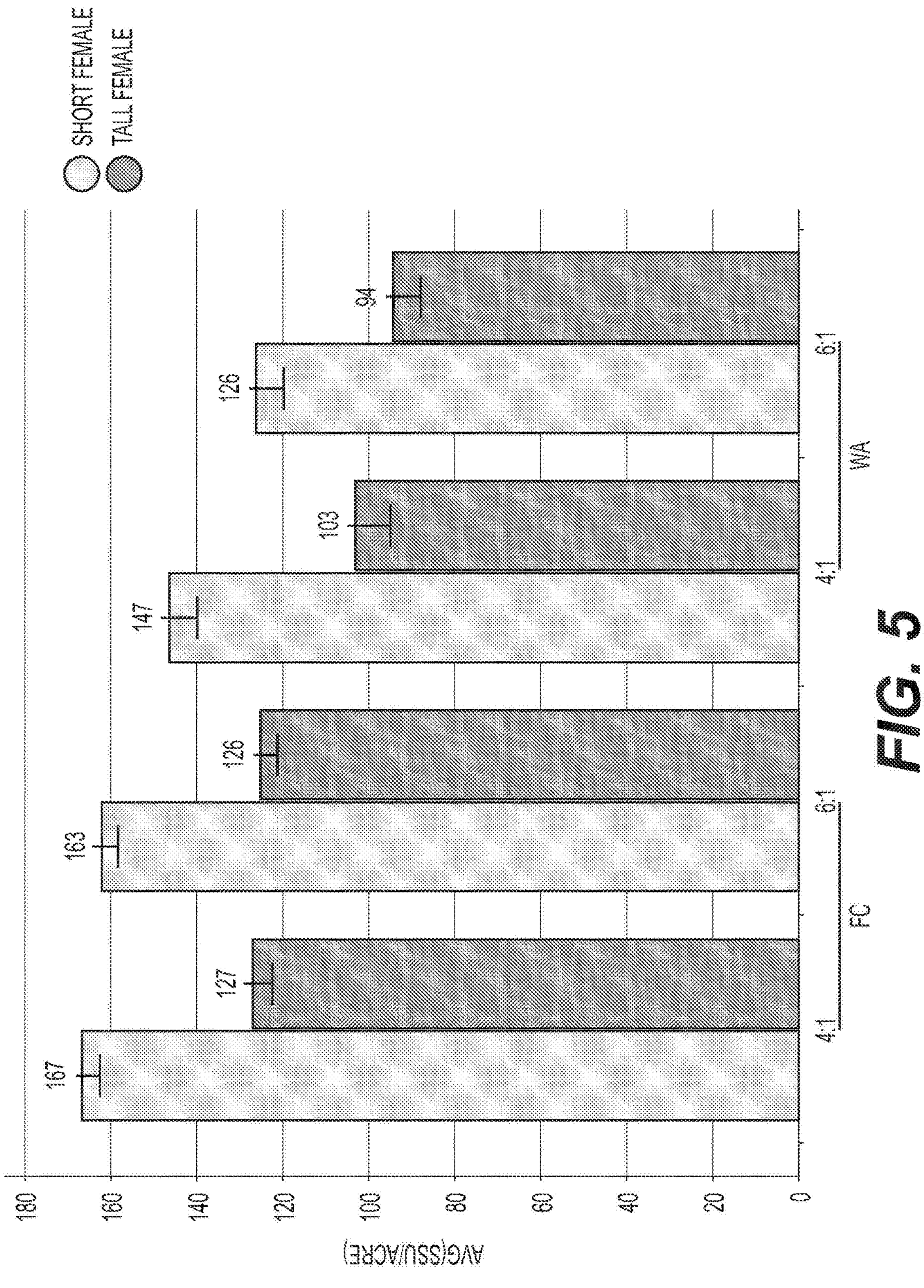
FIG. 5 shows the seed yield in SSU/acre at two testing sites, for both 4:1 and 6:1 female:male row ratio arrangements, averaged over two planting densities.

FIG. 5 shows the seed yield in SSU/acre at the two testing sites, for both 4:1 and 6:1 female:male row ratio arrangements. Seed yield was averaged over the 2 planting densities (described above). In these examples, "WA" is an abbreviation for the first field site, and "FC" is an abbreviation for the second field site. The vertical error bars indicate standard errors for the seed yields. Note the significant improvement in seed yield with shorter female lines, across row planting arrangements at both sites.

Figure 6:
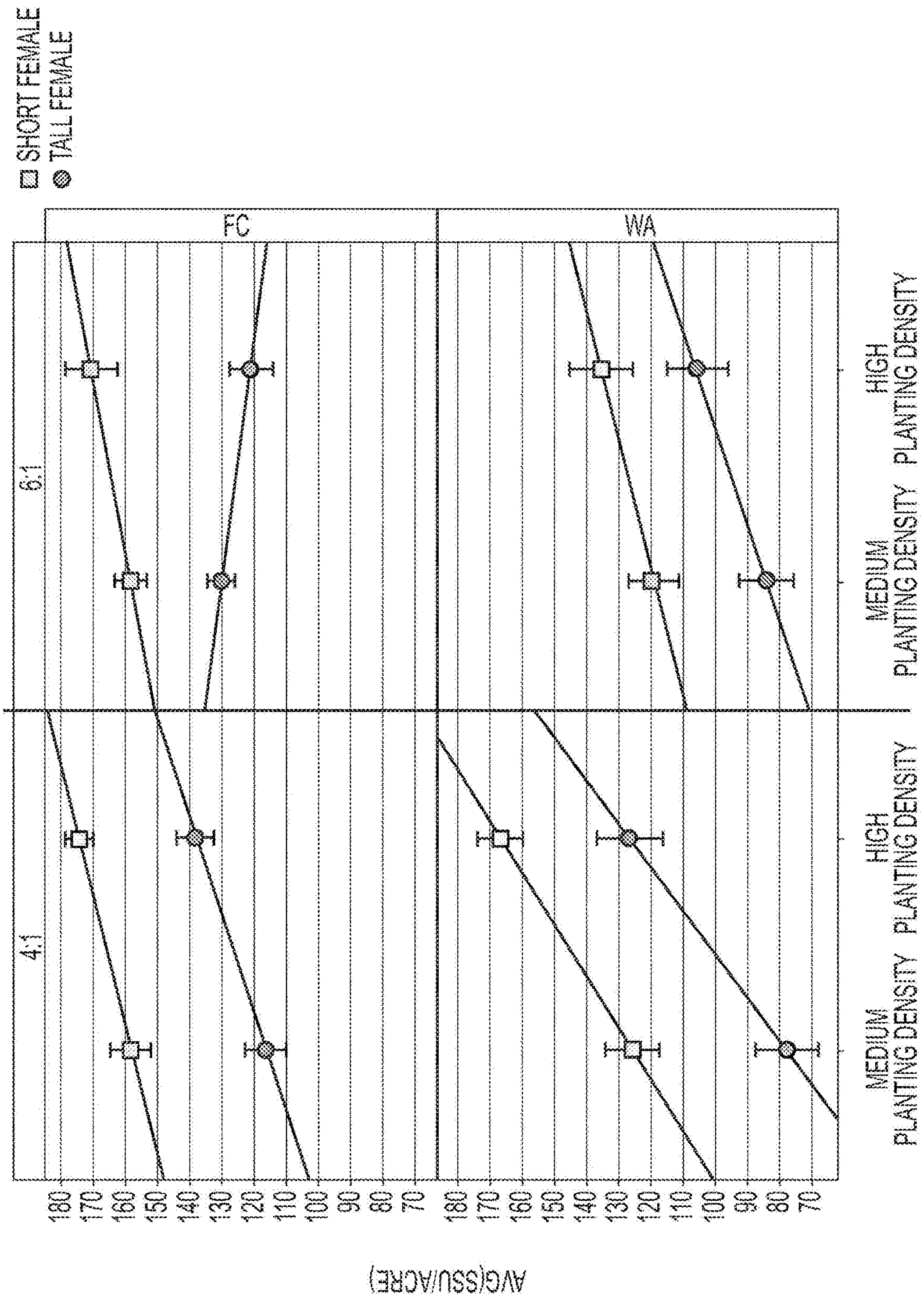
FIG. 6 compares the seed yields of short and tall female lines at two testing sites with 4:1 and 6:1 female-to-male row ratio arrangements, and with two planting densities.

FIG. 6 compares the seed yields of short and tall female lines at two testing sites with 4:1 and 6:1 female-to-male row ratio arrangements, and with two planting densities. "M" indicates medium planting density, and "H" for high planting density. For this experiment, "WA" is an abbreviation for the first site, and "FC" is an abbreviation for the second site. The vertical error bars indicate standard error for the seed yields. Note that the average seed yield is consistently and significantly higher with shorter females than with taller females, at both sites and with both 4:1 and 6:1 female-to-male ratio arrangements of rows, and at both medium and high planting densities. Furthermore, the average seed yield with shorter females is consistently higher at high density relative to medium density planting at both sites and for both of the female-to-male row ratio arrangements.

Example 5. Improved Pollen Production and Distribution with Short Female Parental Line Utilizing short female parental lines in hybrid corn seed production is shown in this example to have direct positive effects on pollen production and dispersion. Without being bound by theory, these positive effects may result from reduced shading of the taller male plants and less physical or wind obstruction to pollen flow from the male tassels by the shorter female plants, resulting in higher seed yields. In this example, direct pollen count measurements are provided over 5 consecutive days of the pollination period, at various female row positions. The "pollination period" is defined as the consecutive five-day period wherein the first day is when the male tassels in the field have reached 10% anthesis.

These five consecutive pollination days can be referred to herein as "Day 1", Day 2", etc.

Pollen trap plates of ~5-inch diameter were placed on level platforms positioned adjacent to the female corn plants in different row positions relative to the closest male row at a height similar to the height of the female corn ears. For the 4:1 female-to-male row ratio planting arrangement, the female rows adjacent to male rows are called the "4-1" position, and the two adjacent inner female rows further away from male rows are called the "4-2" position. Likewise, within the 6:1 female-to-male row ratio planting, the "6-1" position includes the female rows adjacent to male rows, the "6-2" position includes the females rows that are two rows away from the closest male rows, and the "6-3" position includes the two adjacent innermost female rows furthest away from male rows.

600 plates were collected daily from each testing site, with 120 plates collected for each of 5 consecutive days of pollination period, of which 48 plates were collected from plots of 30-inch row spacing, and the other 72 plates from 20-inch plots. To count the number of pollen grains collected on each plate, the collected plates were imaged using a commercial multispectral imaging system, with high-resolution images under strobed LED lights of 19 discrete wavelengths from 365 to 970 nm. The images were further combined into a single multispectral image. An image analysis software was developed to count the number of pollen grains for each plate, and to run the subsequent statistical analysis.

The following experiments and accompanying figures show the average daily pollen counts at different row positions based on the placement of the collection plates. These experiments were carried out at both locations with 4:1 or 6:1 female-to-male row arrangements. The measurements were averaged over all plates for a specific day, at one of the two sites, and for a specific female row position and ratio. The vertical error bars indicate standard errors for the average daily pollen counts.

Figure 7:
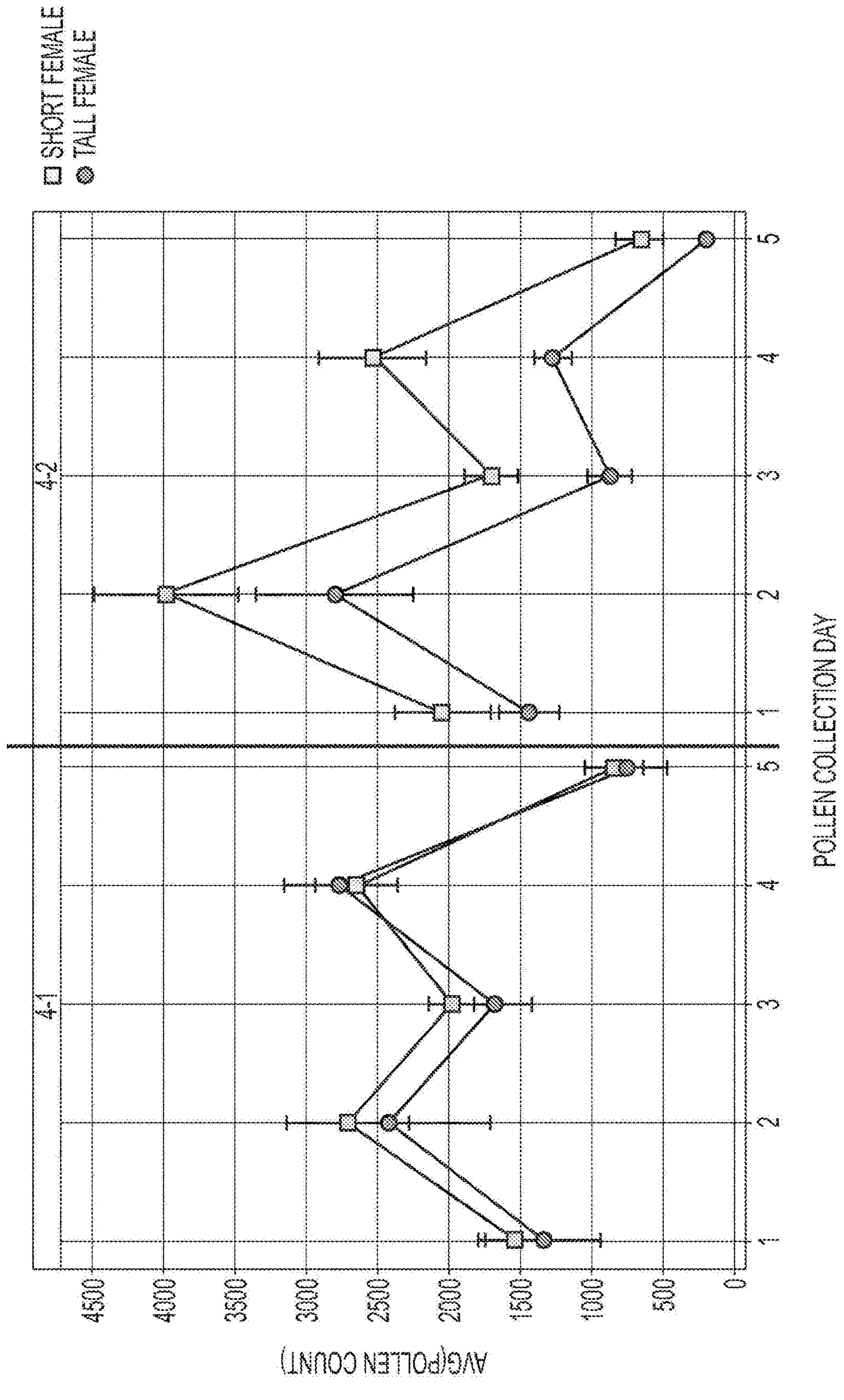
FIG. 7 shows average daily pollen count results for the 4-1 and 4-2 positions at a first field location site with a 4:1 planting arrangement.
Figure 8:
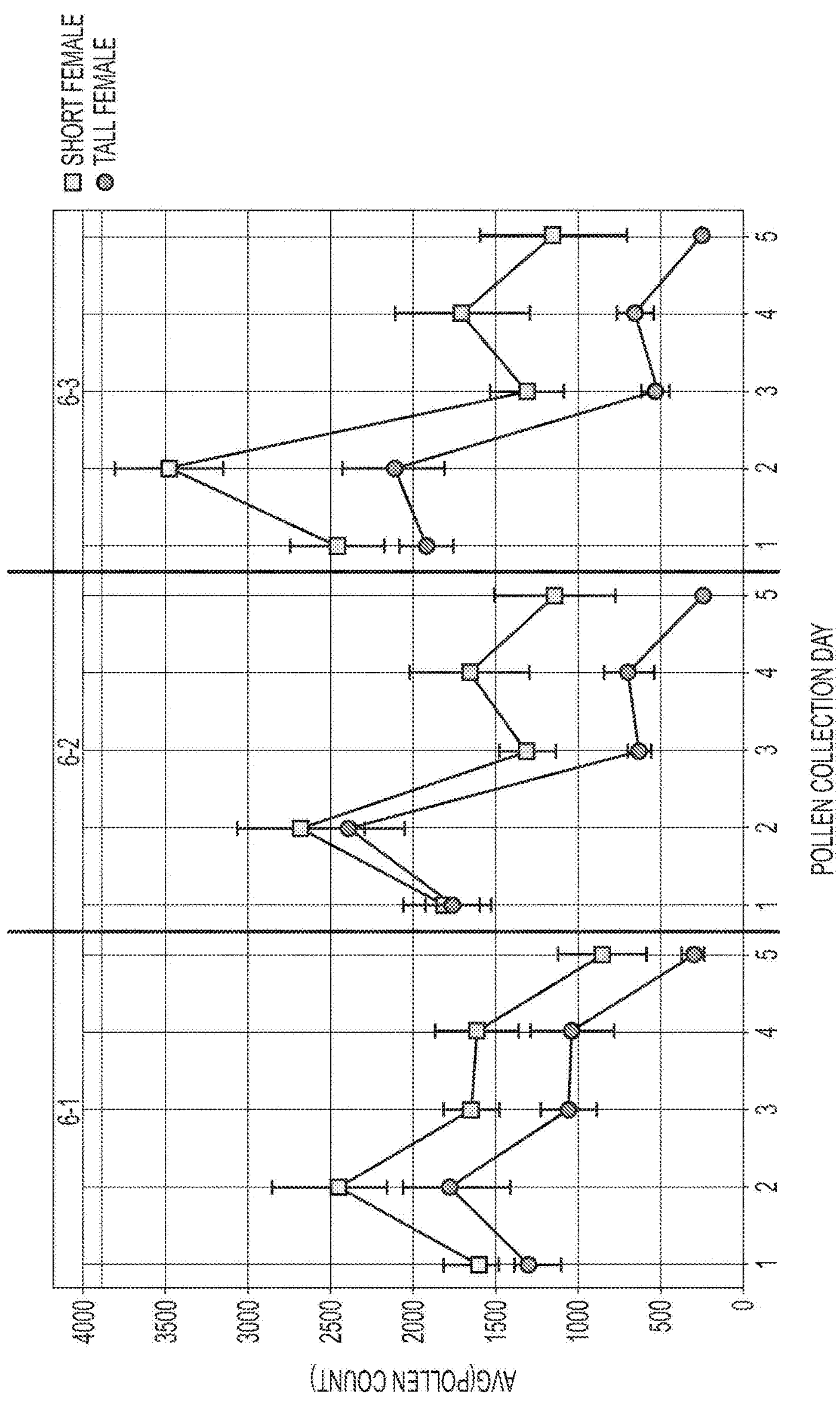
FIG. 8 shows average daily pollen count results for the 6-1, 6-2 and 6-3 positions at a first field location site with a 6:1 planting arrangement.
Figure 9:
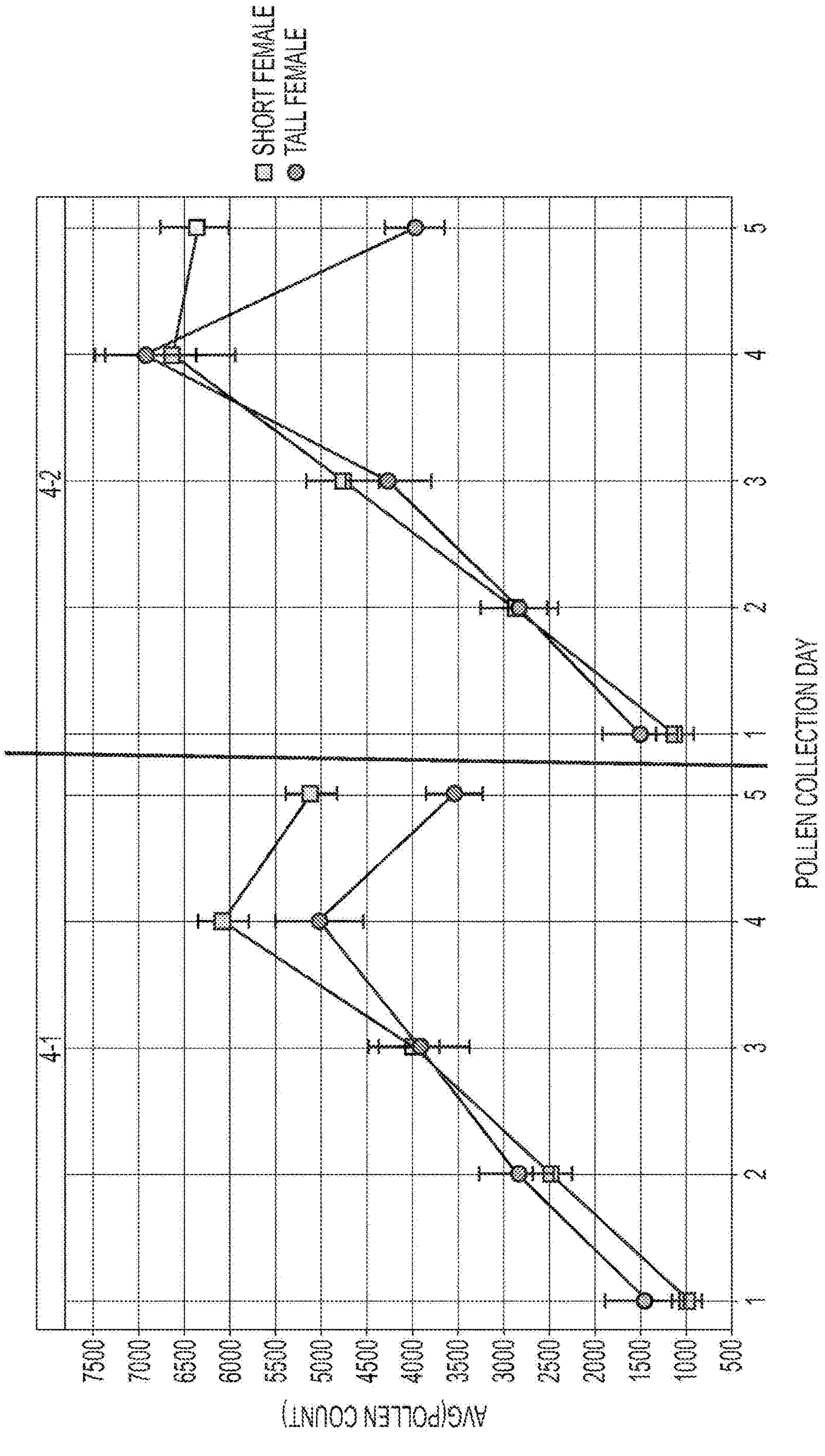
FIG. 9 shows average daily pollen count results for the 4-1 and 4-2 positions at a second field location site with a 4:1 planting arrangement.
Figure 10:
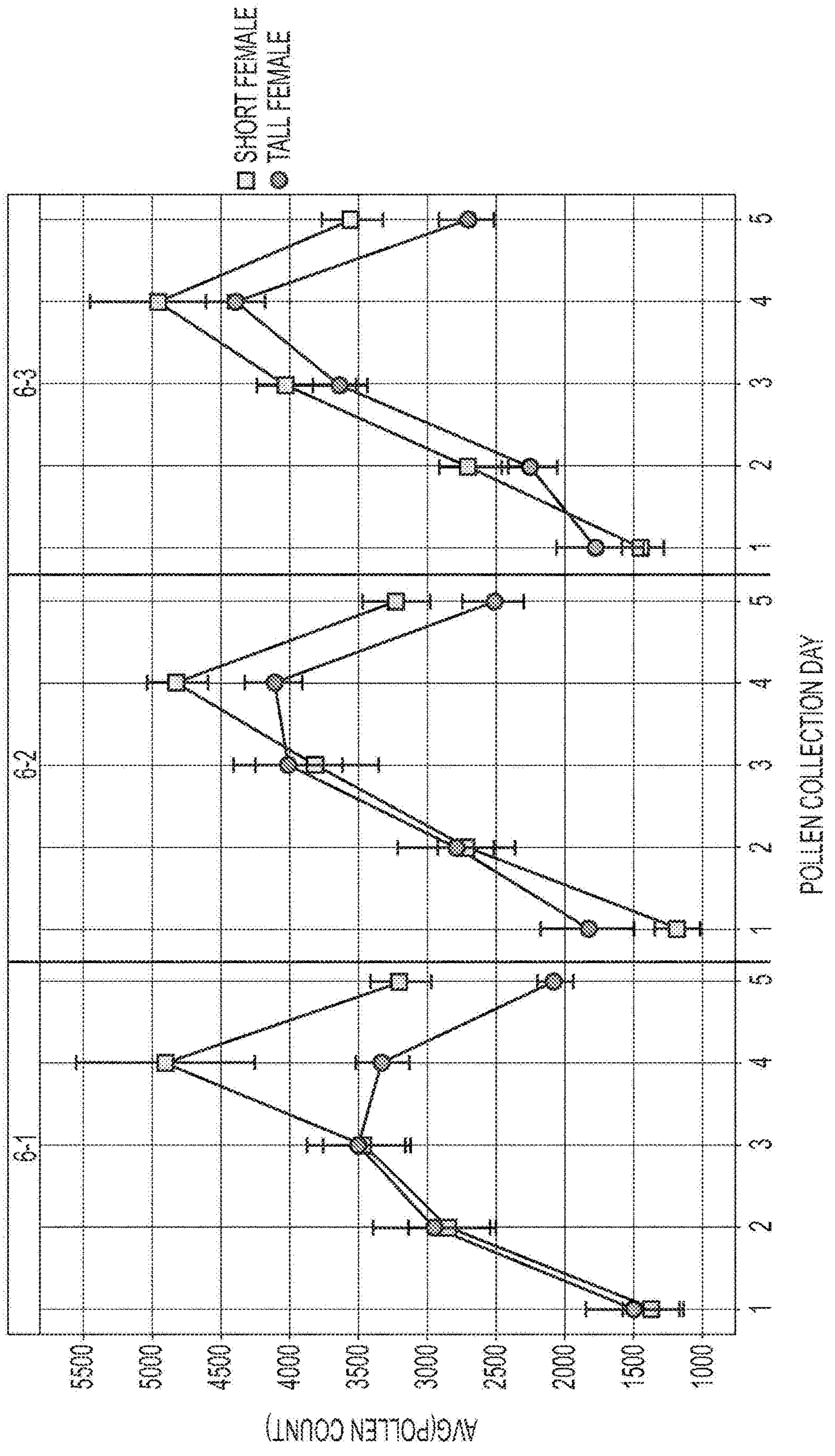
FIG. 10 shows average daily pollen count results for the 6-1, 6-2 and 6-3 positions at a second field location site with a 6:1 planting arrangement.

FIG. 7 shows average daily pollen count results for the 4-1 and 4-2 positions at the first field location site with a 4:1 planting arrangement. In this experiment, position 4-2 showed a significant increase in pollen count with shorter female corn plants, throughout Days 1 to 5. FIG. 8 shows average daily pollen count results for the 6-1, 6-2 and 6-3 positions at the first field location site with a 6:1 planting arrangement. Note the significant increase in pollen count with shorter female corn plants for all positions on Days 3 to 5 and for position 6-3 on Days 1 and 2. FIG. 9 shows average daily pollen count results for the 4-1 and 4-2 positions at the second field location site with a 4:1 planting arrangement. In this experiment, both 4-1 and 4-2 position showed a significant increase in pollen count with shorter female corn plants during Day 5, as well as a significant increase in pollen count with shorter female corn plants at position 4-1 during Day 4. FIG. 10 shows average daily pollen count results for the 6-1, 6-2 and 6-3 positions at the second field location site with a 6:1 planting arrangement. Note the significant increase in pollen count with shorter female corn plants at all row positions (6-1, 6-2 and 6-3) during Day 5 and at row position 6-1 during Day 4. These results show increased pollen collection overall with shorter female plants at both 4:1 and 6:1 female-to-male row ratio planting, with the amounts depending on the ratio of female-to-male rows and the row position.

Without being bound by theory, the increased pollen flow and collection in the rows of shorter female corn plants may at least partially explain and support the increased seed production (SSU/acre) in the production field as shown above.

Example 6. Reduced Male Tassel Skeletonization with Short Female Parental Line Effective pollen production and shedding in hybrid seed production can depend on overall tassel size as well as how fully the tassel develops. In this example, tassel size and development of male inbred plants are observed and measured with either short or tall females. Larger and more developed tassels should produce more pollen leading to greater pollination and seed yields of females. In these experiments, male corn plants next to, or flanked by, shorter female corn plants had larger (data not shown) and more developed tassels with less tassel skeletonization (TSK) (see below), as compared to male corn plants next to, or flanked by, taller female corn plants. Without being bound by theory, it is proposed that the shorter female plants next to the taller male plants permit the male plants to receive more light, perhaps without having to grow as tall, which may improve the development of male reproductive structures.

Tassel skeletonization (TSK), also called "tassel blasting", describes the abortion of glumes and anthers on tassel branches and the main spikelet. It results from an underdevelopment of the tassel and causes reduced pollen production. As known in the art, skeletonization can be measured on the tassels of male parental plants, by a visual rating at 50% pollination stage (P50), on a SKLP scale from 1 to 9, to estimate the level of increasing severity at a plot level. A score of "1" indicates no skeletonization, whereas a score of "9" indicates that the entire tassel is skeletonized. Tassel skeletonization of male corn plants next to either tall or short females was observed and scored according to the above scale. Average SKLP ratings were determined for tassels of male inbred plants flanked in a seed production field by either short female plants (Short) or tall female control plants (Tall) planted at either 20-inch or 30-inch row spacings. For male plants next to taller females, 23 replicates were used for measurement of plants in 30-inch rows, and 26 replicates were used for measurement of plants in 20-inch rows. For male plants next to shorter females, 19 replicates were used for measurement of plants in 30-inch rows, and 26 replicates were used for measurement of plants in 20-inch rows.

Figure 11:
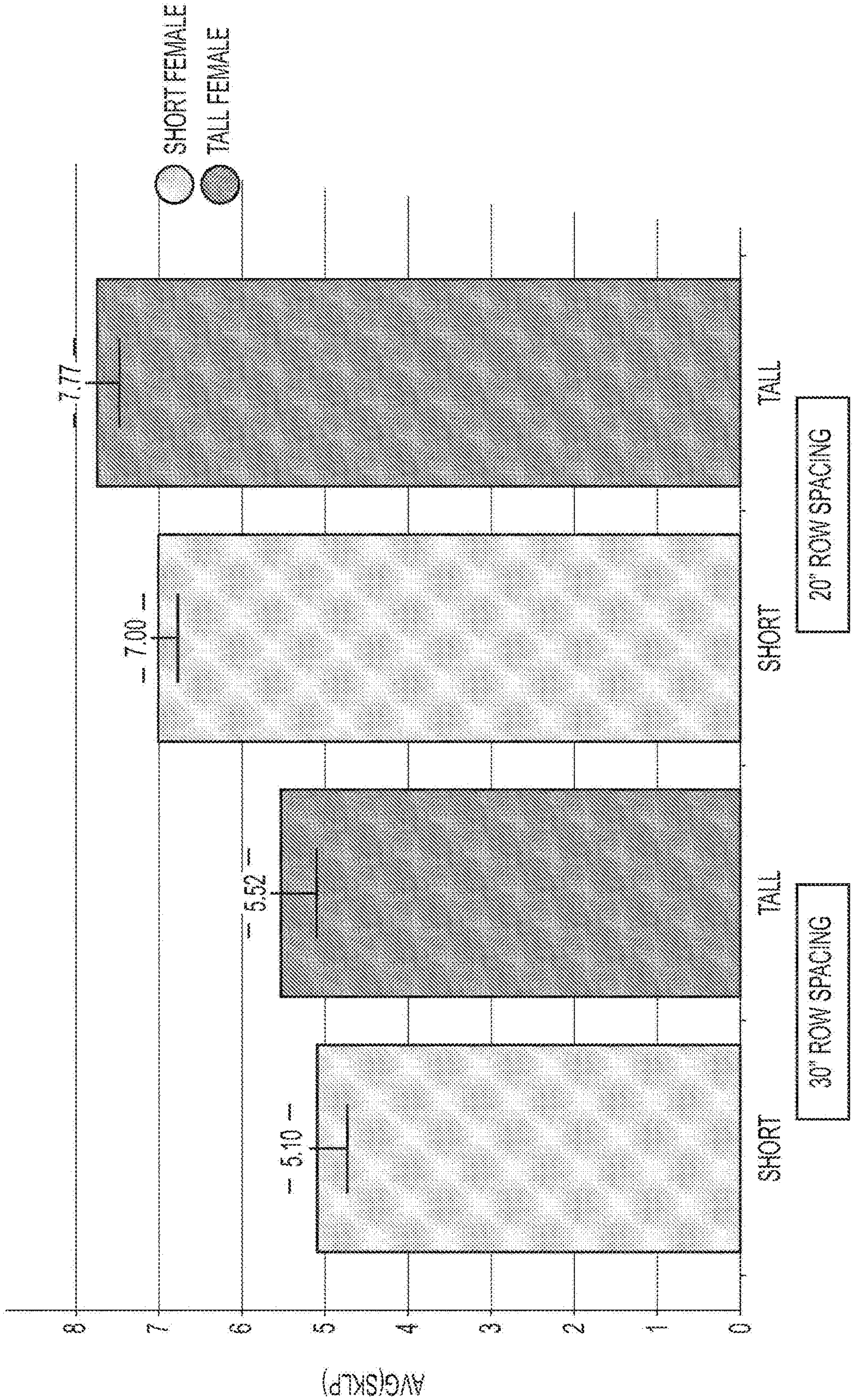
FIG. 11 shows average tassel skeletonization (SKLP) scores of male plants flanked by shorter or taller female plants at 20-inch row spacing and 30-inch row spacing, respectively.

As shown in FIG. 11 for these experiments, male plants flanked by shorter females at 20-inch row spacing had significantly improved (lower) average tassel skeletonization (SKLP) scores (e.g., about 7.0) relative to females planted next to taller females at the same row spacing (e.g., about 7.77). At 30-inch row spacing, average tassel skeletonization (SKLP) scores trended positive toward improvement (e.g., about 5.1), relative to females planted next to taller females at the same row spacing (e.g., 5.52), although the change was not statistically significant. These data indicate that tassel skeletonization of male plants can be reduced with shorter females in corn production fields, which can lead to increased pollen production and shedding.

Without being bound by theory, decreased tassel skeletonization may at least partially explain and support the increased pollen flow and collection in the rows of shorter female corn plants in the production field as shown above.

Example 7. Reduced Plant Lodging with Short Female Parent Line

Corn seed production can be improved if plant lodging is reduced in the production field. It is proposed that the shorter stature female corn plants can have increased lodging resistance relative to taller females, thus leading to improved seed yields in the production field. The shorter stature corn plant may also be more accessible during the growing season with standard height agricultural equipment allowing for over-the-top applications of fertilizer, pesticides, water, etc., to further improve seed yields.

Figure 12:
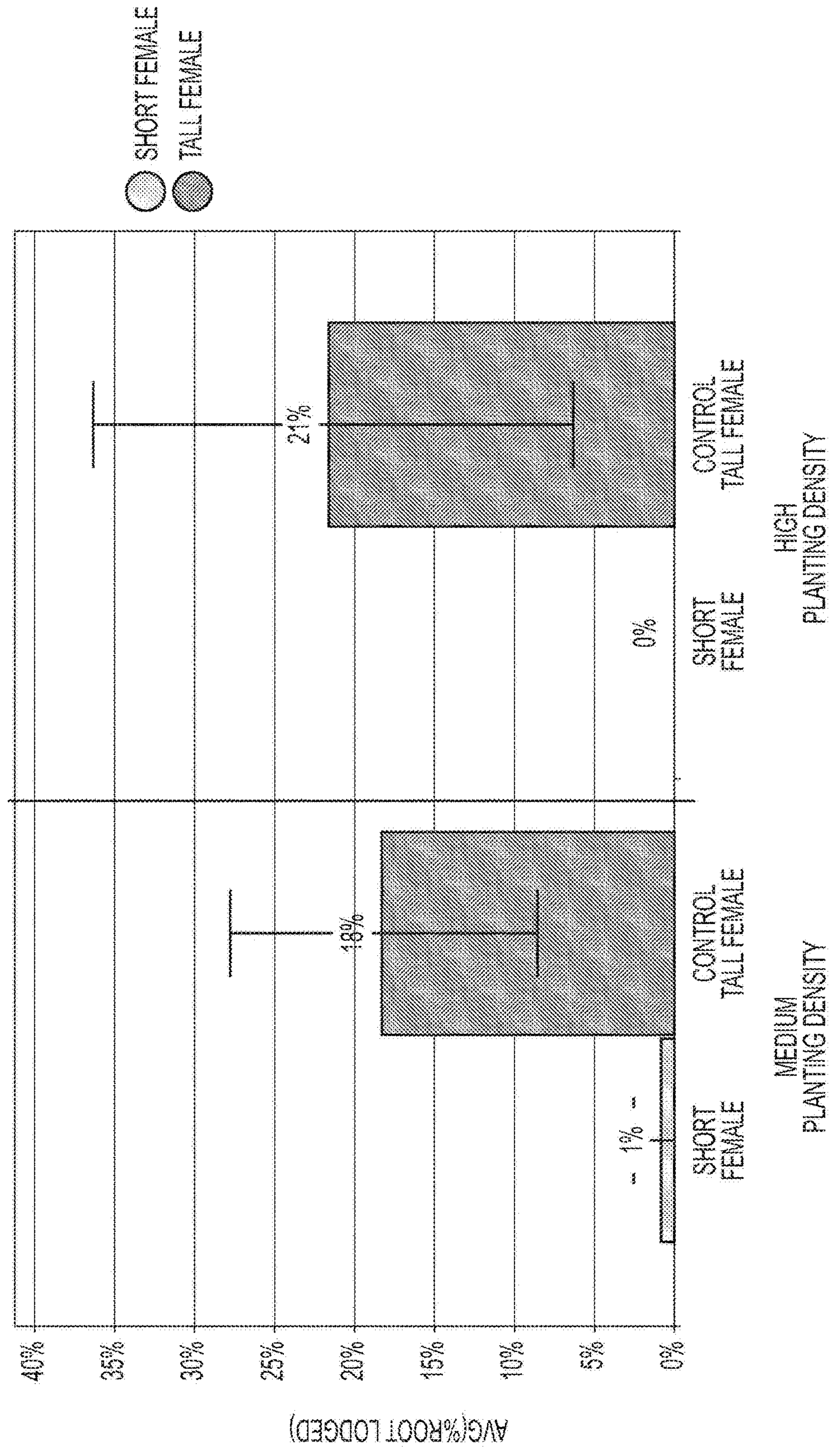
FIG. 12 shows average percentage of root lodged short female plants and root lodged control tall female plants at high and low planting densities.

At one of the corn production field sites, a thunderstorm with high winds caused plant root lodging, particularly among the taller female corn plants in the field. However, the shorter female corn plants exhibited much less lodging at this testing location. Root lodging of female corn plants was measured in a field affected by the storm at both medium (M) and high (H) planting densities. Root lodging data was collected on four female plant rows over the length of the field. A plant was counted as root lodged if it leaned at least 45 degrees from a vertical orientation in the row. 52 replicates were included for both tall and short female corn plants. As shown in FIG. 12, where lodging was significant for the tall control female plants, it was greatly reduced for the short female plants in both medium and high planting density plots. The vertical error bars indicate standard error of average percentage of lodged plants.

Without being bound by theory, the increased lodging resistance of shorter stature female corn plants, in addition to increased pollen flow, may further help to explain and support the increased seed production (SSU/acre) in the production field as shown above.

Having described the present disclosure and inventions in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

The invention claimed is:

1. A method of producing hybrid corn seeds with consistent production stability comprising:

a. fertilizing a plurality of female inbred corn plants with pollen from a plurality of male inbred corn plants to produce hybrid corn seeds, wherein the plurality of female inbred corn plants have an average height that is at least 10% lower than the average height of the plurality of male inbred corn plants, and wherein said female inbred corn plants comprise a mutant allele of a brachytic 2 (br2) locus comprising a mutation or edit in the br2 locus as compared to a wildtype br2 locus; and b. harvesting said hybrid corn seeds from the plurality of the female inbred corn plants, wherein the yield or seed yield of hybrid corn seeds produced in step (b) is less variable and is at least 5% greater as compared to a yield or seed yield of control hybrid corn seeds that are harvested from control female inbred corn plants that have a same or similar average height as control male inbred corn plants, wherein said plurality of female inbred corn plants and said plurality of male inbred corn plants are grown in a corn field, wherein the corn field comprises at least four rows of female inbred corn plants and at least one row of male inbred corn plants, wherein the ratio of female inbred corn plant rows to male inbred corn plant rows is at least 4:1, and wherein the corn field comprises a planting density of the plurality of female inbred corn plants and the plurality of male inbred corn plants of (i) at least 39,560 plants/acre and the corn plant rows are less than 24 inches apart; or (ii) at least 32,000 plants/acres and the corn plant rows are at least 24 inches apart.

2. The method of claim 1, wherein said female inbred corn plants have an average height that is at least 15%, at least 20%, at least 25%, at least 30%, at least 35%, at least 40%, at least 45%, at least 50%, at least 55%, at least 60%, or at least 70% shorter than said plurality of male inbred corn plants.

3. The method of claim 1, wherein said female inbred corn plants have an average height that is between 10% and 50% shorter than said plurality of male inbred corn plant.

4. The method of claim 1, wherein said female inbred corn plants are dwarf corn plants, semi-dwarf corn plants, or brachytic mutant corn plants.

5. The method of claim 1, wherein said female inbred corn plants comprise one or more ears at least 18 inches, at least 19 inches, at least 20 inches, at least 21 inches, at least 22 inches, at least 23 inches, or at least 24 inches above ground level.

6. The method of claim 1, wherein said female inbred corn plants comprise at least one ear that is at least 18 inches above ground level.

7. The method of claim 6, wherein said female inbred corn plants comprise at least one ear that is at least 24 inches above ground level.

8. The method of claim 1, wherein the yield and/or seed yield is increased by at least at least 5.5%, at least 6.0%, at least 6.5%, at least 7.0%, at least 7.5%, at least 8.0%, at least 8.5%, at least 9.0%, at least 9.5%, at least 10%, at least 11%, at least 12%, at least 13%, at least 14%, at least 15%, at least 16%, at least 17%, at least 18%, at least 19%, or at least 20%.

9. The method of claim 1, wherein the yield and/or seed yield of said hybrid corn seeds is increased by between 5% and 20%.

10. The method of claim 1, wherein said female inbred corn plants are detasseled.

11. The method of claim 1, wherein the seed yield is measured in standard seed units (SSUs) per acre.

12. The method of claim 1, wherein the heights of said female inbred corn plants and said at least one male inbred corn plant are measured as the distance between the soil and the ligule of the uppermost fully-expanded leaf.

13. The method of claim 1, wherein the heights of said female inbred corn plants and said plurality of male inbred corn plant are measured as the distance between the soil and the upper leaf surface of the leaf farthest from the soil.

14. The method of claim 1, wherein the heights of said female inbred corn plants and said plurality of male inbred corn plant are measured as the distance between the soil and the arch of the highest corn leaf that is at least 50% developed.

15. The method of claim 1, wherein the heights of said female inbred corn plants and said plurality of male inbred corn plant are measured at R1 stage.

16. The method of claim 1, wherein the yield is measured in bushels per acre.

17. The method of claim 16, wherein the yield is at least 100 bushels per acre, at least 120 bushels per acre, at least 140 bushels per acre, at least 160 bushels per acre, at least 180 bushels per acre, at least 200 bushels per acre, at least 220 bushels per acre, at least 240 bushels per acre, or at least 260 bushels per acre.

18. The method of claim 16, wherein the yield is between 100 and 260 bushels per acre.

19. The method of claim 1, wherein the seed yield is measured in standard seed units (SSUs) per acre.

20. The method of claim 18, wherein the seed yield is at least 80 SSUs per acre, at least 90 SSUs per acre, at least 100 SSUs per acre, at least 110 SSUs per acre, at least 120 SSUs per acre, at least 130 SSUs per acre, at least 140 SSUs per acre, at least 150 SSUs per acre, at least 160 SSUs per acre, at least 170 SSUs per acre, at least 180 SSUs per acre, at least 190 SSUs per acre, or at least 200 SSUs per acre.

21. The method of claim 1, wherein the field comprises multiple rows of female inbred corn plants and multiple rows of male inbred corn plants.

22. The method of claim 21, wherein the seed yield is at least 200 kernels per ear, at least 300 kernels per ear, at least 400 kernels per ear, at least 500 kernels per ear, at least 600 kernels per ear, at least 700 kernels per ear, at least 800 kernels per ear, at least 900 kernels per ear, at least 1,000 kernels per ear, at least 1100 kernels per ear, or at least 1,200 kernels per ear.

23. The method of claim 21, wherein the seed yield is between 200 and 1,200 kernels per ear.

24. The method of claim 1, wherein the yield is measured in dry weight of kernels.

25. The method of claim 24, wherein the yield is at least 0.2 grams per dry kernel, at least 0.25 grams per dry kernel, at least 0.3 grams per dry kernel, at least 0.35 grams per dry kernel, at least 0.4 grams per dry kernel, at least 0.45 grams per dry kernel, at least 0.5 grams per dry kernel, at least 0.55 grams per dry kernel, or at least 0.6 grams per dry kernel.

26. The method of claim 24, wherein the yield is between 0.2 and 0.6 grams per dry kernel.

27. The method of claim 1, wherein the field comprises multiple rows of female inbred corn plants and multiple rows of male inbred corn plants.

28. The method of claim 1, wherein the ratio of female inbred corn plant rows to male inbred corn plant rows is selected from the group consisting of 4:2, 4:3, 6:1, and 6:2.

29. The method of claim 1, wherein the corn field comprises at least 5, at least 6, at least 7, at least 8, at least 9, or at least 10 female rows for every male row.

30. The method of claim 1, wherein said rows of inbred corn plants are spaced at least 14 inches, at least 16 inches, at least 18 inches, at least 20 inches, at least 22 inches, at least 24 inches, at least 26 inches, at least 28 inches, at least 30 inches, at least 32 inches, at least 34 inches, or at least 36 inches apart.

31. The method of claim 1, wherein said rows are spaced between 12 and 36 inches apart.

32. The method of claim 1, wherein the corn field comprises a ratio of at least 5 female inbred corn plants, at least 6 female inbred corn plants, at least 7 female inbred corn plants, at least 8 female inbred corn plants, at least 9 female inbred corn plants, at least 10 female inbred corn plants, at least 15 female inbred corn plants, at least 20 female inbred corn plants, at least 25 female inbred corn plants, at least 30 female inbred corn plants, at least 35 female inbred corn plants, at least 40 female inbred corn plants, at least 45 female inbred corn plants, at least 50 female inbred corn plants, at least 60 female inbred corn plants, at least 70 female inbred corn plants, at least 80 female inbred corn plants, at least 90 female inbred corn plants, or at least 100 female inbred corn plants for every male inbred corn plant.

33. The method of claim 1, wherein the corn field comprises a planting density of at least 33,000 corn plants per acre, at least 36,000 corn plants per acre, at least 39,000 corn plants per acre, at least 42,000 corn plants per acre, at least 45,000 corn plants per acre, at least 48,000 corn plants per acre, at least 51,000 corn plants per acre, at least 54,000 corn plants per acre, at least 57,000 corn plants per acre, or at least 60,000 corn plants per acre.

34. The method of claim 1, wherein the corn field comprises a planting density of between 38,000 and 60,000 corn plants per acre.

35. The method of claim 1, wherein said male inbred corn plants exhibit at least 10% less tassel skeletonization as compared to a control corn field in which said male and female control plants have the same or similar plant heights.

36. The method of claim 35, wherein tassel skeletonization is measured by the percentage of anthers that undergo dehiscence.

37. The method of claim 35, wherein said male inbred corn plants exhibit at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less tassel skeletonization.

38. A method of producing hybrid corn seeds with consistent production stability comprising:

a. crossing a plurality of male inbred corn plants with a plurality of female inbred corn plants to produce hybrid corn seeds, wherein the plurality of female inbred corn plants comprise a mutant allele of a brachytic 2 (br2) locus comprising a mutation or edit in the br2 locus as compared to a wildtype br2 locus; wherein the plurality of female inbred corn plants have an average height that is at least 10% lower than the height or average height of the plurality of male inbred corn plants and; and b. harvesting said hybrid corn seeds from one or more of the female inbred corn plants, wherein the yield or seed yield of hybrid corn seeds produced in step (b) is less variable and is at least 5% greater as compared to a yield or seed yield of control hybrid corn seeds that are harvested from control female inbred corn plants that have a same or similar average height as control male inbred corn plants, wherein said plurality of female inbred corn plants and plurality of male inbred corn plants are grown in a corn field, wherein the field comprises at least one row of female inbred corn plants and at least one row of male inbred corn plants that are spaced at least 12 inches apart, wherein the ratio of female inbred corn plant rows to male inbred corn plant rows is at least 4:1, and wherein the corn field comprises a planting density of at least (i) 39,560 plants/acre and the corn plant rows are less than 24 inches apart; or (ii) at least 32,000 plants/acres and the corn plant rows are at least 24 inches apart.

39. The method of claim 38, wherein the crossing comprises fertilization of said plurality of female inbred corn plants with pollen from said plurality of male inbred corn plants.

40. A method of producing hybrid corn seeds with consistent production stability comprising:

a. planting a plurality of male inbred corn plants in proximity to a plurality of female inbred corn plants to produce hybrid corn seeds, wherein the female inbred corn plants have an average height that is at least 10% lower than the height or average height of the plurality of the male inbred corn plants, and wherein said female inbred corn plants comprise a mutant allele of a brachytic 2 (br2) locus comprising a mutation or edit in the br2 locus as compared to a wildtype br2 locus; and b. harvesting said hybrid corn seeds from one or more of the female inbred corn plants, wherein the yield or seed yield of hybrid corn seeds produced in step (b) is less variable and is at least 5% greater as compared to a yield or seed yield of control hybrid corn seeds that are harvested from control female inbred corn plants that have a same or similar average height as control male inbred corn plants, wherein said plurality of female inbred corn plants and plurality of male inbred corn plants are grown in a corn field, wherein the field comprises at least one row of female inbred corn plants and at least one row of male inbred corn plants that are spaced at least 12 inches apart, wherein the ratio of female inbred corn plant rows to male inbred corn plant rows is at least 4:1, and wherein the corn field comprises a planting density of at least (i) 39,560 plants/acre and the corn plant rows are less than 24 inches apart; or (ii) at least 32,000 plants/acres and the corn plant rows are at least 24 inches apart.

41. The method of claim 1, wherein said female inbred corn plants are homozygous for the mutant allele of the br2 locus.

* * * * *